(12) United States Patent
Jain et al.

(10) Patent No.: US 12,282,408 B1
(45) Date of Patent: Apr. 22, 2025

(54) IMPROVING COMPLIANCE OF PATIENT DATA COLLECTION IN CLINICAL TRIALS WITH PREDICTIVE ANALYSIS

(71) Applicant: Vignet Incorporated, Fairfax, VA (US)

(72) Inventors: Praduman Jain, Fairfax, VA (US); Josh Schilling, Salem, OR (US); Dave Klein, Oakton, VA (US); Mark James Begale, Chicago, IL (US)

(73) Assignee: VigNet Incorporated, Fairfax, VA (US)

( * ) Notice: Subject to any disclaimer, the term of this patent is extended or adjusted under 35 U.S.C. 154(b) by 901 days.

(21) Appl. No.: 17/207,321

(22) Filed: Mar. 19, 2021

Related U.S. Application Data

(63) Continuation of application No. 16/877,162, filed on May 18, 2020, now Pat. No. 11,461,216.

(51) Int. Cl.
  *G06F 11/34* (2006.01)
  *A61B 5/00* (2006.01)
  (Continued)

(52) U.S. Cl.
  CPC ........ *G06F 11/3466* (2013.01); *A61B 5/7275* (2013.01); *G06F 11/3438* (2013.01);
  (Continued)

(58) Field of Classification Search
  CPC . G06F 11/3466; G06F 11/3438; G16H 10/20; G06N 20/00; A61B 5/4806
  (Continued)

(56) References Cited

U.S. PATENT DOCUMENTS 5,547,878 A    8/1996   Kel
5,832,474 A    11/1998   Lopresti et al.
(Continued)

FOREIGN PATENT DOCUMENTS

CN      209085657 U    7/2019
KR    20110133497 A    12/2011
(Continued)

OTHER PUBLICATIONS

US Non-Final Office Action in U.S. Appl. No. 16/876,962, dated Sep. 13, 2021, 32 pages.
(Continued)

*Primary Examiner* — Michael Tomaszewski
(74) *Attorney, Agent, or Firm* — Fish & Richardson P.C.

(57) ABSTRACT

Methods, systems, and apparatus, including computer programs encoded on a computer storage medium, for adapting digital trial to increase protocol compliance and retention. In some implementations, a system accesses (i) study data indicating a type of data to be collected in a research study and (ii) attribute data indicating attributes of participants in a cohort for the research study. The system identifies a set of technology items that are each capable of collecting the type of data indicated by the study data. The system determines a predicted level of compliance for each of the technology items in the set. The system selects a technology item for participants in the cohort to use in the research study based on the predicted levels of compliance. The system updates records for the research study to specify the selected technology item.

21 Claims, 30 Drawing Sheets

(51) Int. Cl.
 *G06N 20/00* (2019.01)
 *G16H 10/20* (2018.01)
(52) U.S. Cl.
 CPC ............. *G06N 20/00* (2019.01); *G16H 10/20* (2018.01); *A61B 5/4806* (2013.01)
(58) Field of Classification Search
 USPC ........................................................ 705/2–3
 See application file for complete search history.

(56) References Cited

U.S. PATENT DOCUMENTS

| | | | |
|---|---|---|---|
| 6,029,144 A | 2/2000 | Barrett et al. | |
| 6,151,586 A | 11/2000 | Brown et al. | |
| 6,514,200 B1 | 2/2003 | Khouri | |
| 6,574,622 B1 | 6/2003 | Miyauchi et al. | |
| 6,663,846 B1 | 12/2003 | McCombs et al. | |
| 6,879,970 B2 | 4/2005 | Shiffman et al. | |
| 7,054,782 B2 | 5/2006 | Hartlaub | |
| 7,113,917 B2 | 9/2006 | Jacobi et al. | |
| 7,251,609 B1 | 7/2007 | McAlindon et al. | |
| 7,415,447 B2 | 8/2008 | Shiffman et al. | |
| 7,752,059 B2 | 7/2010 | Sweeney et al. | |
| 7,809,601 B2 | 10/2010 | Shaya et al. | |
| 7,809,660 B2 | 10/2010 | Friedlander et al. | |
| 7,930,262 B2 | 4/2011 | Friedlander et al. | |
| 8,032,545 B2 | 10/2011 | Setimi | |
| 8,065,180 B2 | 11/2011 | Hufford et al. | |
| 8,157,730 B2 | 4/2012 | LeBouef et al. | |
| 8,380,531 B2 | 2/2013 | Paty et al. | |
| 8,433,605 B2 | 4/2013 | Hufford et al. | |
| 8,527,486 B2 | 9/2013 | Wittig et al. | |
| 8,533,029 B2 | 9/2013 | Hufford et al. | |
| 8,583,453 B2 | 11/2013 | Plummer et al. | |
| 8,684,922 B2 | 4/2014 | Tran | |
| 8,688,475 B2* | 4/2014 | Ferguson | G06Q 10/10 705/2 |
| 8,707,392 B2 | 4/2014 | Birtwhistle et al. | |
| 8,966,548 B2 | 2/2015 | Busse et al. | |
| 9,020,971 B2 | 4/2015 | Bayliss et al. | |
| 9,286,442 B2 | 3/2016 | Csoma et al. | |
| 9,357,939 B1 | 6/2016 | Nosrati | |
| 9,495,651 B2 | 11/2016 | O'Sullivan et al. | |
| 9,514,655 B1 | 12/2016 | Nusbaum et al. | |
| 9,659,254 B2 | 5/2017 | Achin et al. | |
| 9,753,618 B1 | 9/2017 | Jain et al. | |
| 9,813,318 B2 | 11/2017 | Iyoob et al. | |
| 9,848,061 B1 | 12/2017 | Jain et al. | |
| 9,858,063 B2 | 1/2018 | Jain et al. | |
| 9,928,230 B1 | 3/2018 | Jain et al. | |
| 9,983,775 B2 | 5/2018 | Jain et al. | |
| 10,069,934 B2 | 9/2018 | Jain et al. | |
| 10,095,688 B1 | 10/2018 | Jain et al. | |
| 10,231,622 B2 | 3/2019 | Soyao et al. | |
| 10,304,000 B2 | 5/2019 | Birnbaum et al. | |
| 10,452,816 B2 | 10/2019 | Kidd et al. | |
| 10,455,262 B2 | 10/2019 | Rieger et al. | |
| 10,510,438 B2 | 12/2019 | Frazier et al. | |
| 10,521,557 B2 | 12/2019 | Jain et al. | |
| 10,546,339 B2 | 1/2020 | Jiao et al. | |
| 10,565,894 B1 | 2/2020 | Jain et al. | |
| 10,580,531 B2 | 3/2020 | Jiao et al. | |
| 10,636,525 B2 | 4/2020 | Jiao et al. | |
| 10,650,474 B2 | 5/2020 | Jiao et al. | |
| 10,672,519 B2 | 6/2020 | Jiao et al. | |
| 10,756,957 B2 | 8/2020 | Jain et al. | |
| 10,762,990 B1 | 9/2020 | Jain et al. | |
| 10,805,965 B2 | 10/2020 | Vedula et al. | |
| 10,938,651 B2 | 3/2021 | Jain et al. | |
| 11,056,242 B1 | 7/2021 | Jain et al. | |
| 11,061,798 B1 | 7/2021 | Jain et al. | |
| 11,082,487 B1 | 8/2021 | Jain et al. | |
| 11,102,304 B1 | 8/2021 | Jain et al. | |
| 11,107,591 B1 | 8/2021 | Mason | |
| 11,158,423 B2 | 10/2021 | Jain et al. | |
| 11,240,329 B1 | 2/2022 | Jain et al. | |
| 11,281,553 B1 | 3/2022 | Jain et al. | |
| 11,296,971 B1 | 4/2022 | Jain et al. | |
| 11,322,260 B1 | 5/2022 | Jain et al. | |
| 11,328,796 B1 | 5/2022 | Jain et al. | |
| 11,347,618 B1 | 5/2022 | Jain et al. | |
| 11,361,846 B1 | 6/2022 | Jain et al. | |
| 11,392,651 B1 | 7/2022 | McClusky et al. | |
| 11,409,417 B1 | 8/2022 | Schilling et al. | |
| 11,417,418 B1 | 8/2022 | Jain et al. | |
| 11,456,080 B1 | 9/2022 | Jain et al. | |
| 11,461,216 B1 | 10/2022 | Jain et al. | |
| 11,504,011 B1 | 11/2022 | Jain et al. | |
| 11,520,466 B1 | 12/2022 | Schilling | |
| 11,586,524 B1 | 2/2023 | Jain et al. | |
| 11,605,038 B1 | 3/2023 | Jain et al. | |
| 11,645,180 B1 | 5/2023 | Jain et al. | |
| 11,687,437 B1 | 6/2023 | Jain et al. | |
| 11,841,787 B1 | 12/2023 | Jain et al. | |
| 11,886,318 B1 | 1/2024 | Jain et al. | |
| 2002/0099570 A1 | 7/2002 | Knight | |
| 2002/0143563 A1* | 10/2002 | Hufford | G16H 10/40 705/2 |
| 2002/0143577 A1* | 10/2002 | Shiffman | G16H 10/20 705/2 |
| 2002/0143595 A1 | 10/2002 | Frank et al. | |
| 2003/0028413 A1 | 2/2003 | White et al. | |
| 2003/0065669 A1 | 4/2003 | Kahn et al. | |
| 2003/0130871 A1 | 7/2003 | Rao et al. | |
| 2004/0059697 A1 | 3/2004 | Forman | |
| 2004/0098271 A1 | 5/2004 | Hicks et al. | |
| 2004/0172447 A1 | 9/2004 | Miller | |
| 2004/0175700 A1 | 9/2004 | Geesaman | |
| 2004/0210457 A1 | 10/2004 | Sameh | |
| 2004/0235059 A1 | 11/2004 | Warner et al. | |
| 2005/0165626 A1 | 7/2005 | Karpf | |
| 2005/0182657 A1* | 8/2005 | Abraham-Fuchs | G16H 70/20 705/2 |
| 2005/0182664 A1 | 8/2005 | Abraham-Fuchs | |
| 2006/0053094 A1 | 3/2006 | Ravi et al. | |
| 2006/0184493 A1* | 8/2006 | Shiffman | G06Q 90/00 706/47 |
| 2007/0179361 A1 | 8/2007 | Brown et al. | |
| 2007/0250429 A1 | 10/2007 | Walser et al. | |
| 2007/0294110 A1 | 12/2007 | Settimi | |
| 2008/0010945 A1 | 1/2008 | McKenna et al. | |
| 2008/0021287 A1 | 1/2008 | Woellenstein et al. | |
| 2008/0109455 A1* | 5/2008 | Katz | G06Q 10/06393 |
| 2008/0114616 A1* | 5/2008 | Ferguson | G06Q 10/10 705/2 |
| 2008/0114689 A1 | 5/2008 | Psynik et al. | |
| 2008/0140444 A1 | 6/2008 | Karkanias | |
| 2008/0294459 A1 | 11/2008 | Angell et al. | |
| 2009/0163183 A1 | 6/2009 | O'Donoghue et al. | |
| 2009/0228868 A1 | 9/2009 | Drukman et al. | |
| 2009/0299766 A1 | 12/2009 | Friedlander et al. | |
| 2010/0077218 A1 | 3/2010 | Mitchel et al. | |
| 2010/0088245 A1 | 4/2010 | Harrison et al. | |
| 2010/0127891 A1 | 5/2010 | Holzhausen | |
| 2010/0218132 A1 | 8/2010 | Soni et al. | |
| 2010/0318540 A1 | 12/2010 | Svore et al. | |
| 2011/0093796 A1 | 4/2011 | Plummer et al. | |
| 2011/0166628 A1 | 7/2011 | Jain et al. | |
| 2011/0167133 A1 | 7/2011 | Jain et al. | |
| 2012/0029940 A1* | 2/2012 | Hufford | G06Q 10/10 705/3 |
| 2012/0059735 A1 | 3/2012 | Su et al. | |
| 2012/0065987 A1 | 3/2012 | Farooq et al. | |
| 2012/0078648 A1 | 3/2012 | Reiner | |
| 2012/0198049 A1 | 8/2012 | Sangra et al. | |
| 2012/0239414 A1* | 9/2012 | Hufford | G06Q 10/10 705/2 |
| 2012/0310670 A1 | 12/2012 | Pruitt | |
| 2013/0006671 A1 | 1/2013 | Hufford et al. | |
| 2013/0030836 A1 | 1/2013 | Ackerson | |
| 2013/0262140 A1 | 10/2013 | Friedlander et al. | |
| 2013/0268287 A1* | 10/2013 | Hufford | G16H 10/20 705/2 |

(56) References Cited

U.S. PATENT DOCUMENTS

| | | | |
|---|---|---|---|
| 2014/0067596 A1 | 3/2014 | McGovern et al. | |
| 2014/0108032 A1* | 4/2014 | Hufford | G16H 10/20 |
| | | | 705/2 |
| 2014/0187890 A1 | 7/2014 | Mensinger et al. | |
| 2014/0195297 A1 | 7/2014 | Abuelsaad et al. | |
| 2014/0278468 A1 | 9/2014 | Mayer et al. | |
| 2014/0278474 A1 | 9/2014 | McClure et al. | |
| 2014/0297199 A1 | 10/2014 | Osten | |
| 2014/0316793 A1 | 10/2014 | Pruit | |
| 2014/0350954 A1 | 11/2014 | Ellis et al. | |
| 2015/0065830 A1 | 3/2015 | Karp et al. | |
| 2015/0073830 A1 | 3/2015 | Hill et al. | |
| 2015/0178473 A1* | 6/2015 | Hufford | G06Q 10/10 |
| | | | 705/2 |
| 2015/0178474 A1* | 6/2015 | Hufford | G06Q 10/0639 |
| | | | 705/2 |
| 2015/0193588 A1 | 7/2015 | Nemoto et al. | |
| 2015/0199490 A1 | 7/2015 | Iancu et al. | |
| 2015/0228041 A1 | 8/2015 | Naley et al. | |
| 2015/0242572 A1 | 8/2015 | Goltra | |
| 2015/0294090 A1 | 10/2015 | Kodiyan | |
| 2015/0356582 A1 | 12/2015 | Turner, Jr. | |
| 2016/0078186 A1 | 3/2016 | Hill et al. | |
| 2016/0086505 A1 | 3/2016 | Hanlon | |
| 2016/0098541 A1 | 4/2016 | Haskell et al. | |
| 2016/0125171 A1 | 5/2016 | Finken et al. | |
| 2016/0140322 A1 | 5/2016 | Menon et al. | |
| 2016/0253480 A1 | 9/2016 | Cornish | |
| 2016/0262680 A1 | 9/2016 | Martucci et al. | |
| 2016/0267238 A1 | 9/2016 | Nag | |
| 2016/0306945 A1 | 10/2016 | Jiang | |
| 2016/0314257 A1 | 10/2016 | Nolan et al. | |
| 2017/0020444 A1 | 1/2017 | Lurie | |
| 2017/0039324 A1* | 2/2017 | Francois | G16H 10/60 |
| 2017/0039341 A1 | 2/2017 | Shklarski et al. | |
| 2017/0070398 A1 | 3/2017 | Singhal et al. | |
| 2017/0071671 A1 | 3/2017 | Neumann | |
| 2017/0164832 A1 | 6/2017 | Kaib | |
| 2017/0177524 A1 | 6/2017 | Wang | |
| 2017/0199800 A1 | 7/2017 | Johns et al. | |
| 2017/0231528 A1 | 8/2017 | Nathan | |
| 2017/0235894 A1 | 8/2017 | Cox et al. | |
| 2017/0235912 A1 | 8/2017 | Moturu et al. | |
| 2017/0262604 A1 | 9/2017 | Francois | |
| 2017/0286622 A1 | 10/2017 | Cox | |
| 2017/0316482 A1 | 11/2017 | Hisano | |
| 2017/0372348 A1 | 12/2017 | Baluja | |
| 2018/0011772 A1 | 1/2018 | Meyer et al. | |
| 2018/0025125 A1 | 1/2018 | Crane et al. | |
| 2018/0032122 A1 | 2/2018 | Agrawal | |
| 2018/0036591 A1 | 2/2018 | King | |
| 2018/0046780 A1 | 2/2018 | Graiver et al. | |
| 2018/0056130 A1 | 3/2018 | Bitran et al. | |
| 2018/0068083 A1 | 3/2018 | Cohen et al. | |
| 2018/0089376 A1 | 3/2018 | Tucker et al. | |
| 2018/0121605 A1 | 5/2018 | Allen | |
| 2018/0144100 A1 | 5/2018 | Chalas et al. | |
| 2018/0150523 A1 | 5/2018 | Shiffman et al. | |
| 2018/0242860 A1 | 8/2018 | LeBouef et al. | |
| 2018/0300640 A1 | 10/2018 | Birnbaum et al. | |
| 2018/0330824 A1 | 11/2018 | Athey | |
| 2019/0007912 A1 | 1/2019 | Do | |
| 2019/0012434 A1 | 1/2019 | Frazier | |
| 2019/0122266 A1 | 4/2019 | Ramer et al. | |
| 2019/0138656 A1 | 5/2019 | Yang et al. | |
| 2019/0140892 A1 | 5/2019 | Jain et al. | |
| 2019/0164069 A1 | 5/2019 | Zhivotvorev et al. | |
| 2019/0206521 A1 | 7/2019 | Walpole et al. | |
| 2019/0207814 A1 | 7/2019 | Jain et al. | |
| 2019/0227528 A1 | 7/2019 | Abbott et al. | |
| 2019/0244129 A1 | 8/2019 | Tabuchi et al. | |
| 2020/0016745 A1 | 1/2020 | Tang et al. | |
| 2020/0058382 A1 | 2/2020 | Birnbaum et al. | |
| 2020/0065879 A1 | 2/2020 | Hu et al. | |
| 2020/0066412 A1 | 2/2020 | Bender et al. | |
| 2020/0131581 A1 | 4/2020 | Jain et al. | |
| 2020/0203012 A1 | 6/2020 | Kamath et al. | |
| 2020/0211680 A1 | 7/2020 | Sablinski et al. | |
| 2020/0279622 A1 | 9/2020 | Heywood et al. | |
| 2020/0321116 A1 | 10/2020 | Neumann | |
| 2020/0342352 A1 | 10/2020 | Neumann | |
| 2020/0372084 A1 | 11/2020 | Kolobov et al. | |
| 2020/0387810 A1 | 12/2020 | Hodgson | |
| 2021/0055942 A1 | 2/2021 | Guda | |
| 2021/0081486 A1 | 3/2021 | Mattox et al. | |
| 2021/0162261 A1 | 6/2021 | Neumann | |
| 2021/0182878 A1 | 6/2021 | Margolin et al. | |
| 2021/0193297 A1 | 6/2021 | Buckland et al. | |
| 2021/0210170 A1 | 7/2021 | Gardner et al. | |
| 2021/0241137 A1 | 8/2021 | Jain et al. | |
| 2021/0342394 A1 | 11/2021 | Fletcher et al. | |
| 2021/0350890 A1 | 11/2021 | Virkar et al. | |
| 2022/0076822 A1 | 3/2022 | Liu et al. | |
| 2022/0165424 A1 | 5/2022 | Jasik et al. | |
| 2022/0188671 A1 | 6/2022 | Jain et al. | |
| 2022/0325347 A1 | 10/2022 | Ip et al. | |

FOREIGN PATENT DOCUMENTS

| | | |
|---|---|---|
| WO | WO 1995012812 | 5/1995 |
| WO | WO 2015084352 A1 | 6/2015 |
| WO | WO 2015089088 A1 | 6/2015 |
| WO | WO 2016110804 | 7/2016 |
| WO | WO 2017100609 A1 | 6/2017 |
| WO | WO 2020198065 A1 | 10/2020 |

OTHER PUBLICATIONS

Office Action in U.S. Appl. No. 17/173,273, dated Feb. 29, 2024, 12 pages.

Office Action in U.S. Appl. No. 17/176,419, dated Dec. 21, 2022, 34 pages.

Office Action in U.S. Appl. No. 17/327,491, dated Dec. 21, 2022, 40 pages.

US Office Action in U.S. Appl. No. 16/876,962, dated Sep. 28, 2022, 51 pages.

Office Action in U.S. Appl. No. 17/207,439, dated Jan. 18, 2023, 36 pages.

Office Action in U.S. Appl. No. 17/176,419, dated Aug. 24, 2023, 19 pages.

Ispor.com [online], "How mHealth technology is revolutionizing clinical research," Sep./Oct. 2018, retrieved on Apr. 1, 2022, retrieved from URL<https://www.ispor.org/docs/default-source/publications/value-outcomes-spotlight/september-october-2018/ispor-vos-october-2018-toc-mhealth.pdf?sfvrsn=5822a619_2>, 4 pages.

US Final Office Action in U.S. Appl. No. 16/876,962, dated Jan. 26, 2022, 32 pages.

US Non-Final Office Action in U.S. Appl. No. 16/876,856, dated Oct. 6, 2021, 17 pages.

US Non-Final Office Action in U.S. Appl. No. 17/173,264, dated Sep. 16, 2021, 36 pages.

US Notice of Allowance in U.S. Appl. No. 16/876,856, dated Mar. 30, 2022, 14 pages.

US Notice of Allowance in U.S. Appl. No. 16/877,162, dated Mar. 16, 2022, 15 pages.

Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.

Obgyn.com [online], "Neural Networks", published in 2002, retrieved on Jan. 19, 2021, 34 pages.

US Office Action in U.S. Appl. No. 16/800,952, dated Jan. 19, 2021, 24 pages.

US Office Action in U.S. Appl. No. 16/800,952, dated Sep. 1, 2020, 17 pages.

US Office Action in U.S. Appl. No. 16/877,162, dated Apr. 20, 2021, 17 pages.

US Office Action in U.S. Appl. No. 17/163,109, dated Apr. 1, 2021, 16 pages.

(56) References Cited

OTHER PUBLICATIONS

U.S. Appl. No. 17/176,419, filed Feb. 16, 2021, Jain et al.
U.S. Appl. No. 17/207,439, filed Mar. 19, 2021, Jain et al.
U.S. Appl. No. 16/876,962, filed May 18, 2020, Jain et al.
Notice of Allowance in U.S. Appl. No. 17/173,264, dated Jan. 14, 2022, 9 pages.
Notice of Allowance in U.S. Appl. No. 17/246,127, dated Feb. 1, 2023, 9 pages.
Notice of Allowance in U.S. Appl. No. 18/102,875, dated May 24, 2023, 18 pages.
Office Action in U.S. Appl. No. 16/877,162, dated Dec. 8, 2020, 15 pages.
Office Action in U.S. Appl. No. 16/877,162, dated Jul. 8, 2021, 7 pages.
Office Action in U.S. Appl. No. 17/246,127, dated Jul. 8, 2022, 28 pages.
Office Action in U.S. Appl. No. 17/327,491, dated Dec. 21, 2022, 15 pages.
Cancer.gov [online], "NCI Dictionary of Cancer Terms," Jan. 9, 2020, retrieved on Mar. 13, 2020, retrieved from URL<https://www.cancer.gov/publications/dictionaries/cancer-terms/def/research-study>, 1 page.
Coravos et al., "Modernizing and designing evaluation frameworks for connected sensor technologies in medicine", Digital Medicine 3, Mar. 2020.
Ctti-clinicaltrials.org [online], "Clinical Trials Transformation Initiative (CTTI) Recommendations: Advancing the Use of Mobile Technologies for Data Capture and Improved Clinical Trials", published in Jul. 2018, [retrieved on Jan. 7, 2021], retrieved from URL<https://www.ctti-clinicaltrials.org/sites/www.ctti-clinicaltrials.org/files/mobile-devices-recommendations.pdf#Pg2Ln13>.
DeAngelis, "Patient Monitoring, Big Data, and the Future of Healthcare," Wired.com, Aug. 6, 2014, retrieved at URL<https://www.wired.com/insights/2014/08/patient-monitoring-big-data-future-healthcare/>, 6 pages.
Dias et al., "Wearable Health Devices—Vigtal Sign Monitoring, Systems and Technologies," Sensors, Jul. 25, 2018, 18(8):2414.
Flatiron.com [online], "OncoTrials," May 14, 2018, retrieved on Mar. 13, 2020, retrieved from URL <https://flatiron.com/oncology/clinical-trials/>, 4 pages.
Flatiron.com [online], "Press Release: Flatiron Health Announces Three Publications Studying a Feasible, Reliable, Scalable and Meaningful Real-World Progression Endpoint for Oncology Research," Aug. 22, 2019, retrieved on Mar. 13, 2020, retrieved from URL<https://flatiron.com/press/press-release/real-world-progression-2019/>, 4 pages.
Grilo et al. "Pretreatment Patient Factors Predicting Attrition From a Multicenter Randomized Controlled Treatment Study for Panic Disorder," Comprehensive Psychiatry, Nov./Dec. 1998, 39(6):323-332.
Hayhurst, "How Network Monitoring Keeps Healthcare Devices and Patients Safe," HealthTech, May 7, 2020, retrieved at URL<https://healthtechmagazine.net/article/2020/05/how-network-monitoring-keeps-healthcare-devices-and-patients-safe>, 8 pages.
Kakria, "A Real-Time Health Monitoring System for Remote Cardiac Patients Using Smartphone and Wearable Sensors," International Journal of Telemedicine and Applications, Nov. 12, 2015, vol. 2015, Article ID 373474, 11 pages.
Komen.org [online], "Types of Research Studies," Mar. 11, 2015, retrieved on Mar. 13, 2020, retrieved from URL<https://ww5.komen.org/BreastCancer/DifferentTypesofResearchStudies.html>, 5 pages.
Lenane, "Continuous Heart Monitoring Key to Identifying Cause of Cryptogenic Stroke," Diagnostic and Interventional Cardiology, Nov. 16, 2015, retrieved at URL<https://www.dicardiology.com/article/continuous-heart-monitoring-key-identifying-cause-cryptogenic-stroke>, 4 pages.
Med.Standford.edu [online], "Cohort Discovery," retrieved on Mar. 13, 2020, retrieved from URL <https://med.stanford.edu/starr-tools/cohort-discovery.html>, 3 pages.
Michaeljfox.org [online], "Fox Trial Finder," retrieved on Mar. 13, 2020, retrieved from URL<https://www.michaeljfox.org/trial-finder>, 4 pages.
Miksad et al., "Small But Might: The Use of Real-World Evidence to Inform Precision Medicine," Clinical Pharmacology & Therapeutics, Jul. 2019, 106(1):87-90.
Mixpanel.com [online], "What is cohort analysis?," retrieved on Mar. 13, 2020, retrieved from URL <https://mixpanel.com/topics/cohort-analysis/>, 11 pages.
Murphy et al., "Visual Query Tool for Finding Patient Cohorts from a Clinical Data Warehouse of the Partners HealthCare System," Presented at Proceedings of AMIA Symposium, 2000:1174.
Nickelled.com [online], "Chapter 5: Top cohort analysis tools and resources," Dec. 12, 2018, retrieved on Mar. 13, 2020, retrieved from URL<https://www.nickelled.com/cohort-analysis/tools/>, 17 pages.
PaloAltoNetworks.com, "Monitor Device Health," Panorama Administrator's Guide Version 8.1, last updated Jun. 17, 2020, retrieved at URL<https://docs.paloaltonetworks.com/panorama/8-1/panorama-admin/manage-firewalls/device-monitoring-on-panorama/monitor-device-health.html>, 3 pages.
Pennic, "Life Image, Medel.ai Integrates to Support AI-Driven Clinical Trails," Nov. 6, 2018, retrieved from URL<https://hitconsultant.net/2018/11/06/life-image-medel-ai-partner-ai-driven-clinical-trails/#.Xmr7yqhKhZc>, 4 pages.
Phaneuf, "Latest Trends in Medical Monitoring Devices and Wearable Health Technology," BusinessInsider.com, Jan. 31, 2020, retrieved at URL<https://www.businessinsider.com/wearable-technology-healthcare-medical-devices>, 8 pages.
Rogers et al., "Composer: Visual Cohort Analysis of Patient Outcomes," Applied Clinical Informatics, Mar. 2019, 10(2):278-285.
Smith et al., "Performance Measurement for Health System Improvement: Experiences, Challenges and Prospects," Proceedings of WHO European Ministerial Conference on Health Systems, Jun. 25-27, 2008, Tallinn, Estonia, 28 pages.
Tucker, "Five of the Best Health Monitoring Devices," TheGuardian.com, Aug. 21, 2016, retrieved at URL<https://www.theguardian.com/technology/2016/aug/21/five-best-cardio-health-monitoring-devices>, 9 pages.
US Final Office Action in U.S. Appl. No. 16/800,933, dated Oct. 15, 2020, 28 pages.
US Final Office Action in U.S. Appl. No. 16/876,962, dated Jan. 8, 2021, 24 pages.
US Non-Final Office Action in U.S. Appl. No. 16/800,933, dated May 20, 2020, 27 pages.
US Non-Final Office Action in U.S. Appl. No. 16/800,952, dated Sep. 1, 2020, 16 pages.
US Office Action in U.S. Appl. No. 16/876,856, dated Aug. 25, 2020, 16 pages.
US Office Action in U.S. Appl. No. 16/876,856, dated Jan. 7, 2021, 26 pages.
US Office Action in U.S. Appl. No. 16/876,962, dated Sep. 9, 2020, 14 pages.
US Office Action in U.S. Appl. No. 16/877,162, dated Jul. 6, 2020, 12 pages.
Wikipedia.org [online], "Clinical trial," Feb. 17, 2020, retrieved on Mar. 13, 2020, retrieved from URL<https://en.wikipedia.org/wiki/Clinical_trial>, 18 pages.
Wikipedia.org [online], "Observational study," Feb. 17, 2020, retrieved on Mar. 13, 2020, retrieved from URL<https://en.wikipedia.org/wiki/Observational_study>, 4 pages.
Wikipedia.org [online], "Research," Mar. 7, 2020, retrieved on Mar. 13, 2020, retrieved from URL<https://en.wikipedia.org/wiki/Research>, 17 pages.
U.S. Appl. No. 17/173,273, filed Feb. 11, 2021, Jain et al.
U.S. Appl. No. 17/193,717, filed Mar. 5, 2021, Jain et al.
U.S. Appl. No. 17/193,976, filed Mar. 5, 2021, Jain et al.
Corrected Notice of Allowance in U.S. Appl. No. 16/876,856, dated Feb. 1, 2023, 3 pages.
Corrected Notice of Allowance in U.S. Appl. No. 16/876,856, dated Oct. 31, 2022, 3 pages.
Corrected Notice of Allowance in U.S. Appl. No. 16/877,162, dated Aug. 24, 2022, 3 pages.

(56) References Cited

OTHER PUBLICATIONS

Corrected Notice of Allowance in U.S. Appl. No. 16/877,162, dated May 4, 2022, 3 pages.
Corrected Notice of Allowance in U.S. Appl. No. 16/877,162, dated May 6, 2021, 3 pages.
Corrected Notice of Allowance in U.S. Appl. No. 17/163,109, dated Apr. 29, 2021, 2 pages.
Corrected Notice of Allowance in U.S. Appl. No. 17/173,264, dated Feb. 7, 2022, 2 pages.
Corrected Notice of Allowance in U.S. Appl. No. 17/173,264, dated May 2, 2022, 2 pages.
Corrected Notice of Allowance in U.S. Appl. No. 17/327,491, dated Jul. 17, 2023, 2 pages.
Corrected Notice of Allowance in U.S. Appl. No. 17/327,491, dated Nov. 13, 2023, 2 pages.
Corrected Notice of Allowance in U.S. Appl. No. 18/102,875, dated Jun. 9, 2023, 6 pages.
Corrected Notice of Allowance in U.S. Appl. No. 18/102,875, dated Sep. 27, 2023, 2 pages.
Notice of Allowance in U.S. Appl. No. 16/876,856, dated Oct. 24, 2022, 11 pages.
Notice of Allowance in U.S. Appl. No. 16/877,162, dated Nov. 3, 2021, 10 pages.
Notice of Allowance in U.S. Appl. No. 17/173,273, dated Aug. 2, 2024, 8 pages.
Notice of Allowance in U.S. Appl. No. 17/173,273, mailed on Nov. 22, 2024, 6 pages.
Notice of Allowance in U.S. Appl. No. 17/327,491, dated Jun. 20, 2023, 9 pages.
Office Action in U.S. Appl. No. 17/193,976, dated Jun. 7, 2024, 28 pages.
Office Action in U.S. Appl. No. 17/193,717, dated Jun. 21, 2024, 10 pages.
Office Action in U.S. Appl. No. 17/193,976, dated Oct. 11, 2024, 36 pages.
Office Action in U.S. Appl. No. 17/207,439, dated Oct. 13, 2023, 20 pages.
Notice of Allowance in U.S. Appl. No. 17/193,717, mailed on Dec. 4, 2024, 9 pages.

* cited by examiner

Technology Predictions

| Technology | Predicted Success / Failure | Reason for Failure / Warnings |
|---|---|---|
| App A | Failure | Cannot Detect Blood Pressure |
| App B | Failure | Cannot Detect Blood Pressure; Cannot Detect Heart Rate |
| Phone A | Failure | Cannot Detect Heart Rate; Age Group Incompatibility |
| Phone B | *Success | *Warning: Potentially Cost Prohibitive |
| Sensor A | Failure | Cannot Detect Movement; Cannot Detect Heart Rate |
| Bed Sensor C | Success | Cannot Detect Blood Pressure |
| Sensor A & Bed Sensor C | Success | N/A |
| App A & Sensor A | *Success | *Warning: Potentially Insufficient Data Quality |
| App A & Phone A | Failure | Insufficient Data Quality; Age Group Incompatibility |
| ... | ... | ... |

722

Study Data 720

- Measured Data Types:
  - Blood Pressure
  - Sleep *(Heart Rate and Movement)*
- Required Precision:
  - Medium (< ±5%)
- Usage Time:
  - 6-8 hours/day
- Number of Participants:
  - 30 Participants
- Age Range of Participants:
  - 18-40 years old
- Study Length:
  - 45 days
- Study Region:
  - West Coast
- Study Technology Budget:
  - $10,000
- ...

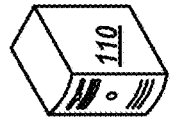
110

Receive Study Data 702 → Use ML Models to Make Predictions 704a → Use Statistical Analysis of Data to Make Predictions 704b → Use Rule-based Analysis to Make Predictions 704c → Generate Technology Predictions 706

FIG. 7

Study Needs 810

- Measured Data Types:
  - Blood Pressure
  - Sleep (*Heart Rate and Movement*)
- Required Precision:
  - Medium (< ±5%)
- Usage Time:
  - 6-8 hours/day
- Number of Participants:
  - 30 Participants
- Age Range of Participants:
  - 18-40 years old
- Study Length:
  - 45 days
- Study Region:
  - West Coast
- Study Technology Budget:
  - $10,000

Recommended Technology 820

General Recommendations

Option 1 – Sensor A & Bed Sensor C
- Score: 0.789
- Cost: $160/Participant (Medium)
- Precision: High (< ±2%)
- Compatible Age Groups: 18-60

Option 2 – Phone B
- Score: 0.649
- Cost: $330/Participant
- Precision: Medium (< ±5%)
- Compatible Age Groups: All Ages

Detailed Recommendations 822

| Group / Participant | Recommended Technology | Reasoning |
|---|---|---|
| Ages 20-35 | Sensor A & Bed Sensor C | N/A |
| Ages 36-40 | Phone B | Usage: Phone B is Predicted to Have Higher Usage Than Bed Sensor C for Those in the 36-40 Age Group |
| Joe (age 38) | Sensor A & Bed Sensor C | Usage: Joe is More Likely to Use Sensor A & Bed Sensor C As There Is No Need to Charge Devices Every Day |
| Sally (age 50) | Phone B | Usage: Sally Is More Likely to Use a Single Device |

FIG. 8A

| Example for a study for research question, "Do activity level and sleep quality have a measurable impact on an individual's mental health?" | | |
|---|---|---|
| | Example Inputs Used by the System | Example Outputs of the System |
| Dependent Metrics (e.g., outcomes or results tracked) | • Responses from study participants for mental health (e.g., depression) surveys | • Indications of which study participants have high or low depression survey scores |
| Types of Measurements (e.g., items to be monitored, types of data to be collected) | Collected measurement data from study participants, e.g.:<br>• Steps per day<br>• Average duration of sleep over one week, or intraday sleep measurements per minute<br>• Indicator of sleep quality (e.g., markers) | Results of analyzing collected data, e.g.:<br>• Fewer steps correlates to higher depression<br>• Consistent sleep duration of 6 hours or greater average per day correlates to lower depression<br>• Good sleep indicating amount and quality of sleep improves overall mental health state |
| Data Quality | • Indication of the quality of data needed to be reported by participants (e.g., accuracy, precision, frequency, etc.) | Recommended study protocol elements or constraints to achieve desired data quality, e.g.:<br>• Total sleep duration needed for 5 days a 7-day period<br>• Step data for 3 days contiguous in the 7-day period |
| Participant Information | • A level of over-recruiting is needed to obtain the expected number of core or active participants (e.g., 75%)<br>• A number of active participants needed to qualify statistical response of data | • Estimate of number of active participants needed (e.g., 90)<br>• Estimate of total number of participants needed to reach the active participant number (e.g., 120)<br>• Actual numbers of active/total participants in the study |
| Reliability of Research Methods/Data Collection Methods | • Methods of data collection (e.g., equipment translation to expected measurement, experimental, research qualified)<br>• Information about research studies (e.g., methods, results, etc.) | • Indication of the level of reliability or validation/qualification of data collection techniques for this study (e.g., the techniques have been successfully used in 100 research studies) |
| Acceptable down time | • Charge cycle of the selected technology<br>• Calibration needs<br>• Replacement ordering of consumables (patches, strips, sample deposits)<br>• DHT availability for measurements | • Indications of requirements needed for successful use of selected technology (e.g., charge once per day outside of measurement activity) |
| Data Transmission Requirements | • Sampling Frequency<br>• Upload / response time<br>• Reporting Cadence | • Expected or actual data transmission requirements (e.g., per day data transfer averages per user) |
| Equipment Cost | • Cost Per Unit<br>• Batch pricing<br>• Subscription pricing<br>• Number of Seats Licensing | • Expected cost of the selected technology (e.g., less than $10 per participant) |
| Likelihood of participant participation | • Participant attributes (e.g., ages or age distribution, etc.)<br>• Requirements for using the selected technology (e.g., duration of use, frequency of use, complexity of use, participant education needed)<br>• Participants' knowledge of similar technologies | Indication of expected or actual level of participation in using the selected technology, e.g.:<br>• Highest participation expected for individuals between 18 and 40<br>• Selected technology requires minimal effort<br>• Overall cohort-level compliance predicted at 82%<br>• Current cohort-level compliance is 87% |

FIG. 13

| DHT (Unique denoted as A, B, C, etc.) | Measures | Precision | Participant Age | Cost | Research Studies | Network Needed | Battery Life | Type |
|---|---|---|---|---|---|---|---|---|
| Wrist Device A | Sleep | Low | 18-40 | 300 | Low Quality | No | Short | Hardware |
| Wrist Device A | Actigraphy | Medium | 18-40 | 300 | Multiple, Qualified | No | Short | Hardware |
| Foot Pedometer B | Actigraphy | High | 40-60 | 50 | Multiple, Qualified | No | Long | Hardware |
| Phone C | Actigraphy | Medium | All Ages | Included | Multiple, Qualified | No | Phone Life | Hardware |
| App D | Actigraphy | High | 18-40 | 5 | Some Qualified | Yes | Phone Life | Software |
| App D | Sleep | Low | 60+ | 5 | Some Qualified | Yes | Phone Life | Software |
| Bed Sensor E | Sleep | High | All Ages | 300 | Some Qualified | Yes | Always On | Hardware |

FIG. 14

| DHT | Measure A Scoring (Actigraphy) | Measure B Scoring (Sleep) | Comprehensive Score | Selection Recommended |
|---|---|---|---|---|
| Wrist Device A | 70 | 40 | 110 | 3 - Cost=$300 |
| Foot Pedometer B | 80 | 0 | 80 | 4 (with Bed Sensor) - Cost =$350 |
| Phone C | 90 | 0 | 90 | 2 (with Bed Sensor) - Cost=$300 |
| App D | 80 | 30 | 110 | 1 - Cost=$5 |
| Bed Sensor E | 0 | 70 | 70 | 2 (With Phone) - Cost=$300 Or 4 (with Foot Pad) - Cost=$350 |

| Technology Option | Adolescent | Young Adult | Elderly | Cost Rank | Usability Analysis | Tailored Score |
|---|---|---|---|---|---|---|
| 1 - Using App D Only | X | | | $ | Medium - confiscated regularly | 3 |
| 1 - Using App D Only | | X | | $ | Best - always available | 1 |
| 1 - Using App D Only | | | X | $ | Poor - sets down regularly | 4 |
| 2 - Using Bed Sensor E with Phone C | X | | | $$$$$ | Medium/Poor - doesn't use bedroom | 2 |
| 2 - Using Bed Sensor E with Phone C | | X | | $$$ | Best - routinely uses bed | 2 |
| 2 - Using Bed Sensor E with Phone C | | | X | $$$$ | Medium - falls asleep on couch | 2 |
| 3 - Using Wrist Device A | X | | | $$$$$ | Poor - forgets at home often | 4 |
| 3 - Using Wrist Device A | | X | | $$ | Medium - forgets to charge | 3 |
| 3 - Using Wrist Device A | | | X | $$$ | Best - routinely uses and charges | 1 |
| 4 - Using Foot Pedometer B with Bed Sensor E | X | | | $$$$$ | Best - regularly uses same shoes | 1 |
| 4 - Using Foot Pedometer B with Bed Sensor E | | X | | $$$$ | Medium - when using same shoes | 4 |
| 4 - Using Foot Pedometer B with Bed Sensor E | | | X | $$$$$ | Medium/Poor - mostly in home, doesn't wear shoes | 3 |

FIG. 16

| Treatment | Pharmaceutical | DHT detected Improvements | DHT detected Toxicities | Possible DHTs utilized |
|---|---|---|---|---|
| Severe nausea and vomiting, anxiety, migraines | Prochlorperazine | Improved Patient Reported Outcomes | Cardiac irregularities, Fever, Low Blood Pressure | Circulatory Shock Detection using 1 or more of a EKG, Thermometer, Blood Pressure Meter - PPG and HRV is also a useful determinate |
| Management of type 2 diabetes | Glimepiride | Glycemic Control | Hypoglycemia | Exercise and Diet Reporting Measures - Actigraphy in conjunction with Glucose meter data and possibly sleep reported data. VO2max can also be useful predictor of effective exercise measures being implemented |

FIG. 22

IMPROVING COMPLIANCE OF PATIENT DATA COLLECTION IN CLINICAL TRIALS WITH PREDICTIVE ANALYSIS

CROSS-REFERENCE TO RELATED APPLICATIONS

This application is a continuation of U.S. application Ser. No. 16/877,162, filed May 18, 2020, now pending, the entire contents of which are incorporated by reference.

FIELD OF INVENTION

This application generally relates to the evaluation, selection, deployment, and monitoring of devices and software capable of reporting sensor measurements and other data.

BACKGROUND

Many different technologies are available for collecting and reporting data. For example, individuals may use phones, smart watches, computers, navigation systems, and other devices, which can obtain information through sensor measurements and user inputs. Software technology, e.g., mobile applications, desktop applications, standard development kits (SDKs), driver modules, etc., can also facilitate collecting and reporting data. Nevertheless, it is often difficult to select which technology items to use out of the various technology options. For example, it can be difficult to determine which technology items are available, what the capabilities of technology items are, and how the technology items will perform under widely-varying conditions of real-world use.

SUMMARY

In some implementations, a computer system is configured to assess various technology items, such as various devices and software packages, and select technology items that are suitable for a user of the system. For example, the system can assist researchers by identifying or inferring data collection needs of a research study, identifying technology options that can meet the data collection needs, and selecting the technology options that the system determines are most suitable for the research study. The system can then recommend the selected technology options to the researcher to use in defining the research study. When evaluating the suitability of a technology option, the system can consider any of various different factors, such as the types of data that can be collected, the accuracy or precision of data collected, battery life, network communication capabilities, reliability, durability, portability, previous rates of successful use by others, and so on. The system can store data indicating the characteristics of various technology items in a database, allowing the system to efficiently The system can assist researchers to design new research studies or to monitor and improve ongoing research studies. In the field of medical and health research, many research studies involve tracking and data collection for a variety of individuals, such as a cohort of individuals enrolled as participants in a study, e.g., a clinical trial. Digital technologies can provide sensing and communication functionality to facilitate the capture of accurate measurements to support a research study. There are vast numbers of digital health technologies available, with different sensing and analysis capabilities. Nevertheless, researchers often don't know what options are available or what the capabilities of available technologies are. The options can change very quickly, for example, as new devices and new software products are introduced and existing products receive updates. Many researchers may not know what types of data can be tracked using software, such as a mobile application on a phone. Researchers also often have misconceptions about what technology options are available and what the capabilities and limitations are. For example, multiple devices may be capable of capturing heart rate data, but the accuracy and precision with which they measure heart rate may differ widely from one device to another. It can be difficult to determine the differences consumer-grade devices and medical-grade devices, which can result in some technologies not meeting researchers' expectations. The systems and techniques disclosed herein can greatly improve the selection of technologies by considering a wide variety of technology options and evaluating the options with respect to the needs of a particular researcher or research study.

One way the system can be used is to generate recommendations of technology items based on information about a study, e.g., a research question to be studied, planned study methods, or study requirements. For example, the system can be configured to receive an indication of the needs for a particular study and to recommend one or more technology items based on the needs for the study. The needs of the study may include a type, precision, or frequency of data collection required by the study. The system selects one or more technologies that meet the needs for the study, e.g., that can collect data of the types of data needed and can do so with a sufficient precision and frequency.

The system can also be used to make predictions about whether a technology option will meet the needs of a research study. For example, the system can predict whether the use of one or more technologies by participants in a study is likely to achieve a target outcome, such as the collection of valid data from at least a minimum number of participants in the study. Several techniques can be used to make these predictions. For example, the system can compare capabilities of technology items with the needs for the study, e.g., the data types, data precisions, and/or data frequencies required by the study. As another example, the system can analyze records of prior use of the technology items or other technology items, to evaluate the rate at which users of technology items achieve the data collection outcomes needed by the study. In some implementations, the predictions can be customized for specific individuals or groups of individuals. For example, the system can use data that describes attributes (e.g., demographic attributes) of a particular individual to identify records of other similar individuals having similar attributes. The system can then use the usage history for the identified similar users to predict how likely the particular individual is to successfully use the technology. The system can be used to generate predictions of the results of a technology item being used by, e.g., (i) a group of individuals in a pool of candidates for a cohort, (ii) a cohort of individuals that are selected or enrolled to participate in a study, (ii) a subset of people within a cohort or a pool of candidates, or (iv) an individual (e.g., an individual participant in a cohort or individual candidate). In some cases, the system can generate predictions of results of selecting a technology option using one or more machine learning models that have been trained based on various examples of technology usage (e.g., by participants in other cohorts or other research studies).

In some implementations, the system is configured to monitor the use of technology items while a research study is carried out. For example, for a given study, the system can receive data collected by the technology items that were selected and deployed for the study. As another example, the system can receive indications of whether and in what manner the technology items are being used by study participants. The data can include various types of information, such as an indication of a time devices are on or operating, an indication of times devices are off or not operating, an indication of the battery life that users of devices experience, an indication of whether the study participants are compliant with the study requirements (e.g., whether they are using the technology items as instructed, performing assigned activities that the technology items are meant to collect data about, etc.), etc. The system can use the collected data to determine if the technology items selected are providing the data needed for the study (e.g., whether the collected data has the type, quantity, quality, consistency, measurement frequency, accuracy, precision, etc.). The system can use the evaluation of collected data and the evaluation of usage of technology items to provide notifications to researchers. If the system determines that the technology items selected for a study are not being used enough or are not providing sufficient data, the system can take actions to remedy the problem. For example, the system can recommend a different set of technology items that is determined to be more likely to provide the desired data collection results. The system can tailor its actions and recommendations to the specific individuals or groups for which results are insufficient. For example, the system can recommend different technology items for different individuals or groups within a study cohort, based on the types of technology items that historical usage information shows to be best adopted for people of similar demographics or other attributes.

In some implementations, the system includes or has access to a technology database used to store technology data, e.g., data that describes the capabilities and characteristics of different technology items. Technology items can be hardware (e.g., devices, such as sensors, peripherals, computing devices, etc.), software (e.g., applications, mobile applications, websites, web applications, etc.), or other types of items. The system can generate and update the content of the technology database using information from a variety of sources. The sources can include marketing literature, specifications, and other information from a technology provider (e.g., manufacturer, distributor, etc.). The system can also update the technology data in the technology database using, for example, monitored data that shows how technology items actually perform in studies, research literature, etc. The system can use the technology data in the technology database to generate scores that indicate the suitability of different technology items, or combinations of technology items, to meet the needs of a study. For example, the technology database can indicate the capabilities of technology items, as specified by the manufacturer and/or as actually observed in practice, and the system can use this information to determine which technologies are most likely to meet the requirements of a research study. More generally, the system can use the technology data in the technology database to recommend one or more technology options, where a technology option includes one or more technology items described in the technology database. The information in the technology database can be used to identify, score, rank, select, and recommend technology items for a variety of uses beyond research studies, such as recommending technology items for clinical use, for providing digital therapeutics, and so on.

In some implementations, the system includes or has access to a research literature database used to store information derived from research literature relating to one or more technologies. The system may collect and store examples of research literature that indicates how different technology items have been used. This can provide real-world examples of the studies and the technology items used, and whether or not the technology items meet the needs of the studies. Among other things, this can provide valuable information about the compliance rates at which people use different technologies, the actual accuracy and precision that can be obtained during real-world use, and so on. For example, a device's specifications may indicate that it can detect heart rate, but research literature for studies that attempted to use this function of the device may indicate that the data was not sufficiently reliable for research use, or even for a specific research purpose such as sleep analysis. As a result, the system can update the technology database to indicate the low reliability of that function of the device. On the other hand, the system can use examples that show successful use of a technology item (or a specific function of a technology item) to validate or certify the ability of a technology item to collect certain data or perform a certain function. The system can use the research literature to validate technology items for different uses, allowing higher confidence that recommended technology items will perform their needed functions. Thus, the system may use the research literature database to update the technology data stored in the technology database, so that the system provides better scoring and recommendation of technology items. For example, the system can use the examples of research literature to validate technologies for certain uses, to identify types of data that can be collected by the technologies, to update data collection precisions of the technologies, to identify software or hardware requirements of the technologies, etc. In some cases, the research literature may reveal that technology items have additional uses or can collect additional types of data that are not specified in literature from the technology provider, and the system can incorporate this into the technology database through analysis of the research literature.

In some implementations, the system includes or has access to a taxonomy that can facilitate natural language processing of research literature, user input, technology specifications, and more. The taxonomy can also be used to associate technology items and their characteristics in some cases. In general, the taxonomy can include data that associates keywords, data types, and uses of various technologies. The associations can be represented in a relational database structure (e.g., columns, rows, tables, and associated relationships), data mappings, metadata, an index, a table, etc. As the system encounters terms in research literature, literature from a technology provider, or other sources, the system can update the taxonomy to add, modify, or adjust elements and relationships in the taxonomy. For example, if a research paper indicates that "sensor X was used to measure resting heart rate (RHR)," the system can update the taxonomy to show that "resting heart rate" is a type of measurable heart rate, that "RHR" can refer to resting heart rate, that item "sensor X" is capable of providing heart rate and RHR, and so on. Then, when a user enters a query or other input, the system can use the taxonomy to interpret the user input. For example, if a user enters the term "RHR," the system can use the taxonomy to identifying matching or related elements in the taxonomy to determine a semantic meaning of the user input and to identify associated technology functions, data types, and technology items related to the user input.

The system can use the one or more machine learning models to analyze study data and to assist in generating one or more technology recommendations. For example, the one or more machine learning models can be used to identify one or more types of data that are required to be collected for the study and/or one or more sensors that are required for the study, e.g., based on the study needs. The study parameters (e.g., the identified data types and/or sensors) can be used by the system in making one or more predictions and/or recommendations.

The system can predict outcomes for the use of technology items. For example, the system can predict the rate of compliance or use of a set of technology items, based on analysis of the usage of technology items in prior studies. In some implementations, the system can train a machine learning model based on the example outcomes (e.g., for individuals, groups of individuals, or studies as a whole) of prior studies that involved different technology items. The predicted outcomes can include, for example, an expected likelihood of success of a technology option for meeting the needs of the study. More fine-grained predictions may be made, such as an expected level of precision of data collection for a given type of data, an expected frequency of data collection for a given type of data, an expected battery life for one or more technologies, an expected participant usage of one or more technologies, etc. The system can use measures (e.g., scores) for predicted outcomes of using technology items to select technology options to be recommended. For example, the predicted outcomes can be used in generating the score for a technology option, e.g., with technology options predicted to have greater use and more successful use being given higher scores. Indications of likelihoods or other predictions may additionally or alternatively be provided for display to a user. For example, along with technology options recommended by the system, or for technology items a user adds to a study, the system can show metrics such as a predicted amount (e.g., number or percentage) of study participants expected to appropriately use the technology item, which can help the researcher determine which of several options to select.

The prediction capability of the system can enable the system to customize the selection of technology for the makeup of a specific cohort and study. For example, different types of technology may have varying usage rates given the attributes of the study participant, e.g., age, gender, geographical location, level of experience with the technology, etc. Similarly, the outcome may depend on parameters of the study (e.g., duration of the study, frequency of use required for the technology item, etc.). The system can use information about a cohort, such as the demographic breakdown of the cohort, to determine different predicted rates of successful technology usage (e.g., likelihood of compliance with study protocols and/or collection of valid, reliable data) among different groups. In some cases, information about attributes of individual cohort members is available, and the system can determine predictions of successful technology usage for each individual. These predictions can be used to recommend different technology options within a cohort, to identify the technology options providing the highest likelihood of being successfully used by individuals, groups, or the cohort as a whole.

The system can be used to identify potential uses of technology items. In many cases, the system can receive an indication of a researcher's needs and identify the technology items that can meet those needs. The system can also perform analysis in the opposite direction, for example, starting with a set of technology items and determining the uses or capabilities for those technologies. For example, one or more technologies can be input to the system. These may be, for example, technology items specified by a researcher, are already in possession of a researcher, are already in possession of the expected participants in a study, etc. From this set of technology items, the system can determine and indicate the set of data types that can be collected (e.g., heart rate data, weight, step count, etc.). This type of "reverse lookup" can provide a researcher with the set of data that is available from technology items on hand, and allow the researcher to design the study appropriately. In some cases, the system can use the taxonomy to translate the functions, uses, and data types that technology items provide (e.g., as specified in the technology database) into research areas or research topics that can be assessed using a user-specified set of technology items. For example, given a set of technology items that provide monitoring of step count, heart rate, and activity, the system may indicate to the researcher that the set would allow data collection to support the study of sleep and exercise as research topics.

In one general aspect, a method performed by one or more computers includes: receiving, by the one or more computers, study data indicating one or more parameters of a research study or an objective of the research study; based on the study data, identifying, by the one or more computers, one or more types of data to be collected during the research study; identifying, by the one or more computers, technology options that each represent one or more technology items that can collect data of the identified one or more types of data to be collected; determining, by the one or more computers, a suitability score for each of the technology options; selecting, by the one or more computers, one or more of the identified technology options based on the suitability scores; and providing, by the one or more computers, output data that indicates the selected one or more technology options for the research study.

In some implementations, receiving the study data includes receiving the study data over a communication network.

In some implementations, the method includes providing data for a user interface for creating the research study, the user interface having one or more controls configured to receive user input specifying at least one of parameters of the research study or an objective of the research study. Receiving the study data includes receiving data indicating interaction with the user interface that provides the study data through the user interface.

In some implementations, identifying the one or more types of data to be collected includes selecting the one or more types of data from among a predetermined set of types of data.

In some implementations, identifying the one or more types of data to be collected includes: identifying one or more keywords in the study data; accessing taxonomy data that indicates relationships between terms and types of data; and determining types of data corresponding to the keywords based on the taxonomy data.

In some implementations, the technology options each represent at least one of a device or a software element.

In some implementations, identifying the technology options includes: accessing a technology data that (i) indicates multiple technology items and (ii) indicates, for each of the multiple technology items, one or more types of data that can be collected using the technology item; and selecting, as the technology options, individual technology items and/or combinations of technology items that the technology data indicates would provide a capability to collect the one or more identified types of data.

In some implementations, the identified one or more types of data to be collected comprise multiple types of data to be collected; and the identified technology options that include one or more technology options that include multiple technology items that in combination provide a capability to collect the multiple types of data to be collected.

In some implementations, the suitability score for a technology option is determined based on characteristics of a technology item represented by the technology option, the characteristics including at least one of an accuracy of measurement using the technology item, a precision of measurement using the technology item, a cost of the technology item, a network capability of the technology item, a battery life of the technology item, types of data that can be collected by the technology item, a compliance rate for users of the technology item, or a validation status for the technology item.

In some implementations, determining the suitability score for each of the technology options includes determining a suitability score for a particular technology option comprising a particular technology item by: determining, for each of the identified one or more types of data, a data collection score indicating a capability of the particular technology item to collect the type of data; and determining a composite score for the technology item based on the data collection scores.

In some implementations, selecting the one or more of the identified technology options includes: ranking the identified technology options based on the suitability scores; and selecting a highest-ranking portion of the identified technology options.

In some implementations, selecting the one or more of the identified technology options includes: comparing the suitability scores with a threshold; and based on the comparison, selecting the technology options that have a suitability score that satisfies the threshold.

In some implementations, providing the output data includes providing an indication of the selected one or more technology options for display in a user interface.

In another general aspect, a method performed by one or more computers includes: receiving, by the one or more computers, information indicating one or more of individuals; accessing, by the one or more computers, attribute data from a database that indicates attributes of the one or more individuals; determining, by the one or more computers, suitability scores for different technology options based on an assessment of the different technology options and the attribute data for the one or more individuals; selecting, by the one or more computers, one or more technology options for the one or more individuals based on the suitability scores; and providing, by the one or more computers, output data that indicates the one or more technology options selected for the one or more individuals.

In some implementations, determining the suitability scores includes generating the suitability scores using one or more machine learning models.

In some implementations, the one or more machine learning models comprise at least one of a neural network, a support vector machine, a classifier, a regression model, a clustering model, a decision tree, a random forest model, a genetic algorithm, a Bayesian model, or a Gaussian mixture model.

In some implementations, the suitability scores are determined based on (i) usage data indicating usage of technology items represented by the technology options by other individuals not in the one or more individuals, and (ii) attributes of the other individuals.

In some implementations, the suitability scores are determined based on rates that other individuals, which are determined to have attributes similar to the one or more individuals, have correctly used the technology options.

In some implementations, the one or more individuals comprise one or more participants in a research study or one or more candidate participants for the research study.

In some implementations, the one or more individuals are (i) a cohort of participants in a research study or (ii) a group of candidate participants for the research study.

In some implementations, the one or more individuals are (i) a proper subset of a cohort of participants in a research study or (ii) a proper subset of a group of candidate participants for the research study.

In some implementations, the one or more individuals are (i) a single individual in a cohort of participants in a research study or (ii) a single individual of a group of candidate participants for the research study.

In some implementations, at least one of the different technology options includes a software technology item and at least one of the different technology options includes a hardware technology item.

In some implementations, at least one of the different technology options includes a single technology item and at least one of the different technology options includes a combination of multiple technology items.

In some implementations, selecting the one or more technology options includes: ranking the technology options based on the suitability scores; and selecting a highest-ranking portion of the identified technology options.

In some implementations, selecting the one or more technology options includes: comparing the suitability scores with a threshold; and based on the comparison, selecting one or more technology options that have a suitability score that satisfies the threshold.

In some implementations, providing the output data includes providing an indication of the selected one or more technology options for display in a user interface.

In another general aspect, a method performed by one or more computers includes: monitoring, by the one or more computers, use of a technology item by one or more individuals assigned to use the technology item; based on the monitoring, generating, by the one or more computers, usage data that indicates usage of the technology item; identifying, by the one or more computers, one or more criteria for evaluating the usage of the technology item by the one or more individuals; determining, by the one or more computers, whether usage data satisfies the one or more criteria; and performing, by the one or more computers, at least one of (i) evaluating an alternative technology item for the one or more individuals, or (ii) providing, for display on a user interface, output data indicating whether the usage data satisfies the one or more criteria.

In some implementations, the technology item includes a software technology item or a hardware technology item.

In some implementations, the one or more computers comprise a server system, and monitoring use of the technology item includes: receiving, by the server system and over a communication network, data transmitted by or generated by the technology item; and storing the received data in association with metadata that describes a context or manner in which the collected data is transmitted or generated.

In some implementations, monitoring use of the technology item includes tracking, for each of the one or more individuals, at least one of a frequency of use of the technology item, times that the technology item is used, or a duration of use of the technology item.

In some implementations, monitoring use of the technology item includes tracking, for each of the one or more individuals, at least one of types of data collected or provided by the technology item, amounts of data collected or provided by the technology item, or data quality of data provided by the technology item.

In some implementations, generating the usage data includes generating data that indicates pattern of usage by the one or more individuals or a series of user interactions with the technology item by the one or more individuals over time.

In some implementations, identifying the one or more criteria includes determining a reference value for a measure of usage of the technology item.

In some implementations, the reference value is determined based on study data describing a research study that one or more individuals are enrolled in as participants.

In some implementations, the reference value is determined based on records of data collected for one or more research studies.

In some implementations, the one or more individuals are a cohort of participants in a medical research study, and each of the participants are assigned to use the technology item as part of the medical research study.

In some implementations, the technology item includes one or more sensors configured to measure a physiological parameter of the user; and monitoring the use of the technology items includes receiving and storing values for the physiological parameter measured.

In some implementations, the method includes evaluating an alternative technology item as a potential substitute for the technology item for the one or more individuals.

In some implementations, the method includes providing, for display on a user interface, output data indicating whether the usage data satisfies the one or more criteria.

In some implementations, the output data includes data indicating (i) a measure of usage of the one or more individuals, (ii) a criterion or reference for the usage of the one or more individuals.

In some implementations, the output data includes data indicating that usage of the technology item by the one or more individuals does not comply with a study protocol for a research study in which the one or more individuals are enrolled as participants.

In another general aspect, a method performed by one or more computers includes: analyzing, by the one or more computers, research literature to determine capabilities of technology items referenced in the research literature; based on the analysis of the research literature, validating, by the one or more computers, technology items for uses referenced in the research literature, including collection of specific types of data, based on comparing results in the research literature to one or more predetermined criteria; updating, by the one or more computers, a technology database to indicate the validated uses of the technology items; and using, by the one or more computers, the information indicating the validated uses in the updated technology database to recommend technology items for a research study.

In another general aspect, a method performed by one or more computers includes: receiving, by the one or more computers, an indication of one or more technology items; receiving, by the one or more computers, outcome criteria indicating characteristics of successful use of the one or more technology items; generating, by the one or more computers, a prediction indicating a likelihood that the one or more technology items will satisfy the outcome criteria; and providing, by the one or more computers, output data that indicates the prediction.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIG. 7 is a diagram that illustrates an example system and process for generating technology predictions.

FIG. 8A is a diagram that illustrates an example recommendation interface.

FIG. 13 is a diagram that illustrates example inputs and outputs of a system for assessing and selecting technologies.

FIG. 14 is a diagram that illustrates an example look-up table.

FIG. 15 is a diagram that illustrates an example of evaluation and scoring of technologies.

FIG. 16 is a diagram that illustrates an example of evaluation and scoring technologies.

FIG. 22 is a diagram that illustrates an example table relating pharmaceuticals and technologies.

Like reference numbers and designations in the various drawings indicate like elements.

DETAILED DESCRIPTION

Figure 1:
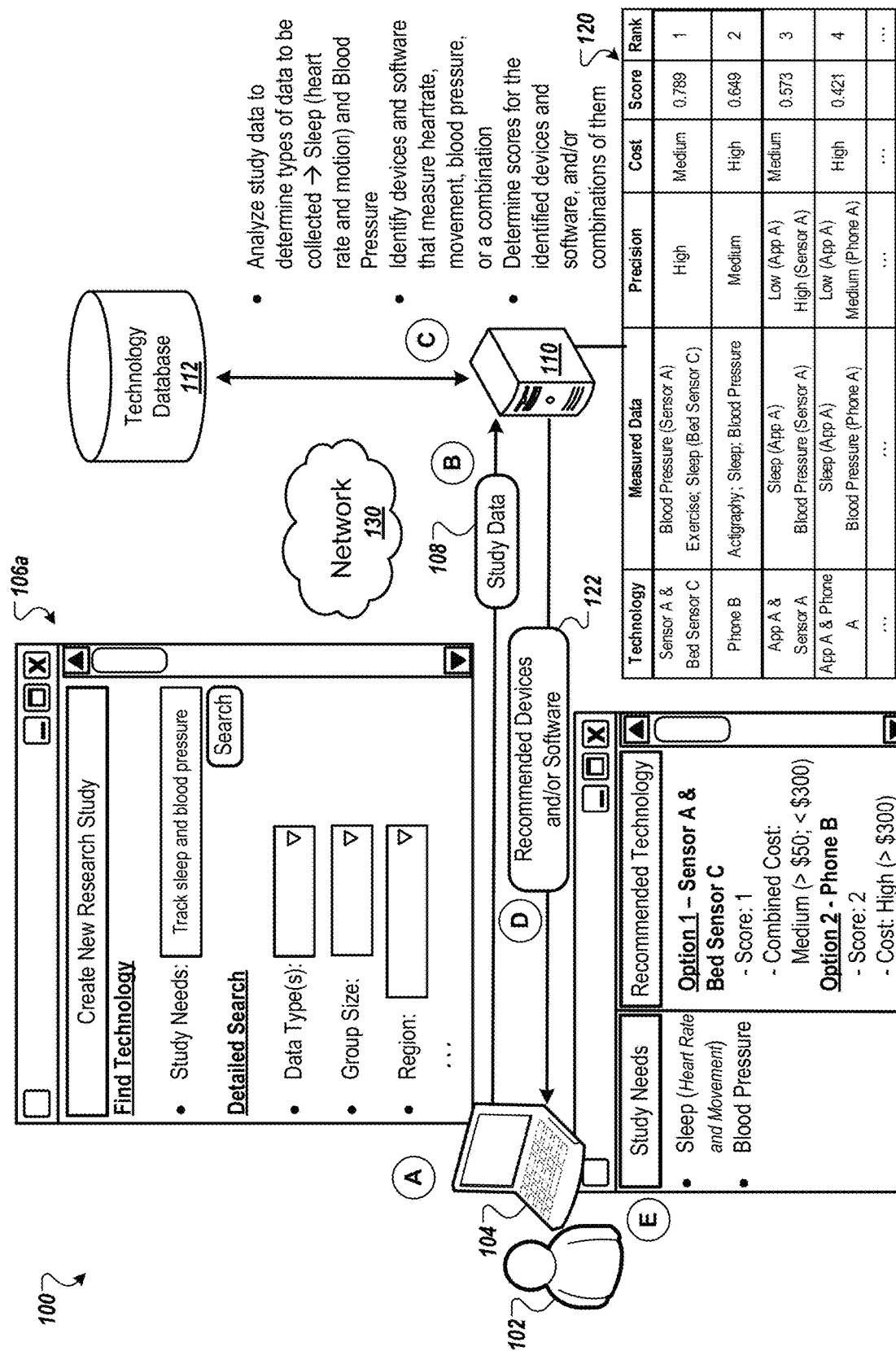
FIG. 1 is a diagram that illustrates an example system for assessing and selecting technologies.

FIG. 1 is a diagram that illustrates an example system 100 for assessing and selecting technologies. Among other uses, the system 100 can be used to select digital health technologies for research studies (e.g., clinical trials, experimental studies, longitudinal studies, correlational studies, case studies, etc.). The system 100 includes a client device 104 and a computer system 110 that includes functionality to assess and select technologies such as digital health technologies (DHTs) from a technology database 112. In general, a DHT can be any technology that gives information about user's health and/or behavior. There are applications for using DHTs in research science, population health, general research, clinical treatment, monitoring, and more.

As illustrated in FIG. 1, the computer system 110 has access to the technology database 112 and also communicates with the client device 104 over a network 130. The computer system 110 can receive data from the client device 104 and can send data to the client device 104 as will be described in more detail below. For example, the computer system 110 can receive data from the client device 104 indicating the requirements for a given study. For example, the client device 104 may provide an interface, with data from the computer system 110, that a researcher uses to design a study (e.g., to define a study protocol). The computer system 110 may also provide data to the client device 104 for interfaces to implement and carry out the study, e.g., to select a members of a cohort, to enroll and obtain consent from members of a cohort, to monitor data collection and compliance of cohort members, to select and deploy technology items for use in the study, and so on. The computer system 110 can send data to client device 104 indicating one or more technologies that it recommends for the study based on the study requirements or other study data that a user provides.

The computer system 110 can be used to assess numerous types of technologies, including hardware, software, and combinations thereof. The technologies can include digital health technologies (DHTs) such as medical devices, medical treatment devices, and/or devices with physiological sensing capability. A few examples include a scale to measure weight, a pulse oximeter, a blood glucometer, and a blood pressure cuff. Nevertheless, even common consumer items can be considered to be digital health technologies. For example, cellular phones can include accelerometers and other sensors to track physical activity, and smart watches can include plesmography sensors and heart rate sensors. Similarly, applications on computing devices, websites, and other software can be digital health technologies that support detection and collection of information about a user's behavior, mood, and other characteristics. Examples of technologies can include sensors, smart phones and other user devices, wearable devices (e.g., activity trackers, smart watches, etc.), and software (e.g., run/walk tracking apps, iHealth, etc.) capable of tracking health-related information. For example, software may be able to track user activity, user locality, user kinematics (e.g., motion tracking, gesture tracking, etc.), environmental factors, etc.

Studies can include various types of research studies, such as clinical trials, experimental studies, longitudinal studies, correlational studies, case studies, and so on. The subject matter of the studies may also vary widely, encompassing studies such as studies of health and disease, pharmaceutical studies, fitness studies, sociological studies, and the like.

As will be described in more detail with respect to FIG. 2 and FIG. 4, the computer system 110 can collect data about various technologies (e.g., DHTs). The computer system 110 can store this technology data in the technology database 112. The computer system 110 can update the technology data in the technology database 112 over time using, for example, monitored data from one or more technologies that are being used in a study, literature (e.g., websites, articles, research journals, etc.), taxonomy (e.g., taxonomy relating technologies, keywords used to described technologies or types of data that can be collected by technologies, types of data that can be collected by technologies, and/or sensors of technologies), technology requirements or specifications (e.g., operating system requirements, RAM requirements, processor requirements, sensor accuracy or precision, etc.), updates from a technology provider or manufacturer (e.g., software updates, updated data precisions, updated capabilities, recalls, etc.), etc.

Some or all of the functions of the computer system 110 can be performed by a server system. In some implementations, functions of the computer system 110 may be implemented on a cloud computing platform (e.g., Amazon Web Services (AWS), Microsoft Azure, and so on).

The network 130 can include public and/or private networks and can include the Internet. The network 130 may include wired networks, wireless networks, cellular networks, local area networks, wide area networks, etc.

The technology database 112 provides data storage and retrieval capabilities to the computer system 110. The technology database 112 may include, but is not required to include, one or more of a relational database, a centralized database, a distributed database, a data warehouse, a noSQL database, an object-oriented database, a graph database, a cloud-computing database, a data repository, a data lake, etc.

The computer system 110 is configured to receive or retrieve data related to technologies from a variety of sources and store the data in the technology database 112. The data can indicate capabilities and characteristics of the technologies. For example the technology data can indicate supported uses of the technologies, data types that can be collected by the technologies, accuracy and/or precision of data collection, physical characteristics (e.g., size, shape, weight, form factor, etc.), compatibility, cost, availability, etc. In some cases, technology data can be provided by technologies themselves, e.g., from network-enabled devices or software installed on a network-enabled device that can indicate capabilities and characteristics. As additional examples, technology data can also be obtained from Internet resources, specifications, other databases (e.g., databases storing literature relating to the technologies), the client device 104 and/or one or more other client devices, providers or manufactures of the technologies, etc.

The computer system 110 is also configured to receive study data from one or more client devices including the client device 104. The study data describes characteristics of the study. The study data may be partial or preliminary, such as representing data describing a study that is still being defined or created using the client device. As another example, the study data may represent a fully defined study about to begin or even a study already in progress. The study data can include, for example, information provided by or for researchers who will conduct the study. The study data can include needs or requirements ("study needs") for the study such as, for example, one or more types of data that need to be collected for the study, a level of data collection precision needed for the study, a minimum frequency of data collection needed for the study, a minimum daily battery life of devices to be used in the study, etc.

The study data can additionally or alternatively include parameters for the study such as, for example, one or more locations where the study is to be conducted, an expected number of participants for the study, a length of the study, an age range of participants for the study, a budget for the study, etc. As will be described in more detail with respect to FIG. 7, the study data can additionally or alternatively include an indication of one or more technology options that are already available for use in the study (e.g., that the researchers already have access to or have already ordered, or that the participants already have access to or have already ordered) and/or a count of each of those one or more technology options that are available for use in the study (e.g., the number of devices that the researchers have access to or have already ordered).

Some data (e.g., technology data) collected in the technology database 112 is obtained as devices automatically send monitored study data, for example, in response to the data being collected by the technologies being used for the study or periodically (e.g., a technology used in a study sends collected data to the computer system 110 at a defined interval, or the computer system 110 updates the technology database 112 with monitored study data at a defined interval). Some data collected in the technology database 112 can be obtained in response to interactions initiated by the computer system 110, for example, to a request stored technology data (e.g., due to receiving study data from a client device).

FIG. 1 illustrates various operations and flows of data represented as stages (A)-(E), which can be performed in the order shown or in a different order. For example, one or more of the stages (A)-(E) can occur concurrently.

In stage (A), a study data is received. This can occur as a new study is defined. The client device 104 can receiving study data as user input from a user 102. The study data can include, for example, an inquiry corresponding to needs for the study (e.g., "track sleep and blood pressure") and/or one or more study parameters. In this case, the study data may represent a query for technologies, a research question or research topic, a series of inputs such as selections of drop-down controls, or other types of input.

The study parameters can include, for example, one or more types of data that are to be collected during the study, an accuracy or precision needed for types of data that are to be collected, a frequency or rate for data that are to be collected (e.g., a required frequency of data collection and/or a required frequency of data upload/submission), a group size (e.g., the number of participants or an expected number of participants) for the study, an age range of participants, a location of the study (e.g., a country, a state, a city, a county, or a region where the study is to take place or where participants reside), a required usage time for the study (e.g., a required battery life for technology options), a budget for the study, etc.

Receiving the study data can include the client device 104 receiving the inquiry and/or the study parameters, e.g., from a user 102. The user 102 can be, for example, a researcher that is designing or administering a study. As an example, the user 102 can submit an inquiry and/or one or more study parameters into the client device 104 through a study interface 106a. The study interface 106a of the client device 104 can provide one or more options for defining a study and/or searching for technology options to be used for the study. For example, as shown, the study interface 106a can include a quick search area where the user 102 can provide an inquiry corresponding to the needs of the study (e.g., "Study Needs"), and a detailed search area where the user 102 can enter/select various study parameters. Here, the user 102 has provided an inquiry, "track sleep and blood pressure", that indicates, for example, that the new study should include one or more technologies (e.g., DHTs) to track sleep and measure blood pressure.

As will be described in more detail below, the technology options can include individual technologies, and/or groupings of multiple technologies. For example, a first technology option can be a mobile computing app for tracking running and walking, a second technology option can be a smart phone that is capable of collecting motion data and location data, and a third technology option can be the combination of the mobile computing app and the smart phone.

The user input can be a natural language inquiry or statement. The natural language user input can be typed, spoken, written, etc. The inquiry can include multiple components, e.g., each corresponding to a different requirement for the new study, which may have been provided at different times, etc.

Although the study data is provided through the interface 106a of the client device 104 in the example of FIG. 1, other interfaces can be used in addition to or in place of the interface 106a. For example, the user 102 can provide the study data through a voice user interface (VUI) such as through a Google Home or Amazon Alexa that can communicate with the client device 104 and/or the computer system 110.

In some implementations, as will be discussed in more detail below with respect FIG. 7, the study data can additionally or alternatively include an indication of one or more technology options that are already available for use in the study (e.g., that a user 102 already has access to or has already ordered) and/or a count of each of those one or more technology options that are available for use in the study (e.g., a number of devices and/or number of software copies that are available/have been purchased).

Study data 108 can be generated. The study data 108 can be or include the study data provided to the client device. For example, the study data 108 can include an inquiry indicating the needs for a new study and/or one or more study parameters for a new study. Here, the study data 108 would include the inquiry, "track sleep and blood pressure." The study data 108 can be generated in response to interactions made through the client device 104, e.g., through the interface 106a of the client device 104. The study data 108 can be generated in response to searching for technology options for a new study/defining a new study, e.g., in response to the user 102 providing the study data to the client device 104 or in response to the client device 104 otherwise receiving the study data. The study data 108 can be generated in response to a new study being submitted, e.g., in response to the user 102 defining the new study and submitting it. As an example, the study data 108 can be generated as a result of the user 102 selecting an interface element on the interface 106a, e.g., the user 102 selecting the "Search" button displayed on the interface 106a.

A request for technology options can be generated along with the study data 108. For example, the request for technology options can be generated in response to interactions made through the client device 104, e.g., through the interface 106a of the client device 104. The request for technology options can be generated in response to searching for technology options for a new study/defining a new study, e.g., in response to the user 102 providing the study data to the client device 104 or in response to the client device 104 otherwise receiving the study data. The request for technology options can be generated in response to a new study being submitted, e.g., in response to the user 102 defining the new study and submitting it. As an example, the request for technology options can be generated as a result of the user 102 selecting an interface element on the interface 106a, e.g., the user 102 selecting the "Search" button displayed on the interface 106a. In some implementations, the study data 108 includes a request for an indication of technology options appropriate for the study.

In stage (B), the study data 108 is sent to the computer system 110. As discussed above, the study data 108 can indicate one or more requirements or parameters for the corresponding study. For example, the study data 108 can include one or more study parameters, and/or can include an inquiry indicating the needs for the study. The study data 108 can be sent to the computer system 110 over the network 130. The study data 108 can include or be sent along with a request for technology options. For example, in some implementations, a user may interact with a user interface control for requesting technology options for the study. In other implementations, the computer system 110 may select and provide recommended technology options without a user requesting a recommendation.

In stage (C), the computer system 110 analyzes the study data 108. In analyzing the study data 108, the computer system 110 can determine one or more study parameters for the new study. For example, in analyzing the study data 108, the computer system 110 can determine one or more data types that need to be collected for the study. Determining one or more study parameters for the new study can include identifying study parameters in the study data 108. Determining one or more study parameters for the new study can additionally or alternatively include extracting study parameters from an inquiry, and/or extracting keywords from the inquiry and using those keywords to identify one or more study parameters. Using keywords to identify one or more study parameters can include the computer system 110 leveraging a taxonomy that associates keywords with study parameters (e.g., with data types, types of sensors, etc.) and/or with technology options. This taxonomy is described in more detail below with respect to FIGS. 2, 5, and 6A-6B.

As an example, the computer system 110 can analyze the inquiry, "track sleep and blood pressure" to identify the keywords "sleep" or "sleep tracking", and "blood pressure."

Using the keyword, "blood pressure" the computer system 110 can determine that blood pressure is type of data that must be collected for the new study. Using the keyword, "sleep" or "sleep tracking," the computer system 110 can determine that the sleep is a type of data that must be collected for the new study. Accordingly, the computer system 110 can determine that the viable technology options must be capable of collecting blood pressure data and sleep data.

The computer system 110 can leverage a taxonomy structure to determine that the collection of sleep data includes collecting heart rate data and motion data. As discussed in more detail with respect to FIG. 3, the computer system 110 can generate a taxonomy structure from example documents, such as various research journals, articles, and websites. The taxonomy structure can indicate for example that collecting sleep data specifically requires collecting heart rate data and motion data, e.g., in the context of the study data 108 (e.g., inquiry) received at the computer system 110. Accordingly, the computer system 110 can determine that the viable technology options for the new research study must be capable of collecting blood pressure data, heart rate data, and motion data.

In some implementations, if the computer system 110 cannot determine one or more particular study parameters and/or cannot determine a sufficient quantity of study parameters for the new study based on the study data 108, the computer system 110 can generate and send a request to the client device 104. The request can indicate (i) one or more particular study parameters that are required, and/or (ii) that additional information is necessary. As an example, the computer system 110 may generate and send a request to the client device 104 if the study data 108 does not indicate the types of data that are to be collected for the new study.

The computer system 110 can access the technology database 112 to retrieve technology data. The technology data can include, for example, a list of various technologies and corresponding information that describes the technologies and their uses. The technologies can include, for example, devices, software, or combinations of devices and software. The technologies can be characterized at different levels, for example, for classes or categories of technologies (e.g., activity trackers in general, or a category of mobile applications), for groups of items (e.g., for activity trackers of a specific brand, or applications of a particular provider), or for specific items (e.g., a specific model of activity tracker, or a specific mobile application, potentially even a specific version such as version 2.1). The corresponding information can indicate capabilities and characteristics of the technologies, and can also indicate how the technologies have been used in the past.

The information for technologies can include, for example, one or more of the types of data that the technologies are capable of collecting (e.g., measuring and recording), the levels of accuracy and/or precision of the technologies in collecting different types of data, validated uses for the technologies, measures of user compliance in using the technologies (e.g., past success rates of users actually using the devices as intended), a cost of the technologies or cost range of the technologies, a battery life of the technologies, an availability of the technologies (e.g., the countries, states, or regions where the technologies are or are not legally permitted, or can or cannot be obtained), age groups that can use or are generally successful at using the technologies (e.g., can indicate which technologies older age groups have difficulty using, which technologies younger age groups have difficulty using, which technologies certain age groups generally fail to use due to, for example, social stigma, etc.), locations where the technologies are generally used successfully or are generally not used successfully (e.g., countries, states, or regions where people generally refuse to use a technology due to, for example, social stigma), the requirements and/or specifications for the technologies (e.g., software version requirements, operating system requirements, RAM requirements, processor speed requirements, etc.), etc.

Availability of a given technology can correspond to whether the technology can be legally obtained in a particular location (e.g., country, state, city, county, region, etc.) For example, for a Sensor B, the technology data can include an indication that Sensor B is available in China but that it is not available in the U.S., e.g., due to not having been approved by the FDA.

The computer system 110 can determine scores and/or viability for the technologies in the retrieved technology data. In determining scores and/or viability for the technologies in the retrieved technology data, the computer system 110 can compare the technology data with the study data 108 and/or with the information extracted or otherwise determined from the study data 108. For example, in determining scores and/or viability for the technologies in the retrieved technology data, the computer system 110 can compare the technology data to the inquiry, "track sleep and blood pressure" and/or to the information extracted or otherwise determined from the inquiry (e.g., that the new study requires the collection of blood pressure data, heart rate data, and motion data).

In comparing the technology data with the study data 108 and/or with the information extracted or otherwise determined from the study data 108, the computer system 110 can identify technology options (e.g., technologies and/or groupings of technologies) that can satisfy the needs of the new study as indicated by the study data 108. The computer system 110 can optionally remove technologies or groupings of technologies from consideration if they are not viable, e.g., if they are unable to satisfy all or a portion of the needs of the new study as indicated by the study data 108. For example, a temperature sensing device can be determined by the computer system 110 to be nonviable due to it not being able to collect blood pressure data, heart rate data, or motion data. Accordingly, the computer system 110 will not consider the temperature sensing device (or, for example, any groupings of technologies that include the temperature sensing device) a technology option.

Once the computer system 110 has identified the technology options that can satisfy the needs of the new study as indicated by the study data 108, the computer system 110 can determine scores for (e.g., can rank) the technology options. In scoring the technology options, the computer system 110 can take into account the precision of the data collected by the technologies in the technology options, the number of devices in the technology options (e.g., the computer system 110 can consider less devices beneficial when scoring the technology options, for example, due to less devices being associated with higher participant utilization, less replacement devices being ordered, reduced participant training, etc.), and/or the cost of the technology options (e.g., the cost of the devices and software that make up the technologies options).

The computer system 110 can also take into account other information when scoring the technology options. For example, the computer system 110 can also take into account one or more of the required usage (e.g., battery life) of the technologies in the technology options (e.g., even if the battery life of a technology has been considered sufficient, if the battery life of the technology only meets or is only slightly above the battery life threshold, then the computer system 110 can consider this a negative factor when scoring the technology options), the location where the study is to take place or the location(s) where the participants reside (e.g., the computer system 110 can take into account the past utilization of the technologies in the technology options by previous study participants in the location where the study is take place or the location(s) where the participants reside), the durability of the devices in the technology options (e.g., the computer system 110 can consider low durability devices as a negative factor, and/or can consider high durability devices as a positive factor when scoring the technology options), the reliability of devices (e.g., the tendency of the sensors installed on the devices to fail) and/or the software in the technology options (e.g., the computer system 110 can consider software that tends to crash as a negative factor, can consider devices or software that fail to consistently collect data or fail to consistently collect data precisely a negative factor, and/or can consider devices that include sensors with high tendency to fail a negative factor when scoring the technology options), reviews of the devices and/or software by previous researchers or previous study participants (e.g., the computer system 110 can consider the reviews of devices and/or software from previous studies when the devices and/or software were used to collect the same type of data as they are expected to collect for the new study), etc.

As shown, in scoring the technology options, the computer system 110 can generate a list or table of scored technology options 120 that includes one or more viable technology options. The one or more viable technology options in the scored technology options 120 can be arranged by their respective score. For example, a first technology option that includes a Sensor A and a Bed Sensor C has the highest score of one, a second technology option that includes a Phone B has the second highest score of two, a third technology option that includes an App A and the Sensor A has the third highest score of four, and a fourth technology option that includes the App A and a Phone A has the fourth highest score of five.

Each of the technology options in the scored technology options 120 can be considered viable by the computer system 110, e.g., due to the computer system 110 determining that each of the technology options can collect sleep data (e.g., heart rate data and motion data) and blood pressure data. For example, the first technology option includes the Sensor A which can collect blood pressure data and the Bed Sensor C which can collect exercise data and sleep data.

In scoring the technology options, the computer system 110 can leverage one or more machine learning models. The one or more machine learning models can be trained using, for example, monitored data (e.g., data collected from technologies used for a study) from one or more previous and/or ongoing studies.

From the scored technology options 120, the computer system 110 can select one or more technology options to recommend. The computer system 110 can determine which of the technology options to recommend by selecting a preset number of technology options with the highest scores, by selecting all technology options that have a score above a threshold score, or by selecting a preset number of technology options (or less than the preset number if the preset number cannot be satisfied) with the highest scores among those technology options that have a score that meets a threshold score.

For example, the computer system 110 can select the first technology option and the second technology option to recommend based on a threshold score being three and a preset number being three. Despite the preset number being three, the computer system 110 would only recommend the first technology option and the second technology option due to them being the only technology options having scores that satisfy the threshold score of three.

The computer system 110 can generate a recommendation 122 that includes the one or more recommended technology options, e.g., that includes the devices and/or software in the one or more recommended technology options. For example, the computer system 110 can generate a recommendation that includes the first technology option and the second technology option, e.g., includes the Sensor A and the Bed Sensor C as a first technology option for the new study, and the Phone B as a second technology option for the new study.

In selecting one or more technology options to recommend, the computer system 110 can leverage one or more machine learning models. The one or more machine learning models can be trained using, for example, monitored data (e.g., data collected from technologies used for a study) from one or more previous and/or ongoing studies.

The recommendation 122 can also include, for example, the information extracted from or otherwise obtained from the study data 108 by the computer system 110. That is, the computer system 110 can add the needs for the study that it determined from the study data 108 to the recommendation 122. For example, the recommendation 122 can include an indication that the computer system 110 has determined that the new study requires the collection of blood pressure data and sleep data, and/or that it has interpreted the collection of sleep data to mean or require the collection of heart rate data and motion data. This can, for example, provide the user 102 (or others) context as to how the computer system 110 identified viable technology options, ranked the viable technology options, and selected one or more technology options to recommend from the viable technology options. Accordingly, the user 102 can use this information to provide updated or modified study data (e.g., that details the needs of the new study in a new or different way through a new inquiry or through the input of additional or different study parameters) if the user 102 determines the recommended technology options in the recommendation 122 are insufficient or off-base.

In stage (D), the computer system 110 sends the recommendation 122 to the client device 104. The recommendation 122 can be sent to the client device 104 over the network 130. The recommendation 122 can include one or more technology options, e.g., one or more devices and/or software that computer system 110 recommends for the new study based on the study data 108.

In some implementations, instead of or in addition to sending the recommendation 122 to the client device 104, the computer system 110 sends the scored technology options 120 to the client device 104. The client device 104 can proceed to select a subset of the technology options from the scored technology options 120 to present to the user 102 (e.g., the researcher of the new research study). Alternatively, the client device 104 can optionally select to present all of the technology options in the scored technology options 120 to the user 102.

In some implementations, the computer system 110 sends the recommendation 122 to one or more devices other than the client device 104. For example, the computer system 110 can send the recommendation 122 to one or more devices belonging to researchers for the new study, one or more devices belonging to participants or potential participants to of the study (e.g., to determine if any participants are likely to refuse to use the devices and/or software of a particular technology option), to one or more digital assistant devices, etc.

In stage (E), the client device 104 presents the recommendation 122. Presenting the recommendation 122 can include, for example, the client device 104 displaying the recommendation on an interface 106b of the client device 104. As shown, the interface 106b includes a first area that presents the study needs that the computer system 110 extracted from or otherwise determined from the study data 108, and a second area that includes the recommended one or more technology options.

In more detail, the first area can present information extracted from or otherwise obtained from the study data 108 by the computer system 110. That is, the client device 104 can present the needs for the study found in the recommendation 122 (or optionally separately sent to the client device 104 by the computer system 110) based on the study data 108. The needs for the study presented in the first area of the interface 106b include the data types that computer system 110 has determined must be collected for the study. The needs for the study can additionally or alternatively include one or more other study parameters. For example, as will be discussed in more detail below with respect to FIG. 8A, the first area can present the required data collection precision(s) for the new study, the required device and/or software usage time(s) for the new study, the number or expected number of participants of the study, the age range of participants for the study, the length or expected length of the study, a location of the study or location(s) where participants of the study reside, a budget for the study, etc.

As an example, as shown, the needs of the study include an indication that blood pressure data must be collected and that sleep data must be collected. The needs of the study also include an indication that the collection of sleep data includes the collection of heart rate data and movement data.

The second area can present the one or more recommended technology options. The second area can optionally present information corresponding to the recommended technology options such as, for example, one or more of the score of each of the recommended technology options, the cost of each of the recommended technologies options, the data that can be collected by the recommended technology options, the precisions in collecting the data by the devices and/or software in the recommended technology options, etc. For example, as shown, the first technology option is displayed in the second area of the interface 106b along with the score for the first technology option (one) and the cost of the first technology option (e.g., between $50 and $300). The second technology option is also displayed in the second area of the interface 106b along with the score for the second technology option (two) and the cost of the second technology option (e.g., greater than $300).

As will be discussed in more detail below, the second area can also include a detailed recommendations area. The detailed recommendations area can provide, for example, more advanced recommendations for particular situations. For example, the detailed recommendations area can provide one or more recommended technology options for particular situations, e.g., for particular participant age groups, for particular study locations, for particular locations where participants reside, for particular people. These recommended technology options can differ from the general, recommended technology options. The detailed recommendations area can also include reasoning to explain why these one or more recommended technology options differ from the one or more general, recommended technology options.

If the user determines that the technology options presented in the second area of the interface 106b are insufficient for the new study or otherwise off-base, the user 102 can use the information provided in the first area of the interface 106b (as well as the information provided in the second area of the interface 106b) to learn how computer system 110 interpreted the study data 108 (e.g., how the computer system 110 interpreted the inquiry, "track sleep and blood pressure). The user 102 can proceed to provide updated or modified study data (e.g., that details the needs of the new study in a new or different way through a new inquiry or through the input of additional or different study parameters) to the computer system 110, e.g., using the interface 106a.

Figure 2:
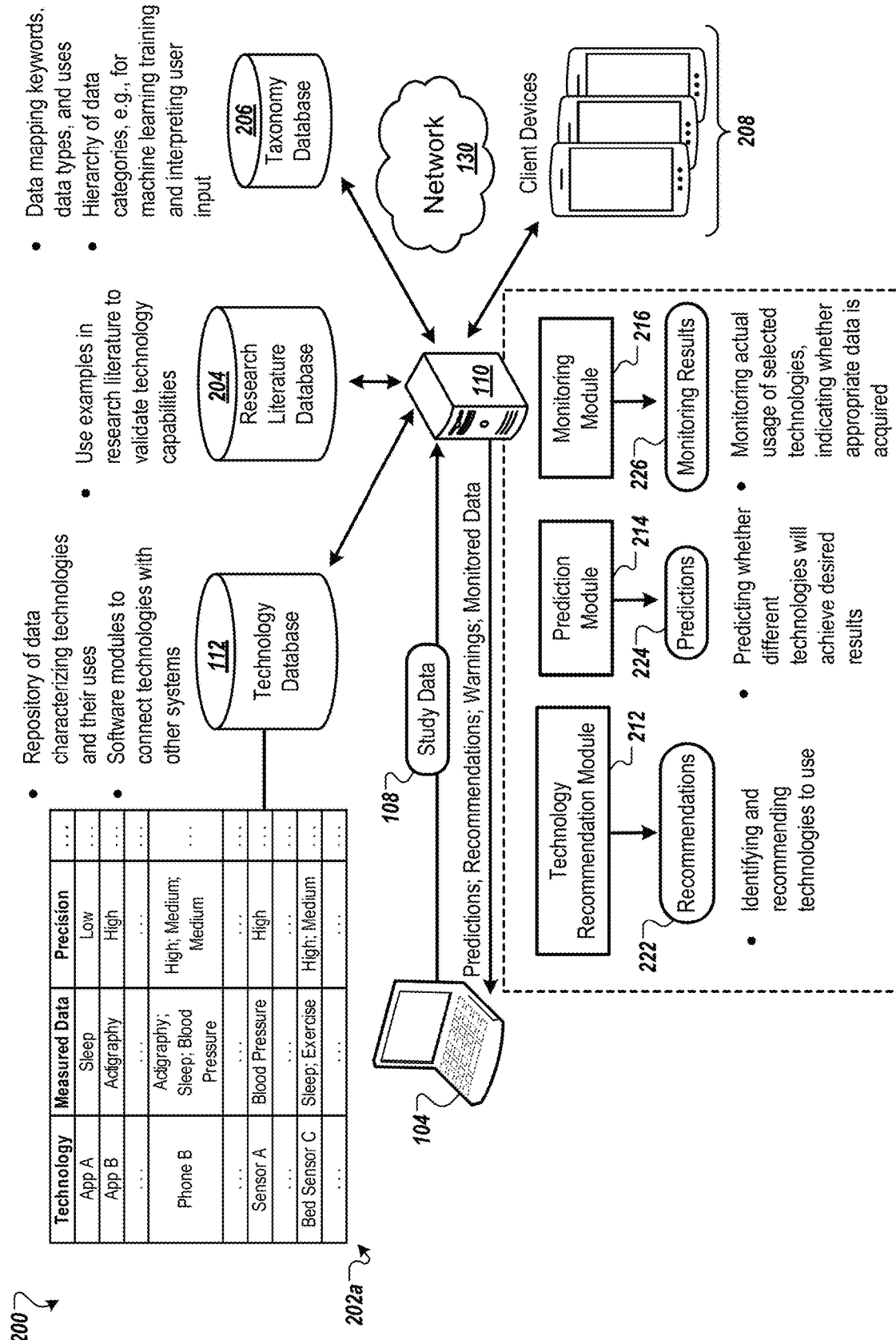
FIG. 2 is a diagram that illustrates an example system for assessing and selecting technologies.

FIG. 2 is a diagram that illustrates an example system 200 for assessing and selecting technologies. In some implementations, the system 200 is the system 100 shown in FIG. 1.

The system 200 includes a client device 104 and a computer system 110. The computer system 110 includes functionality to assess and select technologies such as digital health technologies (DHTs) from the technology database 112.

As illustrated in FIG. 2, the computer system 110 has access to the technology database 112, to a research literature database 204, and to a taxonomy database 206. The computer system can also communicate with the client device 104 and the client devices 208 over the network 130.

The computer system 110 can receive data from the client device 104 and can send data to the client device 104, e.g., over the network 130, as will be described in more detail below. For example, the computer system 110 can receive the study data 108 from the client device 104 indicating the requirements for a given study. The computer system 110 can send predictions (e.g., an indication of the likelihood that a given technology option can be used in study to achieve desired results), recommendations (e.g., one or more recommended technology options), warnings (e.g., warnings indicating low usage of a technology, health alerts corresponding to one or participants indicating that the one or more participants may need medical attention, etc.), and/or monitored data to the client device 104.

The computer system 110 can receive data from the client devices 208 and can send data to the client devices 208, e.g., over the network 130. The client devices 208 can be computing devices belonging to participants of one or more active studies. As an example, the computer system 110 can receive monitored data from the client devices 208 (e.g., data collected from one or more technologies that are currently being used for one or more studies). The computer system 110 can send warnings (e.g., health alerts recommending that the corresponding participant stop an activity, take a medication, refrain from taking a medication, call emergency services, call a healthcare provider, etc.) or notifications (e.g., notifying the corresponding participant of the successful completion of a milestone, notifying the corresponding participant of upcoming tasks, notifying the corresponding participant of task time or percentage remaining, reminding the corresponding participant to use a technology, notifying the corresponding participant that their usage of the technology is too low, etc.) to the client devices 208.

As will be described in more detail with respect to FIG. 4, the computer system 110 can collect data about various technologies (e.g., DHTs). The computer system 110 can store this data in the technology database 112 as technology data 202a. The computer system 110 can update the technology data in the technology database 112 over time using, for example, monitored data received from the client devices 208 and corresponding to one or more technologies that are being used in one or more studies, literature (e.g., websites, articles, research journals, etc.) stored in the research literature database 204, taxonomy (e.g., data mappings relating and/or interrelating technologies, keywords used to described technologies or types of data that can be collected by technologies, types of data that can be collected by technologies, and/or sensors of technologies) stored in the taxonomy database 206, technology requirements or specifications (e.g., operating system requirements, RAM requirements, processor requirements, sensor accuracy or precision, etc.), updates from a technology provider or manufacturer (e.g., software updates, updated data precisions, updated capabilities, recalls, etc.), etc.

As described above with respect to FIG. 1, the technology database 112 provides data storage and retrieval capabilities to the computer system 110. The technology database 112 may include, but is not required to include, one or more of a relational database, a centralized database, a distributed database, a data warehouse, a noSQL database, an object-oriented database, a graph database, a cloud-computing database, a data repository, a data lake, etc. The technology database 112 can include the technology data 202a.

The computer system 110 can use the technology data 202a in the technology database 112 to generate one more predictions as to whether different technologies will achieve desired results for a given study. These predictions can be provided by the computer system 110 to the client device 104. The computer system 110 can use the technology data in the technology database 112 to recommend one or more technology options. These recommendations can be provided by the computer system 110 to the client device 104.

The technology data 202a can include one or more a list of various technologies (e.g., "Technology" column), an indication of the types of data that can be collected by the technologies (e.g., "Measured Data" column), and an indication of the precision of the technologies in collecting the data (e.g., "Precision" column). As will be discussed in more detail below with respect to FIG. 3 and FIG. 4, the technology data 202 can include additional information related to the various technologies. For example, the technology data can include a number of research studies that the technologies were identified as being used in, validated uses for the technologies, a measure of compliance of the technologies (e.g., a success/failure rate of the technologies in the research studies), the cost of the technologies or cost range of the technologies, software and/or hardware requirements for the technologies, an indication as to whether the technologies are portable (e.g., portable if they are battery powered and/or if they are software for a mobile computing device), a battery or usage life for the technologies, an availability for the technologies, age groups that can use the technologies or that have difficulty using the technologies, etc.

The research literature database 204 provides data storage and retrieval capabilities to the computer system 110. The research literature database 204 may include, but is not required to include, one or more of a relational database, a centralized database, a distributed database, a data warehouse, a noSQL database, an object-oriented database, a graph database, a cloud-computing database, a data repository, a data lake, etc. The research literature database 204 can be used to store research literature (e.g., articles, research papers or documents, webpages, etc.) related to various technologies. The research literature database 204 can also be used to store keywords (e.g., digital health related keywords), technology metrics, and links to literature.

The research literature database 204 can be used to store examples of research literature relating to one or more technologies, one or more articles that discuss technologies, one or more webpages that include information relating to technologies, content from one or more data repositories (e.g., that includes data from one or more previously performed research studies), etc. The computer system 110 can, for example, store examples of research literature in the research literature database 204. The computer system 110 can, for example, access examples of research literature from the research literature database 204. The computer system 110 can use the examples of research literature to, for example, update the technology data 202a. That is, for example, the computer system 110 can use the examples of research literature to validate uses (e.g., capabilities) of the technologies, to identify types of data that can be collected by the technologies, to update data collection precision of the technologies, to identify software or hardware requirements of the technologies, etc. The research literature database 204 is described in more detail below with respect to FIG. 3.

The taxonomy database 206 can be used to store data mapping keywords, data types, and uses of various technologies. The computer system 110 can update data stored in the taxonomy database 206 (e.g., one or more data mappings) over time using, for example, research literature stored in the research literature database, updates from a technology provider or manufacturer, etc. The computer system 110 can use the data in the taxonomy database 206 to extract study parameters from the study data 108 provided to the computer system 110, e.g., from the client device 104. For example, the computer system 110 can identify one or more keywords in the study data 108 provided to the computer system 110 from the client device 104, can access one or more data mappings stored in the taxonomy database 206, and can use the one or more data mappings to identify one or more types of data that are required to be collected for the study and/or one or more sensors that are required for the study. The extracted study parameters (e.g., the identified data types and/or sensors) can be used by the computer system 110 in making one or more predictions and/or recommendations. The taxonomy database 206 is described in more detail below with respect to FIG. 5.

In the example of FIG. 2, the computer system 110 includes a technology recommendation module 212, a prediction module 214, and a monitoring module 216. The technology recommendation module 212, the prediction module 214, and the monitoring module 216 can each leverage one or more algorithms, such as one or more static algorithms and/or one or more machine learning algorithms.

As shown, the computer system 110 receives the study data 108 from the client device 104. The computer system 110 can provide the study data 108 to the technology recommendation module 212 and to the prediction module 214.

The technology recommendation module 212 is configured to receive study data 108 (or information extracted from the study data 108) and the technology data 202 as an input. The technology recommendation module 212 is also configured to generate recommendations 222 as an output. The recommendations 222 can include technology options that each contain one or more technology items. As an example, the technology recommendation module 212 can receive the study data 108 related to a particular study from the client device 104 and the technology data 202a as input and generate the recommendations 222 as output for the particular study. The recommendations 222 can include, for example, one or more technology options that the technology recommendation module 212 determines are viable given the study data 108. In some implementations, the recommendations 222 is or includes the recommendation 122 shown in FIG. 1.

As described in more detail below, the technology recommendation module 212 can be configured to additionally receive predictions 224 generated by the prediction module 214 as input. The technology recommendation module 212 can use the predictions 224 in generating the recommendations 222. The predictions 224 can indicate what technology options are viable, e.g., what technology options have a sufficient likelihood of achieving desired results for the study (e.g., given the study data 108, the extracted study parameters, known demographics of the study participants, etc.). Similarly, the predictions 224 can indicate that a subset of the potential technology options that are being considered for the new research are not viable, e.g., due to one or more of an inability to measure or track a data type needed for the study, due to an age group incompatibility with the anticipated participants of the study, due to one or more of the technology items not being available in a location where the study is to take place, due to a technology option or technology item being cost prohibitive, due to insufficient data measurement precision, etc.

In generating the recommendations 222, the technology recommendation module 212 can analyze the study data 108 to extract study parameters from the study data 108. Extracting the study parameters can include identifying one or more keywords in the study data 108 and comparing the keyword with a data mapping accessed from the taxonomy database 206. For example, the study data 108 can be a natural language query. The technology recommendation module 212 can perform natural language processing on the query to identify keywords in the query. For example, with respect to FIG. 1, the technology recommendation module 212 can process the query "track sleep and blood pressure" to identify the keywords "sleep" and "blood pressure." The technology recommendation module 212 can access a taxonomy structure from the taxonomy database 206, and can use the taxonomy structure to determine that the new research study requires collection of blood pressure data, movement data, and heartrate data.

In addition to keywords related to the types of data that are to be collected and/or analyzed for the study, the technology recommendation module 212 can extract other study parameters as well. These parameters can include, for example, an required data measurement precision, an expected data collection time (e.g., hours per day), location where the study is to take place, a size of the study, a budget for the study, a required device/software utilization for the study (e.g., in order to acquire statistically meaningful results from the study), etc. In some implementations, the technology recommendation module 212 provides the extracted one or more study parameters to the prediction module 214. The prediction module 214 can use the study parameters in generating the predictions 224, e.g., by identifying requirements for the new research study from the study parameters and determining what technology options are likely to meet those requirements.

In generating the recommendations 222, the technology recommendation module 212 can compare the extracted study parameters to the technology data 202a accessed from the technology database 112. As a result of comparing the extracted study parameters to the technology data 202a, the technology recommendation module 212 can determine one or more viable technology options. For example, if the study parameters provide that actigraphy data and exercise data are required to be collected for the new research study, the technology recommendation module 212 can generate technology options that only include technology items that are capable of measuring (or analyzing) actigraphy data and/or exercise data.

In some implementations, the recommendations 222 include all potential technology options for a new research study that the technology recommendation module 212 determines are viable and/or that the prediction module 214 indicates are viable. For example, the recommendations 222 can include all technology options that are determined to have a sufficient likelihood of achieving desired results for the new research study (e.g., greater than a 75%, 80%, or 85% chance).

In generating the recommendations 222, the technology recommendation module 212 can score the one or more viable technology options. Scoring the one or more viable technology options is described in more detail above with respect to FIG. 1. Scoring the one or more viable technology options can include, for example, determining as score for each of the technology options by taking into account one or more of the precision of the technologies in the technology options, the cost of the technologies in the technology options, the number of devices in the technologies options, the durability of the devices in the technology options, the reliability of the technologies in the technology options, the ease of use of the technologies of the technologies in the technology options, an anticipated usage of the technologies of the technology options by the study participants, etc.

In generating the recommendations 222, the technology recommendation module 212 can optionally select a subset of the viable technology options to recommend. The subset of technology options can include one or more technology options that the computer system 110 generally recommends, and/or one or more technology options that are recommended for particular situations (e.g., particular age groups if the age group of the participants is currently unknown, a particular location of the study if currently unknown, a particular location where the study participants reside if the participant have yet to be selected, etc.).

Selecting a subset of the viable technology options can include the technology recommendation module 212 comparing the scored, viable technology options to recommendation criteria. Recommendation criteria can include a maximum and/or minimum number technology options to recommend, a minimum acceptable score, a maximum number of devices in each of the technology options (e.g., no more than two devices per technology option), a maximum number of software in each of the technology options (e.g., no more than one mobile computing app per technology option), a maximum price of each of the technology options (e.g., no more than $1000 per technology option), minimum safety requirements, etc.

For example, selecting a subset of the viable technology options can include the technology recommendation module 212 selecting a preset number of viable technology options with the highest scores (e.g., the three viable technologies options with the highest score), selecting all viable technology options that have a score above a threshold score (e.g., all technology options that have a score of three or better), or selecting a preset number of technology options (or less than the preset number if the preset number cannot be satisfied) with the highest scores among those viable technology options that have a score that meets a threshold score.

The prediction module 214 is configured to receive study data 108 (or information extracted from the study data 108) and the technology data 202 as an input, and to generate predictions as an output. For example, the technology recommendation module 212 can receive the study data 108 related to a particular study from the client device 104 and the technology data 202a as input and generate the predictions 224 as output for the particular study. The predictions 224 can indicate the likelihood of one or more technology options (e.g., individual technologies or groupings of technologies) achieving desired results, e.g., the likelihood of the one or more technology options achieving the determined needs of the study as extracted or otherwise determined from the study data 108. Those technology options that are determined to be sufficiently likely to achieve the desired results of the study can be considered viable technology options by the prediction module 214. Technology predications are discussed in more detail below with respect to FIG. 7.

In some implementations, the prediction module 214 can be configured to receive one or more extracted study parameters (e.g., the determined needs for the study) from the technology recommendation module 212 in addition to or in place of the study data 108, as input.

In some implementations, the prediction module 214 can compare the extracted or otherwise determined study parameters to the technology data 202 to generate a list of technology options from the technologies found in the technology data 202a. The technology options can each include one or more technologies.

In generating a list of technology options, the prediction module 214 can identify the technologies in the technology data 202a that are relevant to the study, e.g., that could potentially assist in the study. That is, the prediction module 214 can filter out any technologies from further consideration that are incapable of assisting in the study. For example, the prediction module 214 can identify all technologies in the technology data 202a that can measure at least one type of data that is to be collected in the study (e.g., as indicated by the study data 108) as relevant technologies. As another example, the prediction module 214 can identify all technologies in the technology data 202a that can measure at least one type of data that is to be collected in the study with sufficient precision (e.g., as required by the study data 108) as relevant technologies.

Once the prediction module 214 has identified the relevant technologies, the prediction module 214 can treat each of relevant technologies as a technology option and/or can group relevant technologies together to form technology options. For example, with respect to FIG. 1, the prediction module 214 can group the Sensor A and the Bed Sensor C as a first technology option. The prediction module 214 can group the Sensor A and the Bed Sensor C randomly (e.g., the prediction module 214 can create a technology option for each possible grouping of relevant technologies, can create a technology option for each possible grouping of relevant technologies that include a maximum of three technologies, can create a technology option for each possible grouping of relevant technologies that include a maximum of two devices, etc.), or can group the Sensor A and the Bed Sensor C based on a determination that the Sensor A is insufficient by itself to meet the needs of the study (e.g., cannot collect sleep data).

Alternatively, in some implementations, the computer system 110 generates a conclusive list of technologies options for the prediction module 214 to analyze.

In generating the predictions 224, the prediction module 214 can leverage one or more machine learning models. For example, the prediction module 214 can train and use one or machine learning models to predict the success of each of the technology options, a compliance of participants using the technologies in each of the technology options, a precision of data collected using the technologies in each of the technology options, a reliability of the technologies in the technology options, etc., e.g., in view of the study data 108 and the technology data 202*a*.

As an example, in generating the predictions 224 using one or more machine learning models, the prediction module 214 can determine feature values based on the study needs (e.g., study parameters) extracted from or otherwise determined from the study data 108 received by the computer system 110 from the client device 104. The prediction module 214 can provide the feature values as input to the one or more machine learning models. The prediction module 214 can process the feature data using the one or more machine learning models. The prediction module 214 can obtain one or outputs from the one or more machine learning models that indicate one or more predictions, e.g., a likelihood, a confidence, an expected results, etc. The prediction module 214 can compare the outputs of the one or more machine learning models to a reference or a standard (e.g., a reference or standard that is appropriate for the study) to determine if the technology would succeed.

Alternatively, in generating the predictions 224, the prediction module 214 can use statistical analysis of data. The data can include, for example, usage data (e.g., data received by the computer system 110 from the client devices 208 and collected by one or more technologies used in a study). The data can additionally or alternatively include, for example, study data (e.g., the study data 108 received by the computer system 110 from the client device 104).

As an example, in generating the predictions 224 using statistical analysis of data, the prediction module 214 can use the usage data and/or the study data to identify results that were achieved in the most similar situations (e.g., situations in other studies that are determined to be most similar to the new study based on the study data). The prediction module 214 can average the results of the most similar situations, or can weigh the results of the most similar situations differently based on how similar those previous studies are to the new research study being contemplated (e.g., in terms of study needs and/or study parameters between the previous studies and the new study).

Additionally or alternatively, in generating the predictions 224, the prediction module 214 can use rule-based analysis. For example, the prediction module 214 can perform statistical analysis on data (e.g., study data and/or usage data) in advance to derive rules/heuristics/relationships ("predication criteria") that show compatibility of certain technologies or technology characteristics with certain study parameters or outcomes. The prediction module 214 can proceed to apply the prediction criteria to the current study's data.

For example, the prediction module 214 can apply the prediction criteria to each of the technology options. If the prediction module 214 determines that a given technology options does not meet one or more of the of the prediction criteria, the prediction module 214 can determine that the technology option is unlikely to succeed for the contemplated research study (e.g., that the technology option is not viable). For example, as a result of applying the prediction criteria to the technology options, the prediction module 214 can determine that a given technology option is not viable based on one or more of the technology option including a technology that collects a data type with an insufficient precision, the technology option including a technology that has insufficient usage for a given age group of participants, the technology option including a technology that has an insufficient usage for a given location (e.g., location where the study is to take place and/or where the study participants reside), the technology option including a technology that has an insufficient battery life, the technology option including a technology that has an insufficient reliability (e.g., could be fine for some studies but not for other studies, such as those involving pharmaceuticals where a technology must reliably monitor participant vitals), the technology option including a technology that collects or transfers data with insufficient frequency (e.g., frequency could be important for studies where participant vitals must be closely monitored), etc.

The predictions 224 generated by the prediction module 214 can include, for example, an indication as to the viability of each of the study options. The predictions 224 can be used to filter out potential study options from consideration for the new research study. For example, the prediction module 214 can determine a likelihood of success for each potential technology option for the new research study. The prediction module 214 can apply a threshold likelihood to the determined likelihoods corresponding to the potential technology options. The prediction module 214 can label the technology options that meet the likelihood threshold has viable for the new research study. The predictions 224 can include an indication of which technology options have been labeled as viable and/or which technology options have been labeled as non-viable.

In some implementations, the prediction module 214 can provide the predictions 224 to the technology recommendation module 212. The technology recommendation module 212 can use the predictions 224 in generating the recommendations 222. For example, technology recommendation module 212 can use the predictions 224 to filter out one or more technology options from consideration such that they are not included in the recommendations 222.

The monitoring module 216 is configured to receive collected data from the client devices 208 as input and to generate monitoring results 226 as output. The monitoring results can include, for example, the data collected from the client devices 208, metrics for the technologies generated using the data collected from the client devices 208, warnings (e.g., health alerts), notifications, etc. The monitoring module 216 can send all or part of the monitoring results 226 to the client device 104. The monitoring module 216 can send all or one or more portions to the client devices 208.

In some implementations, the computer system 110 can contact one or more external systems based on the monitoring results 226. For example, if the monitoring results 226 indicate that that one or more of the study participants requires medical attention, the computer system 110 can contact emergency services. Alternatively or additionally, the computer system 110 can alert the client device 104 of the potential emergency event.

The metrics for the technologies generated by the monitoring module 216 using the data collected from the client devices 208 can include, for example, an average usage time (e.g., hours per day) of a given technology, an average battery life for a given technology, an average on-time or off-time for a given technology, a frequency of data collection for a given technology, a frequency of data transmission (e.g., how often the device automatically uploads data to the computer system 110, how often the participants connect a device to a computing device for data upload to the computer system 110, etc.), etc. The metrics can be further broken down by the monitoring module 216 by age groups that the study participants belong to, locations where the data was collected, time of day when the data was collected, etc. The monitoring module 216 can include the generated metrics in the monitoring results 226.

The monitoring module 216 can compare the collected data to monitoring criteria. The monitoring criteria can include one or more study parameters that indicate compliance with the study. For example, the monitoring criteria can include a minimum battery life, a minimum usage time that participants are required to use the technology (e.g., in order for the study to be successful) in a time frame (e.g., two hours per day, twenty hours per week, etc.), a minimum data collection frequency (e.g., device must take twenty measurements a minute, five measurements a second, etc.), a minimum reliability (e.g., software cannot crash more than once per week), etc. If the collected data indicates the one or more monitoring criteria are not met (e.g., for a given day, for a given week, etc.) or are not being met (e.g., after a week of use of the technology, after a month of use of the technology, etc.), the monitoring module 216 can generate a warning notification. The warning notification can indicate the technology that is failing to meet the monitoring criteria, and/or the one or more participants that are associated with the failing examples of the technology, e.g., the one or more participants that are failing to comply with the study requirements (e.g., failing to use the given technology for three hours per day). The monitoring module 216 can send the warning notification to the client device 104 and/or to a subset of the client devices 208 corresponding to the one or more participants that are associated with the failing examples of the technology. The monitoring module 216 can include the warning notification (or the information contained in the warning notification) in the monitoring results 226.

The monitoring criteria can additionally or alternatively include health criteria. The health criteria can include, for example, one or more thresholds that when crossed result in the monitoring module 216 generating a health warning notification. As an example, the health criteria can include a maximum heart rate, a minimum heart rate, a maximum blood pressure, a minimum blood pressure, a maximum blood toxicity level, a minimum blood oxygen level, etc. The monitoring module 216 can generate one or more warning notifications in response to health criteria being met or not met. The monitoring module 216 can send the one or more warning notifications to the client device 104 and/or to a client device of the participant that the warning notification corresponds to. The monitoring module 216 can include the one or more warning notifications (or the information contained in the one or more warning notifications) in the monitoring results 226.

The monitoring criteria can additionally or alternatively include milestones for the study. Milestones can include for example a percent improvement for a given participant from a baseline. Milestones can include, for example, a participant reaching a minimum acceptable level, e.g., of performance, of heart health, of study compliance, etc. The monitoring module 216 can generate one or more notifications in response to a milestone being reached. The monitoring module 216 can send the notification to the client device 104 and/or to a client device of the client devices 208 for the participant that the warning notification corresponds to. The monitoring module 216 can include the one or more notifications (or the information contained in the one or more notifications) in the monitoring results 226.

The computer system 110 can provide one or more of the outputs of the modules 212, 214, and 216 to the client device 104. That is, the computer system 110 can send the recommendations 222, the predictions 224, and/or the monitoring results 226 to the client device 104, e.g., over the network 130.

Figure 3:
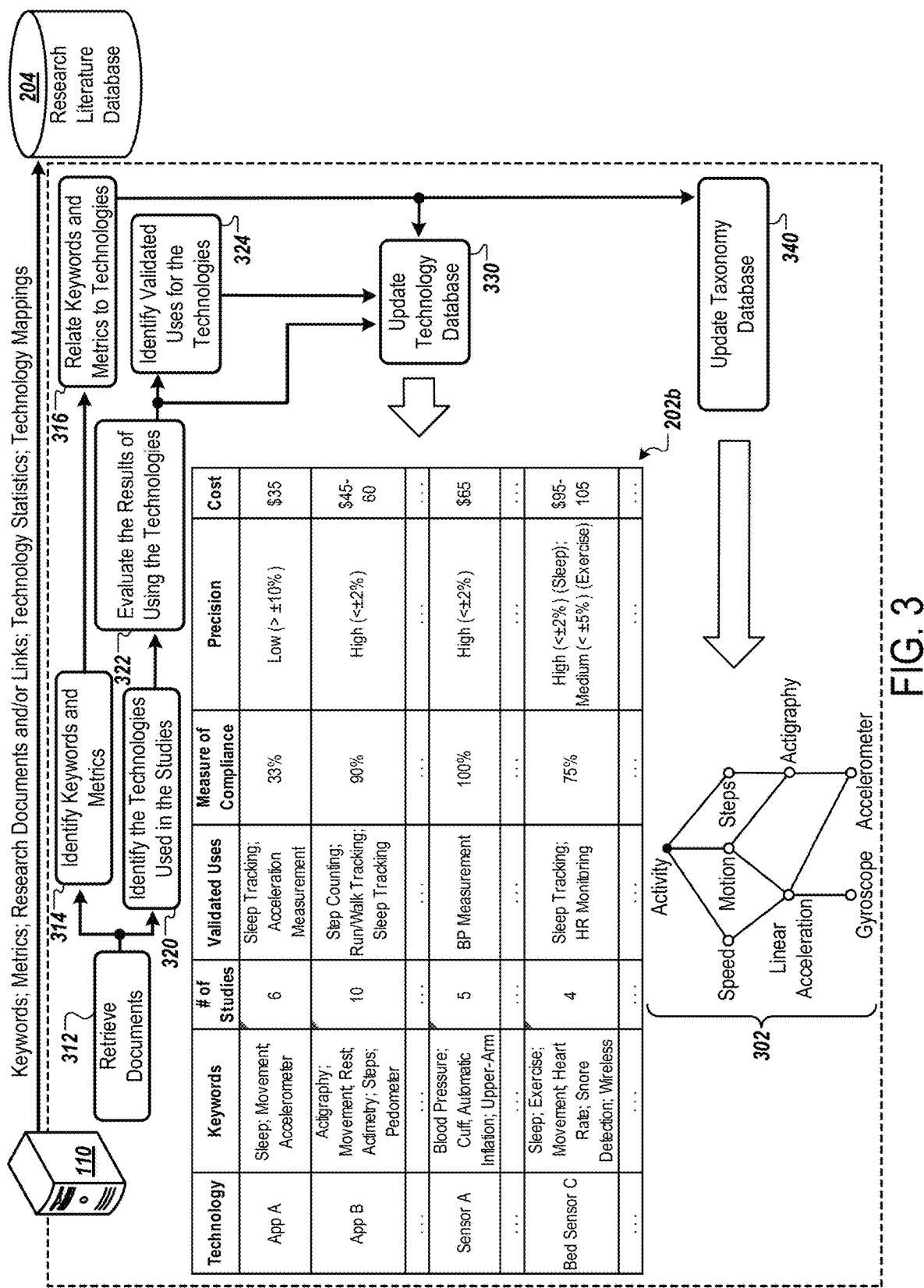
FIG. 3 is a diagram that illustrates an example system and process for updating a research literature database.

FIG. 3 is a diagram that illustrates an example process for updating the research literature database 204. The research literature database 204 can be updated by the computer system 110. The research literature database 204 can be updated to include one or more keywords, technology metrics, research documents, links to research documents, technology statistics, and/or technology mappings.

In the example of FIG. 3, the computer system 110 can retrieve documents (312). The documents can include, for example, web pages, articles, research documents, etc. Retrieving the documents can include, for example, crawling web pages, web articles, databases containing research documents, databases containing articles, etc.

The computer system 110 can identify keywords and metrics in the retrieved documents (314). The keywords that the computer system 110 attempts to identify (e.g., searches the retrieved documents for) can included keywords that are stored in the taxonomy database 206 shown in FIG. 2 (e.g., as part of one or more data mappings), keywords that have previously been associated with one or more technologies (e.g., as indicated by the technology data 202 stored in the technology database 112), keywords identified by one or more study researchers (e.g., keywords provided by the user 102 as part of the study data 108 shown in FIG. 1), etc. The keywords can include, for example, types of data, particular sensors, types of sensors, technologies, etc. The metrics can include, for example, data collection precisions, technology costs, technology specifications, technology requirements, data collection frequencies, etc.

The computer system 110 can relate the identified keywords and metrics to technologies. For example, in identifying the keywords and metrics in the retrieved documents, the computer system 110 can identify the keyword, "accelerometer" and a related precision metric of ±11% in an article describing a previously conducted research study. The computer system 110 can relate the keyword, "accelerometer" and the precision metric of ±11% to a mobile computing app technology ("App A") upon determining that the keyword and the precision metric are associated with App A. The computer system 110 can determine that the keyword and the precision metric are associated with App A based on, for example, the structure of the sentence/paragraph/passage that the keyword, metric, and technology label were found in; the technology label being found in the same sentence/paragraph/passage as the keyword and the metric; a determination that the App A was the only technology used in the study or the only technology described in the research document; etc.

The computer system 110 can use the related keywords, metrics, and technologies to update the technology database 112 (330). For example, the computer system 110 can update the technology data 202b in the technology database 112 to add a technology to the technology data 202b, to associate a new keyword with a technology, and/or to update the metrics of a technology. For example, the computer system 110 can update the technology data 202b to associate the keyword, "accelerometer" with the App A, and to update the precision of the App A, e.g., from medium to low. In updating one or more metrics in the technology data 202, the computer system 110 can determine the average metric value, e.g., the computer system 110 can take the average of all metric values for a given technology and for a given metric type (e.g., a precision metric or a precision metric associated with a particular type of data collection) that have been identified and/or collected.

The computer system 110 can use the related keywords, metrics, and technologies to update the taxonomy database 206 (340). For example, the computer system 110 can update a data mapping 302 in the taxonomy database 206. Updating the data mapping 302 can include, for example, the computer system 110 adding a node to the data mapping 302 and/or forming a new connection between nodes of the data mapping 302. Adding a node to the data mapping 302 can include the computer system 110 adding a node for a technology, adding a node for a technology type, adding a node for a data type, adding a node for a sensor, or adding a node for a sensor type. As an example, the computer system 110 can use the related keywords, metrics, and technologies to add the identified keyword, "accelerometer" to the data mapping 302. The relationships between the keywords, metrics, and technologies can indicate that the keyword accelerometer should be associated with both the keywords "linear acceleration" and "actigraphy." Accordingly, the computer system 110 can form a connection between the new accelerometer node and the linear acceleration node. Similarly, the computer system 110 can form a connection between the new accelerometer node and the actigraphy node.

In some implementations, as will be described in more detail below with respect to FIG. 5, the computer system 110 can be provided an initial or a previously generated taxonomy (e.g., data mapping) that is updated by the computer system 110 over time.

The computer system 110 can identify the technologies used in the studies (320). Identify the technologies used in the studies can include searching the retrieved documents for known technologies (e.g., iPhone 6S, Fitbit, etc.) or known types of technologies (e.g., wearables, smart phones, ECG heart rate monitors, etc.).

The computer system 110 can evaluate the results of using the technologies (322). Evaluating the results of using the technologies can include, for example, the computer system 110 identifying the way in which the technologies were used in the studies, determining study parameters for the studies (e.g., the needs/requirements for the studies), and determining if the technologies were successfully used or not for the studies (e.g., determining if the technologies were able to be used in the way the studies required and with sufficient performance so as to meet the study parameters).

The computer system 110 can identify the validated uses for the technologies (324). For example, the computer system 110 can determine a validated use for a technology based on one or more studies The computer system 110 may require that for a use of a given technology to be validated, the technology must have been used in this way in a threshold number of studies (e.g., at least one study, at least two studies, at least three studies, etc.), must have been used successfully in this way in a threshold number of studies, and/or must have been used in this way in threshold number of studies while providing performance that the computer system 110 considers sufficient (e.g., technology can provide a precision of at least ±3% when used in this way). In determining if performance of a technology is sufficient, the computer system 110 can compare the identified metrics related to the technology to one or more criteria (e.g., performance criteria). The criteria can include, for example, a minimum level of precision, a minimum data collection frequency, a minimum level of reliability, etc.

The computer system can use the evaluation of the results of using the technologies in the studies and/or the validated uses for the technologies to update the technology database (330). For example, the computer system 110 can update the number of unique studies that each of the technologies are used in, to update a list of validated uses associated with each of the technologies, to update a measure of compliance of each of the studies, etc. The measure of compliance can be, for example, a success rate of the technology in the studies that it has been used in, the rate at which the technology would be considered successful by the computer system 110 in the studies that it has been used in (e.g., when compared to performance criteria), or a rate determined from both the success rate of the technology and the rate at which the technology would be considered successful by the computer system 110.

Figure 4:
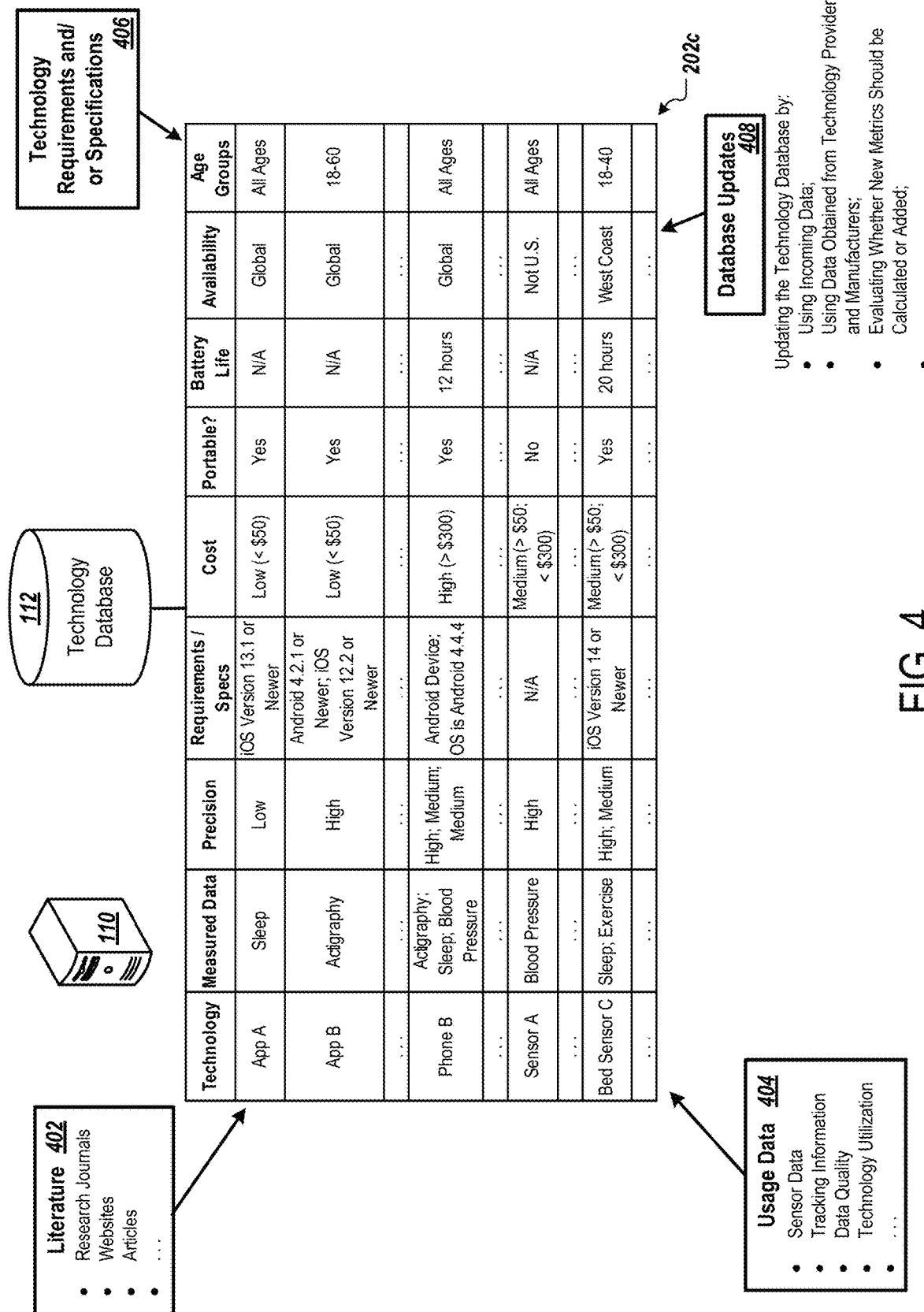
FIG. 4 is a diagram that illustrates an example system and process for updating a technology database.

FIG. 4 is a diagram that illustrates an example process for updating the technology database 112.

The computer system 110 or another system can update the technology database 112 using, for example, literature 402, usage data 404, technology requirements and/or specifications 406, and/or database updates 408. The updates to the technology database 112 can be made by the computer system 110.

The literature 402 can include, for example, research journals, websites, articles, content from one or more external data repositories, etc. The literature 402 can be stored in the research literature database 204 as shown in FIG. 2. The literature 402 can be obtained by the computer system 110 crawling through one or more webpages or databases. The computer system 110 can analyze the literature 402 as described in more detail above with respect to FIG. 3 to extract data from the literature 402. The computer system 110 can use the extracted data to update the technology data 202c stored in the technology database 112.

The usage data 404 can include, for example, usage data from previously performed and ongoing studies. The usage data 404 can include data collected from the technology items that are currently being used or have been used by actual participants. The usage data 404 can be obtained by the computer system 110 shown in FIG. 2 from the client devices 208. The computer system 110 can use the usage data 404 to update the technology data 202c.

The usage data 404 can include sensor data, such as the measurements being taken of the participants by the technology items. For example, the usage data 404 can include blood pressure measurements, heart rate measurements, and pulse rate measurements for various participants of ongoing and past studies.

The usage data 404 can additionally or alternatively include tracking information, such as locations of the participants, distances traveled by the participants, speeds of the participants, steps taken by the participants, etc.

The usage data 404 may also indicate the quality of the data being collected. For example, the usage data 404 may explicitly provide an indication of the precisions of the measurements that are being collected by the technology items. However, the usage data 404 may indirectly indicate the precisions of the measurements that are being collected by the technology items, e.g., based on the range of measurements collected by the technology items for a particular participant, particular cohort of participants, across all participants of a given study, or across all participants for all studies that used the technology items in question.

The usage data 404 may also indicate the utilization of the technology items by participants. The utilization can be, for example, an indication of the amount of time that participants are using the technology items compared to a time that they are supposed to be using the technology items. For example, if a group of participants in an ongoing study are on average measuring their blood sugar three times a day but the study requires that they take their blood sugar four time a day to be compliant, the computer system 110 can use the usage data 404 to determine that the average utilization (at least with respect to this study) of a particular glucometer used in the study is 75%.

The technology requirements and/or specifications 406 can include, for example, software requirements for the technologies, hardware requirements for the technologies (e.g., a required memory, a required processor speed, a required number of processors, etc.), an expected battery life the technologies, an indication of durability or survivability of the technologies (e.g., an IPX7 rating), etc. The computer system 110 can obtain the technology requirements and/or specifications 406 from manufacturers and/or providers of the technologies. For example, the computer system 110 can extract the technology requirements and/or specifications of a given technology from a website of the technology's manufacture. The computer system 110 can use the technology requirements and/or specifications 406 to update the technology data 202c.

The database updates 408 can include, for example, the computer system 110 updating the technology database 112 using one or more of incoming data (e.g., from one or more research study participants, from one or more researchers, etc.), using data obtained from technology providers and manufacturers, evaluating whether new metrics should be calculated or added, etc.

As shown, the technology data 202c is depicted as a data table having multiple rows and columns. The first column of the technology data 202c ("Technology") includes identifications and/or brief descriptions of various technology items. The technology items can include, for example, sensors, devices, software, or combinations thereof. The technology items can include digital health technologies (DHTs) as described above. DHTs may be capable of measuring one or more types of health data, such as, for example, cardiac activity, temperature, blood pressure, glucose levels, toxicity levels, etc.

The second column of the technology data 202c ("Measured Data") includes types of data the technology items in the first column can measure. For example, the Sensor A can measure blood pressure data. Additionally or alternatively, the second column includes an indication of types of data that the technology items in the first column can use, e.g., receive as input to track and/or analyze. For example, the App A may be capable of tracking sleep data that is measured by one or more sensors (e.g., the Bed Sensor C) over time. The App A may be capable of analyzing the sleep data to determine sleep data metrics, such as, for example, an average length of sleep per night for a corresponding user (e.g., 7.2 hours), an average sleep time for the corresponding user (e.g., 12:06 AM), an average wakeup time (e.g., 7:18 AM), sleep trends (e.g., averaging 0.2 hours less sleep per night over the last month), etc.

Continuing with this example, information in the database updates 408 from a developer of the App A can provide that the App A is capable of analyzing sleep data to determine sleep data metrics. The computer system 110 can update the technology data 202c to include an indication that the App A is capable of analyzing sleep data to determine sleep data metrics. This indication may be provided in the second column of the technology data 202c or in a different column of the technology data 202c. Alternatively, the computer system 110 can store information indicating the capability of the App A elsewhere in the technology database 112.

Similarly, information from research journals in the literature 402 can provide that the App A has been successfully used to determine an average length of sleep per night, an average sleep time, an average wakeup time, and sleep trends for study participants, such as participants of a clinical trial for a new sleep medication. In response, the computer system 110 can find that determining an average length of sleep per night, an average sleep time, an average wakeup time, and sleep trends are all validated uses for the App A. Additionally or alternatively, the usage data 404 from previously performed or ongoing studies can be used by the computer system 110 to confirm (e.g., to validate) the potential uses of the App A. The computer system 110 can proceed to update the technology data 202c to include an indication of each of these validated uses of the App A. This indication may be provided in the second column of the technology data 202c or in a different column of the technology data 202c. Alternatively, the computer system 110 can store information indicating the validated uses of the App A elsewhere in the technology database 112.

The third column of the technology data 202c ("Precision") includes indications of precisions of data that can be measured and/or generated by the technology items for a given data type. For example, the high precision indicator for the Sensor A indicates that the Sensor A is capable of measuring blood pressure with a high precision. What is considered a high precision can be set by a researcher of the study, can be determined from the technology requirements and/or specifications 406 (e.g., that indicate the expected measurement precision of the Sensor A), can be determined from the usage data 404 (e.g., acquired from one or more on going or previously performed usage studies that used the Sensor A), can be determined from the database updates 408 (e.g., provided by a manufacturer of the Sensor A), and/or can be determined from the literature 402 (e.g., high precision can be equal to or greater than a precision that is always found to be sufficient based on research journals).

The fourth column of the technology data 202c ("Requirements/Specifications") includes software and/or hardware requirements of the technology items. For example, the App A requires iOS Version 13.1 or newer. The fourth column can indicate the compatibility of the technology items with other devices, such as devices of study participants and/or researchers. For example, because the App A requires iOS Version 13.1 or newer, the App A can only be installed on Apple devices. This could potentially pose an issue for a study if the study participants are required to install software on their own devices for the research study. The fourth column can be populated by the computer system 110 using the technology requirements and/or specifications 406. The information from the technology requirements and/or specifications 406 can be pulled from, for example, websites and/or documents of manufacturers' or developers' of the technology items.

The fifth column of the technology data 202c ("Cost") includes prices, ranges of prices, and/or cost indicators for the technology items. For example, the cost of the App A is determined to be low (e.g., less than $50.00). The cost information that the computer system 110 uses to populate the fifth column can be determined from one or more of the database updates 408 (e.g., prices provided by the manufacturers' and/or developers' of the technology items), and/ or from the literature 402 (e.g., from websites, research journals, articles, etc. that indicate a cost of the technology items). In determining a price for a given technology item, the computer system 110 may weigh more recent information (e.g., price from website that is currently selling the technology item) more heavily than older information (e.g., prices from research study from over a year ago). Similarly, in determining a price for a given technology item, the computer system 110 can weigh information identified from the literature 402 more heavily than information provided by the manufacturer, e.g., as the literature 402 may indicate a real-world price while the manufacturer is likely to provide a suggested retail price.

The sixth column of the technology data 202c ("Portability") includes indicators of the portability of the technology items, the dimensions of the technology items (e.g., if applicable), and/or the weight of the technology items (e.g., if applicable). Software, such as the App A, can be assumed by the computer system 110 to portable. Alternatively, software, such as the App A, can assume the portability of the device that it will be installed on or the device(s) that it can be installed on. For example, a software technology item that can only be used computer (e.g., desktop computer or laptop computer) can be determined to be not portable. The portability of the technology items can be determined from one or more of the database updates 408 (e.g., as indicated by manufacturers' of the technology items), from the technology requirements and/or specifications 406 (e.g., that can indicate the dimensions and/or weight of the technology items), from the literature 402 (e.g., that may indicate the dimensions and/or weight of the technology items, and a finding as to whether the technology items were portable), and/or from the usage data 404 (e.g., the technology utilization along with tracking information can indicate whether the technology items are portable).

The seventh column of the technology data 202c ("Battery Life") includes battery lives of the technology items (e.g., if applicable). For example, the battery life for the Phone B is shown to be twelve hours. The battery lives of the technology items can be determined from one or more of the database updates 408 (e.g., an maximum battery life provided by manufacturers of the technology items), the technology requirements and/or specifications 406 (e.g., which can provide a maximum battery life of the technology items), the literature 402 (e.g., the research journals, websites, and/or articles can indicate a real-world battery life for the technology items), and the usage data 404 (e.g., the data collected from the technology items used in previous and/or ongoing studies can provide real-world battery lives for the technology items, and/or can indicate how certain actions, such as running specific software, affects the battery life of the technology items).

The computer system 110 can calculate expected real-world battery lives for the technology items using the obtained information. In calculating the expected battery lives, the computer system 110 can take into account, for example, other technology items that are anticipated to be used with the technology items (e.g., specific software, software that will use GPS tracking, software that will use a Bluetooth connection, etc.). The computer system 110 can take into account the location where the study is expected to take place when calculating the expected battery lives (e.g., if the study requires collecting data outside and the region is particularly hot or cold, the computer system 110 can take these factors into account). The computer system 110 can take into account the expected types of connectivity and/or lengths of connectivity time (e.g., study will require five hours of Bluetooth connection per day and the usage data 404 indicates that this will generally require a phone that has a stated maximum battery life of fourteen hours or better).

The eighth column of the technology data 202c ("Availability") includes locations (e.g., geographic areas) where the technology items can be legally obtained. As previously mentioned, availability of a given technology can correspond to whether the technology can be legally obtained in a particular location (e.g., country, state, city, county, region, etc.) For example, the computer system 110 can use the literature 402 to determine that the Sensor A is not available in the U.S., e.g., due to not having been approved by the FDA.

The ninth column of the technology data 202c ("Age Groups") includes age ranges and/or age indicators of participants who are determined to successfully use the technology items. For example, the computer system 110 can populate the age groups for the technology items using one or more of the literature 402 (e.g., which can indicate whether participants of external studies successfully utilized the technology items) and/or the usage data 404 (e.g., the technology utilization can indicate how likely study participants of different age groups were to use the technology items in previously performed and/or ongoing studies).

In some implementations, the technology data 202c also includes an indication of technology usage in various locations. This usage data can indicate locations (e.g., countries, states, counties, cities, or regions) where the technologies are generally used successfully (e.g., usage percent greater than 75%, 85%, 95%, etc.) or are generally used unsuccessfully (e.g., usage percent less than 70%, 80%, 90%, etc.). Additionally or alternatively, this usage data can indicate the usage percentage of the technologies at various locations. For example, the technology data can include an indication of the usage percent for the technologies for every state in the U.S. Specifically, for Sensor A, the technology data can indicate, for example, that the usage percentage in CA is 95%, in NY is 80%, in GA is 30%, etc. The usage percentages can be determined by the computer system 110 from one or more previously conducted studies and/or ongoing studies.

Figure 5:
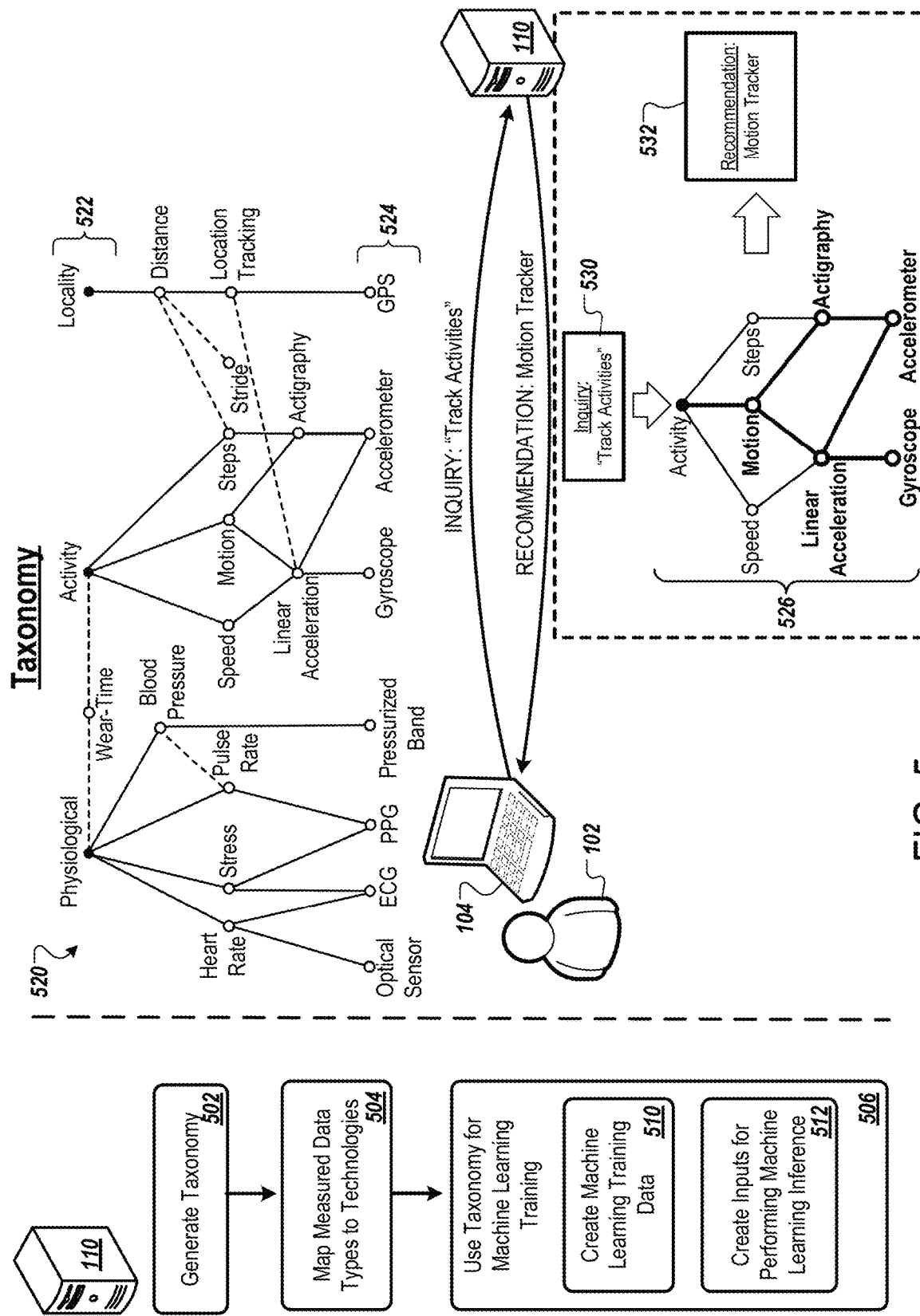
FIG. 5 is a diagram that illustrates an example system and process for generating and using a taxonomy.

FIG. 5 is a diagram that illustrates an example system and process for generating and using a taxonomy. The system can be the system 100 described above with respect to FIG. 1. The system can be the system 200 described above with respect to FIG. 2. The process for generating and using a taxonomy can be performed by the computer system 110.

The process for generating and using a taxonomy can include generating a taxonomy structure (502). For example, the computer system 110 can be used to generate a taxonomy structure 520. The taxonomy structure 520 can be generated from data stored in the research literature database 204. For example, the taxonomy structure 520 can be generated using research journals, websites, articles, etc. Generating a taxonomy structure can include the computer system 110 using data stored in the research literature database 204 to generate nodes that correspond to data types, types of technologies (e.g., types of devices or software), and/or types of sensors (e.g., that may be included in a type of device or used by a type of software). Generating a taxonomy structure can include using the computer system 110 using data stored in the research literature database 204 shown in FIG. 2 to form relationships between the nodes.

Relationships between nodes can include hierarchal relationships, e.g., hierarchal relationships between data types and/or technology types. For example, the relationships between nodes can include a connection between a node corresponding to a category of data (e.g., activity) and a node corresponding to a subcategory of data (e.g., speed, motion, and steps). A relationship between nodes can include a connection between a node corresponding to a type data (e.g., linear acceleration) and a node corresponding to a type of sensor that can be used to obtain the data (e.g., gyroscope and accelerometer). These relationships between nodes corresponding to various The process for generating and using a taxonomy can include mapping measured data types to technologies (504). The computer system 110 can form connections between nodes corresponding to types of data and particular technologies (e.g., particular devices or software that can be used to obtain the types of data). The computer system 110 can use the data stored in the research literature database 204 shown in FIG. 2 to form these connections, e.g., to determine what technology items can provide the measured data types found in the taxonomy structure 520. For example, with respect to FIG. 6B, the computer system 110 can use the data in the research literature database 204 to identify particular technologies that can provide the measured data types and to form corresponding connections. As shown in FIG. 6B, the computer system 110 can form a connection between the blood pressure node and a node for the iHealth technology item.

In cases, the process for generating and using a taxonomy includes mapping sensor types to technologies. The computer system 110 can form connections between nodes corresponding to types of sensors and particular technologies (e.g., particular devices that include sensors belonging to the types of sensors or software that use sensors belonging to the types of sensors). The computer system 110 can use the data stored in the research literature database 204 shown in FIG. 2 to form these connections, e.g., to determine what technology items include or can make use of the types of sensors found in the taxonomy structure 520. For example, the computer system 110 can use the data stored in the research literature database 204 to determine that a Phone C includes an accelerometer. Accordingly, the computer system 110 can form a connection between the accelerometer node of the taxonomy structure 520 and the Phone C.

The process for generating and using a taxonomy can include using the taxonomy structure for machine learning training (506). For example, the computer system 110 can use the taxonomy structure 520 for machine learning training, e.g., to train one or more machine learning models. The machine learning models can include machine learning models of the technology recommendation module 212, the prediction module 214, and/or the monitoring module 216 shown in FIG. 2.

As an example, the taxonomy structure 520 can be used to train a machine learning model that receives information related to a given technology item as input and outputs classification(s) of the technology item with respect to the taxonomy structure 520. The input information can include, for example, an ID of the technology item (e.g., a name or other identifier). The input information can additionally or alternatively include known characteristics of the technology item (e.g., an input vector that indicates characteristics such as battery life, precision, cost, etc. of the technology item). The classifications can provide, for example, a relationship between a given technology item and nodes of the taxonomy structure 520. For example, if the specifications of a new technology item, a Phone C, are provided to the machine learning model as input, the machine learning model can provide output that indicates the nodes of the taxonomy structure 520 that the Phone C should be associated with.

Specifically, the specifications may provide that the Phone C includes an accelerometer. The output of the machine learning model can provide that the Phone C should be associated with the linear acceleration node, the speed node, and the activity node of the taxonomy structure 520 (e.g., indicating that the Phone C can measure acceleration data, speed data, and activity data). However, in this example, the output of the machine learning model does not provide that the Phone C should be associated with the actigraphy node or the motion node. This may be due to the machine learning model taking into account usage data from one or more previous or ongoing studies, literature, and/or database updates that indicate that the Phone C should not be associated with the actigraphy node and the motion node despite the taxonomy structure 520 indicating that they should be related on the basis of the Phone C having an accelerometer.

In some cases, the computer system 110 uses one or more machine learning models to generate the taxonomy structure 520 and/or to update the taxonomy structure 520. For example, a machine learning model can receive the literature 402 and the usage data 404 shown in FIG. 4 as input. The literature 402 and/or the usage data 404 can indicate devices having gyroscopes consistently are able to measure linear acceleration. The output of the machine learning model can indicate that a relationship should therefore exist between gyroscopes and linear acceleration. Accordingly, in generating the taxonomy structure 520 or updating the taxonomy structure 520, the computer system 110 can, in response to the output of the machine learning model, add a connection between the gyroscope node and the linear acceleration node.

As an example, one or more machine learning models can be trained using the taxonomy structure 520. The one or more machine learning model can, for example, identify one or more terms that a research likely means when a different, related term is received (e.g., as part of study data). Alternatively or additionally, the one or more machine learning model can, for example, identify one or more data types that are required for a study when one or more terms are received (e.g., as part of study data). Alternatively or additionally, the one or more machine learning models can, for example, identify one or more sensors that are required for a study or can be used for a study when one or more terms are received (e.g., as part of study data). Alternatively or additionally, the one or more machine learning models can, for example, identify one or more technologies or types of technologies that can be used for a study when one or more terms are received (e.g., as part of study data).

Using the taxonomy structure for machine learning training can include creating machine learning training data (510). For example, the computer system 110 can use the taxonomy structure 520 to create machine learning training data from data found in the research literature database 204, e.g., from research journals, webpages, articles, data from external repositories etc. The computer system 110 can use the taxonomy structure 520 to generate and attach labels for data found in the research literature database 204, and/or to classify data found in the research literature database 204. The resulting labelled and/or classified data can be used as training data for one or more machine learning models of the computer system 110, e.g., machine learning models for the technology recommendation module 212, the prediction module 214, and/or the monitoring module 216 shown in FIG. 2.

As an example, the computer system 110 can use the taxonomy structure 520 to create machine learning training data by determining labels for known technology items that will be used to generate sample input for training a machine learning model. For example, the technology items in the technology data 202 can be associated with one or more nodes of the taxonomy structure 520. For a model configured to predict output of the capabilities or uses of a technology, these nodes can serve as labels, e.g., as the desired output of the machine learning model. For example, the App B may be a technology item that has already been associated with the actigraphy node, the motion node, the steps node, the distance node, the locality node, and the activity node. Accordingly, the computer system 110 can identify the actigraphy node, the motion node, the steps node, the distance node, the locality node, and the activity node as representing desired output for a machine learning model being trained to predict types of data that a technology can measure and report. The input of the machine learning model can be an identifier for App B (e.g., its name or other identifier) and/or input features indicating other characteristics of the App B, e.g., as determined from the technology data 202. For example, the input of the machine learning model can include feature values that indicate characteristics of the App B (e.g., that it can measure actigraphy data, that it has a high precision in measuring actigraphy data, that it has a low cost, that it is portable, values quantifying these and other capabilities, etc.). Accordingly, the output labels (e.g., the desired output of the machine learning model) and the input information (e.g., the ID or an input vector that indicates characteristics of the corresponding technology item) can serve as training data for the machine learning model.

Using the taxonomy structure for machine learning training can include creating inputs for performing machine learning inference (512). For example, one or more machine learning models of the computer system 110 can use the taxonomy structure 520 to modify input data and/or in generating an output. As an example, a machine learning model can use the taxonomy structure 520 to label and/or classify input data (e.g., a research journal, a webpage, an article, content of a data repository, etc.), to identify keywords in the input data, to identify technology items in the input data, etc.

As an example, creating input for machine learning interference can include creating an identifier and/or an input vector for a new or existing technology item. For example, for a new Sensor X, the computer system 110 can create an entry in the technology data 202 for the Sensor X. In creating the entry, the computer system 110 can assign an identifier to the Sensor X (e.g., provide it a name or another identifier). The computer system 110 can also add any information known about the Sensor X to the technology data 202 and associate it with the Sensor X. The identifier of the Sensor X can be used as input to the machine learning model. The machine learning model can use the denier to locate information associated with the Sensor X from the technology data 202. Additionally or alternatively, the computer system 110 can generate an input vector out of the information in the technology data 202 associated with Sensor X (e.g., it may be known that the Sensor X is or includes a Gyroscope). This input vector can serve as input to the machine learning model.

The taxonomy structure 520 can be a data mapping that relates various technology types, data types, and/or sensor types. As shown, the taxonomy structure 520 can include one or more node levels corresponding to categorical hierarchies. For example, the taxonomy structure 520 includes a higher level 522 of nodes that correspond to broad data types and/or broad descriptions of data types. The taxonomy structure 520 also includes a lower level 524 of nodes that correspond to particular data types, types of sensors, and/or types of technologies. For example, as shown, the lower level 524 includes types of sensors including gyroscopes, accelerometers, GPS units, and optical sensors. The lower level 524 can also include particular types of technologies such as electrocardiogram (ECG) and photoplethysmography (PPG). As described in more detail below with respect to FIG. 6B, the taxonomy structure 520 can include a lowest level of nodes that correspond to particular technologies (e.g., iPhone 6S, Fitbit, etc.), types of devices (e.g., smart phone, smart watch, activity tracker, etc.), and/or types of software (e.g., fitness tracker, health tracker, nutrition app, etc.).

The logical relationships that exist between the nodes of the taxonomy structure 520 are such that when the computer system 110 associates a technology item with a lower level node (e.g., a node having one or more parent nodes), the technology item is automatically associated with all related nodes that are of a higher level (e.g., higher in the hierarchy of nodes). For example, if the computer system 110 associates a Fitness Tracker A with the accelerometer node in the lower level 524 (e.g., based on a determination that the Fitness Tracker A includes an accelerometer), the computer system 110 can, in response, associate the Fitness Tracker A with the actigraphy node, the linear acceleration node, the location tracking node, the steps node, the motion node, the speed node, the distance node, the activity node of the higher level 522, and the locality node of the higher level 522. However, the logical relationships that exist between the nodes are such that when a technology item is associated with a higher level node (e.g., a node that has one or more child nodes), then the technology item is not necessarily associated with a related lower level node. For example, if the computer system 110 associates the Fitness Tracker A with the motion node (e.g., based on a determination that a validated use for the Fitness Tracker A is tracking motion wearer), the computer system 110 can, in response, associate the Fitness Tracker A with the activity node of the higher level 522. However, the computer system 110 may not automatically associate the Fitness Tracker A with the actigraphy node, the linear acceleration node, the gyroscope node, or the accelerometer node without more information.

Using these logical relationships, the computer system 110 can use the taxonomy structure 520 to help fill in the technology data 202, e.g., for technology items where information is missing or incomplete. For example, with respect to the Fitness Tracker A, the computer system 110 may create a new row in a data table representing the technology data 202 for the Fitness Tracker A. With respect to the Fitness Tracker A, the technology data 202 may only contain an indication that the Fitness Tracker A includes an accelerometer. The computer system 110 can proceed to use the taxonomy structure 520 to update the technology data 202 with respect to the Fitness Tracker A such that it includes an indication that the Fitness Tracker A can measure actigraphy data, can measure linear acceleration data, can perform location tracking, can measure motion data, can measure speed data, can track steps, can track distance, can measure activity data, and can measure locality data.

In some cases, the computer system 110 marks information added to the technology data 202 that was obtained from the taxonomy structure 520 as requiring validation (e.g., from the literature 402 and/or the usage data 404). For example, with respect to the Fitness Tracker A, the computer system 110 may add to the technology data 202 an indication that the Fitness Tracker A can likely measure steps but also include an indication that this use has yet to be validated.

In the example of FIG. 5, the computer system 110 receives the inquiry 530 to "tack activities." The computer system 110 can provide the inquiry 530 as input to one or more machine learning models (e.g., one or more machine learning models that are part of and/or leveraged by the technology recommendation module 212 shown in FIG. 2). The computer system 110 can identify a lookup taxonomy 526 based on the inquiry 530. This lookup taxonomy 526 can represent a subset of the overall taxonomy graph, e.g., a proper subset of the nodes that would satisfy a criterion used for technology lookup.

For example, as shown, the computer system 110 can match "activities" in the inquiry 530 to the "activity" node in the taxonomy structure 520. The computer system 110 then extracts the activity node and the child nodes of the activity node that can be used for tracking activities (e.g., all of the child nodes in this particular situation) to generate the lookup taxonomy 526.

In some cases, machine learning model(s) are trained using the taxonomy structure 520 and/or the lookup taxonomy 526. The machine learning model(s) can be trained as described above, e.g., using entries of the technology data 202 to generate inputs of training examples and using the taxonomy structure 520 to identify desired outputs of training examples.

The computer system 110 can provide the inquiry 530 to the machine learning model(s), or can generate an input set based on the inquiry 530 and provide it to the machine learning model(s) as input. For example, the computer system 110 can generate an input set that includes input bits. The input bits can each correspond to a node of the taxonomy structure 520 (e.g., there can be an input bit for the activity node). The input bits can be on (e.g., have a value of one) or can be off (e.g., have a value of zero). The input bits can have a default value of zero, e.g., are default off. An input bit can be set to a value of one, e.g., can be set to on, when the study data indicates that a corresponding sensor, sensor type, device type, technology type, data type, etc. is required for a new research study. For example, the computer system 110 can determine that the inquiry 530 indicates that activity data needs to be measured for the new research study (e.g., based on the inquiry 530 including the keyword "activities" and/or the keyword "track"). In response to this determination, the computer system 110 can generate an input set that includes one or more input bits. Here, the computer system 110 would set the input bit that corresponds to the activity node in the taxonomy structure 520 (and in the lookup taxonomy 526) to a value of one (on) and include it in the input set for the machine learning model(s). The input set can also include input bits for all other nodes in the taxonomy structure 520, and/or all other nodes in the lookup taxonomy 526. The other input bits in the input set can have a value of zero (off).

The computer system 110 may determine feature values, including binary input feature values (e.g., binary bits to turn set to a value of one or zero, based on logical relationships within the taxonomy structure 520. For example, if the computer system 110 determines that an inquiry indicates that measurement of pulse rate data is required for a clinical trial, the computer system 110 could generate an input set that includes an input bit corresponding to the pulse rate node in addition to an input bit corresponding to the blood pressure node and an input bit corresponding to the physiological node. The computer system 110 can set the values of each of these three input bits to the value of one.

The output of the machine learning model(s) can vary depending on the desired use of the models. For example, models can be trained to predict the uses for a technology based on characteristics of a technology, to predict whether a technology will be effective for a use or function based on characteristics of the technology, to predict the characteristics of a technology that are needed for a study based on an indication of needs of the study (e.g., data types or taxonomy nodes representing the needs of the study), to predict which technology items can meet the needs of a study, etc.

The computer system 110 can use the output of the one or more machine learning models in generating a recommendation 532. The recommendation 532 includes one or more recommended technology options. As shown, the recommendation 532 includes a motion tracker device as a recommended technology option. The computer system 110 can recommend the motion tracker device after, for example, determining that the motion tracker device includes both a gyroscope and an accelerometer, that the motion tracker device is capable of measuring linear acceleration data and actigraphy data, and/or that the motion tracker device is capable of tracking motion.

Figure 6A:
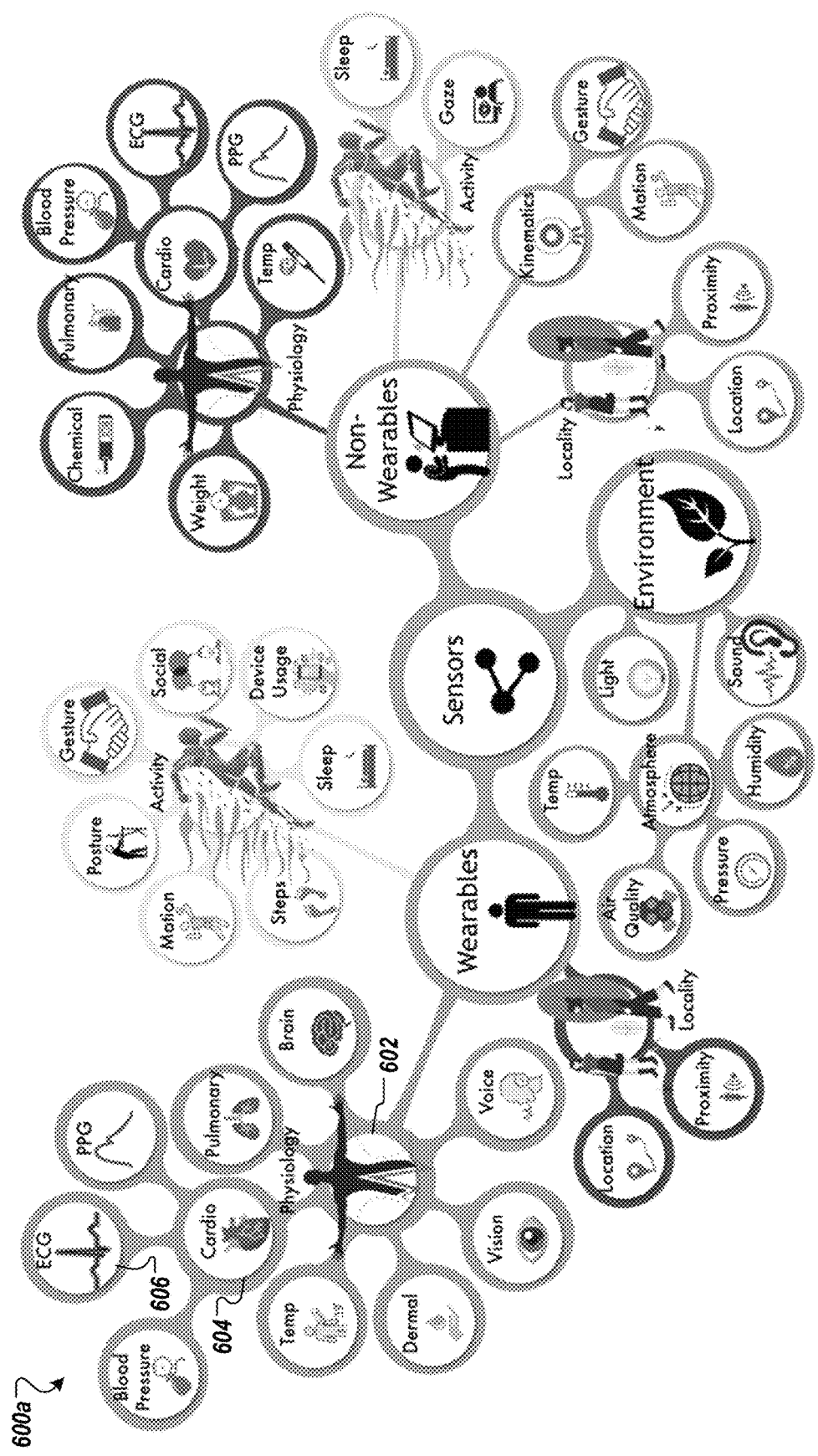
FIGS. 6A-6B are diagrams that illustrate example taxonomy structures.
Figure 6B:
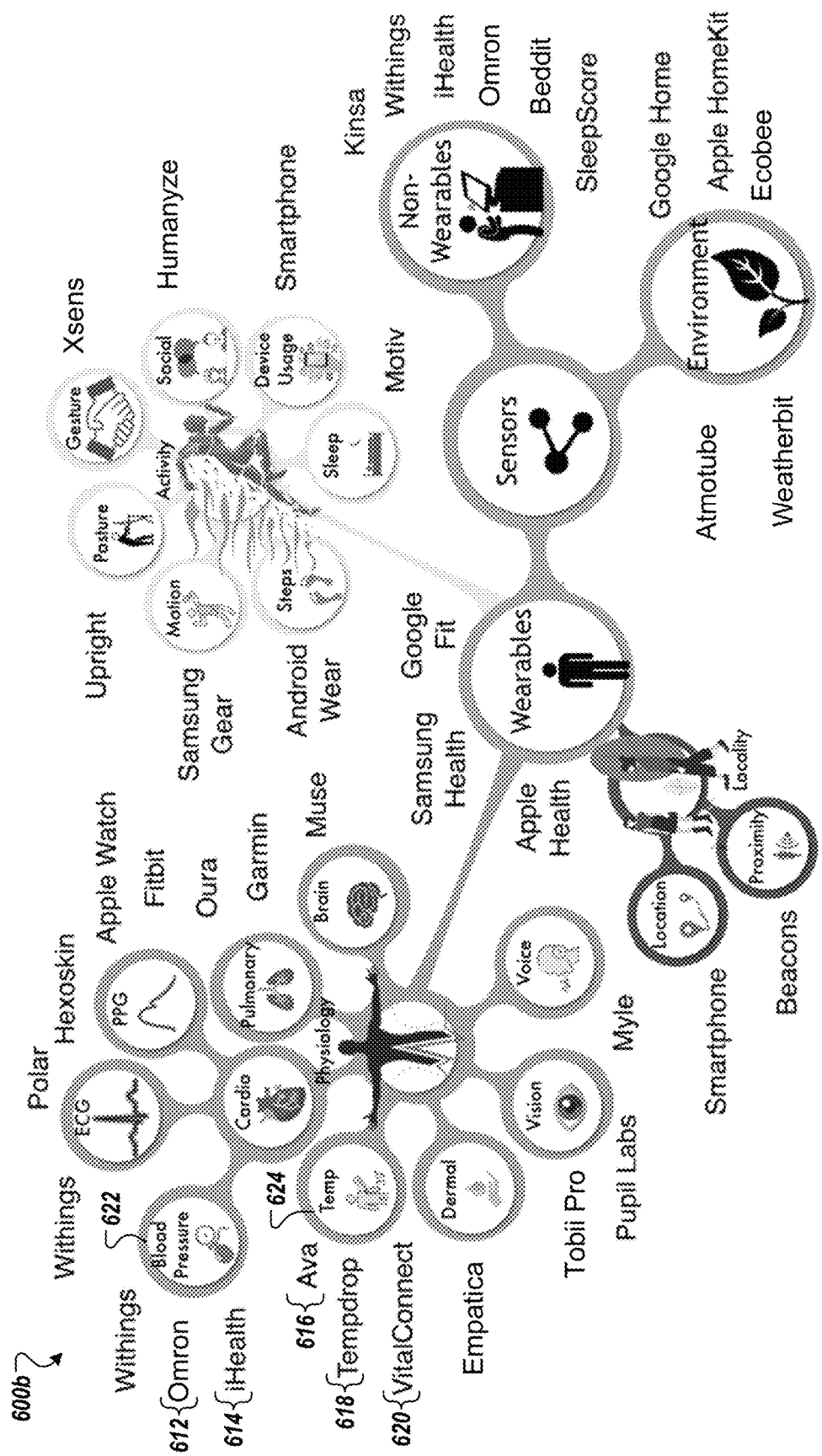

FIGS. 6A-6B are diagrams that illustrate example taxonomy structures. In the example of FIG. 6A, a first taxonomy structure 600a is shown. The taxonomy structure 600a can be data that associates various technology types, data types, and/or sensor types. For example, the taxonomy can include a mapping of data elements to indicate relationships among the data elements. The computer system 110 can generate data that represents the taxonomy structure 600a when generating the taxonomy.

The taxonomy structure 600a can be generated by the computer system 110, e.g., from data stored in the research literature database 204 shown in FIG. 2. The taxonomy structure 600a can be stored in the taxonomy database 206.

As shown, the taxonomy structure 600a can include various categories and subcategories of data types (e.g., that a researcher may want to measure and/or track for a study), technology types, device types, sensor types, etc. Each type of data, technology, device, sensor, etc. can have a corresponding one or more nodes. For example, with respect to wearable devices, the taxonomy structure 600a includes a node 602 for physiology data, a node for activity data, and a node for locality data. The taxonomy structure 600a can also include an indications of relationships between the various nodes. These relationships can be depicted between the nodes. For example, the physiology node 602 is related to a cardio node 604 as shown by the connection between the two nodes. Similarly, the cardio node 604 is related to an ECG node 606 as shown by the connection between the two nodes.

The connections between nodes can represent hierarchies that exist between the types of data, technologies, devices, sensors, etc. For example, as shown, the cardio node 604 can be considered a child node of the physiology node 602. Similarly, the ECG node 606 can be considered a child node of the cardio node 604, and a grandchild node of the physiology node 602.

Lower level nodes such as the ECG node 606 can correspond to more specific types of data, technologies, devices, sensors, etc. than higher level nodes such as the physiology node 602. The logical relationships that exist between the nodes of the taxonomy structure 600a are such that when a technology item is associated with a lower level node, the technology item is automatically associated with all related nodes that are of a higher level (e.g., higher in the hierarchy of nodes). For example, if the computer system 110 associates a Sensor C with the ECG node 606 (e.g., based on a determination that performing ECG tests are a validated use for the Sensor C), the computer system 110 can, in response, associate the Sensor C with the cardio node 604 and the physiology node 602. However, the logical relationships that exist between the nodes are such that when a technology item is associated with a higher level node (e.g., a node that has one or more child nodes), then the technology item is not necessarily associated with a related lower level node, e.g., is not automatically associated with a related lower level node. For example, if the computer system 110 associates the Sensor C with the cardio node 604 (e.g., based on a determination that the Sensor C can obtain cardio data), the computer system 110 can, in response, associate the Sensor C with the physiology node 602. However, the computer system 110 will not automatically associate the Sensor C with the ECG node 606 as, without more information, it would be possible for the Sensor C to be related to a blood pressure node, a PPG node, or another node that has yet to be added to the taxonomy structure 600a in place of or in addition to the ECG node 606.

As shown, the taxonomy structure 600a can also include sensors and/or type of sensors. For example, the taxonomy structure 600a can includes nodes for types of sensors. These nodes can be arranged in one or more hierarchies, e.g., by the computer system 110. For example, the highest level node of the taxonomy structure 600a is a sensors node. The child nodes of the sensors node include a wearables node (e.g., corresponding to wearable devices or sensors that can be found in wearable devices), an environment node (e.g., corresponding to sensors that can track or measure environment data), and a non-wearable node (e.g., corresponding to non-wearable devices or sensors that can be found in non-wearable devices). Wearable sensors and/or devices can include, for example, wrist-worn devices, clothing, smart phones (including apps), glasses, keychains, etc. Non-wearable sensors and/or devices can include, for example, tabletop blood pressure monitors, glucose meters, bed-side sleep monitors, etc. Environment sensors and/or devices can include home monitoring devices, weather-based sensors, etc. These nodes for sensors and/or types of sensors can be related, e.g., by the computer system 110, to nodes for different data types. For example, the computer system 110 can relate the environment node to a light data node, a sound data node, and an atmosphere data node that includes a number of own child nodes.

In the example of FIG. 6B, a second taxonomy structure 600b is shown. The taxonomy structure 600b can be data that associates technologies with various technology types, data types, and/or sensor types.

The taxonomy structure 600b can be generated by the computer system 110, e.g., from data stored in the research literature database 204 shown in FIG. 2. Alternatively, the computer system 110 can generate the taxonomy structure 600b from the taxonomy structure 600a shown in FIG. 6A and from technology items stored in the technology database 112. For example, as described in more detail below, the computer system 110 can identify nodes in the taxonomy structure 600a that relate to the technology items in the technology data 202a. The computer system 110 can identify a relationship between a given technology item and a node if, for example, the technology item belongs to a technology type that corresponds to the node, if the technology item can be used to measure (or analyze) a data type that correspond to the node, and/or if the technology item includes a sensor or type of sensor that corresponds to the node.

The taxonomy structure 600b can be stored in the taxonomy database 206. For example, after generating the taxonomy structure 600b, the computer system 110 can store the taxonomy structure 600b in the taxonomy database 206. The computer system 110 can update the taxonomy structure 600b over time, e.g., as new documents are acquired in the researcher literature database 204 and/or as new technology items are added to the technology database 112.

The computer system 110 can form connections between the technology items and the nodes of the taxonomy structure 600a to generate the taxonomy structure 600b. The computer system 110 can form connections between nodes of the taxonomy structure 600a and technology items that it determines a relationship exists. The computer system 110 can determine that a relationship exists between a given technology item and a node of the taxonomy structure 600a if, for example, the technology item belongs to a technology type that corresponds to the node, if the technology item can be used to measure (or analyze) a data type that correspond to the node, and/or if the technology item includes a sensor or a type of sensor that corresponds to the node.

As an example, the computer system 110 can form a connection between the technology item 612 ("Omron") and a blood pressure node 622 based on determining that a validated use for the technology item 612 is to measure blood pressure data, e.g., as indicated by the technology data 202. Similarly, the computer system 110 can form a connection between the technology item 614 ("iHealth") and the blood pressure node 622 based on determining that a validated use for the technology item 614 is analyzing blood pressure data, e.g., obtained by the technology item 612.

The computer system 110 can use the taxonomy structure 600b to quickly identify technology items that may be suitable for a new research study. For example, the computer system 110 can determine that the study parameters for a new clinical trial require temperature data. In response, the computer system 110 (e.g., the technology recommendation module 212 shown in FIG. 2) can refer to the temperature node 624 of the taxonomy structure 600b and use the taxonomy structure 600b to identify any technology items related the temperature node 624. For example, the computer system 110 can use the taxonomy structure 600b to identify a technology item 616 ("Ava"), a technology item 618 ("Tempdrop"), and a technology item 620 ("VitalConnect") that are each related to the temperature node 624. The computer system 110 can further analyze the technology items 616-620 to determine their suitability for the new clinical trial.

By referring to the taxonomy structure 600b, the computer system 110 can benefit from improved efficiency as the computer system 110 would not need to reform the connections between the technology items and the nodes of the taxonomy structure 600b later on (e.g., unless the computer system 110 updated the taxonomy structure 600b based on new documents and/or to include additional technology items).

The computer system 110 can update the taxonomy structure 600b over time. For example, the computer system 110 can update the taxonomy structure 600b to include additional connections between technology items and nodes of the taxonomy structure 600b as additional uses for the technology items are validated (e.g., based on new or newly acquired research journals, based on usage data confirming a use of a technology item as a validated use from one or more ongoing or previously performed studies, etc.). The computer system 110 can also update the taxonomy structure 600*b* to include additional technology items, and/or to remove technology items (e.g., where a use is determined to no longer be a validated use for a given technology item). As an example, usage data collected from the client devices 208 shown in FIG. 2 can indicate that the precision of the technology item 618 is too low (e.g., greater than ±2% accuracy), e.g., in general or for most research studies. In response, the computer system 110 can determine that measuring temperature is no longer a validated use. In response to determining that measuring temperature is no longer a validated use, the computer system 110 can update the taxonomy structure 600*b* to disassociate the technology item 618 with the temperature node 624, e.g., to remove the connection between the technology item 618 and the temperature node 624.

FIG. 7 is a diagram that illustrates an example system and process for generating technology predictions. The system can be the system 100 described above with respect to FIG. 1. The system can be the system 200 described above with respect to FIG. 2.

The process for generating technology predictions can be performed by the computer system 110. For example, the process for generating technology predictions can be performed by the prediction module 214 shown in FIG. 2 of the computer system 110. The technology predictions 722 can be the predictions 224 shown in FIG. 2 generated by the prediction module 214.

The process for generating technology predictions can include receiving study data (702). For example, the computer system 110 can receive study data 720 from a client device, e.g., a device of a researcher. The study data 720 can include study needs and/or study parameters. The study data 720 can include, for example, an indication of data types to be measured (or analyzed), a required precision for measuring data, a required frequency for obtaining data, a required usage time, a number of participants, age range of participants, a length of the study, a region where the study is to be performed, a budget for the study, etc. With respect to FIGS. 1-2, the study data 720 can be or be included in the study data 108. In some cases, the study data 720 can be extracted by the computer system 110 from the study data 108.

The study data 720 can additionally or alternatively include detailed information related to the participants of the study. For example, the study data 720 can include names of known participants (e.g., participants who have already signed up for the study, and/or participants who have participated in one or more ongoing or previously performed studies).

Receiving study data can include receiving study data from a client device such as the client device 104 shown in FIGS. 1-2. As described above, the client device 104 can be a device of researcher who will be conducting the new research study. Accordingly, a researcher can use a client device to send the study data to the computer system 110.

In some cases, the study data has multiple sources. For example, the computer system 110 can receive different study parameters from different client devices, e.g., devices belonging to multiple researchers (e.g., who can each add requirements for the study through their respective client devices), and/or devices belonging to known/expected participants (e.g., who can indicate what technology items they own, to confirm that they are comfortable using a particular technology item, to indicate that they are unlikely to use a particular technology item, etc.).

In some cases, receiving study data includes extracting one or more study parameters from the study data. For example, the computer system 110 can use using keyword matching, a taxonomy structure stored on the taxonomy database 206, or a combination of keyword matching and using the taxonomy to identify study parameters in the study data. In using the taxonomy structure to extract study parameters, the computer system 110 can determine if any of nodes in the taxonomy structure have identifiers (e.g., names) that appear in the study data. The identifiers that do appear in the study data can be determined by the computer system 110 to be data types that need to be measured for the new research study.

If any identifiers appear in the study data, the computer system can further use the taxonomy structure to extract study parameters by identifying related nodes. Related nodes can be those that are connected in the taxonomy structure.

In some cases, receiving study data includes using literature stored in the research literature database 204 to identify study data from other, similar studies that have been previously performed. As an example, the research studies stored in the research literature database 204 can indicate that studies involving the collection of sleep data require medium or high precision sensors to succeed.

The process for generating technology predictions can optionally include generating one or more technology options based on the study data. Generating one or more technology options is described in more detail below with respect to FIG. 8B. As an example, in generating one or more technology options based on the study data, the computer system 110 can use the study data 720 to filter the technology data 202 shown in FIG. 2 for one or more technology items that can provide at least one of the data types to be measured, e.g., that can measure blood pressure data, heart rate data, and/or movement data. In some cases, in generating one or more technology options based on the study data, the computer system 110 can additionally filter the technology items by one or more a required data collection precision, a required data collection frequency, a required reliability, a required battery life, a required location availability, etc. as indicated by the study data 720. In some cases, in generating one or more technology options based on the study data, the computer system 110 can form technology options from single technology items that can provide all the data types to be measured, and/or can form technology options from multiple technology items that can each provide at least one of the data types to be measured. Providing a data type to be measured can include the technology item being capable of measuring data of that data type. Providing a data type to be measured can include the technology item being capable of analyzing data of that data type.

The process for generating technology predictions can optionally include using one or more machine learning models to make predictions (704*a*). As an example, optionally using one or more machine learning models to make predictions can include the prediction module 214 shown in FIG. 2 training and using the one or machine learning models to predict the success of each of the technology options, a compliance of participants using the technologies in each of the technology options, a precision of data collected using the technologies in each of the technology options, a reliability of the technologies in the technology options, etc., e.g., in view of the study data 720.

As an example, in using one or more machine learning models to make predictions, the prediction module 214 can determine feature values based on the study data 720 (e.g., extracted from, contained in, or otherwise determined from the study data 108 received by the computer system 110 from the client device 104). The prediction module 214 can provide the feature values as input to the one or more machine learning models. The prediction module 214 can process the feature data using the one or more machine learning models. The prediction module 214 can obtain one or more outputs from the one or more machine learning models that indicate one or more predictions, e.g., a likelihood, a confidence, an expected results, etc. The prediction module 214 can compare the outputs of the one or more machine learning models to a reference or a standard (e.g., a reference or standard that is appropriate for the study) to determine if the technology would succeed. The reference or standard can be, for example, a percent threshold.

The process for generating technology predictions can optionally include using statistical analysis of data to make predictions (704*b*). As an example, optionally using statistical analysis of data to make predictions can include using the prediction module 214 shown in FIG. 2 to perform statistical analysis of usage data (e.g., data received by the computer system 110 from the client devices 208 and collected by one or more technologies used in a study) and/or of study data (e.g., the study data 108 received by the computer system 110 from the client device 104).

As an example, in using statistical analysis of data to make predictions, the prediction module 214 can use the usage data and/or the study data to identify results that were achieved in the most similar situations (e.g., situations in other studies that are determined to be most similar to the new study based on the study data). The prediction module 214 can average the results of the most similar situations, or can weigh the results of the most similar situations differently based on how similar those previous studies are to the new research study being contemplated, e.g., based on the similarity of the study data 720 for the contemplated study to the study data for one or more previous studies.

The process for generating technology predictions can optionally include using rule-based analysis to make predictions (704*c*). As an example, optionally using rule-based analysis to make predictions can include using the prediction module 214 shown in FIG. 2 to perform rule-based analysis on the study data 720. For example, the prediction module 214 can perform statistical analysis on data (e.g., the study data 720 and/or usage data) in advance to derive rules/heuristics/relationships ("predication criteria") that show compatibility of certain technologies or technology characteristics with certain study parameters (e.g., found in the study data 720) or outcomes. The prediction module 214 can proceed to apply the prediction criteria to the study data 720.

For example, in using rule-based analysis to make predictions, the prediction module 214 can apply the prediction criteria to each of the technology options. If the prediction module 214 determines that a given technology options does not meet one or more of the of the prediction criteria, the prediction module 214 can determine that the technology option is unlikely to succeed for the contemplated research study (e.g., that the technology option is not viable). For example, as a result of applying the prediction criteria to the technology options, the prediction module 214 can determine that a given technology option is not viable based on one or more of the technology option including a technology that collects a data type with an insufficient precision, the technology option including a technology that has insufficient usage for a given age group of participants, the technology option including a technology that has an insufficient usage for a given location (e.g., location where the study is to take place and/or where the study participants reside), the technology option including a technology that has an insufficient battery life, the technology option including a technology that has an insufficient reliability (e.g., could be fine for some studies but not for other studies, such as those involving pharmaceuticals where a technology must reliably monitor participant vital signs), the technology option including a technology that collects or transfers data with insufficient frequency (e.g., frequency could be important for studies where participant vitals must be closely monitored), etc.

The process for generating technology predictions can include generating technology predictions (706). For example, the computer system 110 can use the study data 720 to generate the technology predictions 722. The technology predictions 722 can be and/or indicate the output of one or more machine learning models that were used by the computer system 110 to make predictions. The technology predictions 722 can be and/or indicate the outcome of a statistical analysis performed by the computer system 110 on the study data 720. The technology predictions 722 can be and/or indicate the outcome of a rule-based analysis performed by the computer system 110 on the study data 720.

The technology predictions 722 can be generated by the computer system 110 shown in FIG. 2, e.g., by the prediction module 214 of the computer system 110. In some implementations, the technology predictions 722 are the predictions 224.

The technology predictions 722 can include an indication as to the viability of each of the technology options. For example, as shown, the technology option that includes the Sensor A and the Bed Sensor C is determined by the computer system 110 to be a viable option as indicated by the predicted "Success". The technology predictions 722 can additionally include an indication as to why a technology option was determined by the computer system 110 to not be viable. For example, the technology option that includes an App A and a Phone A was determined to not be viable due insufficient data quality (e.g., cannot collect data with a sufficient frequency, with sufficient precision, etc.) and age group incompatibility (e.g., it was anticipated that those in the age group range of 18-40 years old would fail to meet the utilization requirements for the study if the Phone A was selected for the study).

FIG. 8A is a diagram that illustrates an example recommendation interface 800.

The interface 800 can be an interface of a client device, e.g., the client device 104 shown in FIGS. 1-2. In some implementations, the interface 800 is the interface 106*b* shown in FIG. 1, e.g., an expanded view of the interface 106*b* shown in FIG. 1.

The interface 800 includes a first area 810 that presents the study needs and/or study parameters that the computer system 110 extracted from or otherwise determined from the study data 108, and a second area 820 that includes recommended technology options. The second area 820 also includes a detailed recommendation area 822 that provides recommended technology options for particular situations, for particular groups of persons who will be study participants, for particular locations, for particular age groups, and/or for particular persons who will be study participants.

In more detail, the first area 810 can present information extracted from or otherwise obtained from the study data received by the computer system 110, e.g., from a researcher. The needs for the study presented in the first area 810 of the interface 800 include the data types that computer system 110 has determined must be collected for the study. The needs for the study can additionally or alternatively include one or more other study parameters. For example, as shown, the first area 810 can present the required data collection precision(s) for the new research study, the required device and/or software usage time(s) for the new research study, the number or expected number of participants of the new research study, the age range of participants for the new research study, the length or expected length of the new research study, a location of the study or location(s) where participants of the new research study reside, a budget for the new research study, etc.

As an example, as shown, the needs of the study include an indication that blood pressure data must be collected and that sleep data must be collected. The needs of the study also include an indication that the collection of sleep data includes the collection of heart rate data and movement data, e.g., as determined by the computer system 110 shown in FIGS. 1-2 based on study data 108 received by the computer system 110.

The second area 820 can present the one or more recommended technology options. The second area can optionally present information corresponding to the recommended technology options such as, for example, one or more of the score of each of the recommended technologies options, the cost of each of the recommended technologies options, the data that can be collected by the recommended technology options, the precisions in collecting the data by the devices and/or software in the recommended technology options, etc. For example, as shown, the first technology option is displayed in the second area of the interface 106b along with the score for the first technology option (one), the cost of the first technology option ($160 per participant), the average precision of the technologies in the first technology option (e.g., less than ±2%), and compatible age groups for the technologies in the first technology option (e.g., participants of ages 18-60 are anticipated to use the technologies for a sufficient amount of time and/or with a sufficient frequency). The second technology option is also displayed in the second area 820 of the interface 800 along with the score for the second technology option (two), the cost of the second technology option ($330 per participant), the average precision of the technologies in the first technology option (e.g., less than ±5%), and compatible age groups for the technologies in the first technology option (e.g., participants of all ages are anticipated to use the technologies for a sufficient amount of time and/or with a sufficient frequency).

The second area 820 also includes the detailed recommendations area 822. The detailed recommendations area 822 can provide, for example, recommendations for particular situations, for particular groups of persons who will be study participants, for particular locations (e.g., regions where the study may be performed), for particular age groups of participants, and/or for particular persons who are anticipated to be study participants (e.g., those that have already signed up for the study). These recommended technology options can differ from the general, recommended technology options. The detailed recommendations area 822 can also include reasoning to explain why these one or more recommended technology options differ from the one or more generally recommended technology options (e.g., the first technology option and the second technology option).

For example, with respect to those participants in the age group of 36-40, the technology recommendation module 212 of the computer system 110 recommends the second technology option (e.g., Phone B) over the first technology option (e.g., the Sensor A and the Bed Sensor C). With respect to FIG. 2, the technology recommendation module 212 can include an indication in the recommendations 222 of how it came to determine that the second technology option should be recommended over the first technology option for this particular age group. The interface 800 can display these indications in the detailed recommendations area 822. As shown, the interface 800 provides that the technology recommendation module 212 came to the determination of recommending the second technology option over the first technology option for participants belonging to the age group of 36-40 due to anticipated usage of the technology items in the technology options. Specifically, the technology recommendation module 212 can determine that the second technology option should be preferred due to it predicting that participants belonging to the age group of 36-40 are anticipated to have higher usage of the Phone B than the Bed Sensor C of the first technology option.

Figure 8B:
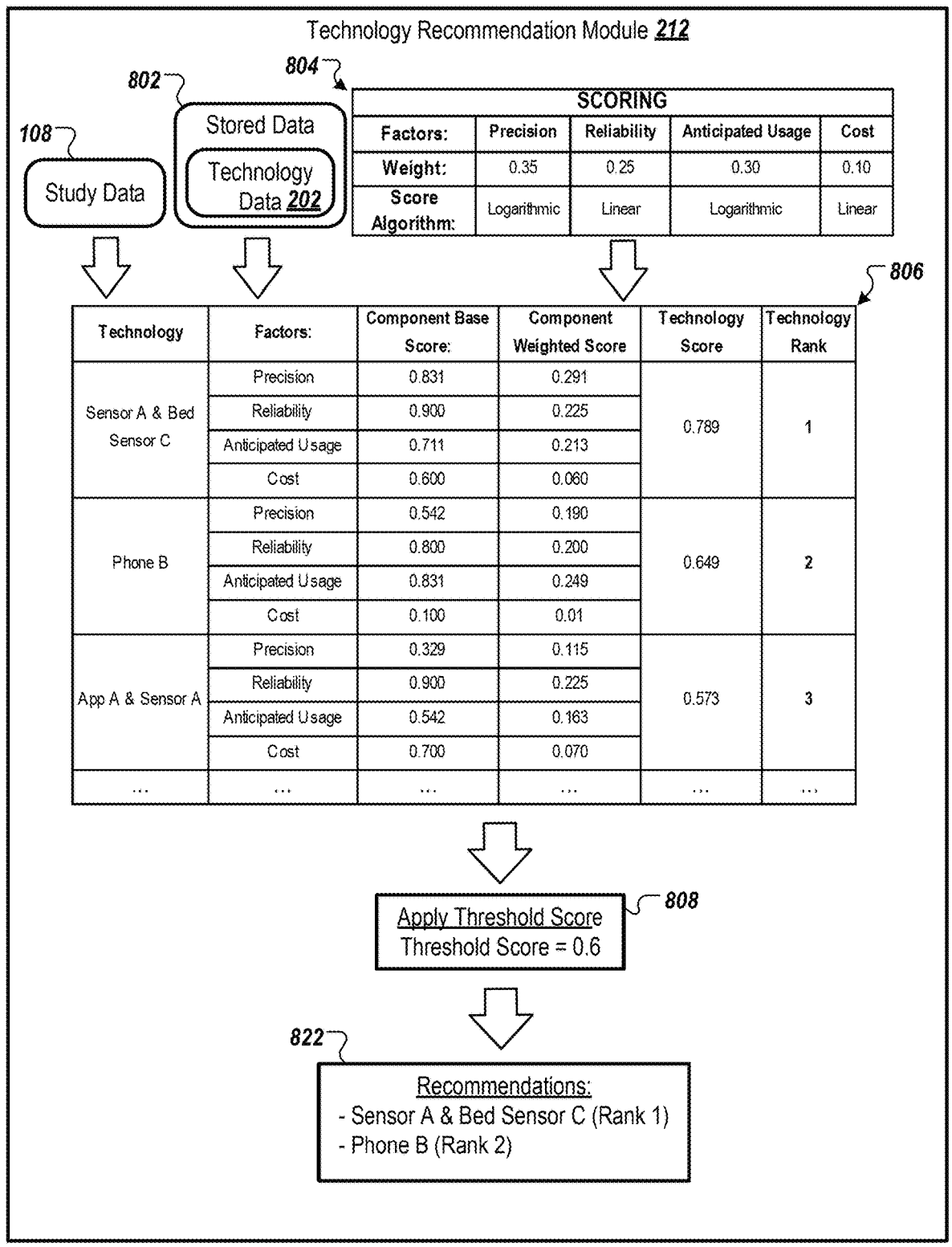
FIG. 8B is a diagram that illustrates an example recommendation module for generating recommendations.

FIG. 8B is a diagram that illustrates an example recommendation module for generating recommendations. As shown, the technology recommendation module 212 is used to generate the recommendations 822. In some implementations, the recommendations 822 are the recommendations 222 shown in FIG. 2.

The technology recommendation module 212 can use the study data 108, stored data 802, and scoring data 804 to score and rank various technology options. The stored data 802 includes the technology data 202. The stored data 802 can additionally or alternatively include taxonomy data from the taxonomy database 206 shown in FIG. 2, such as, for example, the data mapping 302 shown in FIG. 3, the taxonomy structure 520 shown in FIG. 5, the taxonomy structure 600a shown in FIG. 6A, and/or the taxonomy structure 600b shown in FIG. 6B. The stored data 802 can additionally or alternatively include research literature data from the research literature database 204 shown in FIG. 2, such as, for example, the literature 402 shown in FIG. 4, As an example, the technology recommendation module 212 can use the study data 108, the stored data 802, and the scoring data 804 to generate the scoring table 806 for various technology options. As shown, the technology options include the first technology option of the Sensor A and the Bed Sensor C, the second technology option of Phone B, and the third technology option of the App A and the Sensor A.

The technology options can be generated by the technology recommendation module 212 using, for example, the study data 108 and the technology data 202. Alternatively, the technology options to be scored and ranked by the technology recommendation module 212 can be generated by the prediction module 214 shown in FIG. 2. For example, the technology options to be scored and ranked can be those that the prediction module 214 predicted would be successful, e.g., as found in 722 shown in FIG. 7. That is, the first technology option of the Sensor A and the Bed Sensor C, the second technology option of Phone B, and the third technology option of the App A and the Sensor A.

In generating the technology options, the technology recommendation module 212 and/or the prediction module 214 can first filter the technologies in the technology data 202. For example, the technology recommendation module 212 and/or the prediction module 214 can filter the technologies found in the technology data 202 using the study data 108. For example, the technology recommendation module 212 can determine one or more data types to measure from the study data 108 and can use the one or more data types to filter out those technologies in the technology data 202 that are unrelated to the one or more data types. Specifically, the technology recommendation module 212 can remove those technologies in the technology data 202 from consideration if they are unable to collect (or otherwise obtain) or analyze data of one of the determined one or more data types.

The technology recommendation module 212 and/or the prediction module 214 can additionally or alternatively filter the technologies in the technology data 202 based on other criteria. For example, the technology recommendation module 212 can identify additional or alternative study needs from the study data 108, such as a required precision for the collection data (e.g., ±5%), a required precision for the collection of a specific type data (e.g., ±2% for heart rate data), a required sensor type, a required technology type, one or more types of sensors that must be avoided, one or more technology types that must be avoided, a minimum battery life (e.g., ten hours), a minimum data collection frequency (e.g., twenty readings per minute), a minimum level of data quality (e.g., data collection consistency), etc.

In generating the technology options, the technology recommendation module 212 and/or the prediction module 214 can determine what individual technologies and combinations of the technologies of the technologies that made it through filtering are possible technology options for the current study. For example, the technology recommendation module 212 may not consider any individual technologies as technology options if the respective individual technology cannot collect and/or analyze a particular type of data needed for the current study, cannot collect a particular type of data at a precision needed for the current study, cannot collect a particular type of data at a frequency needed for the current study, cannot collect a particular type of data at a quality (e.g., consistency) need for the current study, cannot analyze a particular type of data needed for the current study, and/or has insufficient reliability with respect to a particular type of data.

In combining two or more technologies to form a technology option, the technology recommendation module 212 and/or the prediction module 214 can take into account the satisfactory functions for the technologies given the study data 108, e.g., given the study needs determined from the study data 108. The satisfactory functions for the technologies can be those functions that meet the study needs and/or study parameters for the current study, e.g., that meet the required data precision, data collection frequency, and/or data quality for the current study. The technology recommendation module 212 and/or the prediction module 214 can avoid combining technologies that perform redundant or only redundant satisfactory functions. For example, if the technology recommendation module 212 determines from the study data 108 that two data need to be collected, the technology recommendation module 212 will not combine a device technology that can satisfactorily collect only the first type data with a second device technology that can satisfactorily collect only the first type data.

In combining two or more technologies to form a technology option, the technology recommendation module 212 and/or the prediction module 214 can take into account whether a given technology in a potential technology option is, for example, a device or is software. For example, where a potential technology option includes a device technology that performs a first function and a software technology that performs the same function, the technology recommendation module 212 may not consider the functions performed by each of the technologies as redundant. The technology recommendation module 212 may not consider the functions performed by each technologies as redundant due to the first technology being a device technology and due to the second technology being a software technology. Similarly, the technology recommendation module 212 may not consider the functions performed by each technologies as redundant due to the first technology being a device technology and due to the second technology being a software technology that the technology recommendation module 212 determines can be installed and/or run on the device technology.

The scoring data 804 can include one or more scoring factors. For example, the scoring factors can include one or more of a precision of measurement of the one or more technologies in a given technology option, the reliability of the one or more technologies in a given technology option, the anticipated usage of the one or more technologies in a given technology option, and/or the cost of the one or more technologies in a given technology option. The scoring factors can include additional or alternative scoring factors such as, for example, data collection frequency of the one or more technologies in a given technology option, quality (e.g., consistency) of data collected by the one or more technologies in a given technology option, portability of the one or more technologies in a given technology option, battery life of the one or more technologies in a given technology option, etc.

The scoring data 804 can include a scoring weight for each of the scoring factors. The scoring weight can be based on the study data 108. The study data 108 can indicate, for example, which scoring factors are relevant and/or most relevant for the new research study. As an example, if the study data 108 provides a budget for the study, the computer system 110 may determine a higher weight for the cost factor than if the study data 108 did not include an indication of a budget for the study. The scoring weight for the scoring factors can be determined by one or more machine learning models, e.g., that are trained using data collected from one or more ongoing or previously conducted studies. The scoring weight for each of the scoring factors can indicate the importance of each of the scoring factors to, for example, the success of studies overall and/or the success of the current study given the study data 108. The scoring weights for the scoring factors can add up to 100% (e.g., add up to one).

The scoring data 804 can include an indication of how the score for the scoring factors are calculated. For example, as shown, the scoring data 804 can include a scoring algorithm (e.g., linear based algorithm, logarithmic based algorithm, etc.) for each of the scoring factors. The scoring algorithms can include static algorithms. Additionally or alternatively, the scoring algorithms can include machine learning techniques (e.g., trained machine learning models). The scoring algorithms can be linear based such that, for example, a percent decrease from a baseline value will result in the same percent decrease from a baseline score (e.g., one). The scoring algorithms can be logarithmically based such that values that are near a baseline value are emphasized and/or values that do not meet the baseline value deemphasized. For example, in the scoring table 806, the precision component base score of 0.831 can correspond to a determination that the precision of the first technology option is 95% of a baseline precision value, the precision component base score of 0.542 can correspond to a determination that the precision of the second technology option is 80% of a baseline precision value, and precision component base score of 0.329 can correspond to a determination that the precision of the third technology option is 60% of a baseline precision value.

In some cases, the scoring data 804 can include a scoring scale. The scoring scale can be applied to all of the scoring factors. Alternatively, different scoring scales (e.g., having different constant values) can be applied to the different scoring factors. As an example, the scoring factors can be linearly scaled. Alternatively, the scoring factors can be logarithmically scaled.

The technology recommendation module 212 can use the scoring data 804, the determined technology options, and the technology data 202 to generate the scoring table 806. As shown, the scoring table 806 can include component base scores for each of the scoring factors for each of the technologies options. The technology recommendation module 212 can determine the component base score using, for example, values obtained from the technology data 202 corresponding to each of the scoring factors and the scoring data 804. For example, the technology recommendation module 212 can obtain a first precision value corresponding to the Sensor A and a second precision value corresponding to the Bed Sensor C, and can proceed to average the precision values (or, alternatively, calculate component base scores for each of the precision values and proceed to average the two precision component base scores). The technology recommendation module 212 can use the scoring data 804 to calculate a component base score for the precision factor for the first technology option based on the precision values for the first technology option.

After calculating the component base scores for a given technology option, the technology recommendation module 212 can apply weighting to each of the component base scores. The weight that the technology recommendation module 212 applies can be determined from the scoring data 804. For example, the technology recommendation module 212 can identify a weight to apply to a component base score based on the scoring factor that corresponds to the component base score.

As a result of applying weights to the component base scores, the technology recommendation module 212 calculates component weighted scores. For example, the technology recommendation module 212 applies a weight of 0.35 to the precision component base score of 0.831 to obtain a precision component weighted score of 0.291.

The technology recommendation module 212 can add the component weighted scores calculated for a given technology option to obtain a technology score (e.g., a suitability score) for the technology option. For example, the technology recommendation module 212 can add the precision component weighted score of 0.291, the reliability component weighted score of 0.225, the anticipated usage component weighted score of 0.213, and the cost component weighted score of 0.060 to obtain a technology score of 0.789 for the first technology option.

After the technology recommendation module 212 has calculated technology scores (e.g., suitability scores) for each of the technology options, the technology recommendation module 212 can rank the technology options based on their technology score. For example, as shown, the first technology option is ranked first based on its technology score of 0.789 being greater than the technology score of 0.649 for the second technology option and the technology score of 0.573 for the third technology option.

In determining one or more technology options to recommend, the technology recommendation module 212 can apply a threshold score 808 to the technology scores (e.g., suitability scores) to obtain the recommendations 822. The recommendations 822 can include the technology options that each have a respective technology score that meets the threshold score 808. For example, the technology recommendation module 212 can apply the threshold score 808 of 0.6 to the technology options, resulting in the technology recommendation module 212 determining that the first technology option and the second technology option meet the threshold score 808.

Alternatively, in determining the one or more technology options to recommend, the technology recommendation module 212 selects a predetermined number of technology options based on their rank. For example, if the predetermined number is one, the technology recommendation module 212 would recommend only the first technology option. In some cases, the technology recommendation module 212 identifies technologies to recommend by selecting a predetermined number of technology options based on their rank if the none of the technology options have a technology score (e.g., a suitability score) that meets the threshold score 808, or if only one of the technology options has a technology score that meets the threshold score 808. For example, if a threshold score of 0.7 was applied to the technology scores of the technology options, the technology recommendation module 212 can recommend the first technology option and can proceed to select the next highest ranking technology option to recommend along with the first technology option, e.g., the second technology option.

The technology recommendation module 212 can send the recommendations 822 to the client device 104 shown in FIGS. 1-2. In some implementations, the recommendations 822 are the recommendations 122 shown in FIG. 1.

The recommendations 822 can be used by the client device 104 to generate the interface 800 shown in FIG. 8A.

Figure 9A:
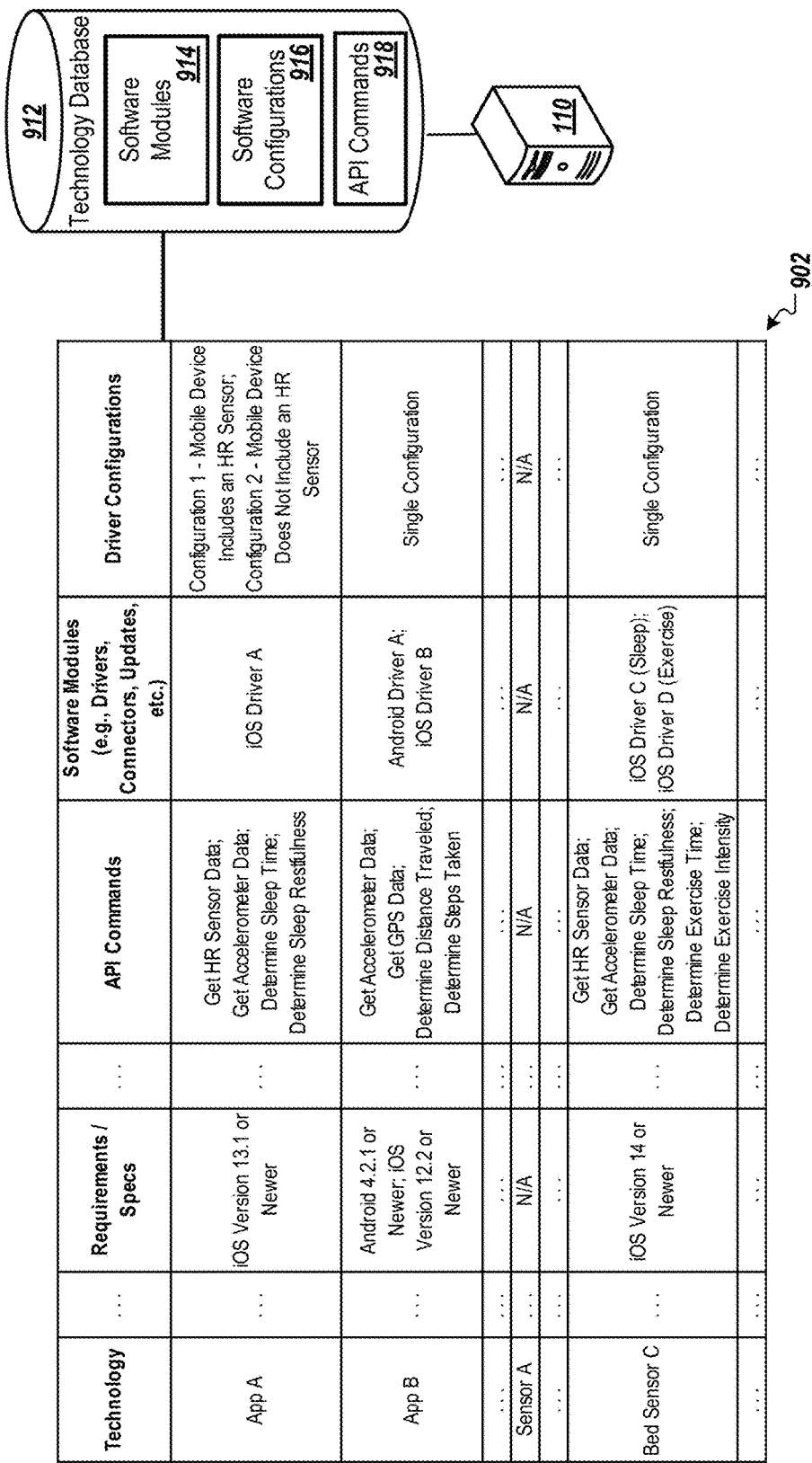
FIGS. 9A-9B are diagrams that illustrate an example system for assessing and selecting technologies.
Figure 9B:
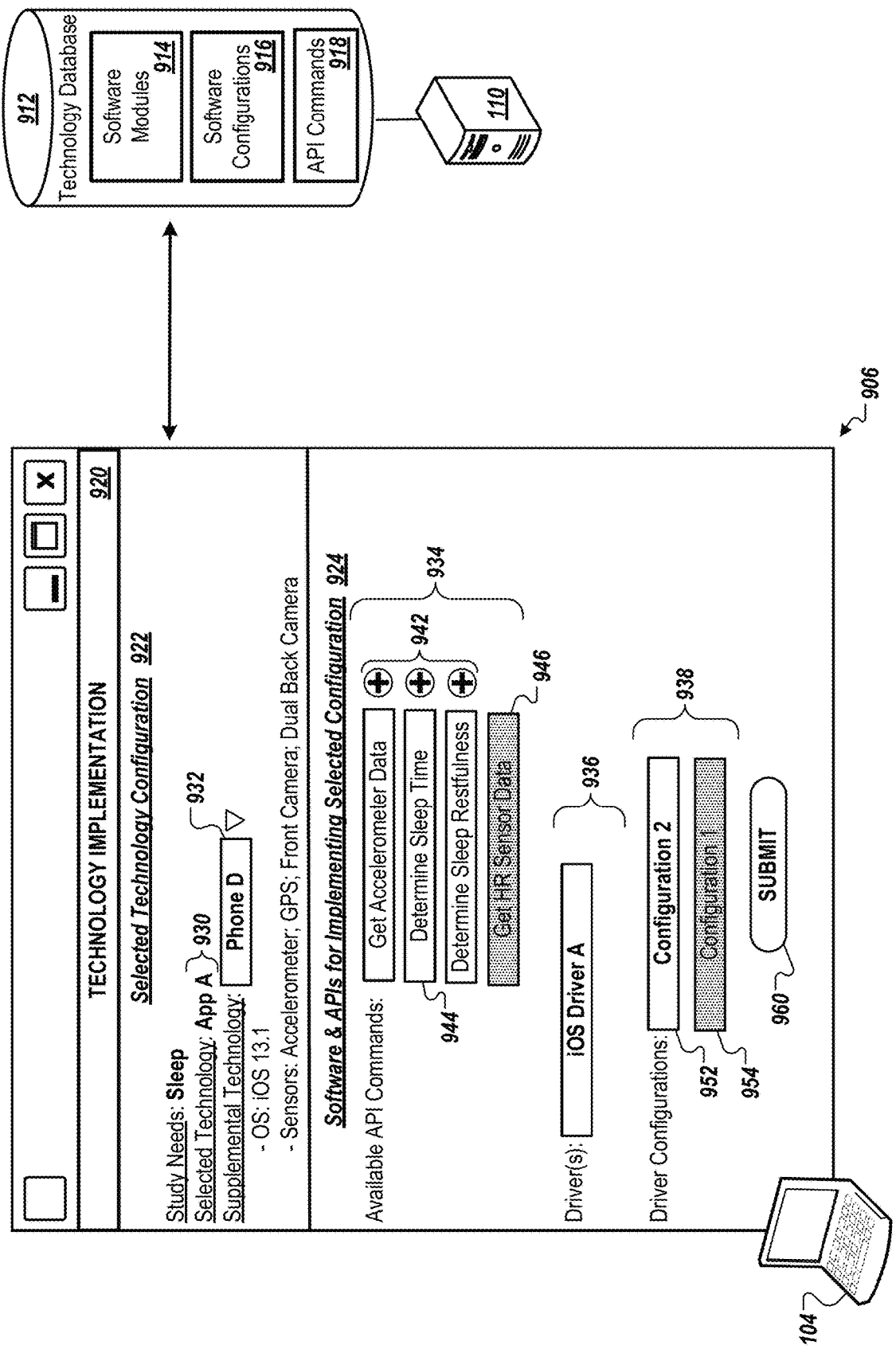

FIGS. 9A-9B are diagrams that illustrate an example system for assessing and selecting technologies. The system can be the system 100 described above with respect to FIG. 1. The system can be the system 200 described above with respect to FIG. 2.

In the example of FIG. 9A, the computer system 110 is can access a technology database 912. The technology database 912 includes software modules 914, software configuration 916, and API commands 918. The software modules 914 can include, for example, drivers for the technologies, software connectors for the technologies, software updates or multiple software versions for the technologies, etc. The software configurations 916 can include, for example, different driver configurations for the technologies, different software configurations for the anticipated age group of the technology, different software configurations for different types of data collection, different software configurations for different types of data collection and/or data transmission frequency, etc. In some implementations, the technology database 912 is the technology database 112 shown in FIGS. 1-2.

The technology database 912 also stores technology data 902. The technology data 902 can include various technologies and corresponding information. The information can include, for example, software and/or hardware requirements for each of the technologies, API commands that can be used with each of the technologies, software modules (e.g., software drivers, connectors, updates or versions, etc.) that can be used with each of the technologies, different driver configurations for the technologies, other software configurations, etc. In some implementations, the technology data 902 is the technology data 202 shown in FIG. 2.

As an example, the software configurations 916 can include profiles. These profiles can include, for example, Bluetooth profiles. These profiles can define values and/or ranges of values for values in software packets. As an example, these profiles can be used by the computer system 110 to establish a communication channel between the client devices 208 shown in FIG. 2 and the computer system 110 and/or the client device 104. Once this channel is defined, it can be customized for wireless messaging, packet types and content, etc.

As an example, the software modules 914 can include a web connector, e.g., an API to a third-party service. The third-party service can use OAuth security credential authentication. A token can be provided to the user 102 of the client device 104 and/or can be received at the computer system 110. The token can be used with a known communication protocol and communication specification to pull in data, e.g., from a database, a webpage, etc. This can be used for client side specifications and on the server side (e.g., for connecting to a API endpoint).

In the example of FIG. 9B, an interface 906 is presented that allows for configuring the implementation of a given technology for a study. The interface 906 can be, for example, presented on a client device such as the client device 104 shown in FIGS. 1-2. As shown, the interface 906 displays a technology implementation page 920. The interface 906 (e.g., specifically the displayed technology implementation page 920) includes a first area 922 corresponding to an area where users can view and/or select the technology items that they want to configure for a new research study, e.g., a new clinical trial. The interface 906 (e.g., specifically the displayed technology implementation page 920) also includes a second area 924 corresponding to an area where users can select (e.g., customize) a software and API configuration for implementing the one or more technologies.

Through the interface 906, a user such as a researcher can make various selections. For example, in the first area 922 of the interface 906, a user can select one or more technology items that are to be used in a new research study. The user can select the technology item that they wish to configure. Alternatively, the client device 104 can automatically select the technology item that is to be configured (e.g., based on the technology option that has been selected for the study and/or there being a single technology item in the selected technology option that can be configured). As shown, a technology item 930 (App A) has been selected by the user of the client device 104 and/or has been automatically selected by the client device 104. Accordingly, the technology item 930 is the technology item that has been selected to be configured.

As an example, the first area 922 can also include an option for one or more supplemental technology items to be considered in during the configuration of the technology item 930. As shown, Phone D has been selected from a dropdown menu 932. The dropdown menu 932 may be populated by the client device 104 with the technology items other than the technology item 930 that are in the technology option that has been selected for the new research study. By selecting the Phone D from the dropdown menu 932, the user has indicated, for example, that they plan on installing the technology item 930 (App A) on the Phone D. In some cases, the client device 104 automatically populates the supplemental technology section based on the technology option selected for the new research study. For example, the client device 104 may automatically select the Phone D as a supplemental technology based on the Phone D being the only other technology item in the selected technology option that can have software installed on it (e.g., as being the only computing device that was selected for the study).

The interface 906 can present information corresponding to the selected technologies in the first area 922. For example, as shown, the interface 906 presents information corresponding to the Phone D technology, e.g., accessed from the technology data 902 shown in FIG. 9A. As shown, the information corresponding to the Phone D technology includes in indication that the Phone D has iOS 13.1 as its operating system, includes an accelerometer, includes a GPS unit, includes a front camera, and includes a dual back camera.

In the second area 924, a user can select (e.g., customize) a software and API configuration for implementing the one or more technology items. For example, the second area 924 can include an API area 934, a driver selection area 936, and a software configuration area 938. The API commands presented in the API area 934 can be those that are found in the API commands 918 and that are associated with the selected technology item 930 (App A). As an example, a user (e.g., the user 102 shown in FIG. 1) can indicate which of the available API command's they want the selected technology item 930 to be capable of using during the study. The API area 934 can provide interface elements 942 that allow the user to add API commands to the implementation of the selected technology item 930. For example, the user can select the middle interface element of the interface elements 942 to add the "Determine Sleep Time" API command 944 to the implementation of the selected technology item 930 such that this functionality of the selected technology item 930 (e.g., the App A's ability to determine a sleep time and send it to the computer system 110) can be used during study.

The API area 934 can also present an indication as to which API commands the computer system 110 recommends (e.g., based on the study needs, study parameters, the supplemental technology items or other technology items in the selected technology option for the study, etc.). For example, the client device 104 may highlight API commands in the API area 934 that the computer system 110 recommends.

The API area 934 can indicate some API commands that are not currently available, e.g., due to incompatibility with one or more of the selected supplemental technology items. For example, as shown, the "Get HR Sensor Data" API command 946 is not available due to the Phone D not having a heart rate sensor as indicated by the technology data 902 shown in FIG. 9A.

The interface 906 can also present one or more drivers for the selected one or more technologies in the driver selection area 936. For example, a single driver "iOS Driver A" is presented in the driver selection area 936. The iOS Driver A can be automatically selected by the computer system 110 due to it being the only available driver for the selected technology item (App A).

The interface 906 can also present one or more software configurations in the software configuration area 938, such as one or more driver configurations. For example, as shown, the software configuration area 938 includes two configurations for the App A technology, a first software configuration 952 and a second software configuration 954. The client device 104 can optionally highlight one or more recommended configurations, e.g., based on recommendations received from the computer system 110. The client device 104 can optionally indicate one or more configurations that are not available, e.g., due to incompatibility with one or more of the supplemental technologies. For example, because the supplemental technology, Phone D does not have a heart rate sensor, the client device 104 can determine that only the software configuration 952 ("Configuration 2") can be used. Accordingly, the computer system 110 can automatically select the software configuration 952 due to it being the only available software configuration (e.g., driver configuration) given the technology selections made by the user and/or by the client device 104, and/or can indicate that the software configuration 954 is not available for selection (e.g., by being shaded, not selectable, removed from display, etc. in the interface 906).

In some cases, the software configuration area 938 additionally or alternatively include other software configurations that a user may be able to choose from and/or choose settings for. For example, the software configuration area 938 may be able to present indications of different software configurations for the anticipated age group of the technology, different software configurations for different types of data collection, different software configurations for different types of data collection and/or data transmission frequency, etc. that a user could choose from for the selected technology item 930 (App A) and/or could select settings for.

In general, the computer system 110 can provide various techniques and features to assist researchers in deploying a selected technology. The computer system 110 can provide instructions, and deploy them to client devices of study participants, to indicate what data to sense, how to sense it, and which external devices to connect with. One example technique for assisting deployment is to store profiles for communication, e.g., profiles for BLUETOOTH or BLUETOOTH LOW ENERGY (BLE) or other communication protocols, and selectively enabling a profile needed for a selected technology. As another example, the system may enable or provide elements of a software development kit (SDK). The computer system 110 may enable or distribute a software module or build needed software and configurations into a composite software module (e.g., a custom module for the study). The computer system 110 may cause devices to download an application or to connect to an external service, e.g., over the Internet. The applications or study-related software models may have are different modes that can be turned on based on the delivery mechanism selected and the technologies selected for use.

Figure 10:
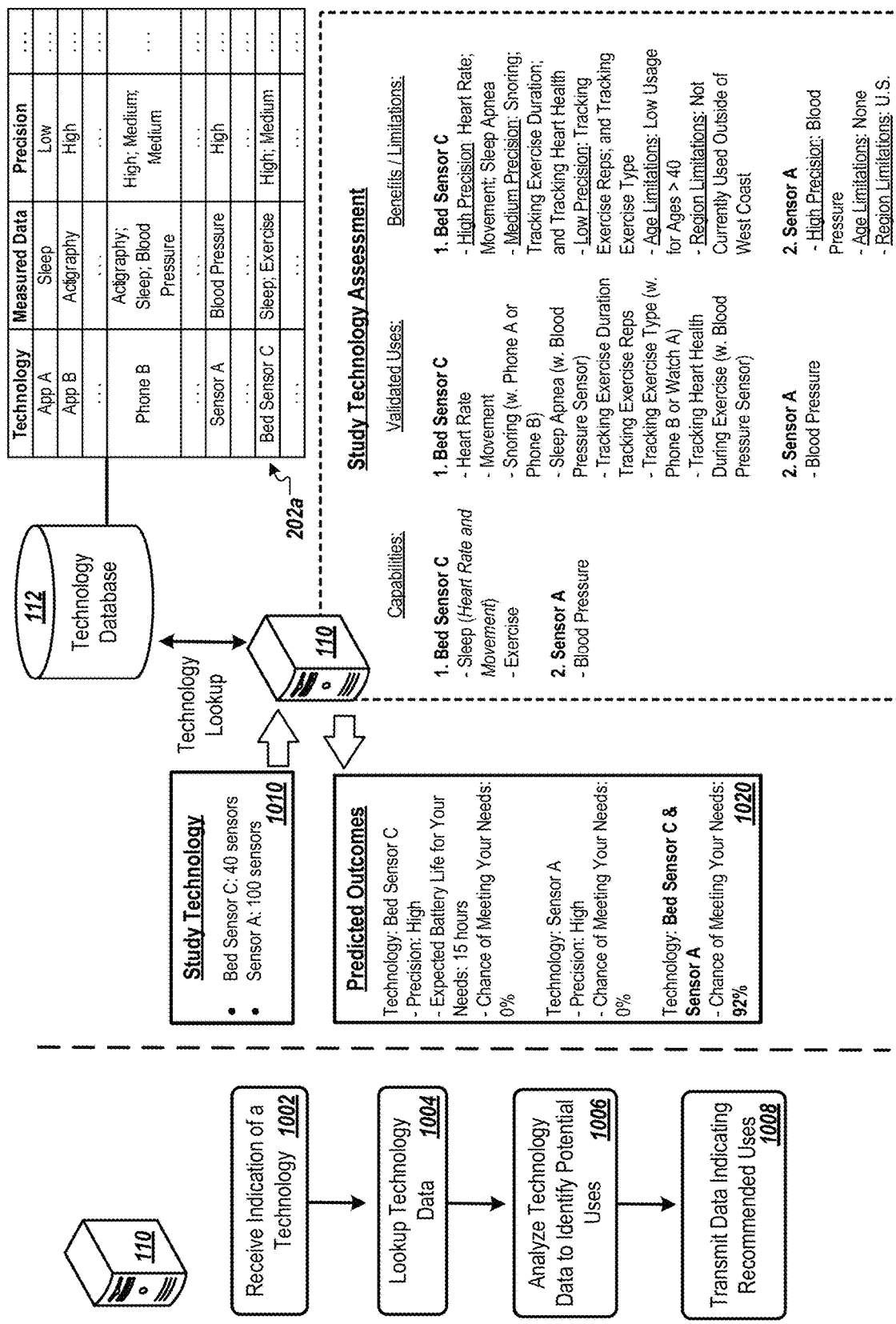
FIG. 10 is a diagram that illustrates an example system and process for assessment of capabilities of technologies.

FIG. 10 is a diagram that illustrates an example system and process for assessment of capabilities of technologies. The system can be the system 100 described above with respect to FIG. 1. The system can be the system 200 described above with respect to FIG. 2. The techniques of FIG. 10 can be used to determine the potential uses for a technology item.

While the examples of FIGS. 1 and 2 started with input of a desired use or outcome and select a technology that could support that use, the example of FIG. 10 does the reverse, e.g., starting with a technology item or items and identifying the uses or functions that this technology can support. This can be considered a "reverse look-up" or a "reverse assessment" compared to the technique of selecting a technology. The techniques of FIG. 10 can be used to indicate to a researcher other data that can be gathered with the existing selection of technology, potentially allowing the researcher to expand the scope of collected data or topics studied without needing to add additional technologies. Similarly, the researcher may already have certain technologies available (e.g., from prior studies) and may use the techniques of FIG. 10 to determine what those technologies may be used for, e.g., to help explore what may be researched in future studies. Although the examples are described in the context of research studies, the technology assessment may be done for any technology, separate from any research study.

The process for reverse assessment of technologies can include receiving an indication of a technology (1002). For example, the computer system 110 can receive user input that identifies technology item(s) 1010 (e.g., "study technology 1010") currently selected for a research study. The study technology 1010 may be a technology option that the user entered manually, or a technology option recommended by the computer system 110 that the user selected to use in a study. The study technology 1010 can include an indication of one or more technology items, e.g., one or more technology items that researcher(s) already have access to or that the researcher(s) have already ordered. The technology items in the study technology 1010 can be those that one or more researchers already have access to, that one or more researchers have ordered, that participants have access to, that participants have ordered or will be required to order, etc. The study technology 1010 can include an indication of one or more quantities of technology items, e.g., a quantity of a given technology item that researcher(s) already have access to or a quantity of the technology item that the researcher(s) have already ordered. The study technology 1010 can include an indication of one or more version numbers or model names of one or more technology items. For example, the study technology 1010 can include an indication that there are twenty iPhones available for the study, and that the iPhones are each an iPhone 8 running iOS 11.

The process for reverse assessment of technologies can include looking up technology data (1004). For example, the computer system 110 can use the technology data 202a in the technology database 112 to identify data corresponding to the one or more technology items in the study technology 1010.

The process for reverse assessment of technologies can include analyzing technology data to identify potential uses or functions of the technology (1006). For example, the computer system 110 can analyze the technology data 202a to identify potential types of data that can be measured (e.g., resting heart rate, step count, etc.) or even broad research topics (e.g., sleep, diet, exercise, etc.) that can be assessed using the one or more technology items in the study technology 1010.

Analyzing the technology data to identify potential studies can include the computer system 110 identifying the capabilities of the one or more technology items in the study technology 1010. For example, if the study technology 1010 includes the Bed Sensor C, the computer system 110 can use the technology data 202a to determine that the Bed Sensor C can measure sleep data (e.g., specifically heart rate data and movement data) with high precision, and can measure exercise data with medium precision.

Analyzing the technology data to identify potential uses of the study technology 110 can include the computer system 110 identifying validated uses for the one or more technology items in the study technology 1010. The validated uses for the one or more technology items in the study technology 1010 can be determined by the computer system 110 from the technology data 202a. As discussed above with respect to FIG. 3, the validated uses for the one or more technology items in the study technology 1010 can be determined by the computer system 110 from data stored in the research literature database 204 shown in FIGS. 2-3. A use for a given technology item can be considered a validated use if the technology item was used successfully in one or more prior studies (e.g., studies previously performed by the current researcher, studies indicated in research literature, studies indicated in one or more webpages, studies indicated in one or more articles, etc.), if the manufacturer or developer indicates the use as proper (e.g., on a website belonging to the manufacturer or developer, in material provided by the manufacturer or developer, etc.), and/or if the performance of the technology item during the use met one or more standardized metrics (e.g., met a required frequency of data collection, met a required precision of data collection, met a minimum battery life requirement, met a waterproof requirement, etc.).

In some cases, a validated use can be for a group of technology items. For example, a given technology item may have a validated use only when it is used with one or more other technology items (or types of technology items). As shown, the Bed Sensor C has a validated use of tracking an exercise type performed by the wearer but only when the Bed Sensor C is also used with the Phone B or the Watch A.

Analyzing the technology data to identify potential uses can include the computer system 110 identifying one or more benefits and/or limitations for the one or more technology items in the study technology 1010. For example, the computer system 110 can identify the types of data that each of the one or more technology items can provide with high precision (e.g., <±0.5%, <±1%, <±2%, etc.), with medium precision (e.g., <±5%), and/or with low precision (e.g., >15%). The computer system 110 can consider the precision of data collection by the one or more technology items in the study technology 1010 when making the predicted outcomes 1020. For example, if the needs for a given study require a data type that a technology item can measure with high precision, the computer system 110 can consider this need being met or likely being met. Accordingly, the computer system 110 may calculate a higher likelihood of a technology option meeting the study needs if the technology option includes the technology item (e.g., can assign a higher suitability score for the technology option). Similarly, if the needs for a given study require a data type that a technology item can only measure with low precision, the computer system 110 can consider this need not being met or unlikely to be met. Accordingly, the computer system 110 may calculate a lower likelihood of a technology option meeting the study needs if the technology option includes the technology item (e.g., can assign a lower suitability score for the technology option).

The computer system 110 can also identify other benefits and/or limitations. For example, the computer system 110 can identify a cohort of participants that are likely to use a given technology item (e.g., a group of participants that share one or more characteristics), a cohort of participants that are unlikely to use a given technology item, groups of participants that are likely to use a given technology item (e.g., participants belonging to a certain age group, participants living in a certain region, participants with a given health condition, an already formed group of participants, etc.), can identify groups of participants that are unlikely to use a given technology item (e.g., participants belonging to a certain age group, participants living in a certain region, participants with a given health condition, an already formed group of participants, etc.), can identify particular participants that are likely to use a given technology item (e.g., based on their characteristics and/or passed usage), and/or can identify particular participants that are unlikely to use a given technology item (e.g., based on their characteristics and/or passed usage). The computer system 110 can take into account this anticipated usage of a technology item in determining a likelihood of a given technology option meeting the study needs if the technology option includes the technology item.

As another example, the computer system 110 can take into account the availability of a given technology item in determining a likelihood of a given technology option meeting the study needs if the technology option includes the technology item. For example, if the FDA has not approved the use of the technology item in the U.S. and the study must be performed in the U.S., the computer system 110 can calculate a likelihood of 0% for a technology option that includes the technology item due to the technology item being unavailable. This likelihood can be used by the computer system 110 to generate a suitability score. For example, the computer system 110 can generate a suitability score for the technology items by ranking them based on, or based in part on, the determined likelihoods. Additionally or alternatively, in generating a suitability score, the computer system 110 can apply a likelihood threshold (e.g., 0.80, 0.85, 0.90, etc.) to the determined likelihoods. Additionally or alternatively, in generating a suitability score, the computer system 110 can use the determined likelihoods as input to an algorithm for determining suitability scores. The algorithm can take into account other inputs (e.g., variables other than likelihood of success).

Identifying potential uses can include the computer system 110 determining one or more potential technology options to be used in the study. For example, given the Bed Sensor C and the Sensor A, the computer system 110 can determine that the potential technology options can include the Bed Sensor C alone, the Sensor A alone, and the Bed Sensor C with the Sensor A.

Identifying potential uses can include the computer system 110 determining the viability of the one or more potential technology options meeting the needs of the study. For example, the computer system 110 can take into account one or more of the capabilities of each of the technology items in each of the potential technology options, the validated uses of each of the technology items in each of the potential technology options, and/or the benefits and/or limitations of each of the technology items in each of the potential technology options. In determining the viability of the one or more potential technology options meeting the needs of the study, the computer system 110 can calculate a likelihood of the each of the potential technology options meeting the needs of the study, e.g., based on the capabilities, validated uses, and/or benefits and/or limitations of the technology items in each of the potential technology options. For example, as shown, the computer system 110 generates the predicted outcomes 1020 that includes a prediction of 0% likelihood of success for a potential technology option only including the Bed Sensor C, a prediction of 0% likelihood of success for a potential technology option only including the Sensor A, and a prediction of 92% likelihood of success for a potential technology option including the Bed Sensor C and the Sensor A.

Identifying potential uses can include the computer system 110 determining one or more technology options to recommend. For example, the computer system 110 can recommend any of the potential technology options that have a likelihood that meets a threshold percent (e.g., 70%, 80%, 90%, etc.). Alternatively, the computer system 110 can recommend a predetermined number of potential technology options with the highest likelihood of success. Alternatively, the computer system 110 can recommend a predetermined number of potential technology options with the highest likelihood of success as long as the likelihood of the potential technology options meets a threshold percent.

Analyzing the technology data to identify potential uses can include the computer system 110 identifying one or more data types to track and/or measure for a study. For example, the computer system 110 can use the capabilities, the validated uses, and/or the benefits and/or limitations of the technology items in the study technology 1010 to determine one or more data types that can likely be successfully obtained (e.g., tracked or measured) using the technology items in the study technology 1010. These one or more data types can be included in the predicted outcomes 1020 by the computer system 110.

Analyzing the technology data to identify potential uses can include the computer system 110 identifying one or more study parameters and/or study parameter limitations (e.g., minimums and/or maximum values for study parameters) for the study. For example, the computer system 110 can use the study technology 1010, the capabilities, the validated uses, and/or the benefits and/or the limitations of the technology items in the study technology 1010 to determine a maximum number of participants for the study, a minimum number of participants for the study (e.g., in order for the study to have a sufficient likelihood of achieving statistical significance given anticipated usage of the one or more technology items used in the study), a recommended age group of participants (e.g., in order to maximize the likelihood of participants utilizing the one or more technology items used in the study), a recommended study location (e.g., in order to maximize the likelihood of participants utilizing the one or more technology items used in the study), etc. These one or more study parameters and/or study parameter limitations can be included in the predicted outcomes 1020 by the computer system 110.

Analyzing the technology data to identify potential uses can include the computer system 110 identifying one or more studies previously performed using one or more of the technology items in the study technology 1010. For example, the computer system 110 can use the study technology 1010 and data in the research literature database 204 shown in FIG. 2 to identify one or more previously performed studies used one or more of the technology items in the study technology 1010. The computer system 110 can filter the previously performed studies by those where one or more of the technology items in the study technology 1010 were successfully used in the study. The computer system 110 can filter the previously performed studies by those where the performance of one or more of the technology items in the study technology 1010 was sufficient to meet one or more standardized metrics. The computer system 110 can filter the previously performed studies by those that only used one or more of the technology items in the study technology 1010. An indication of the one or more studies previously performed can be included in the predicted outcomes 1020 by the computer system 110.

The process for reverse assessment of technologies can include and transmitting data indicating recommended uses or functions of the technologies 1010 (1008). For example, the computer system 110 can transfer information indicating the predicted outcomes 1020 to the client device 104 shown in FIGS. 1-2. Optionally, the predicted outcomes 1020 can include an indication of only the uses that the computer system 110 recommends, e.g., those that are validated or have a least a minimum likelihood of success or rate of success. Alternatively, a more expansive set of uses can be indicated, and the rates of success can be indicated with the respective uses. The predicted outcomes 1020 can include an indication of all potential uses and their corresponding likelihoods of success. The predicted outcomes 1020 can include an indication of which of the potential uses, and/or combinations and subcombinations of the study technology 1010, the computer system 110 recommends.

Figure 11:
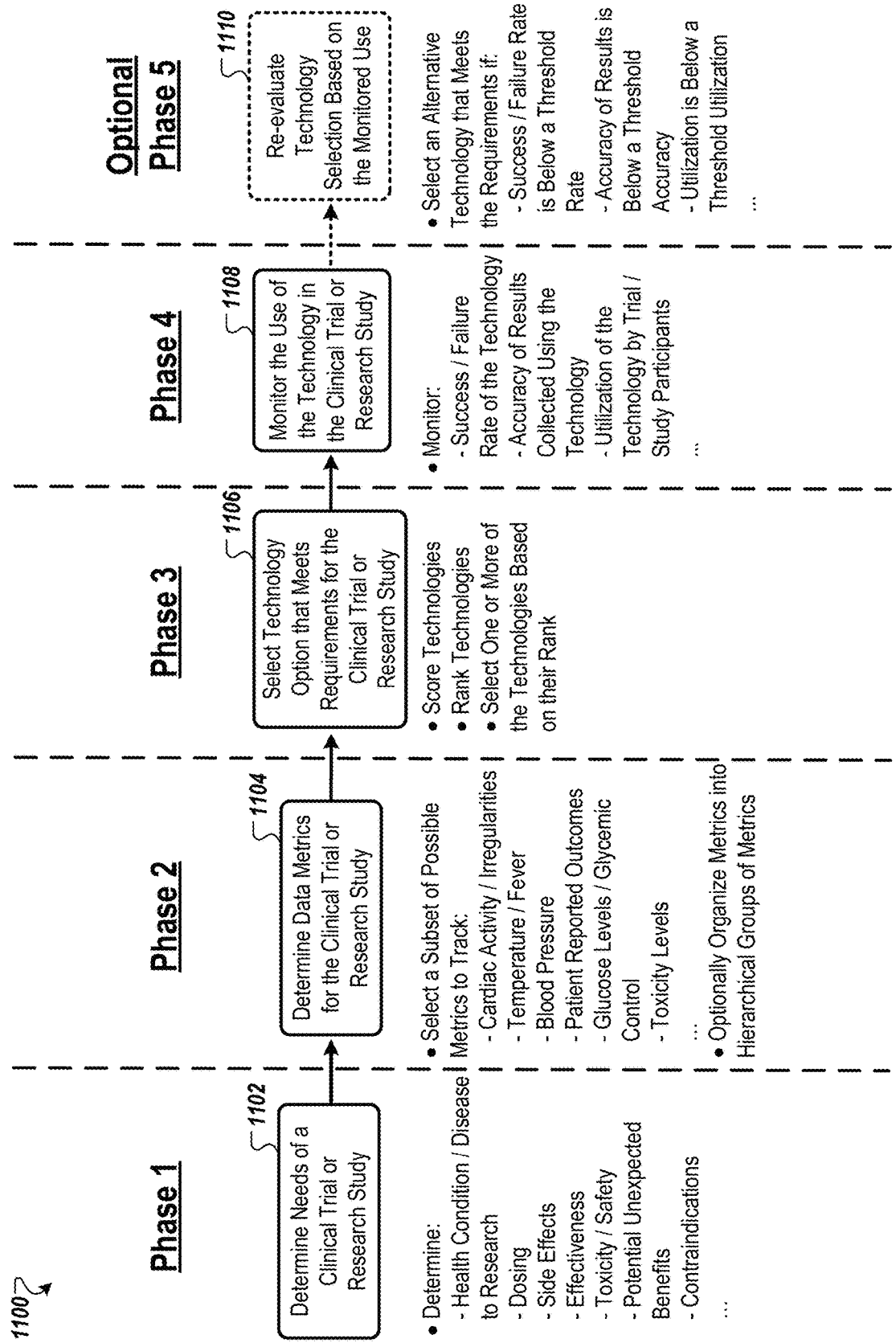
FIG. 11 is a diagram that illustrates an example process for using technologies in pharmaceutical development or research.

FIG. 11 is a diagram that illustrates an example process 1100 for using technologies in pharmaceutical development or research. The process 1100 may be performed by one or more computers, such as the computer system 110 shown in FIGS. 1 and 2. As another example, the process 1100 may be performed in whole or in part by a client device, such as device 104 of FIGS. 1 and 2. Similarly, the operations of the process 1100 may be distributed among one or more servers, one or more client devices, and/or other computing systems.

Technology, e.g., digital health technologies (DHTs), can be used in many different ways to support pharmaceutical research, including to facilitate drug discovery, dosing, facilitating clinical trials, and so on. Even before clinical trials, the monitoring that technology items provide can be used to detect the results of dosing, e.g., to measure the effects of different doses of a drug, including to detect changes in outcomes due to changing dosage (e.g., increasing or decreasing) and to detect interactions between drugs. Digital technologies are especially suited for measuring the context of an individual (e.g., vital signs, physiological status, type of activity, level of activity, mood, stress level, location, environmental conditions, etc.) given that network-connected mobile devices can measure and report aspects of health and behavior, and do so frequently and with low latency, even in real-time or near-real-time in some cases. This can be used to detect and characterize the effects of different drugs, as well as different dosages of drugs and different combinations of drugs in different dosages, in general and in specific contexts. For example, context data provided by technology items helps the computer system 110 and researchers characterize whether risks are higher when other behaviors or conditions present, and to identify those behaviors or conditions.

Even before a clinical trial is developed for a drug, technology items can be used to collect information to determine dosing models. An example is to detect and quantify a dose response, e.g., to determine whether and how changing a dose changes the type and magnitude of effects experienced by a patient. The collected information can then be used to determine the nature and parameters of a study related to the drug. Technology items can be used to measure information for different purposes, such as to detect or verify safety, effectiveness, toxicity, health risks, side effects, contraindications, and unexpected benefits.

The process 1100 includes four or five phases or steps that can be used in creating and administering a study related to pharmaceutical development or research. The first phase involves determining the needs for a clinical trial or study. The second phase involves determining the parameters for the clinical trial or study. The third phase involves selecting technology options to be used in the clinical trial or study. The fourth phase involves monitoring the use of technologies of the selected technology options during the clinical trial or study. The optional fifth phase involves re-evaluating the selection of technology options, and potentially selecting different technologies based on the monitored use.

In the first phase, the process 1100 includes determining needs of a clinical trial or research study (1102). Determining needs of a clinical trial or research study can include, for example, the computer system 110 shown in FIG. 2 determining one or more of a health condition or disease to research (e.g., based on study data provided by a researcher), dosing, side effects, effectiveness, toxicity/safety, potential for unexpected benefits, contraindications, etc. For example, determining needs of a clinical trial regarding Pharmaceutical A can include determining one or more dosing amounts to administer to study participants (e.g., a first cohort of participants can receive a first dose amount, a second cohort of participants can receive a second dose amount, etc.), determining known or potential side effects of the Pharmaceutical A (e.g., cannot be used if pregnant, potential loss of hair, increased risk to those with Factor V Leiden, hives, etc.), determining Pharmaceutical A's effectiveness or potential effectiveness for treating one or more conditions (e.g., hair loss, lack of sleep, etc.), determining a maximum dose and/or ingestion of Pharmaceutical A to avoid drug toxicity (e.g., maximum amount of 15 mg per day), and determining Pharmaceutical A's potential for unexpected benefits (e.g., prior studies indicate correlation between Pharmaceutical A and certain benefits, Pharmaceutical A has a similar molecular structure to one or more other drugs that are known to have benefits, Pharmaceutical A is compound similar to one or more other drugs that are known to have benefits, etc.).

In the second phase, the process 1100 includes determining data metrics for the clinical trial or research study (1104). Determining data metrics for the clinical trial or research study can include, for example, the computer system 110 shown in FIGS. 1-2 determining one or more of data types, data precision, and data frequency required for the clinical trial or study. As an example, determining one or more of data types, data precision, and frequency required for the clinical trial or study can include the computer system 110 selecting a subset of possible metrics to track (e.g., cardiac activity/irregularities, temperature/fever, blood pressure, patient reported outcomes, glucose levels/glycemic control, toxicity levels, etc.). The tracked metrics can be used by the computer system 110 to monitor the health of the clinical trial's participants over the trial period. If any of the tracked metrics indicate that a given participant requires medical attention, the computer system 110 can alert emergency services, a doctor, a nurse, etc. For example, if the monitored toxicity level of a participant in a clinical trial involving the taking of the Pharmaceutical A meets a threshold toxicity level (e.g., a maximum toxicity level for the Pharmaceutical A that indicates potential harm if exceeded), the computer system 110 can notify emergency services of the event and provide them a current location of the participant. Determining one or more of data types, data precision, and frequency required for the clinical trial or study can optionally include, for example, the computer system 110 organizing the metrics into hierarchical groups of metrics.

In the third phase, the process 1100 includes selecting a technology option that meets requirements for the clinical trial or research study (1106). Selecting a technology option can include, for example, the computer system 110 shown in FIG. 2 selecting a technology option that includes one or more technologies (e.g., DHTs). Selecting a technology option can include, for example, the computer system 110 scoring multiple technology options, ranking the technology options using their respective scores, and selecting one or more technologies options based on their rank. For example, for a clinical trial involving the taking of the Pharmaceutical A, the computer system 110 can select a technology option that includes a Sensor G for measuring temperature and a Device F for monitoring the participants' toxicity levels based on this technology option having the highest suitability score for the clinical trial.

In the second and/or third phases, the computer system 110 can use the nature of the drug, the types of primary effects and side effects to be monitored, the evaluation stage for the drug (e.g., experimental, dosing analysis, clinical phase I/phase II/phase III trials, etc.), and other information to determine the types of data to be monitored and the technology requirements that are needed. For example, the system 110 can store data, in a taxonomy or other data set, that relates types of measurements to be performed with, e.g., different classes of drugs, different primary effects or desirable effects to monitor, different side effects to monitor, etc. For example, for cardiovascular drugs, there may be a set of parameters to measure, e.g., resting heart rate, peak heart rate, blood pressure, etc. to measure how the target body system is responding. In addition, there may be potential side effects for drugs of this category (e.g., for the use in treating similar ailments, or for the same chemical family as the new drug, etc.), and the potential side effects may affect behavior, such as alertness, exercise or physical activity levels, etc. When a researcher or other user indicates that a cardiovascular drug or cardiovascular effect is being tested, the computer system 110 can use its data mappings to find the data types and data quality needed (e.g., frequency of measurement, level of precision, etc.) to measure both the primary effects and side effects (e.g., changes in alertness, exercise, etc.) that are related to this area of research.

The system 110 can store mappings of measurement types and measurement requirements, and/or other technology functions that may be needed, to many different types of medical research areas, diseases or health conditions to be studied (e.g., cancer, diabetes, heart disease, etc.), positive effects, side effects, chemical compounds or chemical compound families, study types or study goals (e.g., safety testing, effectiveness testing, dosing, etc.), and so on. Thus, when a user enters study data or the system accesses study data indicating a drug to be tested, a purpose of the test, and/or expected or desired outcomes of the test, the computer system 110 can compile a list of the types of measurements, reporting, patient interaction, and other requirements. For example, the computer system 110 can assemble sets of requirements retrieved for any or all of the items that the user specifies for the study, e.g., mapping general safety monitoring to a first set of technology functions needed, mapping a side effect that the researcher wants to watch for to a second set of technology functions needed, mapping a desired effect of the drug to a third set of technology functions needed, etc., with the overall set of requirements or needed data metrics to be collected combining the first, second, and third requirements. In many studies, especially safety studies, experimental studies, etc., a broad base of monitoring may be needed to detect various side effects that may be unknown. This is an instance where the stage of the study can be used by the computer system 110 to better tailor monitoring for the study (e.g., selecting a predetermined set of broad-based monitoring for early-stage studies, where effects are not able to be anticipated).

In the fourth phase, the process 1100 includes monitoring the use of the technology in the clinical trial or research study (1108). Monitoring the use of the technology can include, for example, the computer system 110 shown in FIGS. 1-2 monitoring one or more of the success and/or failure rate of the technology, the accuracy of results collected using the technology (e.g., data measured by the technology), the utilization of the technology by clinical trial or research study participants, etc. Similarly, monitoring the use of the technology can include, for example, the client device 104 shown in FIGS. 1-2 monitoring one or more of the success and/or failure rate of the technology, the accuracy of results collected using the technology (e.g., data measured by the technology), the utilization of the technology by clinical trial or research study participants, etc. For example, the monitored usage data can indicate that the utilization for Sensor G is over 96% for the study requirements (e.g., measuring temperature four times a day), but that the utilization for Device F is only 55% (e.g., monitor toxicity levels six times per day). This can indicate to the computer system 110 that another technology item may be needed to replace the Device F, e.g., one that is easier to use or more convenient.

With respect to FIGS. 9A-9B, the computer system 110 and/or the client device 104 can use one or more software modules of the software modules 914 (e.g., one or more web connectors in the software modules 914), one or more software configurations of the software configurations 916 (e.g., one or more Bluetooth profiles in the software configurations 916), and/or one or more API commands of the API commands 918 to monitor the use of the technology in the clinical trial or research study. For example, computer system 110 can use a web connector in the software modules 914 to obtain usage data from one of the technology items in use for a study. Continuing with the example of the clinical trial of Pharmaceutical A, the computer system 110 can use a web connector in the software module 914 to obtain toxicity level data from the Device F. The Device F may be configured by the researchers of the clinical trial, e.g., using the interface 906, to measure toxicity levels and to send the toxicity level measurements to the computer system 110 in response to a new measurement.

In some implementations, monitoring the use of the technology in the clinical trial or research study is not performed by the computer system 110. For example, one or more external (e.g., remote) systems can be used to monitor the use of the technology in the clinical trial or research study. The monitored data can be sent to the computer system 110 by the one or more external systems.

In the optional fifth phase, the process 1100 includes re-evaluating technology selection based on the monitored use (1110). Re-evaluating technology selection based on the monitored use can include, for example, the computer system 110 shown in FIG. 2 selecting a different technology based on the monitored use (e.g., the next highest ranked technology option). Selecting a different technology can include, for example, the computer system 110 selecting a new or different technology option that includes one or more technologies (e.g., DHTs). The computer system 110 can determine to select a different technology option due to one or more technologies of the previously selected technology option having an insufficient success rate (e.g., below 90%, below 70%, below 60%, etc.), collecting data with insufficient accuracy (e.g., an accuracy error of more than ±2%, ±5%, ±10%, etc.), having insufficient utilization by the trial or study participants (e.g., utilization below 90%, below 80%, below 70%, etc.), etc.

Continuing with the example of the clinical trial of Pharmaceutical A, the computer system 110 can select a new technology item to replace the Device F or can select an entire new technology option (e.g., the technology option with the second highest suitability score if that technology option does not include the Device F) based on the utilization of the Device F being below a threshold utilization of 60% over the first week of the clinical trial.

In some implementations, re-evaluating technology selection based on the monitored use is not performed by the computer system 110. For example, one or more external (e.g., remote) systems can be used to re-evaluate the technology selection based on the monitored use. The evaluations data (e.g., the results of the re-evaluation) can be sent to the computer system 110 by the one or more external systems.

Figure 12:
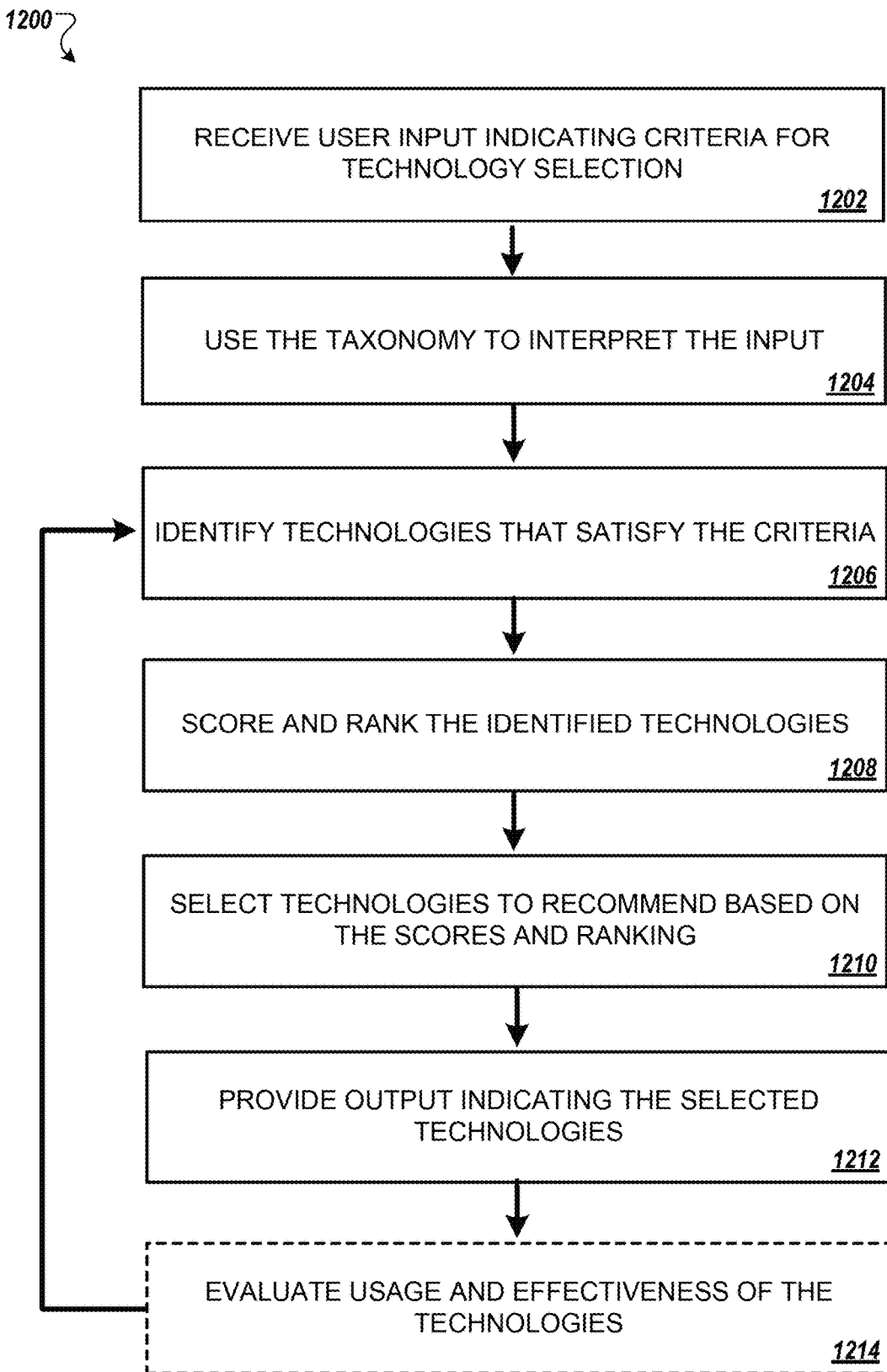
FIG. 12 is a flowchart diagram that illustrates an example process for assessing and selecting technologies.

FIG. 12 is a flowchart diagram that illustrates an example process 1200 for assessing and selecting technologies. The process 1200 may be performed by one or more computers, such as the computer system 110 shown in FIGS. 1 and 2. As another example, the process 1200 may be performed in whole or in part by a client device, such as device 104 of FIGS. 1 and 2. Similarly, the operations of the process 1200 may be distributed among one or more servers, one or more client devices, and/or other computing systems.

The process 1200 includes receiving user input indicating criteria for technology selection (1202). As an example, with respect to FIGS. 1-2, the input can be the study data 108 that is sent the computer system 110 from the client device 104. The input can include or indicate one or more study needs. The study needs can include, for example, study parameters such as the data types to measure, precision levels, and/or frequency of a measurement required for the current study. The input can include a natural language query that indicates one or more study needs, e.g., "track sleep and blood pressure" as shown in FIG. 1.

The process 1200 includes using the taxonomy to interpret the input (1204). Using the taxonomy to interpret the input can include the computer system 110 shown in FIG. 2 to access on or more taxonomy structures stored in the taxonomy database 206. The computer system 110 can identify keywords in the input and match those keywords to corresponding nodes in the taxonomy structure, such as the taxonomy structure 520 shown in FIG. 5 or the taxonomy structure 600*a* shown in FIG. 6A.

In using the taxonomy to interpret the input, if the input is or includes a natural language query, the computer system 110 can translate the natural language query, e.g., "track sleep activity and blood pressure", into a standardized format. In translating the natural language query into a standardized format, the computer system 110 can obtain structured data with predefined feature types or categories that are used in the technology database 112, e.g., that are used in the technology data 202. For example, the computer system can analyze the natural language query to identify that two types of data need to be collected (e.g., based on "track") for the study, that the first data type is associated with the keywords "sleep" and "activity", and the second data type is associated with the keyword "blood pressure." The computer system 110 can proceed use a taxonomy structure to translate the analyzed input. In doing this, the computer system 110 can generate a comprehensive set of technology features from the input.

As an example, the computer system 110 can identify the keyword "activity" in the input. The computer system 110 can proceed to match the keyword "activity" with a node for "activity" in taxonomy structure 520 shown in FIG. 5. The computer system 110 can obtain the activity node and the child nodes of the activity node that are defined as providing sleep data (based on the keyword "sleep"), e.g., the motion node, the linear acceleration node, the actigraphy node, the gyroscope node, and the accelerometer node from the taxonomy structure 520. This provides the computer system 110 the set of standardized device features (e.g., acceleration sensing, location sensing, motion sensing, etc.) any of which would satisfy the overall criteria for "track sleep activity." The computer system 110 can proceed to match the keyword "blood pressure" with a node for "blood pressure" in taxonomy structure 520 shown in FIG. 5. The computer system 110 can obtain the blood pressure node and the child nodes of the blood pressure node, e.g., the pulse rate node, the PPG node, and the pressurized band node.

The computer system 110 can use the keywords obtained from analyzing the input to, for example, determine the study needs and/or the study parameters for the current study. For example, the keyword "track" from the input can signal that data needs to be measured over a period of time. The computer system 110 can also identify "sleep", "activity", and "blood pressure" as keywords or "sleep activity" and "blood pressure" as keywords. The computer system 110 can use these keywords along with the "track" keyword to determine that sleep activity and blood pressure are data types that need to be measured for the current study. As discussed above, the computer system 110 can search the taxonomy structure 520 shown in FIG. 5 for example to identify nodes that correspond to "sleep", "activity", "sleep activity", and/or "blood pressure," e.g., nodes in the taxonomy structure 520 that can provide sleep data, activity data, sleep activity data, and/or blood pressure data.

The portion of a taxonomy structure (e.g., the taxonomy structure 520 shown in FIG. 5) that the computer system 110 determines relates to the input can be identified by the computer system 110 as a lookup taxonomy representing a subset of the overall taxonomy. For example, the computer system 110 can generate the lookup taxonomy 526 based on the input and the taxonomy structure 520. The computer system 110 can further leverage static or machine learning models to determine a subset of nodes from the lookup taxonomy 526 that are most relevant and/or that the client most likely meant for the current study based on the input.

The process 1200 includes identifying technologies that satisfy the criteria (1206). For example, the computer system 110 shown in FIGS. 1-2 can identify particular technologies from the identified technology features, e.g., the nodes in a technology structure that were determined to relate to the input. The computer system 110 can use, for example, the taxonomy structure 600b to identify the technologies that can be used for the current study, e.g., that can serve as a technology option or be combined with one or more other technologies to serve as a technology option. The technologies identified can be those that the computer system 110 determines would provide at least one of the features that it previously identified using the taxonomy structure, e.g., the taxonomy structure 520 shown in FIG. 5.

As an example, using the taxonomy structure 600b, the computer system 110 can determine a set of technology features that could meet the "sleep" measurement requirement (e.g., the sleep node and the motion node) and another set of technology features that could meet the "blood pressure" measurement requirement (e.g., the blood pressure node). The computer system 110 could proceed to use the taxonomy structure 600b to identify particular technologies that are associated with those technology features, e.g., the technologies that could be used to conduct the current study. With respect to FIG. 6B, the computer system 110 could identify the "Motiv" technology item and the "Samsung Gear" technology item as technologies that could meet the "sleep" measurement requirements. The computer system 110 could also identify the "Withings" technology item, the "Omron" technology item, and the "iHealth" technology item as technologies that could provide the "blood pressure" measurement requirement. The computer system 110 could use these technology items to generate technology options. For example, the computer system 110 could generate technology options that include one of the technologies related to sleep measurement and one of the technologies related to blood pressure measurement. This would result in the computer system 110 generating the following technology options: Motiv and Withings, Motive and Omron, Motiv and iHealth, Samsung Gear and Withings, Samsung Gear and Omron, and Samsung Gear and iHealth. The computer system 110 can optionally remove technology options that are not compatible. For example, the computer system 110 could remove the technology option of Samsung Gear and iHealth due to incompatibility.

In identifying technologies that satisfy the criteria, the computer system 110 shown in FIGS. 1-2 can use a previously identified lookup taxonomy. Specifically, the computer system 110 can use the nodes of a previously identified lookup taxonomy to identify technologies that are associated with the nodes of the lookup taxonomy. For example, with respect to FIG. 5, the computer system 110 can identify the technologies that are associated with each of the nodes in the lookup taxonomy 526 and/or the sub-portion of the lookup taxonomy 526 that includes the activity node, the motion node, the linear acceleration node, the actigraphy node, the gyroscope node, and the accelerometer node.

As an example, with respect to FIG. 6B, the term "activity" is mapped to the activity node in the taxonomy structure 600b. The computer system 110 can use the activity node to identify the child nodes of the activity node (e.g., a steps node, a motion node, a posture node, a gesture node, a social node, a device usage node, and a sleep node) or the child nodes of the activity node that can provide sleep data (e.g., the motion node and/or the sleep node). The computer system 110 can treat the activity node and the one or more child nodes as a lookup taxonomy. The computer system 110 can proceed to use the taxonomy structure 600b to identify the technology items mapped to the identified nodes as possible technology items to be used for the current study, e.g., for meeting the sleep activity needs for the current study. For example, the computer system 110 can identify the technology items Android Wear, Samsung Gear, Upright, Xsens, Humanyze, Smartphone, and/or Motiv as technology items that might be recommended for use in the current study.

In some cases, identifying technologies that satisfy the criteria includes generating one or more technology options from the identified technologies. For example, with respect to FIGS. 1-2 and FIG. 7, the computer system 110 can use the technology recommendation module 212 and/or the prediction module 214 to generate technology options that each include one or more of the identified technologies. As described in more detail above with respect to FIG. 2 and FIG. 7, if the prediction module 214 determines that a technology option is unlikely to result in a successful study, the computer system 110 can remove the technology option from consideration.

The process 1200 includes scoring and ranking the identified technologies (1208). With respect to FIGS. 1-2 and FIG. 8B, the computer system 110 can score and rank the identified technologies. For example, the computer system 110 can score and rank technology options that include the identified technologies using the technology recommendation module 212.

In scoring the technology options, the computer system 110 can use one or more scoring factors to generate component scores corresponding to each of the scoring factors, e.g., the scoring factors of the scoring data 804 shown in FIG. 8B. The scoring factors can include, for example, precision of data collection by one or more of the technology items in the technology option, reliability of the one or more technology items in the technology option, the frequency of data collection by one or more of the technology items in the technology option, the anticipated usage of one or more of the technology items in the technology option by participants or a subset of participants (e.g., by participants belonging to a certain age group, by participants residing in a certain region, by particular participants, etc.), etc.

In some cases, in scoring the technology options, the computer system 110 applies scoring weights to each of the component scores to generate component weighted scores for the technology options. The scoring weights can correspond to the scoring factors. For example, as shown in FIG. 8B, the precision scoring factor has a corresponding weight of 0.35, the reliability scoring factor has a corresponding weight of 0.25, the anticipated usage scoring factor has a corresponding weight of 0.30, and the cost scoring factor has a corresponding weight of 0.10. The sum of the scoring weights can be equal to one. In applying the scoring weights to each of the component scores, the computer system 110 can multiply a given component base score corresponding to a particular scoring factor by the scoring weight for that scoring factor. For example, with respect to the first technology option in FIG. 8B (e.g., the technology option that includes the Sensor A and the Bed Sensor C), the computer system 110 can multiple the component base score of 0.831 for the precision scoring factor by the precision scoring weight of 0.35 to obtain a weighted precision score of 0.291.

In some cases, in scoring the technology options, the computer system 110 sums the component weighted scores corresponding to each of the technology options to generate technology scores (e.g., suitability scores) for the technology options. For example, with respect to FIG. 8B, the computer system 110 can sum the weighted precision score of 0.291, the weighted reliability score of 0.225, the weighted anticipated usage score of 0.213, and the weighted cost score of 0.060 to obtain a technology score of 0.789 for the first technology option.

In some cases, in ranking the technology options, the computer system 110 organizes the technology options based on their respective technology scores (e.g., suitability scores). For example, with respect to FIG. 8B, the computer system 110 can rank the first technology option first due to having a technology score of 0.789 that is greater than the technology score of 0.649 for the second technology option and the technology score of 0.573 for the third technology option.

The process 1200 includes selecting technologies to recommend based on the scores and ranking (1210). With respect to FIGS. 1-2 and FIG. 8B, selecting technologies to recommend based on the scores and ranking can include the computer system 110 selecting a predetermined number of the highest ranking technology options. For example, if the predetermined number is one, the computer system 110 would select the first technology option that includes the Sensor A and the Bed Sensor C as shown in FIG. 8B due to it being the highest ranked technology option. Alternatively, selecting technologies to recommend based on the scores and ranking can include the computer system 110 applying a threshold score (e.g., a threshold technology score or threshold suitability score) to the technology options. For example, with respect to FIG. 8B, the computer system 110 can apply the threshold score of 0.6 to the technology options in the scoring table 806. Due to the first technology option and the second technology option both having technology scores (e.g., suitability scores) greater than the threshold score of 0.6, the computer system 110 could recommend the first technology option and the second technology option.

The process 1200 includes providing output indicating the selected technologies (1212). For example, with respect to FIG. 1, the output indicating the selected technologies can be the recommendation 122. The recommendation 122 can be used by the client device 104 to generate the interface 106b. Similarly, with respect to FIG. 2, the output indicating the selected technologies can be the recommendations 222 that are generated by the technology recommendation module 212. The output can include an indication of the one or more technology options that the computer system 110 recommends. The output can optionally include an indication of how the computer system 110 interpreted the input, e.g., can include an indication of the study needs and/or study parameters that the computer system 110 extracted from the study data 108. The output can optionally include an indication of one or more technology options that are recommended for particular groups of participants (e.g., those belonging to particular age groups, those residing in particular regions, those having a particular health condition, etc.) or particular participants (e.g., based on their characteristics such as age, observed passed usage, etc.).

The process 1200 optionally includes evaluating usage and effectiveness of the technologies (1214). With respect to FIG. 2, evaluating usage and effectiveness of the technologies can include the computer system 110 receiving monitored data from the client devices 208 after a study has begun. The client devices 208 can be devices belonging to participants (or researchers) of study. The technologies can include one or more of the technologies recommended by the computer system 110, e.g., the one or more technology items in the technology option selected by the user 102 of the client device 104 for the study. The computer system 110 can provide the monitored data to the monitoring module 216. As described in more detail above, the monitoring module 216 can analyze the monitored data to track the utilization of the one or more technologies for the study by the study participants, data collection frequency by the one or more technologies for the study, data collection precision by the one or more technologies for the study, the reliability of the one or more technologies for the study, etc. If the monitoring module 216 determines that utilization is insufficient, e.g., due to the tracked utilization of one or more of the technologies for the study being below a utilization threshold, then the monitoring module 216 can include an indication of poor utilization in the monitoring results 226. Similarly, if the monitoring module 216 determines that data precision/data frequency/technology reliability is insufficient, e.g., due to the data precision/data frequency/technology reliability of one or more of the technologies for the study being below one or more thresholds, then the monitoring module 216 can include an indication of poor effectiveness in the monitoring results 226. The computer system 110 can send the monitoring results 226 to the client device 104.

One or more steps of the process 1200 can be repeated. For example, in some cases, the usage and effectiveness of the technologies is used for identifying new technologies that satisfy the criteria (1206). For example, with respect to FIGS. 1-2, the user 102 can choose to select a new technology options based on the monitoring results 226 indicating that the currently implemented technology option includes one or more technologies that are being insufficiently utilized and/or that are not effective (e.g., fail to collect data a required level of precision, fail to collect data at a required frequency, fail battery life requirements, fail reliability requirements, etc.).

FIG. 13 is a diagram that illustrates example inputs and outputs of a system for assessing and selecting technology items. The example inputs and outputs of the system are presented in a table 1300.

In some cases, the system for assessing and selecting technology items is the computer system 110 described above.

As shown, the table 1300 corresponds to an example inquiry (e.g., research question) for a new research study. The inquiry is "Do activity level and sleep quality have a measurable impact on an individual's mental health?" As an example, with respect to FIG. 1, this inquiry can be sent to the computer system 110 from the client device 104, e.g., by the user 102 (e.g., a researcher of the new research study).

The inputs and outputs of the system for assessing and selecting technology items can correspond to particular categories. These categories are presented in a first column of the table 1300. These categories can correspond to requirements for a new research study (e.g., study needs and/or study parameters), e.g., requirements to meet study quality standards, to ensure that the results of the study meet statistical standards, etc. These categories can include, for example, dependent metrics (e.g., outcomes or results tracked), types of measurements (e.g., items to be monitored, types of data to be collected), data quality (e.g., accuracy, precision, frequency, etc. of data obtained by technology items), participant information, relatability of research methods/data collections methods, acceptable down time, data transmission requirements, equipment cost, and likelihood of participant participation.

The second column of the table 1300 includes example inputs used by the system for assessing and selecting technology items. For example, with respect to dependent metrics, the input to the system can include responses from study participants for mental health (e.g., depression) surveys.

With respect to types of measurements, the input to the system can include collected measurement data from study participants. For example, the input can include the number of steps per day, the average during of sleep over one week (or intraday sleep measurements per minute), and/or indications of sleep quality (e.g., markers) for a cohort of participants in a given research study.

With respect to the data quality, the input to the system can include an indication of the quality of data needed to be reported by participants, e.g., a minimally acceptable accuracy, precision, frequency, etc. of data collection.

With respect to the participant information, the input to the system can include a level of over-recruiting that is needed to obtain the expected number of core or active participants (e.g., 75%). Alternatively or additionally, the input to the system can include a number of active participants needed to qualify statistical response of data.

With respect to the reliability of research methods/data collection methods, the input to the system can include methods of data collection. For example, the input to the system can include equipment translation to expected measurement, experimental, research qualified, etc. Alternatively or additionally, the input to the system can include information about research studies. For example, the input to the system can include methods and results of one or more previously performed research studies.

With respect to acceptable down time, the input to the system can include a charge cycle of the selected technology. Alternatively or additionally, the input to the system can include calibration needs. Alternatively or additionally, the input to the system can include replacement ordering of consumables, such as, for example, replacement ordering of patches, strips, sample deposits, or other medical supplies. Alternatively or additionally, the input to the system can include DHT availability for measurements.

With respect to data transmission requirements, the input to the system can include one or more of sampling frequencies, upload/response times, and reporting cadence.

With respect to equipment cost, the input to the system can include one or more of cost per unit, batch pricing, subscription pricing, and number of seats licensing.

With respect to likelihood of participant participation, the input to the system can include participant attributes, such as, for example, ages of participants, age distribution of participants, locations of participants, education of participants, etc. Additionally or alternatively, the input to the system can include requirements for using the selected technology. The requirements can include, for example, duration of use of the selected technology, frequency of use of the selected technology, complexity of use of the selected technology, participant education needed for use of the selected technology, etc. Additionally or alternatively, the input to the system can include participants' knowledge of similar technologies. For example, the input to the system can include an indication that a participant is familiar with smartphones as they currently own and use a smartphone, that a participant is familiar with the iOS operating system as their smartphone is an Apple device, etc.

The third column of the table 1300 includes example outputs generated by the system for assessing and selecting technology items. The outputs of the system can include observations such as observed patterns (e.g., participant behavioral patterns, patterns in the usage of technology items, patterns in the performance of technology items, etc.), recommendations, and/or results. The outputs can be generated by the system in response to receiving the corresponding inputs. As an example, with respect to dependent metrics, the output of the system can include indications of which study participants have high or low depression survey scores With respect to types of measurements, the output of the system can include results of analyzing collected data. For example, the output can include an indication that fewer steps correlates to higher depression, that consistent sleep duration of six hours or greater average per day correlates to lower depression, that good sleep indicating amount and quality of sleep improves overall mental health state, etc.

With respect to the data quality, the output of the system can include recommended study protocol elements or constraints to achieve desired data quality. For example, the output can include an indication of the total sleep duration needed for five days in a 7-day period, and/or step data for three days contiguous in the 7-day period.

With respect to the participant information, the output of the system can include an estimated number of active participants needed (e.g., 90 participants). Alternatively or additionally, the output of the system can include an estimated total number of participants needed to reach the active participant number (e.g., 120 participants). Alternatively or additionally, the output of the system can include an actual number of active/total participants in the study (e.g., thirty total participants with twenty-five active participants).

With respect to the reliability of research methods/data collection methods, the output of the system can include an indication of the level of reliability or validation/qualification of data collection techniques for this study. For example, the output can include the techniques that have been successfully used in 100 research studies.

With respect acceptable down time, the output of the system can include indications of requirements needed for successful use of selected technology. For example, the output can include an indication that a charge once per day outside of measurement activity is required for the selected technology item.

With respect to data transmission requirements, the output of the system can include expected or actual data transmission requirements. For example, the output of the system can include an indication that an expected data transmission is a one data transfer per day per user.

With respect to equipment cost, the output of the system can include an expected cost of the selected technology. For example, the output of the system can provide that the expected cost for the study is less than $10 per participant.

With respect to likelihood of participant participation, the output of the system can include an indication of expected or actual level of participation in using the selected technology. For example, the output of the system can include an indication of the highest participation expected for individuals between 18 and 40, an indication that the selected technology requires minimal effort, an indication that the overall cohort-level compliance predicted at 82%, an indication that the current cohort-level compliance is 87%, etc.

As an example, the inputs can be provided to the computer system 110 shown in FIGS. 1-2. The outputs can include outputs generated by the computer system 110, e.g., by the technology recommendation module 212 as part of the recommendations 222, by the prediction module 214 as part of the predictions 224, and/or by the monitoring module 216 as part of the monitoring results 226.

FIG. 14 is a diagram that illustrates an example look-up table 1400.

The look-up table 1400 can be a representation of the technology data 202 shown in FIG. 2. The look-up table 1400 can be stored in the technology database 112, e.g., as an example of the technology data 202 or as a representation of at least a portion of the technology data 202. Of course, the table 1400 shows only a few examples of the many types of data that can be included in the technology database 112.

Each row in the table 1400 can represent an entry for a technology item, e.g., a particular hardware device, software module, network technology, web site, cloud computing-based service, web-based or Internet based technology, etc. Technology items can be characterized differently for different functions or uses of the technology item. For example, there are two rows that represent the "Wrist Device A," which represent the same device but represent different uses. The first entry refers to using the device measuring sleep (e.g., as indicated in column 2), and the second entry refers to using the device to measure actigrapy. Note that these two uses of the device also have different levels of precision and also different levels of qualification or validation based on prior results and research literature. Thus, although the "Wrist Device A" can measure both sleep and actigraphy, the data in the table 1400 indicates to the system 110 that if better than low precision sleep data is needed, it would be better to use a different device (e.g., one having medium or high precision for sleep tracking). This is one way that the system 110 and database 112 can characterize different uses or functions of a device separately, to allow better technology selection to be better suited to the needs of a researcher, clinician, etc. Another way to express this may be to include multiple levels of scoring within an entry for a technology item, rather than including the technology item listed twice. Regardless of the data format, the information can be used by the computer system 110 to generate the technology options, e.g., individual technology items or combinations of technology items, that best meet the combinations of constraints and needs of a user.

As shown, the first column of the look-up table 1400 ("DHT") includes identifications and/or brief descriptions of various technology items. The technology items can include, for example, sensors, devices, software, or combinations thereof. The technology items can include digital health technologies (DHTs) as described above. DHTs may be capable of measuring one or more types of health data, such as, for example, cardiac activity, temperature, blood pressure, glucose levels, toxicity levels, etc.

The second column of the look-up table 1400 ("Measures") includes types of data the technology items in the first column can measure. For example, the Wrist Device A can measure actigraphy data. Additionally or alternatively, the second column includes an indication of types of data that the technology items in the first column can use, e.g., receive as input to track and/or analyze. For example, the App D may be capable of tracking sleep data that is measured by one or more sensors (e.g., the Bed Sensor E) over time. The App D may be capable of analyzing the sleep data to determine sleep data metrics, such as, for example, an average length of sleep per night for a corresponding user (e.g., 7.2 hours), an average sleep time for the corresponding user (e.g., 12:06 AM), an average wakeup time (e.g., 7:18 AM), sleep trends (e.g., averaging 0.2 hours less sleep per night over the last month), etc.

The third column of the look-up table 1400 ("Precision") includes indications of precisions of data that can be measured and/or generated by the technology items in the first column for a given data type. For example, the high precision indicator for the Sensor A indicates that a Foot Pedometer B is capable of tracking the steps of a wearer with a high precision. What is considered a high precision can be set by a researcher of the study, can be determined from acquired specifications of the Foot Pedometer B, can be determined from usage data (e.g., acquired from participants using the Foot Pedometer B in ongoing studies, and/or acquired from participants that used the Foot Pedometer B in past studies), can be determined from the database updates corresponding to the Foot Pedometer B (e.g., provided by a manufacturer of the Foot Pedometer B), and/or can be determined from stored literature.

The fourth column of the look-up table 1400 ("Age Groups") includes age ranges and/or age indicators of participants who are determined to successfully use the technology items. For example, the computer system 110 can populate the age groups for the technology items using one or more of stored literature (e.g., which can indicate whether participants of external studies successfully utilized the technology items) and/or usage data (e.g., that can indicate the utilization of the technology items in the first column with respect to different ages or different age groups of study participants).

The fifth column of the look-up table 1400 ("Cost") includes prices, ranges of prices, and/or cost indicators for the technology items. For example, the cost of the Wrist Device A is determined to be $300. The cost information that the computer system 110 uses to populate the fifth column can be determined from one or more of database updates (e.g., prices provided by the manufacturers' and/or developers' of the technology items), and/or from stored literature (e.g., from websites, research journals, articles, etc. that indicate a cost of the technology items). In determining a price for a given technology item, the computer system 110 may weigh more recent information (e.g., price from website that is currently selling the technology item) more heavily than older information (e.g., prices from research study from over a year ago). Similarly, in determining a price for a given technology item, the computer system 110 can weigh information identified from the stored literature more heavily than information provided by the manufacturer, e.g., as the stored literature may indicate a real-world price while the manufacturer is likely to provide a suggested retail price.

The sixth column of the look-up table 1400 ("Research Studies") includes indicators of the trustworthiness of the technology items. The trustworthiness can indicate, for example, whether the technology items found in column one of the look-up table 1400 can be relied on to measure/analyze the types of data found in the second column. The trustworthiness can indicate whether a use (e.g., measurement/analysis of a given data type) is validated (e.g., qualified) or not. The trustworthiness can indicate whether a use (e.g., measurement/analysis of a given data type) has been validated and/or the amount of times the use has been validated.

As an example, the sixth column can indicate that for a given use (e.g., measurement of sleep data) a corresponding technology item should not be trusted for the use (e.g., "low quality") based on stored literature and/or obtained usage data indicating that the technology item has not successfully performed the use or has successfully performed the use below a threshold number of times (e.g., successful performance of use in four/three/two prior research studies). Similarly, the sixth column can indicate that for a given use a corresponding technology item may be trusted for the use with low/medium confidence (e.g., "some qualified") based on stored literature and/or obtained usage data indicating that the technology item has successfully performed the use a threshold number of times (e.g., successful performance of use in four/three/two prior research studies) but not a second threshold number of times (e.g., successful performance of use in seven/six/five prior research studies), Additionally, the sixth column can indicate that for a given use a corresponding technology item may be trusted for the use with high confidence (e.g., "multiple qualified") based on stored literature and/or obtained usage data indicating that the technology item has successfully performed the use the second threshold number of times (e.g., successful performance of use in seven/six/five prior research studies).

The seventh column of the look-up table 1400 ("Network Needed") includes an indication as to whether the technology items in the first column require a network to function (e.g., for the particular use that the technology items are being used for). For example, the App D requires a network in order to function (e.g., so that it can communicate with a sensor that is collecting sleep data such as the Bed Sensor E).

The eighth column of the look-up table 1400 ("Battery Life") includes indicators of the battery lives of the technology items. The indicators can include, for example, "short" (e.g., for a battery life below 5/4/3 hours), "medium" (e.g., for a battery life between Dec. 11, 2010 hours and 5/4/3 hours), and "long" (e.g., for a battery life of at least Dec. 11, 2010 hours). The indicators can additionally or alternatively include "always on" (e.g., to indicate that the technology item is plugged into a power source), and "phone life" (e.g., to indicate that the battery life for software installed on a mobile device is the same as the mobile device's battery life).

The ninth column of the look-up table 1400 ("Type") includes indicators of the technology items being hardware devices or software. For example, the ninth column can indicate that the Wrist Device A is a hardware device and that the App D is software.

FIG. 15 is a diagram that illustrates an example of technologies and corresponding scores represented in a table 1500.

The table 1500 can, for example, represent the output of the computer system 110 after scoring various technology options. For example, the table 1500 can be generated by the technology recommendation module 212 shown in FIG. 2 as the recommendations 222.

As shown, the first column of the table 1500 includes individual technology items. These technology items include the Wrist Device A, the Foot Pedometer B, the Phone C, the App D, and the Bed Sensor E. Each of these technology items may represent a technology option having a single technology item. Accordingly, the table 1500 may provide for the scoring of technology options. Alternatively, the technology items may be part of technology options that include two or more technology items. As such, the table 1500 may provide for the scoring of individual technology items.

In some cases, the first column of the table 1500 includes technology options that each include one or more technology items. For example, the first column may include an entry for the Bed Sensor E and the Phone C. The first column may include another entry for the Bed Sensor E with the Foot Pedometer B.

The table 1500 may be generated in response to the computer system 110 determining that the study needs for a new research study require measuring actigraphy data and also require measuring sleep data. For example, the computer system 110 can use the study data 108 shown in FIGS. 1-2 to determine that actigraphy data and sleep data both need to be measured for a study. Accordingly, the table 1500 includes a second column for the scoring of the technology options/items in the first column with respect to measuring actigraphy data, and a third column for the scoring of the technology options/technology items with respect to measuring sleep data.

As an example, the computer system 110 can use the technology recommendation module 212 and/or the prediction module 214 to generate a list of technology options that can potentially measure the actigraphy data and/or the sleep data, e.g., based on the technology data 202 stored in the technology database 112. These technology options can be used by the computer system 110 to populate the first column of the table 1500.

The computer system 110 can proceed to generate a score for each of the technology options/items for each data type to be measured/analyzed for a new research study (e.g., a new clinical trial).

For example, the computer system 110 can proceed to calculate a score for measuring actigraphy data for each of the technology options. The actigraphy score can be generated based on, for example, the precision that each of the technology options can measure the actigraphy data, the frequency that each of the technology options can measure actigraphy data, etc. The actigraphy score can also be based on other factors such as the battery life of each of the technology options.

Similarly, the computer system 110 can proceed to calculate a score for measuring sleep data for each of the technology options. The sleep score can be generated based on, for example, the precision that each of the technology options can measure the sleep data, the frequency that each of the technology options can measure sleep data, etc. The sleep score can also be based on other factors such as the battery life of each of the technology options.

The computer system 110 can generate a comprehensive score for each of the technology options/items, e.g., as shown in the fourth column of the table 1500. The comprehensive scores can be generated by, for example, summing the data type scores for each of the technology options. As an example, for the technology option including the Wrist Device A, the computer system 110 can sum the actigraphy score of 70 for the Wrist Device A with the sleep score of 40 for the Wrist Device A to obtain a comprehensive score of 110 for the Wrist Device A.

In some cases, prior to summing the data type scores, the computer system 110 applies a weight to one or more of the data type scores. The weight applied can be determined for the particular study, e.g., as indicated by the study data 108 shown in FIGS. 1-2. For example, if actigraphy data is explicitly mentioned in the study data 108 and sleep data is only inferred by the computer system 110 from the study data 108 (e.g., by the computer system 110 using a taxonomy structure stored in the taxonomy database 206 shown in FIG. 2), the computer system 110 can apply a larger weight to the actigraphy score than the weight applied to the sleep score.

As provided in the fifth column of the table 1500 ("Selection Recommended"), the computer system 110 can rank the technology options/items. In ranking the technology options/items, the computer system 110 can determine suitability scores for the technology options/items. As an example, the computer system 110 can rank the technology options/items based on their respective comprehensive scores. As another example, the computer system 110 can take into account one or more other factors in ranking the technology options/items, such as cost. In some cases, these rankings serve as suitability scores.

As an example, the computer system 110 has determined that App D has the highest suitability score with a score of one, that the Bed Sensor E has a suitability score of two when combined with the Phone C or a suitability score of four when combined with the Food Pedometer B, the Wrist Device A has a suitability score of three, and the Foot Pedometer B has the lowest suitability score with a score of four.

FIG. 16 is a diagram that illustrates an example of technologies and corresponding scores represented in a table 1600.

In the example of FIG. 16, a table 1600 of technologies and corresponding scores indicates various technology options and their viability across demographics. Likely study participants (e.g., those belonging to certain age groups) may need participant tailored messaging in representing technologies (e.g., DHTs) for which they can interact with. In some cases, rules may prohibit certain technology options from being presented when more than one technology selected by a researcher is made available to the participants. As an example, adolescents are not given options to purchase equipment, or for young adults where specific tools or apps are sponsored through respective marketplaces (e.g., Google Play, or Amazon) based on factors such as affordability versus predicted usability.

The table 1600 can be generated by the computer system 110, e.g., can be generated by the technology recommendation module 212 as the recommendations 222 shown in FIG. 2.

The computer system 110 can analyze each of the technology options for one or more cohorts of participants, groups of participants, and/or particular participants. For example, the computer system 110 can generate a usability analysis for each of the technology options depending on the age group of the study participants (e.g., adolescent, young adult, or elderly).

The computer system 110 can use the results of the usability analysis to calculate a suitability score ("tailored score") for each of the technology options, e.g., given a particular cohort of participants, groups of participants, and/or particular participants. In calculating the suitability scores, the computer system 110 can take into account other factors such as cost of the technology items in the technology options.

Figure 17:
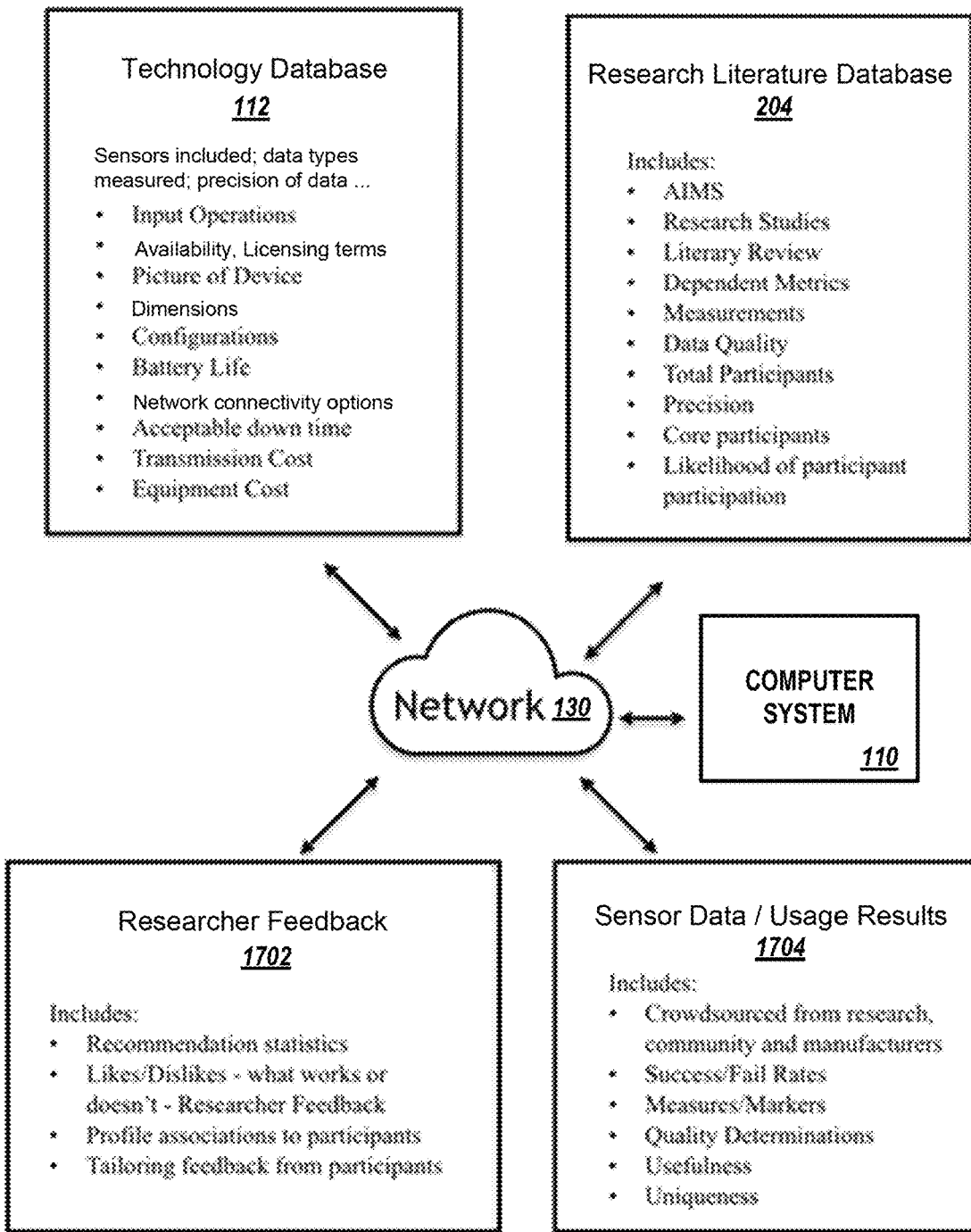
FIG. 17 is a diagram that illustrates an example system for assessing and selecting technologies.

FIG. 17 is a diagram that illustrates an example system 1700 for assessing and selecting technologies. In some implementations, the system 1700 is the system 100 shown in FIG. 1. In some implementations, the system 1700 is the system 200 shown in FIG. 2.

The system 1700 includes the computer system 110. The computer system 110 can communicate with the technology database 112 and the research literature database 204 over the network 130. The computer system 110 can receive research feedback 1702 over the network 130. The computer system 110 can receive sensor data/usage results 1704 over the network 130.

The technology database 112 can include, for example, the technology data 202 shown in FIG. 2. The technology data 202 can include one or more technology items, sensors included in and/or used by the one or more technology items, data types measured by the technology items, data types analyzed by the technology items, precision of data measured by the technology items, frequency of data measured by the technology items, etc. The technology database 112 can also include input operations, an indication of the availability of the one or more technology items, licensing terms for the one or more technology items, a picture of one or more of the technology items (e.g., for those that are devices), dimensions for one or more of the technology items (e.g., for those that are devices), configurations for one or more of the technology items, an estimated battery life for one or more of the technology items (e.g., for those that are devices), network connectivity options for one or more of the technology items, acceptable down time for one or more of the technology items, transmission cost for one or more of the technology items, cost for one or more of the technology items, etc.

The research literature database 204 can include, for example, the literature 402 shown in FIG. 4. The research literature database 204 can include, for example, AIMS, research studies that used one or more technology items, literary reviews, dependent metrics, measurements taken using one or more technology items, indications of data quality that can be acquired by one or more technology items (e.g., precision of data collection and/or frequency of data collections, etc.), an indication of total participants (e.g., in the research studies), a precision of data collected by one or more technology items, an indication of core participants (e.g., of the research studies), a likelihood of participant participation (e.g., based on the characteristics of the participants, based on the prior usage data obtained on the participants, etc.), content of one or more external repositories, content of one or more webpages, etc. Some of the information contained in the research literature database 204 can be determined from the computer system 110 analyzing one or more research studies, articles, webpages, etc. as described in more detail above with respect to FIG. 3.

The research feedback 1702 can include feedback provided by one or more participants and/or one or more researchers. The research feedback 1702 can be provided through the client device 104 and/or through the client devices 208 shown in FIG. 2. The research feedback 1702 can include recommendation statistics, e.g., the percentage that recommended technology options are selected and/or used for a study, the percentage that recommended technology options are successfully used in a study given a researcher's assessment or metrics, or the percentage that recommended technology options successfully used in a study based on standardized metrics. The research feedback 1702 can include a researcher requesting new recommendations, e.g., not selecting one or more recommended technology options from a first set of recommended technology options. The research feedback 1702 can include likes and/or dislikes by one or more researchers. The research feedback 1702 can include likes and/or dislikes by one or more participants of studies. The research feedback 1702 can include profile associations to participants (e.g., profiles can take into account the age of the participant, the location where the participant resides, technology item usage habits or patterns of the participant, health conditions of the participant, etc.).

The sensor data/usage results 1704 can be provided by the client devices 208 shown in FIG. 2. The sensor data/usage results 1704 can be received by the computer system 110, e.g., can be provided to the monitoring module 216 of the computer system 110. In some cases, the sensor data is obtained by one or more external systems. The one or more external systems can analyze the sensor data to determine usage results, and can send the usage results to the computer system 110 and/or the client device 104.

The sensor data/usage results 1704 can include, for example, data crowdsourced from research (e.g., one or more research studies or clinical trials), from one or more communities, and/or from one or more manufacturers. The sensor data/usage results 1704 can include, for example, one or more of success rates and/or failure rates of one or more technology items, measures and/or markers provided by one or more technology items, quality determinations corresponding to one or more technology items, usefulness determinations for one or more technology items, uniqueness determinations for one or more technology items, etc.

Figure 18:
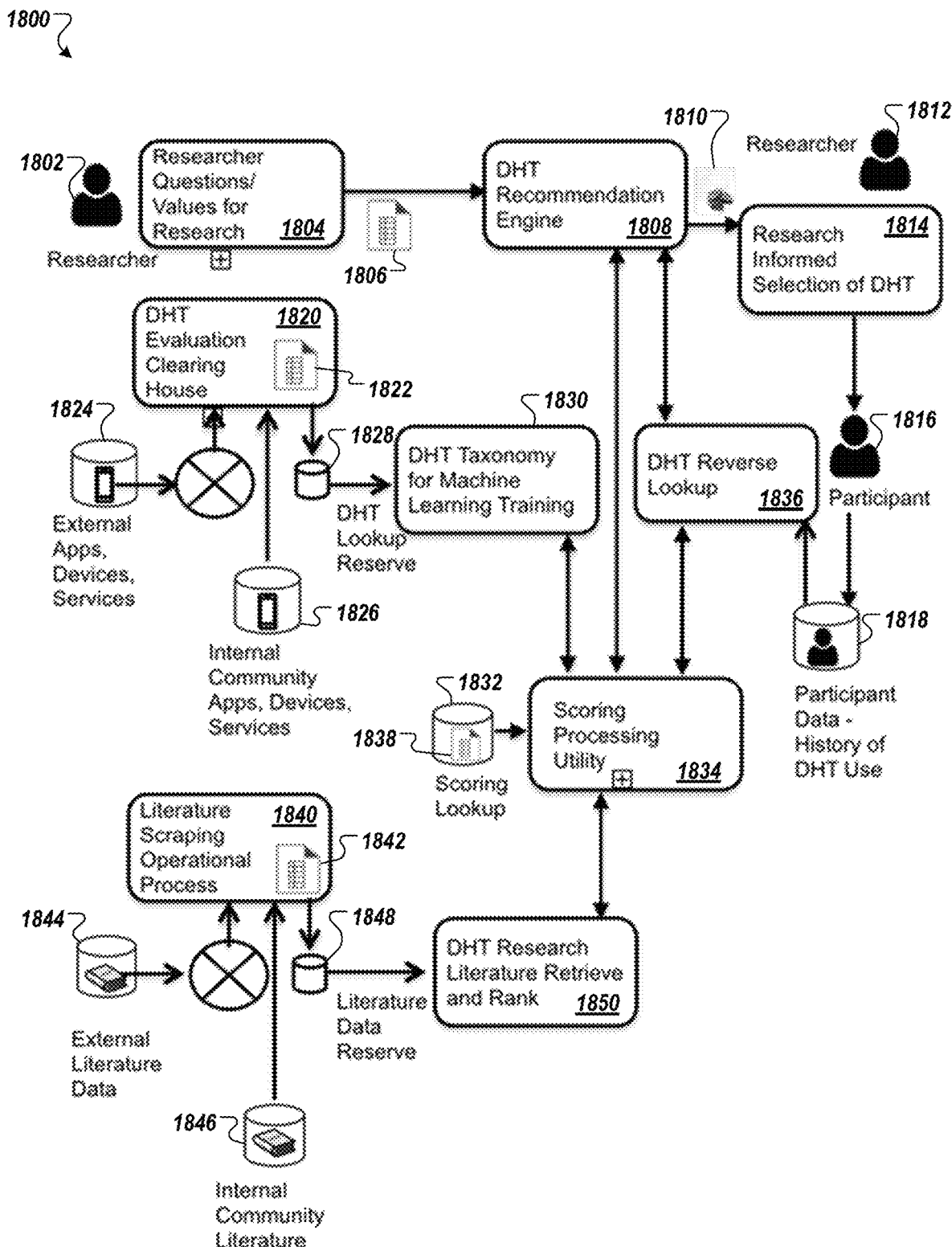
FIG. 18 is a diagram that illustrates an example processing flow of a system for assessing and selecting technologies.

FIG. 18 is a diagram that illustrates an example processing flow 1800 of a system for assessing and selecting technologies.

The processing flow 1800 describes an example flow of data and the processing of the data by a recommendation engine 1808, and its interactions with the scoring processing utility 1834 and related lookup processes, that produce the informed selection 1814. The informed selection 1814 can be the selection of a technology option that includes one or more technology items (e.g., one or more devices and/or software).

A researcher 1802 can provide researcher questions/values for research 1804. The researcher 1802 can be the user 102 shown in FIG. 1. The researcher 1802 can provide the researcher questions/values for research 1804 through the client device 104 shown in FIGS. 1-2. The researcher questions/values for researcher 1804 can include or indicate the needs for a potential research study. The researcher questions/values for researcher 1804 can include or indicate one or more study parameters for a potential research study.

In some implementations, the researcher questions/values for research 1804 are sent to the computer system 110 shown in FIGS. 1-2 by the client device 104.

As a result of providing the researcher questions/values for researcher 1804, study data 1806 is generated and sent to the recommendation engine 1808. The study data 1806 can be the study data 108 shown in FIGS. 1-2.

The recommendation engine 1808 can analyze the study data 1806 and, in response, generate recommendations 1810. The recommendations 1810 can include one or more technology options that the recommendation engine 1808 recommends based on the study data 1806. The recommendations 1810 can include one or more predictions, such as suitability scores of one or more technology options, likelihoods that one or more technology options will meet the needs of the study, one or more types of data that can be collected using known (e.g., available) technology items, one or more studies that can be performed using known (e.g., available) technology items, etc. The recommendation engine 1808 can be part of the computer system 110 shown in FIGS. 1-2. The recommendation engine 1808 can be, or be part of, the technology recommendation module 212 shown in FIG. 2 and FIG. 8B. The recommendations 1810 can be the recommendations 222 shown in FIG. 2. The recommendations 1810 can be the predicted outcomes 1020 shown in FIG. 10.

In some implementations, in generating the recommendations 1810, the recommendation engine 1808 uses the output of a scoring processing utility 1834. For example, the recommendation engine 1808 can use scores associated with technology options, and/or scores associated with technology items (e.g., that are each included in a technology option) in selecting the one or more technology options to include in the recommendations 1810.

In some implementations, in generating the recommendations 1810, the recommendation engine 1808 uses the output of a reverse lookup 1836. For example, the reverse lookup 1836 can use one or more known technology items to identify information associated with the known technology items. The information can be accessed from a clearing house 1820. The recommendation engine 1808 can use the information in generating the recommendations 1810.

The clearing house 1820 can store and/or produce information associated with various technology items. For example, the clearing house 1820 can store and/or produce technology data 1822. The technology data 1822 can be the technology data 202 shown in FIG. 2. With respect to FIG. 2, the clearing house 1820 can be the technology database 112, can be part of the technology database 112, or can be otherwise part of the computer system 110.

The clearing house 1820 can receive information associated with various technologies from one or more external apps, devices, and/or services 1824. Data outputted by the one or more external apps, devices, and/or services 1824 can be analyzed to extract the information associated with various technologies, e.g., by the computer system 110 shown in FIGS. 1-2. The clearing house 1820 can receive information associated with various technologies from one or more internal community apps, devices, and/or services 1826.

The clearing house 1820 can use the received information to generate the technology data 1822. For example, the operations associated with the clearing house 1820 can be performed by the computer system 110 shown in FIGS. 1-2 to produce the technology data 1822. The technology data can be stored in the technology database 1828. For example, the computer system 110 can store the technology data 1822 in the technology database 1828. The technology database 1828 can be the technology database 112 shown in FIGS. 1-2.

A taxonomy 1830 can be generated using data stored in the technology database 1828. For example, the taxonomy 1830 can be generated by the computer system 110 shown in FIGS. 1-2 using the technology data 1822 stored in the technology database 1828. The taxonomy 1830 can be stored on the taxonomy database 206 shown in FIG. 2. The taxonomy 1830 can be the taxonomy structure 520 shown in FIG. 5. The taxonomy 1830 can be the taxonomy structure 600*a* shown in FIG. 6A. The taxonomy 1830 can be the taxonomy structure 600*b* shown in FIG. 6B. The scoring processing utility 1834 can use the taxonomy 1830 to score and/or rank one or more technology options. The taxonomy 1830 can be used to train one or more machine learning models, e.g. one or more machine learning models of or used by the recommendation engine 1808, the scoring processing utility 1834, the reverse lookup 1836, etc.

The scoring processing utility 1834 can access scoring data 1838 from a database 1832. The scoring data 1838 can include an indication of one or more scoring factors, one or more scoring weights (e.g., for each of the scoring factors), one or more algorithms, etc. The scoring data 1838 can be the scoring data 804 shown in FIG. 8B.

In scoring and/or ranking one or more technology options, the scoring processing utility 1834 can receive output from the research literature retrieve and rank 1850. The output of the research literature retrieve and rank 1850 can include for example one or more keywords and/or metrics associated with a given technology item, an indication of how many studies the technology item has appeared in, an indication of the success of the technology item in the one or more studies, an indication of the effectiveness of the technology item (e.g., when compared to one or more standardized metrics), an indication of one or more validated uses of the technology, etc. The output of the research literature retrieve and rank 1850 can include all or of a portion of research data 1842, e.g., can include a portion of the research data 1842 that corresponds to the one or more technology items that the scoring processing utility 1834 is analyzing (e.g., scoring and/or ranking).

The literature scraping operational process 1840 one or more of identifying keywords and/or metrics associated with technology items, how many studies the technology items have appeared in, the success of the technology items in the one or more studies, the effectiveness of the technology items (e.g., when compared to one or more standardized metrics), validated uses of the technology, etc. using data such as documents obtained from an external literature database 1844 and/or from an internal community literature database 1846. For example, the literature scraping operational process 1840 can include one or more of the operations 312, 314, 316, 320, 322, 324, 330, and/or 330 shown in FIG. 3 and described above. The literature scraping operational process 1840 can be performed by the computer system 110 shown in FIGS. 1-3.

The research data 1842 is produced as a result of the literature scraping operational process 1840. The research data 1842 can be stored on the researcher literature database 1848. The research literature database 1848 can be the research literature database 204 shown in FIGS. 2-3. The research data 1842 can be used, e.g., by the computer system 110 shown in FIGS. 1-3, to update the technology data 1822.

Figure 19:
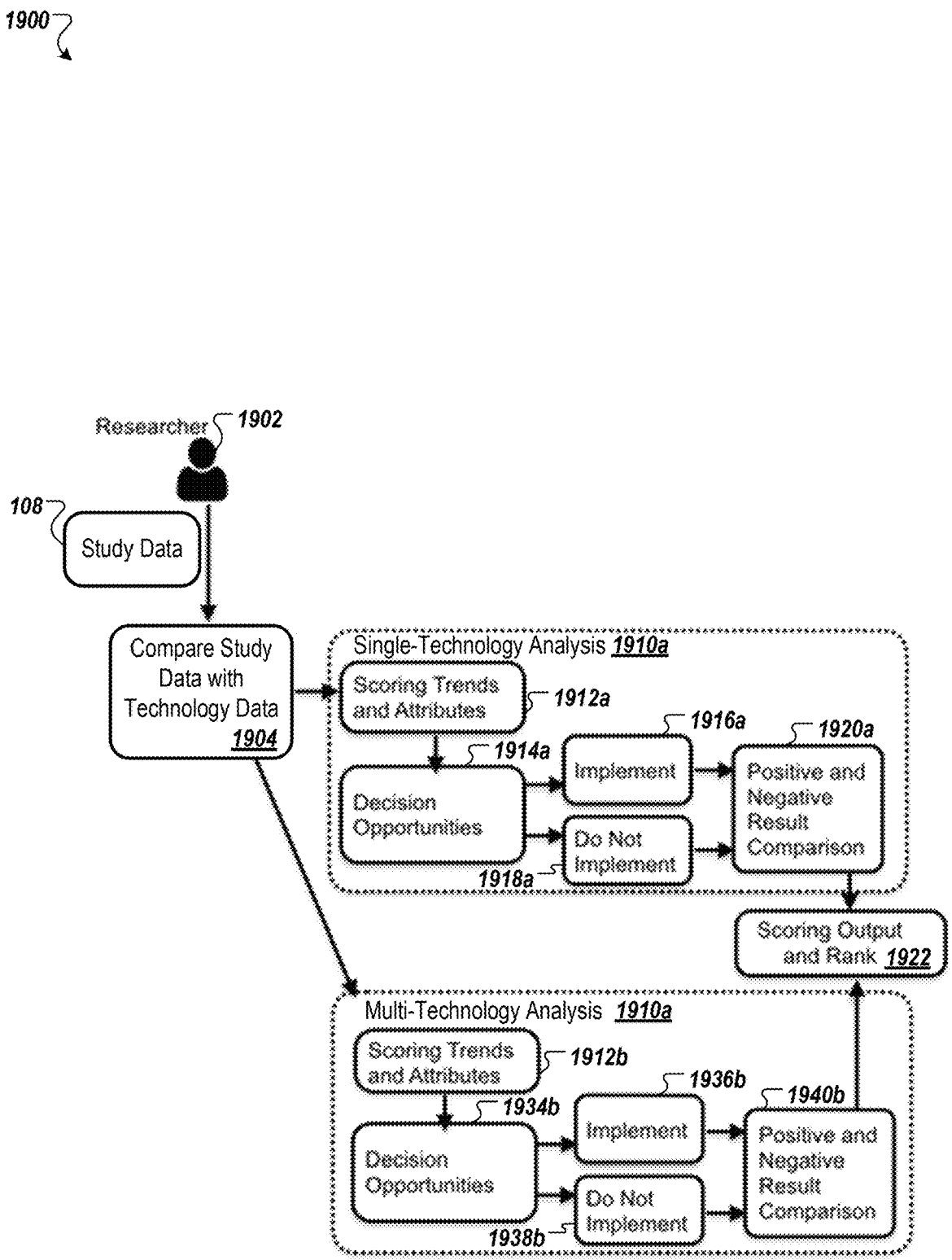
FIG. 19 is a diagram that illustrates an example scoring process of a system for assessing and selecting technologies.

FIG. 19 is a diagram that illustrates an example scoring process 1900 of a system for assessing and selecting technologies.

The process 1900 describes a scoring processing utility which can use two different analyses depending on the number of technology items in a given technology option. For example, as described in more detail below, the scoring processing utility can use a single-technology analysis 1910*a* when a technology option includes a single technology item. Alternatively, the scoring processing utility can use a multi-technology analysis 1910*a* for assessing a technology option that includes multiple technology items. The scoring processing utility can leverage machine learning models, taxonomy structures, and databases as described in more detail below with respect to FIGS. 1-2.

In some cases, the scoring processing utility can be the scoring processing utility 1834 shown in FIG. 18.

The process 1900 includes receiving study data. For example, the computer system 110 shown in FIGS. 1-2 can receive the study data 108 from a researcher 1902. The study data 108 can include study needs (e.g., one or more objectives for a study) and/or study parameters. The study data 108 can include an indication of one or more technology features that are required for the study. The study data 108 can indicate one or more cohorts of participants, groups of participants, and/or individual participants for the study.

The process 1900 includes comparing study data with technology data (1904). The study data can be compared with the technology data to identify technology items that are potentially suitable for a new research study. For example, with respect to FIG. 2, the computer system 110 can compare the study data 108 with the technology data 202 stored in the technology database 112. Comparing the study data with the technology data can include analyzing the study data to determine data types that need to be measured and/or analyzed for the new research study. For example, if the study data is in the form of a natural language query, analyzing the study data can include the computer system 110 identifying keywords in the natural language query, using a taxonomy structure from the taxonomy database 206 to identify technology nodes related to the identified keywords, using the technology nodes to identify technology items that have been associated with those nodes, etc.

In some cases, in analyzing the study data 108, the computer system 110 can use one or more machine learning models to identify keywords in the study data 108, to identify study needs or study parameters from the study data 108, to identify technology items based on the study data 108, etc. The one or more machine learning models can receive the study data 108 as input. The output of the one or more machine learning models can be, for example, one or more features/attributes required for the study, keywords (e.g., corresponding to data types needed for the study), and/or technology items that are potentially suitable for the new research study. Similarly, the output of the one or more machine learning models can be, for example, one or more feature/attribute values or ranges of values required for the study. The one or more machine learning models can use previously identified trends (e.g., trends in utilization of various technology items), one or more taxonomy structures accessed from the taxonomy database 206, and/or the technology data 202 to generate the output.

In some cases, comparing the study data with the technology data includes filtering technology items in the technology data. For example, the computer system 110 can filter the technology data 202 using the study data 108. The computer system 110 can remove technology items from consideration that are incompatible with the study. For example, the computer system 110 can remove technology items in the technology data 202 from consideration if they do not provide a type of data required for the study as indicated by the study data 108, if they do not technology feature/attribute required for the study as indicated by the study data 108 (e.g., don't have a sufficiently long battery life), if they do not provide every type of data required for the study (e.g., if the study data 108 indicates that only a single technology item can be used for the study), etc.

In some cases, comparing the study data with the technology data includes generating one or more technology options. For example, the computer system 110 can generate one or more technology options from the technology items that made it through the filtering process. The technology recommendation module 212 and/or the prediction module 214 of the computer system 110 can be used to generate the one or more technology options, e.g., from the study data 108 and the technology data 202.

The process 1900 optionally includes performing the single-technology analysis (1910a). The computer system 110 shown in FIGS. 1-2 can perform the single-technology analysis. Performing the single-technology analysis can include identifying individual technology items that are compatible for the study, e.g., the technology options that include a single technology item and that meet the study needs and/or study parameters as indicated by the study data 108. Identifying individual technology items that are compatible for the study can include identifying individual technology items that are compatible with the study needs, the study parameters, features/attributes required for the study, one or more cohorts of participants, one or more groups of participants, and/or one or more individual participants.

The single-technology analysis 1910a can be performed for one or more technology items. For example, the single-technology analysis 1910a can be performed by the computer system 110 shown in FIGS. 1-2 for each technology item in the technology data 202 or for a subset of technology items in the technology data 202 (e.g., after performing one or more filtering operations on the technology data 202). The subset of technology items in the technology data 202 can include those that were not filtered out by the computer system 110 using the study data 108.

For a given technology item, the single-technology analysis includes scoring trends and attributes for the technology item (1912a), considering decision opportunities for the technology item (1914a), choosing to implement the technology item (1916a) or choosing not to implement the technology item (1918a), and comparing the positive and negative results corresponding to the technology item (1920a).

In performing the single-technology analysis, the computer system 110 can use one or more machine learning models. For example, the computer system 110 can use a machine learning model to generate scores (e.g., suitability scores) for one or more technology options including a single technology item.

The process 1900 optionally includes performing the multi-technology analysis (1910b). The computer system 110 shown in FIGS. 1-2 can perform the multi-technology analysis. Performing the multi-technology analysis can include identifying groupings of technology items that are compatible for the study, e.g., the technology options that include a multiple technology items and that meet the study needs and/or study parameters as indicated by the study data 108. Identifying groupings of technology items that are compatible for the study can include identifying groupings of technology items that are compatible with the study needs, the study parameters, features/attributes required for the study, one or more cohorts of participants, one or more groups of participants, and/or one or more individual participants.

The multi-technology analysis 1910b can be performed for one or more technology options that include two or more technology items. For example, the multi-technology analysis 1910b can be performed by the computer system 110 shown in FIGS. 1-2 for various combinations of technology items in the technology data 202, e.g., where the combinations are selected by the technology recommendation module 212 and/or by the prediction module 214.

For a given technology option including two or more technology items, the multi-technology analysis includes scoring trends and attributes for the technology option (1912b), considering decision opportunities for the technology option (1914b), choosing to implement the technology option (1916b) or choosing not to implement the technology option (1918b), and comparing the positive and negative results corresponding to the technology option (1920b).

In performing the multi-technology analysis, the computer system 110 can use one or more machine learning models. For example, the computer system 110 can use a machine learning model to generate scores (e.g., suitability scores) for one or more technology options including two or more technology items.

With respect to the single-technology analysis and/or the multi-technology analysis, in scoring trends and attributes for the technology item(s), the computer system 110 shown in FIGS. 1-2 can, for example, obtain the technology data associated with the technology item from the technology data 202 stored on the technology database 112. The technology data can include one or more features/attributes of the technology item(s). In scoring trends and attributes for the technology item(s), the computer system 110 can additionally or alternatively access one or more previously identified trends for the technology item(s) and/or for a technology type (e.g., wearable devices, non-wearable devices, smart phones, smart watches, tablets, etc.) that includes the technology item(s). In scoring trends and attributes for the technology item(s), the computer system 110 can additionally or alternatively analyze stored data (e.g., usage data and/or sensor data) from one or more previously performed studies to identify trends for the technology item(s) and/or for a technology type that includes the technology item(s). In scoring trends and attributes for the technology item, the computer system 110 can additionally or alternatively analyze stored data (e.g., usage data and/or sensor data) from one or more previously performed studies to identify an attribute to associate with the technology item(s) and/or for a technology type that includes the technology item(s).

For example, the computer system 110 can leverage a machine learning model to determine, based on the characteristics of the participants (e.g., age, location, weight, sex, etc.) in one or more previous studies and/or the usage of the technology item(s) in those studies, that a new attribute should be associated with the technology item(s). For example, a machine learning model can be used to identify a utilization pattern of the technology item(s) and use this pattern for pattern matching/clustering. If the utilization pattern falls into a particular cluster associated with a bulky/large attribute (e.g., cluster that includes technology items that typically identified as bulky/large by participants, have previously been assigned a bulky/large attribute, etc.), the computer system 110 can determine that a bulky/large attribute should be associated with the technology item due to having been assigned to the cluster. The cluster can also be associated with certain participant characteristics (e.g., an age range of participants, a location where participants reside, a particular cohort of participants, a particular group of participants, a particular participant, etc.). The characteristics of participants from the one or more previous studies or of a subset of participants from the one or more previous studies (e.g., characteristics of the participants of the previous one or more studies with low utilization of the technology item) can be determined to match the participant characteristics of the cluster, e.g., prior to performing the clustering/matching.

For example, the utilization data can indicate that those between the ages of ten and twenty generally failed to wear a smart ring device. The computer system 110 can identify a machine learning model associated with an age group of participants that includes ages between ten and twenty and can proceed to use the machine learning model to analyze the utilization data. The machine learning model can associate with the smart ring with a particular cluster of technology items that share a bulky/large attribute. The computer system 110 can proceed to use the output of the machine learning model to associate the smart ring with a bulky/large attribute (e.g., the attribute can be conditional such that it is only applied when participants of a study include or include a threshold percent of participants that are younger than twenty years old).

With respect to the single-technology analysis and/or the multi-technology analysis, in considering decision opportunities for the technology item, the computer system 110 shown in FIGS. 1-2 can, for example, determine what aspects of the study can be fulfilled by the technology item(s) and/or adjust one or more features/attributes for the technology item(s) for the study (e.g., based on the study data 108).

In some cases, adjusting one or more features/attributes for the technology item(s) includes the computer system 110 adjusting one or more feature values based on the study needs and/or study parameters extracted from the study data 108. For example, the computer system 110 can leverage a machine learning model to identify the anticipated battery life for a particular smart phone based on the smart phone needing to be paired with a Bluetooth device (e.g., smart watch) for five hours a day for the study and the expected use time for the smartphone being eight hours a day for the study. The computer system 110 can, for example, provide the required/expected daily use time of the smartphone, the required/expected daily time that the smartphone will be paired to a Bluetooth device, and the smartphone's typical or maximum battery life (e.g., as indicated in the technology data 202) to calculate an estimated battery life for the smartphone.

In some cases, adjusting one or more features/attributes for the technology item(s) includes the computer system 110 ignoring or recognizing an attribute for the technology based on the study needs and/or study parameters extracted from the study data 108. For example, the study parameters can indicate that the study is to be performed at a first location. Based on the first location, the computer system 110 can determine that an "ugly" attribute should be enabled for a particular technology item. The ugly attribute can indicate low utilization (e.g., below 70%, below 60%, below 50%, etc.) for participants if the technology item is to be used in public. That is, the computer system 110 can take into account that participants residing in the first location historically have low utilization of this technology item (and/or of the type of technology that the technology item belongs to) in public spaces. However, if the study parameters instead indicate that the study is to be performed at a second location, the computer system can instead determine that an "attractive" attribute should be enabled for this same technology item (e.g., instead of the ugly attribute). The attractive attribute can indicate high utilization (e.g., above 70%, above 80%, above 90%, etc.) for participants if the technology item is to be used in public. That is, the computer system 110 can take into account that participants residing in the second location historically have high utilization of this technology item (and/or of the type of technology that the technology item belongs to) in public spaces.

With respect to the single-technology analysis and/or the multi-technology analysis, in choosing to implement the technology option, the computer system 110 shown in FIGS. 1-2 can, for example, simulate the study using the technology option. For example, the computer system 110 can simulate the use the of the technology item(s) given the study parameters, how the technology item(s) will be used in the study (e.g., based on the study needs), adjusted feature values for the technology item(s) for the study, enabled attributes for the technology item(s) for the study, etc. The computer system 110 can identify any benefits in using the technology item(s) in the technology option for the study, e.g., high precision of data being collected, high frequency of data being collected, high utilization, etc. The computer system 110 can identify any negatives in using the technology item(s) in the technology option for the study, e.g., low precision of data being collected, low frequency of data being collected, low utilization, etc.

With respect to the single-technology analysis and/or the multi-technology analysis, in choosing not to implement the technology option, the computer system 110 shown in FIGS. 1-2 can, for example, simulate the study without using the technology option (e.g., using one or more alternative technology options). For example, the computer system 110 can simulate the use of one or more alternative technology options that include technology item(s) given the study parameters, how the technology item(s) will be used in the study (e.g., based on the study needs), adjusted feature values for the technology item(s) for the study, enabled attributes for the technology item(s) for the study, etc. The computer system 110 can identify any benefits in using the technology item(s) in the one or more alternative technology options for the study, e.g., high precision of data being collected, high frequency of data being collected, high utilization, etc. The computer system 110 can identify any negatives in using the technology item(s) in the one or more alternative technology options for the study, e.g., low precision of data being collected, low frequency of data being collected, low utilization, etc.

With respect to the single-technology analysis and/or the multi-technology analysis, in comparing the positive and negative results corresponding to the technology option, the computer system 110 shown in FIGS. 1-2 can, for example, determine the success of the technology option for the study. For example, the computer system 110 can determine a suitability score for the technology option that includes the technology item(s) and/or one or more alternative technology options. As another example, the computer system 110 can determine a suitability score for the technology item(s) themselves. In comparing the positive and negative results corresponding to the technology options, the computer system 110 can identify the highest performing technology options. For example, the computer system 110 can rank the technology options based on the positive and/or negative results obtained from simulating the study.

The process 1900 includes scoring output and rank (1922). For example, the computer system 110 shown in FIGS. 1-2 can use the results of the single-technology analysis and/or the results of the multi-technology analysis to determine scoring output and rank of one or more technology items. Specifically, the computer system 110 can use the technology recommendation module 212 shown in FIG. 2 to perform the single-technology analysis and/or the multi-technology analysis. The technology recommendation module 212 can use the results from the single-technology analysis and/or the multi-technology analysis to determine suitability scores for the one or more technology options (e.g., each including one or more technology items), and to rank the technology options based on their suitability scores.

In general, the computer system can use the technology database 112 and the taxonomy to normalize data formats and lookup information about technologies. The information from research literature and past studies can be used as a filter or risk indicator to aid selection. The first-line analysis can include using the technology database 112 information to select and score candidate technology options. The computer system 110 can further refine scoring and selection by looking at how prior attempts resulted in actual practice. This can reveal issues such as whether compatibility with other devices is an issue, whether other researchers have researchers tried to use the technology and what rate they succeeded or failed, and scoring or ranking can be adjusted the ranking based on these factors. The computer system 110 also considers, at various steps in the process whether the performance or likelihood of success may be improved if a technology item is combined with another device, potentially creating a technology option that provides a greater rate of success.

Figure 20:
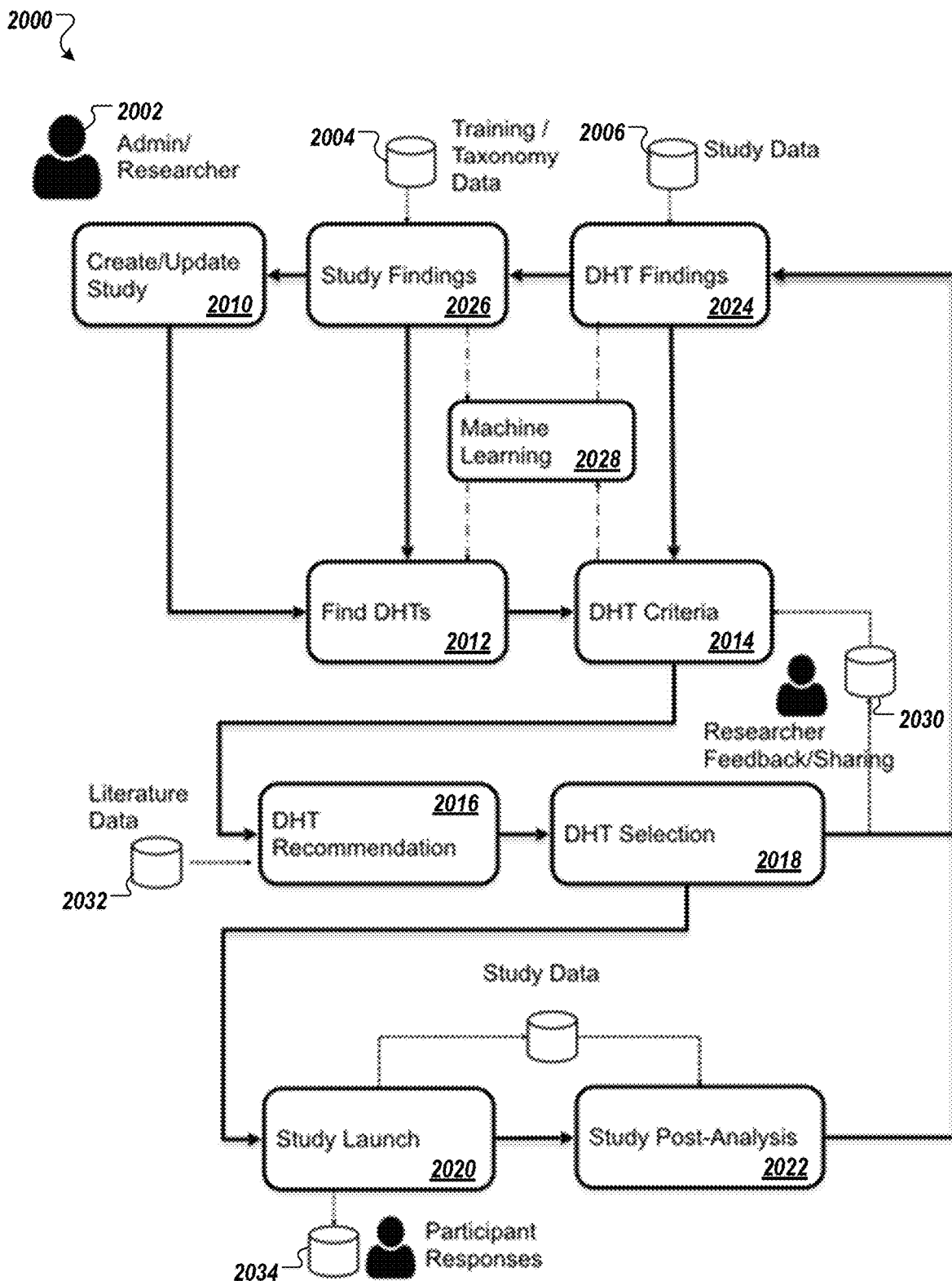
FIG. 20 is a diagram that illustrates an example interaction process of a system for assessing and selecting technologies.

FIG. 20 is a diagram that illustrates an example interaction process 2000 of a system for assessing and selecting technologies.

The process 2000 can indicate the research facing interactions of, for example, the computer system 110 shown in FIG. 2. The process 2000 shows an example creation of or modification to a study based on study findings or initial questions related to the study. As an example, the computer system 110 can find technology items (e.g., DHTs) based on criteria and machine learning suggestions that ultimately guide the admin/researcher 2002 into selecting a technology option. The findings, e.g., the selected technology options and/or the data collected from implemented technology items of the selected technology options, can be shared through a community of researchers or accessed by related literature showing relevance for additional citations to the research performed.

The process 2000 includes creating or updating a study (2010). For example, an admin/researcher 2002 can create or update a study. The admin/researcher 2002 can be the user 102 shown in FIG. 1 and can create a study by sending the study data 108 to the computer system 110.

The process 2000 includes finding technology items (2012). The operation for finding the one or more technology items can be based on previous study findings. As an example, with respect to FIGS. 2, the computer system 110 can identify one or more technology items from the technology data 202, e.g., using data provided by the admin/researcher 2002.

The process 2000 includes comparing the technology items to technology criteria (2014). The criteria can be based on previous findings, such as previous technology findings. The criteria can additionally or alternatively be based on the data provided by the admin/researcher 2002. The criteria can additionally be based on feedback received from one or more researchers (e.g., the admin/researcher 2002), or on data shared by one or more researchers such as previous technology option selections previously made by one or more researchers. As an example, the technology recommendation module 212 of the computer system 110 can be used to compare the technology options to study needs and/or study parameters extracted from the study data 108, and/or to other criteria determined from findings of one or more previous or ongoing studies. The criteria can be accessed from a database 2030. The database 2030 can store, for example, information indicating previously selected technology options, feedback from one or more researchers regarding a technology option or a specific technology item, etc.

The process 2000 includes generating a technology recommendation (2016). For example, a the computer system 110 shown in FIGS. 1-2 can select one or more technology options to recommend, e.g., based on the comparison of the technology items to the technology criteria. The computer system 110 can use the technology recommendation module 212 to generate the technology recommendation. The technology recommendation can be or included as part of the recommendations 222. Data stored in a literature database 2032 can be used, e.g., by the computer system 110, to make the technology recommendation. The literature database 2032 can be the research literature database 204 shown in FIG. 2.

The process 2000 includes selecting a technology option (2018). For example, the admin/researcher 2002 can select one of the recommended technology options to use for the study. An indication of the admin/researcher 2002's selection can be stored in the database 2030.

The process 2000 includes launching the study (2020). Launching the study can include the computer system 110 shown in FIGS. 1-2 sending one or more notifications to study participants or potential study participants (e.g., asking them to confirm participation). Launching the study can include the computer system 110 shown in FIGS. 1-2 transmitting one or more software modules, one or more software installers, one or more software configurations/profiles, etc. to the participant devices.

Once the study is launched, feedback can be received from the participants. For example, the admin/researcher 2002 can configure the study to ask for participant feedback once every day, every week, every month, etc. The participant responses can be stored in a database 2034. In some cases, the computer system 110 can recommend one or more alternative technology options and/or technology items based on the participant responses.

Once the study is launched, study data can be collected from the technology items used in the study. The study data can include usage data indicating the utilization of the technology items in the study by the study participants. The study data can include sensor data such as measurements collected by the technology items used in the study. With respect to FIG. 2, the study data can be collected and analyzed by the monitoring module 216 of the computer system 110 and can be used in generating the monitoring results 226. In some cases, the computer system 110 can recommend one or more alternative technology options and/or technology items based on the study data.

The process 2000 includes performing a study post-analysis (2022). Performing a post-analysis can include, with respect to FIG. 2, the computer system 110, analyzing the study data and/or the participant responses. Performing a post-analysis can additionally include the computer system 110 obtaining (e.g., requesting and receiving) feedback from one or more researchers of the study including, for example, the admin/researcher 2002.

The process 2000 includes determining technology findings (2024). With respect to FIG. 2, determining technology findings can include, for example, the computer system 110 (e.g., through the monitoring module 216) using the results of the study post-analysis to identify an overall utilization of the technology items used in the study by the study participants, determining an average battery life for one or more technology items over the course of the study, determining the precision of data collection by one or more technology items over the course of the study, determining the frequency of data collection by one or more technology items over the course of the study, etc. The technology findings can be used to, for example, update the technology criteria. The technology findings can be used in determining study findings as described below. The technology findings can be provided to one or more machine learning models as input and/or can be used as training data to train one or more machine learning models.

The process 2000 includes determining study findings (2026). With respect to FIG. 2, determining study finding can include, for example, the computer system 110 (e.g., through the monitoring module 216) using the results of the study post-analysis and/or the technology findings to determine an overall percent of active participants (e.g., those that are reporting), to determine an overall utilization of one or more technology items by active participants, to determine whether a technology item in the study was successful or not using one or more standardized metrics, etc. The study findings can be used to, for example, update the process for finding technology items (e.g., to update the filtering process for selecting technology items, to add one or more attributes to a technology item, to remove one or more attributes to a technology item, to adjust a feature value for a technology item, etc.). The study findings can be provided to one or more machine learning models as input and/or can be used as training data to train one or more machine learning models.

The study findings can be used for updating the study. For example, the admin/researcher 2002 can use the study finding to determine that one or more technology items being used for the study need to be replaced due to low utilization, poor data precision, poor data collection frequency, etc.

The process 2000 optionally includes using one or more machine learning models (2028). For example, the study findings and the technology findings can be used to train one or more machine learning models. The output of the machine learning models can be used to find (e.g., lookup) technology items, to adjust how technology items are found, to add attributes to technology items, to remove attributes from technology items, to adjust feature values for technology items, to modify technology criteria, etc. For example, the feedback from participants and/or sensor data for the study can indicate that the real-world battery life of one of the technology items selected for the study is about 20% less than expected. The feedback and/or sensor data can be provided to a machine learning model as input. One or more study parameters may also be provided to the machine learning model as input such as, for example, an indication of how the technology item was being used in the study, an indication of any devices that the technology item was connected to (e.g., Bluetooth paired devices), an indication as to whether the technology item was being connected to a network (e.g., Wi-Fi or cellular network), etc. The machine learning model can provide output that indicates that the technology criteria for this study is that the battery life for a suitable technology item is 30% greater than the prior battery life requirement.

Figure 21:
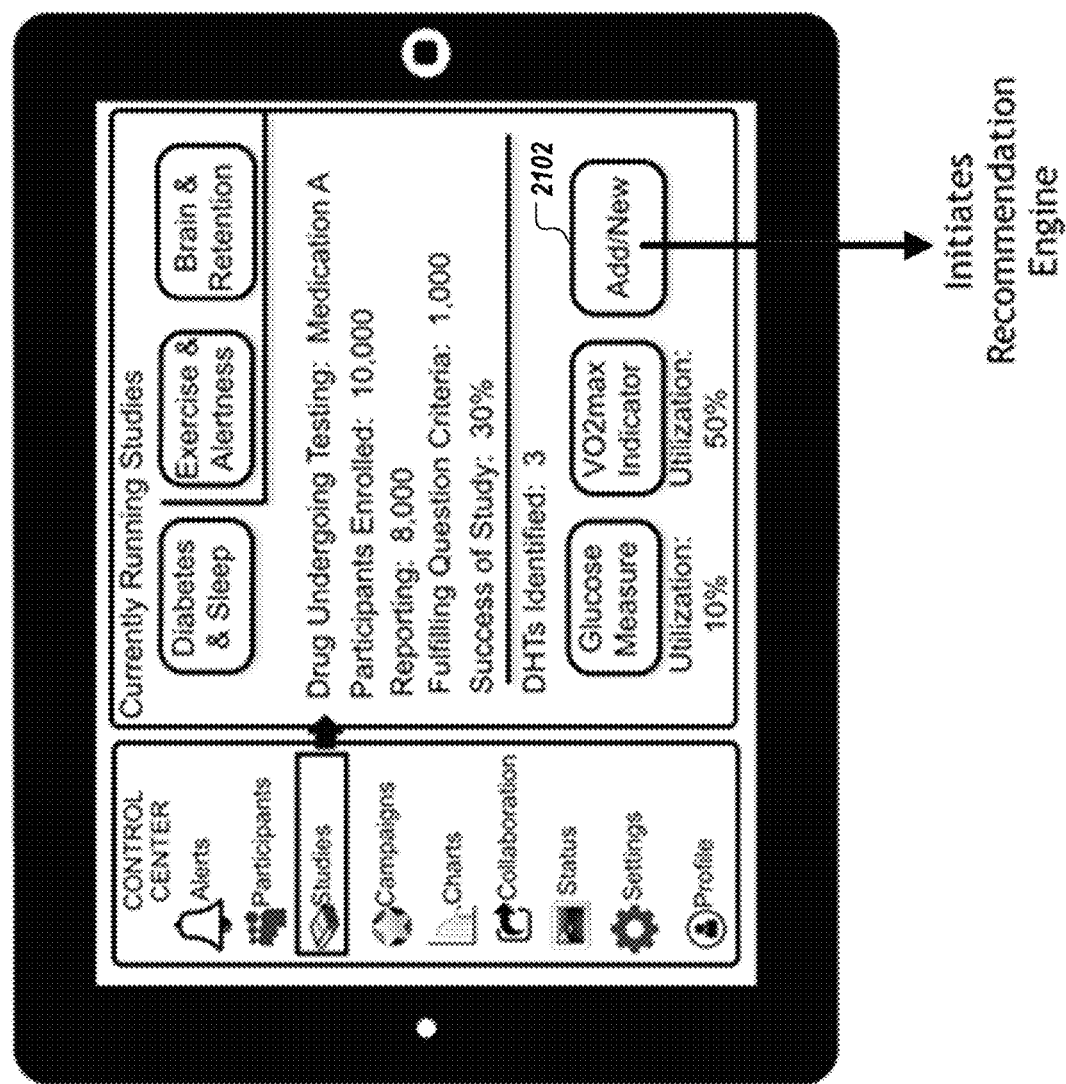
FIG. 21 is a diagram that illustrates an example interface for monitoring technologies.

FIG. 21 is a diagram that illustrates an example interface 2100 for monitoring technologies.

The interface 2100 can be presented on a client device, such as the client device 104 shown in FIGS. 1-2. The interface 2100 can be that of a mobile application running on the client device or of a web portal related to a researcher for one or more studies (e.g., the user 102). For example, the researcher can use the interface 2100 to configure one or more upcoming studies, to make changes to one or more currently running studies, to review sensor data collected and/or usage results for one or more currently running studies, etc. The interfaces 2100 can allow a researcher, for example, to select from among a list of currently running studies to view in more detail. For example, as shown, a researcher has selected the "Diabetes & Sleep" study that is currently running. The interface 2100 can present more detailed information for the research study selected. For example, as shown, the interface 2100 can provide the researcher an indication of one or more pharmaceuticals that are being tested with the study, the number of participants enrolled in the study, the number or percent of participants that are reporting data (e.g., sensor data to the computer system 110), the number or percent of participants that are meeting the study criteria (e.g., utilization criteria), the number or percent of participants that are providing feedback, an overall success of the study (e.g., can be based, at least in part, on the overall utilization, and/or on a comparison of the utilization to study criteria), etc.

The interface 2100 can also include an indication of the one or more technology items that are being used in the selected study. For example, as shown, the selected diabetes and sleep study includes glucose measure technology item and VO2max Indicator technology item. The interface 2100 can also include an indication of the current utilization of each of the technology items used in the study. For example, as shown, the utilization for the glucose measure technology item is presently only 10%, and the utilization for the VO2max indicator is presently 50%. These utilizations can be used to determine the current success of the study.

The interface 2100 can also include an interface element 2102 to add a new technology item to the selected study, e.g., to the diabetes and sleep study. By selecting the interface element 2102, the computer system 110 can be notified that a user of the client device (e.g., the client device 104) is requesting a recommendation. The computer system 110 can receive study data for the currently selected study (e.g., the diabetes and sleep study) along with the request for a recommendation, or can lookup study data previously provided to the computer system 110 using an identifier for the currently selected study that is sent along with the request for a recommendation. The computer system 110 can provide the request and/or the study data for the currently selected study to the technology recommendation module 212. The technology recommendation module 212 can generate a technology recommendation for the researcher that includes one or more technology items that can be used with the preexisting technology items that are already in use in the study (e.g., the glucose measure technology item and the VO2max indicator technology item), or can be used to replace one or more of the preexisting technology items (e.g., can be used to replace the glucose measure technology item and/or the VO2max indicator technology item).

In some implementations, the interface element 2102 is additionally or alternatively an interface element to replace one or more preexisting technology items in use in the selected study.

In some implementations, the interface 2100 includes an interface element for replace one or more preexisting technology items in use in the selected study.

As study inputs, the system (e.g., the computer system 110) is aware of the categorical needs of the study, for example Diabetes and Sleep. There are metrics as to the overall monitoring of the success of the study outcomes. These metrics can be used to evaluate the statistical relevance based on individuals reporting. For new technologies (e.g., DHTs), there is a utilization factor presented based on the scoring to help describe what can be enabled and to what extent will it be used. Once deployed, the researcher can check back for success improvements.

FIG. 22 is a diagram that illustrates an example table 2200 relating pharmaceuticals and technologies. Pharmaceutical development includes monitoring the therapeutic target and the absorption while considering the necessary volume of distribution and ensuring that toxicity and interactions are understood and manageable.

The table 2200 and/or its data can be stored in the technology database 112 shown in FIG. 2, e.g., as part of the technology data 202. The table 2200 and/or its data can be stored in the research literature database 204 shown in FIG. 2.

As indicated by the table 2200, many pharmaceuticals can manage multiple therapeutic targets, through indications and off-label usage. Having multi-therapeutic targets or polypharmacology, can lead to varying screening methodologies in the development phase. These methods then undergo testing through discovery, pre-clinical and clinical trials as the drug is manufactured and regulatory authorizations such as a premarket approval (PMA) is acquired.

The toxicity of a given dosage can be detectable using technologies such as DHTs. As limits are reached, detectable conditions such as convulsions detectable by changes in movement through actigraphy using accelerometers and six degrees of freedom related sensing, ECG/EKG changes, cardiac arrhythmias, heart rate variability (HRV) common with stress related detection, respiratory changes through photoplethysmography (PPG), blood oxygen levels using SpO2, and respiration, body temperature consistent with fevers, and reactions such as hypotension (e.g., hypotension can be measured as blood pressure in response to circulatory shock).

The system 100 described with respect to FIG. 1 or the system 200 described with respect to FIG. 2 can be applied to the needs of pharmaceutical research phases through drug discovery, drug development, and assessing drug interactions through clinical trials and regulatory PMAs to help observe participants through effective evaluations, selections, and implementations of technology items (e.g., DHTs). For instance, the success of a study can be improved for various indicators of success, such as health improvements and toxicity considerations.

The table 2200 provides examples of representative technology items (e.g., DHTs) in varying situations of treatment.

The one or more technology items can be recommended by the computer system 110 shown in FIGS. 1-2, e.g., for participants undergoing a particular treatment and/or using a particular pharmaceutical. The one or more technology items can be recommended by the technology recommendation module 212 shown in FIG. 2. The one or more technology items can form a technology option recommended by the technology recommendation module 212.

The computer system 110 can obtain sensor data and usage data from the client devices 208. The client devices 208 can belong to, for example, participants undergoing treatment using a pharmaceutical. The sensor data obtained by the computer system 110 from the client devices 208 can include, for example, detected toxicity levels (e.g., Hypoglycemia indications, cardiac irregularities, fever, low blood pressure, etc.). The computer system 110 can provide the sensor data to the monitoring module 216. The monitoring module 216 can compare the sensor data to one or more expected values or ranges of values. If the sensor data corresponding to one or more participants goes beyond an expected value, beyond a range values, falls below an expected value, falls below a range of values, goes a threshold percent beyond an expected value, goes a threshold percent beyond a range of values, falls a threshold percent below an expected value, and/or falls a threshold percent below an expected range of values, then the monitoring module 216 can generate one or more alerts. These alerts can be included in the monitoring results 226. When an alert is generated, the computer system 110 can notify the client device 104, can notify a doctor for the corresponding participant, can notify emergency services (e.g., by sending the alert to an external emergency services system), etc.

Figure 23:
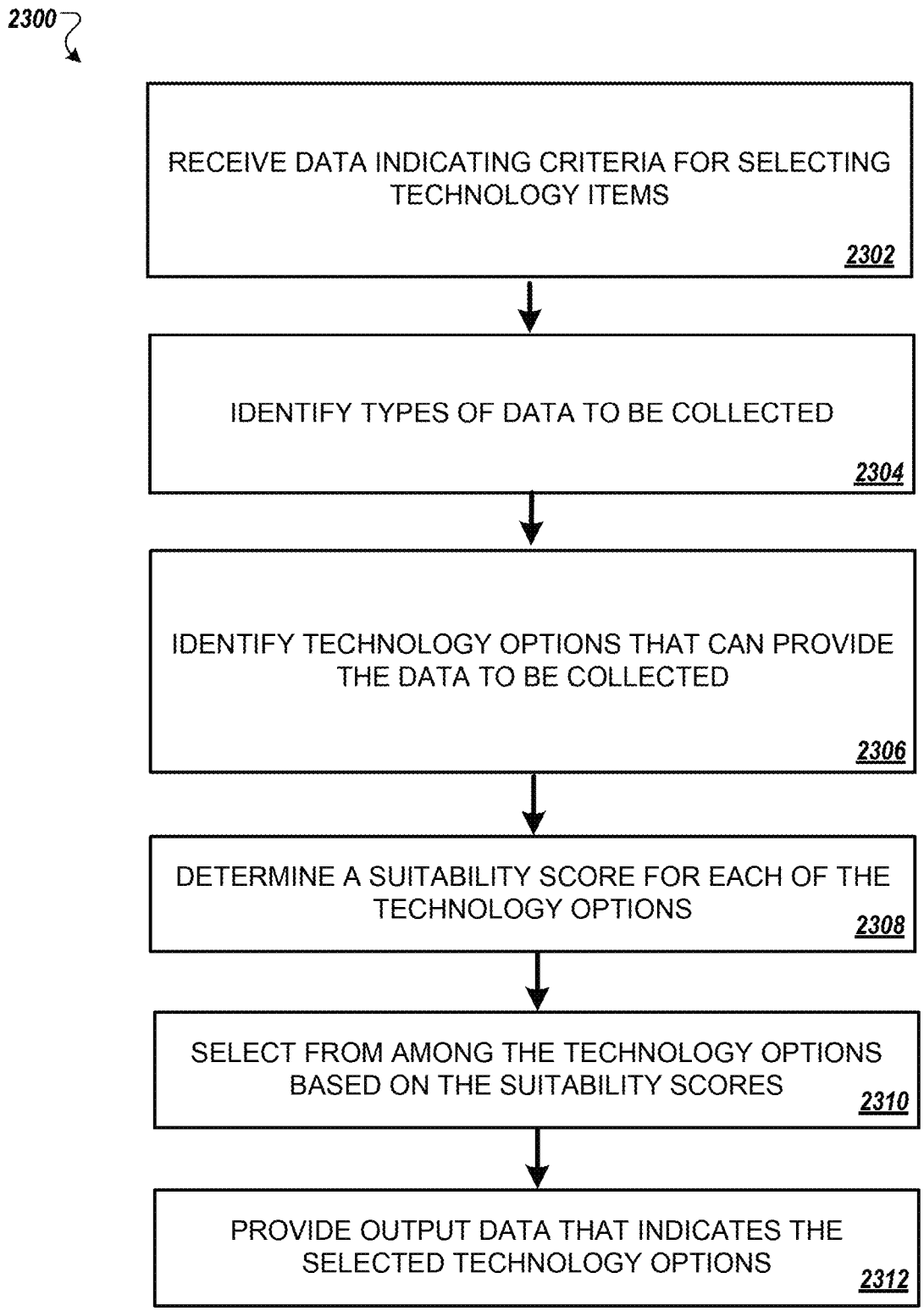
FIG. 23 is flowchart diagram that illustrates an example process for recommending technologies.

FIG. 23 is a flowchart diagram that illustrates an example process 2300 for recommending technologies. For example, the process 2300 can be used to evaluate the various technology items and recommend technology items determined to have the characteristics likely to meet the needs of, for example, a cohort, a group of individuals, an individual, etc. The technology items can be selected based on a set of selection criteria, such as desired functions or capabilities of the technology items, a desired use of the technology items, a type of data to be collected, communication abilities (e.g., types of network connectivity), cost, size, availability, and/or other factors. The process 2300 may be performed by one or more computers, such as the computer system 110 shown in FIGS. 1 and 2. As another example, the process 2300 may be performed in whole or in part by a client device, such as device 104 of FIGS. 1 and 2. Similarly, the operations of the process 2300 may be distributed among one or more servers, one or more client devices, and/or other computing systems.

The process 2300 includes receiving data indicating criteria for selecting technology items (2302). In some implementations, the criteria may specify features or characteristics of the technology, such as a desired level of battery life, a size constraint, or a function or use the technology would need to support. This level of specificity is not required however. In many situations, the computer system 110 is able to take data representing a topic, use case, or situation and infer some or all of the capabilities that suitable technology items would need. For example, using the taxonomy discussed above, if the general use of "tracking sleep" is indicated by a user, the computer system 110 can identify the node in a taxonomy graph (see FIGS. 5, 6A, 6B) that corresponds to sleep, and from connections to that node identify the related data gathering capabilities needed (e.g., activity or movement tracking, heart rate tracking, etc.), and potentially even identify technology types (e.g., device types, application types, etc.) or specific technologies (e.g., specific models of devices or specific applications) that would be effective. More simply, the computer system 110 may store taxonomy data that maps keywords (e.g., individual terms or phrases) to corresponding criteria. In other situations, the computer system 110 may use a semantic model or a machine learning model to determine constraints or requirements that technologies would need to meet, based on a description of a study, study protocol, or other study data.

As an example, the computer system may receive study data that indicates parameters of a research study or an objective of a research study. The study data can include information about the purpose, type, or design of the study, which may or may not specify any specific technology features, uses, or characteristics. For example, with respect to FIGS. 1-2, the study data can be the study data 108 that indicates a natural language statement of a desired component of the study, e.g., to "track sleep and blood pressure." This data can be provided through a user interface, such as a desktop application, a mobile application, a web page, a web application, etc. The data can be provided to the computer system 110 through an application programming interface (API) in some implementations.

In some cases, the computer system provides data for a user interface for creating or updating a research study. The user interface can include one or more controls configured to receive user input specifying at least one of parameters of the research study or an objective of the research study. The user interface can then receive data indicating interaction with the user interface that provides the study data through the user interface. The one or more controls can include text input fields, buttons, sliders, drop-down menus, radio buttons, check boxes, controls to select from among predetermined parameters or enter new parameters, and so on. In this manner, the study data can relate to a new research study being created, an existing study, an ongoing research study, etc. In some cases, such as for re-evaluating the technology for an existing study, the study data can be retrieved from records for the existing study.

The parameters of a study can include, for example, a time duration of the study, one or more locations where the study will be conducted, one or more locations where study participants are located, identifying information for one or more cohorts of participants or individual members of cohorts, cohort inclusion criteria for selecting members of a cohort, data types for data to be collected in the study, a frequency of data collection for the study, activities or conditions to be monitored during the study, etc. Other types of study parameters include cohort size (e.g., number of participants), number of locations, geographical distribution of locations or participants involved, types of participants (e.g., demographic attributes, medical status, etc.), procedures to be used to collect data, precision and accuracy needed, types of participant outcomes to be measured, study requirements (e.g., whether the study is double-blind, randomized, controlled, etc.), and so on. Any or all of these parameters may potentially affect the selection of technology items for a cohort. For example, for a study with a small number of participants, the computer system 110 may favor a more expensive device with high accuracy and high rates of successful use (e.g., use in compliance with study protocols). However, for a study with a large cohort, the computer system 110 may rank a less expensive device as more recommended, even if accuracy and success rates are lower, given the need to purchase the device for a larger number of people. In general, the parameters of the research study can include the protocol, process, settings, characteristics, requirements, needs, constraints, or other data used to define or describe the research study and how it will be conducted. The parameters can be input by a user or may be determined by the system (e.g., added, inferred, or recommended based on user input that does not directly specify the parameters).

The objective for a study can refer to the purpose or goal of the research study, such as the type of information intended to be gained through the study. In some cases, the objective may be expressed through a research question to be addressed, one or more topic(s) of a study, a disease or condition for the study to address, a natural language statement or query (e.g., statement of intended activities or actions in the study), etc. The objective may also refer to the type of study. For example, different types or phases of clinical trials can have different objectives, which can affect the types of data to be collected and conditions to be monitored and thus affect the technology options that are selected by the computer system 110. A phase 0 trial may be experimental, with the aim to determine how a drug is processed by the body. A phase I trial may be used to evaluate drug safety and dosage, for example, to find the best dose of a drug that has limited side effects, by gradually increasing dosage until side effects become too severe or positive effects are observed. A phase II trial can be used to assess safety as well as effectiveness of a drug, potentially evaluating effects of a drug in combination with other drugs or other factors. A phase III trial may be used to further assess safety and effectiveness of a drug, for example, to compare effectiveness of a drug with a reference, such as a current standard-of-care drug. As different types of trials have different monitoring and reporting needs, the computer system 110 can use these parameters to determine the needed features of technology items and then determine which technology items provide the needed features.

The process 2300 includes identifying types of data to be collected during the research study (2304). For example, the computer system 110 can use the study data to determine types of data that technology items will need to collect and provide over the course of the study. The types of data that may be biological, physiological, behavioral, mental, emotional, environmental, social, or other types of information. For example, examples of physiological data types include weight, muscle mass, heart rate, sleep, nutrition, exercise, lung capacity, brain activity, etc. As another example, mental or emotional data types may include indicators of mood, mental health, alertness, etc. In general, "types of data" or "data types" herein refers to the characteristics or attributes to be monitored, e.g., the class or category of content to be detected or measured, not merely to the form of the data representation for that content (e.g., whether the data is expressed in binary, floating point, text, file type, media type, or other forms). Nevertheless, the form of data representation may be an important in some instances, and may be an indicator of the level of precision or usability of the collected data, and so may optionally be identified and considered by the computer system 110 in selecting technology options.

The computer system 110 can extract data types from the study data. For example, the study data may indicate user selections of predetermined types of data, indicating that the selected types should be selected. The computer system 110 can also use natural language statements or other study data to identify data types to be collected. The computer system 110 can store a list of known data types, for example, as part of a taxonomy. The computer system 110 can then identify keywords in natural language input, and then use taxonomy data that indicates relationships between terms and types of data to identify types of data corresponding to the keywords. For example, the taxonomy can be used to map a term such as "diabetes" in study data to a data type to be measured, such as blood glucose level or Hemoglobin A1C level. Similarly, a reference to "weight" in study data may be used to identify data types such as exercise tracking (e.g., step count, actigraphy, etc.), diet tracking, nutrition tracking, and so on. Direct keyword matching is not required. For example, the computer system 110 can use natural language to identify a topic based on the keywords or study data overall, and then map the identified topic(s) (e.g., "exercise") to data types using the taxonomy. The taxonomy can thus provide a mapping of key terms or topics to predetermined data types, which the computer system 110 can use to identify the data types most relevant to the current study data. As discussed above, the system 110 can learn which data types correspond to different keywords or topics from research literature examples and other data sources.

The process 2300 includes identifying technology options that can provide the data to be collected (2306). The technology options can each include one or more technology items. In other words, a technology option may represent a single item (e.g., a single device or software module) or may include a combination of multiple items (e.g., multiple devices, multiple software modules, a combination of hardware and software, etc.). Examples of categories of technology items include computing devices, wearable devices, medical devices, sensors, software applications, and software modules (e.g., drivers, software libraries, etc.). The technology items used to generate the technology options can indicate a specific type of item, e.g., a smart phone or smart watch, and/or specific models of devices and specific software modules. In this manner, the computer system 110 can be used to evaluate and recommend specific devices from among multiple devices in a product line of a manufacturer, or to evaluate and select between different versions of a device or software product.

Identifying technology options can include identifying one or more technology items that can provide (e.g., collect) one of the identified types of data. For example, the computer system 110 can access a technology database 112 that (i) indicates multiple technology items and (ii) indicates, for each of the multiple technology items, one or more types of data that can be collected using the technology item.

Identifying technology options can include filtering the broad set of technology items from the technology database to those items that provide the capability to collect at least one of identified types of data to be collected in the study. The computer system 110 can then generate technology options from the filtered set of items. For example, if a study is determined to need collection of two types of data, the technology options can include (i) individual technology items that can collect both types of data, as well as (ii) combinations of multiple technology items that together can provide both types of data, even if they individually could not.

In some implementations, the computer system 110 may filter the technology options further based on the study data, for example by eliminating technology options that fail to meet criteria expressed in or derived from the study data. Additionally or alternatively, the computer system 110 can incorporate information about technology options that do not meet study needs into the process of generating a suitability score.

The process 2300 includes determining a suitability score for each of the technology options (2308). The suitability score for a technology option can indicate a degree of relevance or match between one or more technology item(s) and the criteria for technology selection. For example, a suitability score can indicate how well the capabilities and characteristics of a technology item satisfy the needs of a research study, as indicated in or inferred from the study data. The suitability scores can be determined based on a variety of factors. In general, the computer system 110 may compare the characteristics of technology items, as indicated by the technology database 112, with the needs (e.g., criteria or requirements) of the study, as indicated by or inferred from the study data. Technology options that meet the needs of a study are scored to have high suitability, while technology options that do not fully meet the needs of the study are indicated to have lower suitability. In addition, the computer system 110 can identify any incompatibilities between a technology option and the study needs, and can lower indicated suitability in response.

The suitability scores can indicate, e.g., can be at least a factor in determining, the rank of the technology options as discussed above. The suitability scores can be determined by, for example with respect to FIGS. 2 and 8B, the technology recommendation module 212 of the computer system 110. For example, the suitability score can be a technology score determined by the technology recommendation module 212. In some implementations, the suitability score for a technology option can indicate the anticipated level or likelihood of success for the technology option if used in the research study.

In determining the suitability scores, the primary or highest-weighted factors considered are those for which the study data indicates a constraint or requirement. For example, results of comparing the capabilities of technology options and the capabilities required for the study have the highest influence on the suitability scores. The computer system 110 can set the suitability scores using various factors, regardless of whether the study data does specifies a constraint for that factor. For example, factors such as higher reliability, lower cost, higher durability, greater availability, greater accuracy, greater precision, greater network connectivity options, longer battery life, faster processing capability, higher interoperability, and so on can boost the suitability score even in the absence of any study-specific requirements for those factors. The computer system 110 may use data in the technology database 112 to assess these factors, and may generate a combined score (e.g., a weighted score or composite score) that takes into account the various factors.

The types of data that a technology option can collect may affect the suitability score. Although the computer system 110 may filter the set of technology options to those providing at least the minimum set of types of data (e.g., in step 2308), the ability of some technology options to provide additional data types not strictly required for the study can be an advantage that boosts the usefulness of the technology and thus the suitability score. In other words, even if all of the technology options being considered provide the base set of necessary data collection, some technology options provide additional data collection capabilities (or other functions or capabilities more generally) which may benefit the study or provide researchers with added versatility.

In generating the suitability scores, the computer system 110 can use data describing historical usage rates of technology items. For example, the technology database 112 or other data sets may indicate rates at which users asked or assigned to use a given technology item actually used or successfully used the technology item. Incorporating this information into the suitability score can help steer technology selection toward technologies that are easier to use and are more acceptable to users, and away from those that are more difficult to use. Thus, the suitability score for a technology option can be boosted or decreased based on actual real-world usage rates and success rates for using the technology item(s) that make up the technology option. As with other factors considered in determining the suitability scores, the computer system 110 can generate a sub-score for this factor, with the value varying based on the historical usage data, and then combine the different factors scores, e.g., using a weighted average of different sub-scores.

Optionally, the suitability score can take into account the attributes and needs of individuals or groups of individuals who will use the technology items. This allows the computer system 110 to generate the suitability scores in a way that customizes the scoring, and ultimately the technology selection, for individual preferences and tendencies. This can be done by identifying historical usage rates or success rates for subsets of users that have certain attributes, e.g., determining different usage rates for users in different age ranges. As an example, the demographic makeup (e.g., age distribution, sex distribution, etc.) of a cohort for a study can affect the suitability scores, as some options may be more appropriate for some age groups than others. In some cases, in addition to or instead of using historical usage rates or success rates, a machine learning model or statistical analysis can be used to generated a predicted usage rate or success rate tailored to the attributes of the cohort.

To take into account the differing needs of individuals or groups related to a study, the computer system 110 can generate, for each technology option evaluated, a set of different suitability scores for different groups of individuals involved in a study. For example, a particular technology option may be assigned a first suitability score for a first portion of the cohort having a first demographic profile, based on historical or predicted usage rates or success rates for the first demographic profile. The same particular technology option may be assigned a second suitability score for a second portion of the cohort having a different, second demographic profile, based on historical or predicted usage rates or success rates for the second demographic profile. In some cases, a single technology option may be assigned a different suitability score for each study participant or candidate for the study. The different suitability scores can result in different technology options being selected and recommended for different members of a cohort for a study. Actions to customize selection of technology for individuals and groups is described in further detail with respect to FIG. 24.

The process 2300 includes selecting from among the technology options based on the suitability scores (2310). The computer system 110 may select a single technology option, e.g., the one assigned the suitability score that indicates the best fit for the needs of the study. The computer system 110 may select multiple different technology options as alternatives for a user to select among. For example, the computer system 110 can rank the technology options based on the suitability scores and select one or more of the highest-ranking options. For example, the computer system 110 can select the technology option with the score that indicates the highest suitability for the study or select a predetermined number or portion of the technology options (e.g., the top 3 options, the top 5 options, the top 5%, the top 10%, etc.).

In some implementations, the computer system 110 applies a threshold to the suitability scores and selects each technology option assigned a suitability score that satisfies the threshold. The computer system 110 can apply a threshold in addition to selection based on ranking or selection of the option having the highest score. For example, the top 5 technology options may be identified based on the scores, but the computer system may further filter that set of options to include only the options that have at least a minimum suitability score.

As discussed, above, the computer system 110 can select one or more technology options to recommend to a researcher associated with the research study. For example, the technology recommendation module 212 can use the suitability scores for each of the technology options in determining one or more technology options for the recommendations 222. The technology recommendation module 212 can select, for example, a predetermined number of technology options having the highest suitability scores, all technology options having a suitability score above a threshold score, or a predetermined number of technology options having the highest suitability scores provided that the technology options also have a suitability score above a threshold score. As another example, the computer system 110 can use the suitability scores as an input to an algorithm or function to determine one or more technology options to recommend.

The process 2300 includes providing output data that indicates the selected technology options for the research study (2312). In many cases, the information is provided to a researcher or other user that is creating or reviewing a study. The selected technology options can be provided as recommendations of technologies to add to a study, e.g., for participants in a cohort to use during the study. Accordingly, the selected technology options can be provided as recommendations for updating the data collection procedures or study protocol for the study. In some implementations, technologies can be selected and recommended for other purposes that may be independent of a study, such as for clinical use by a patient, for use by a doctor or researcher (e.g., as opposed to a patient or study participant), for delivery of digital therapeutics, for diagnostic use, etc.

The process 2300 of selecting technology options and indicating the selected options can be performed in response to a request, such as a query entered by a user, a message through an API, a user activating functionality to request a recommendation, etc. Alternatively, the computer system 110 may automatically generate recommendations simply as part of a workflow or when a certain user interface screen is generated. The computer system 110 may also generate and provide recommendations of technology options when the computer system 110 detects other events or conditions such as: a change in study data (e.g., prompting re-evaluation of the suitability of different technologies for the updated set of technology selection criteria or study characteristics); a change in technology options that are available (e.g., in response to updates to the technology database 112 adding or removing technology items or updating listed characteristics); or monitoring of technology use in the study indicates that a study is not generating a desired level of usage by participants or that collected data does not meet standards for the study (e.g., when the type, quantity, frequency, accuracy, or consistency of data is insufficient).

The output data can be provided in any of various forms. For example, an indication of the selected one or more technology options can be displayed on a user interface, outputted through an application programming interface (API), sent over a communication network to one or more devices (e.g., client devices, servers, storage devices, etc.), provided for display through a web page or application on a client device, provided as an electronic message (e.g., an e-mail, a notification or alert through a mobile device, a short message service (SMS) text message, output of a voice interface or digital conversational assistant, etc.), and so on. For example, the output data can be included in a notification, e.g., sent by the computer system 110 shown in FIG. 2. In many cases, the output data causes an indication of the selected technology options to be provided on a user interface for designing, updating, or monitoring a study.

The output data can include scores that indicate the relative suitability of different technology options. These can be, for example, the suitability scores, the rankings of the technology options, scores that indicate how well each option meets the needs of the study (e.g., a percentage indicating what percentage of study needs are met by the technology option), etc. The output data can include the ranking of the selected technology options so the options are displayed in rank order or otherwise distinguished based on rank. The output data can include data describing each selected technology option, such as a list of technology items included in that option, capabilities and characteristics of the technology items (e.g., features, functions, specifications, etc.), descriptive information (e.g., a technology item name, a model number, a manufacturer name, a classification or type for the technology item, a text summary or description of the technology item, a web link to a page providing more information, etc.), limitations or constraints on use of the technology item, and so on.

To assist users in selecting an appropriate technology option, the output data can indicate criteria from the study data or technology selection criteria and an indication of how well each technology option meets those criteria. For example, if study data indicates three requirements for technology, then for each of the selected technology options the output data can indicate a score for each of the three criteria. The scores may be indicated as numbers, color coding, icons (e.g., a check mark to show a feature is present or an "X" to show the feature is missing), and so on. This can demonstrate the needs of the study that the respective technology options satisfy and those that the options do not satisfy. The computer system 110 can use sub-scores generated earlier (e.g., as components for generating the suitability score) for this purpose, and may permit ranking other indication of how well each technology option fits different aspects or needs of the study.

In some implementations, the output data includes a table or list showing a comparison of features of the selected technology options. Based on information from the technology database 112, the computer system 110 can provide indicators (e.g., ratings, scores, icons, etc.) for factors such as capabilities, data collection abilities, battery life, size, cost, and so on. In addition, or as an alternative, the output data can include measures of historical or predicted usage of the technologies, e.g., by study participants in the current study and/or other studies. This can include providing historical or predicted compliance by study participants with specific elements of the study (e.g., usage of specific functions of the technology items, collection of a specific type of data) or with the protocol of the study as a whole. The output data can include estimates of data quality (e.g., frequency, accuracy, precision, etc.) of the data types that the computer system 110 identified as needed for the study, with the estimates generated based on historical data quality measures for other studies.

In some implementations, the output data can be provided along with user interface controls enabling a user to select one of the technology options to add it to the study. The computer system 110 can receive data indicating user interaction with these controls, and in response, can update the data that defines the study to add the use of the selected technology option to the study protocol or other study data. In this way, the computer system 110 can aid researchers in quickly adding technology items to a study. In some implementations, the user interface can include controls to reserve or acquire technology items that a user selects. The computer system 110 can receive data indicating user selection of these technology items and respond by reserving, purchasing, or otherwise securing the technology items for the researcher.

The computer system 110 can store and provide providing connector elements (e.g., configuration data, settings, software modules, etc.) to incorporate a user-selected technology option into the study, thus facilitating active use of the user-selected technology option in the study. For example, the study may have an associated application or software module. When a researcher selects a technology option to add to the study, the computer system 110 may look-up configuration data, settings, drivers, API commands, software libraries, code, scripts, or other elements that facilitate incorporating the selected technology option. The elements could be, for example, drivers to communicate with another device (e.g., a peripheral device, a sensor, a medical device, etc.), configuration data to change the behavior or function of an application, settings that change the types of data collected by a device or application (and/or the frequency, precision, context, triggers, or other factors related to data collection), settings that change the manner of reporting data collected, and so on. The computer system 110 may then provide the connector elements to the researcher, or in some cases directly to devices of study participants (e.g., members of a cohort).

In some implementations, the computer system 110 may distribute connector elements to devices of one or more study participants over a communication network, e.g., the Internet. For example, if the researcher selects to add the use of a particular software module to the study, the computer system 110 can distribute that software module to phones or other devices of study participants. As another example, if the researcher selects to use a particular device in the study, the computer system 110 can distribute a driver, set of configuration settings, or other software or data to phones or other devices of study participants, enabling or causing the user devices to communicate with the particular device. For example, the computer system 110 can distribute, to members of a cohort that each have an mobile application installed on a phone, a configuration file or software module that enables the mobile application to communicate with, and in some cases control or trigger functions of, other devices or software.

Various variations to the process 2300 can be made. For example, the computer system 110 may combine some steps or further divide some steps. In some cases, the computer system 110 may combine the steps of identifying technology options that meet certain criteria (step 2306), determining suitability scores (step 2308), and selecting based on the scores (step 2310) in a single general step of selecting technology options based on the study data and data in the technology database 112. As discussed below, machine learning techniques can be used for evaluation and selection of technologies, where machine learning models are used to perform one or more steps of the process 2300. The one or more machine learning models, like any of the other machine learning models discussed herein, may include at least one of a neural network, a support vector machine, a classifier, a regression model, a reinforcement learning model, a clustering model, a decision tree, a random forest model, a genetic algorithm, a Bayesian model, or a Gaussian mixture model.

In some implementations, the computer system 110 can use one or more machine learning models to select technology options. One of the advantages of machine learning in the process is the ability to incorporate the effects of factors that affect success but may not be easy to discern or define as rules. For example, users may avoid using a bulky device, even though the bulkiness disadvantage may not be apparent from published materials or even comments from the users. Nevertheless, when machine learning models are trained based on examples of technologies that were successfully used and/or examples of those that were not successfully used, the models can learn the options that result in greater use and better data quality, based on the usage results and data results. For example, based on usage data and reports of data collected, the models may learn to score a bulky device lower than other similar devices, even for situations when the specifications of the bulky device would seem to be a good fit. Various different arrangements of machine learning models can be used.

One example machine learning model is configured to receive input features representing (i) criteria for technology selection (e.g., study data and/or technology requirements derived from the study data), and (ii) characteristics of a technology option (e.g., from data about the technology option in the technology database 112) and/or an identifier for a technology option. The model can be trained to provide an output, such as a likelihood score, confidence score, or classification score, indicating how well the model predicts the technology option described by the input features meets the criteria indicated by the input features. The model can be trained based on examples of prior studies, including positive examples where technology options successfully met the corresponding criteria as well as negative examples where technology options did not meet the corresponding criteria of the studies. The computer system 110 may also generate additional training examples from the data in the technology database 112 and sample criteria or generated criteria. For example, for training, the computer system 110 can generate examples where the selection criteria includes blood glucose monitoring, creating an example for each of the technology items and assigning a training target label whether the technology item can provide blood glucose monitoring. Similar examples can be generated for other criteria, including combinations of multiple technology functions or uses. The computer system 110 can use a model trained in this manner to generate a suitability score for technology items and combinations of technology items. For example, the computer system 110 can generate a set of input feature data for each of various technology items in the technology database 112, where each set of input feature data includes the same set of selection criteria feature values (e.g., based on the study data) but a different set of technology characteristic feature values (e.g., being determined for each particular technology option based on its respective entries in the technology database 112). The outputs of the model can then be used as a suitability score for respective technology options, or may be used to generate the suitability scores (e.g., by combining with other factors or applying further processing).

Another example of a machine learning model that may be used is a model that receives input indicating selection criteria and outputs a score for each of a set of technology options, where the scores indicate their relative suitability to meet the criteria. This model may be trained based on examples of technologies that were successfully employed and the study characteristics or other criteria the technologies needed to satisfy. For example, the model may be implemented as a neural network, with the input layer receiving a set of input feature values indicating the selection criteria (e.g., study characteristics, study topics, or other study data). The output layer of the neural network can have a value for each of a predetermined set of technology items. When a set of input features is provided to the model, the model can output a value for each of the predetermined set of technology items. Each output value may be, for example, a score classifying how suitable the model predicts the corresponding technology option to be for the criteria indicated at the input layer. Thus, the output layer can indicate suitability scores for each of many different technology options.

Another example can include a set of machine learning models each trained to classify the expected suitability of technology options with respect to a different uses or functions. The models may each be configured to receive input feature values representing characteristics of a technology option (e.g., as determined from data in the technology database 112), but the output of each model can indicate suitability with respect to a different predetermined criterion or set of criteria. For example, a first model may be trained to predict whether technology options, having features as indicated by the input to the model, will serve to track sleep of a user. A second model may be trained to predict whether technology options will serve to track exercise of a user. A third model may be trained to predict whether technology options will effectively track both sleep and exercise. In this manner, the computer system 110 can use a set of the trained models to determine scores indicating the suitability of different technology options. The computer system 110 can select a proper subset of the trained models that represents the needs of the research study or other reason for technology selection. For example, if only exercise tracking is needed, the computer system 110 selects the second model that corresponds to exercise tracking. The computer system 110 then a set of input features for each technology option to consider, provides each set of input features to the selected model(s), and obtains output scores from the selected model(s) for each technology option. This permits the computer system 110 to obtain scores for the suitability of any technology in the technology database 112 with respect to any of the criteria (or combinations of criteria) for which a model has been trained. As with other machine learning models discussed herein, the training examples for model training can be derived from the literature database, the technology database 112, records of studies designed or carried out using the computer system 110, user input specifying suitability of technologies for different purposes, and so on.

Figure 24:
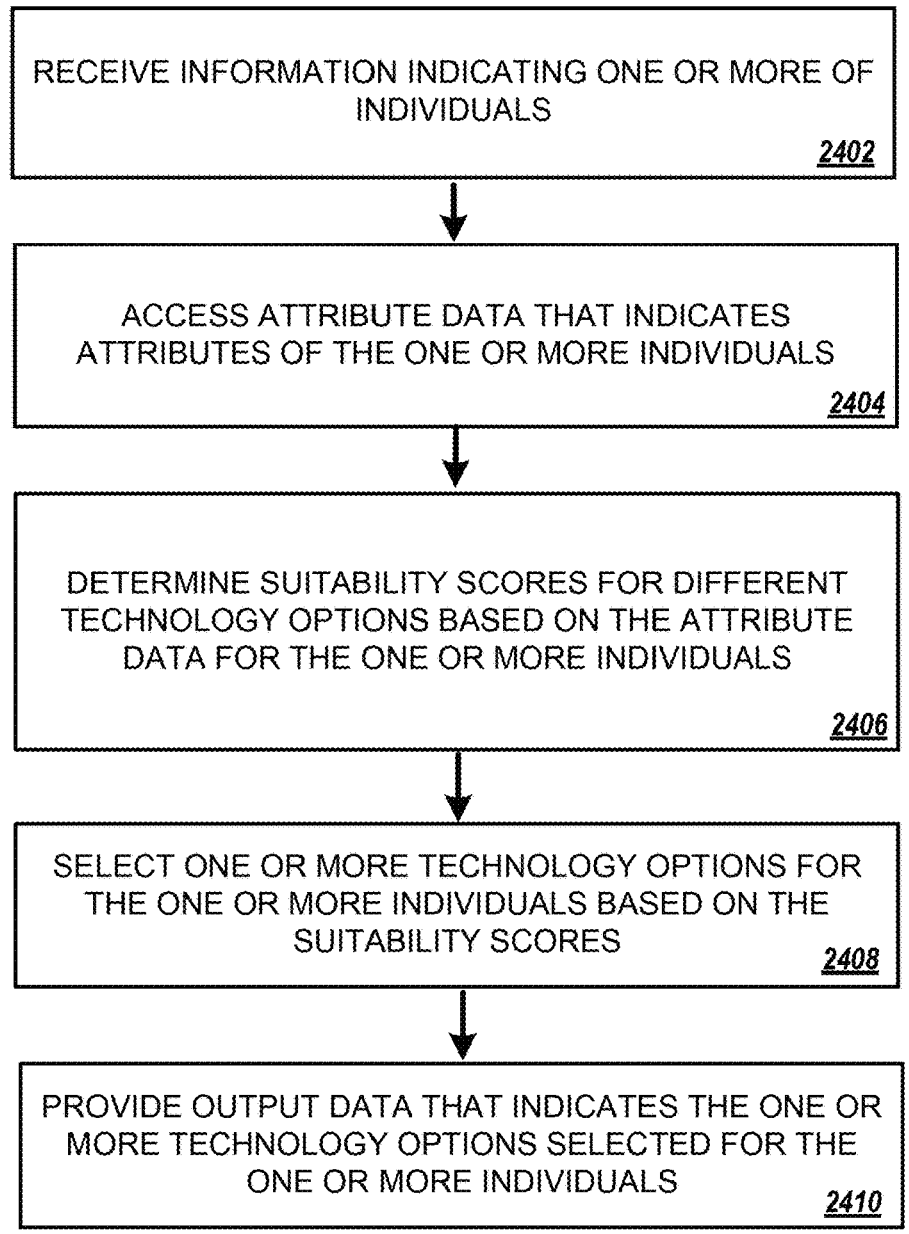
FIG. 24 is flowchart diagram that illustrates an example process for recommending technologies that can be tailored for one or more individuals.

FIG. 24 is a flowchart diagram that illustrates an example process 2400 for customizing recommendations for a cohort, group, or individual. The process 2400 may be performed by one or more computers, such as the computer system 110 shown in FIGS. 1 and 2. As another example, the process 2400 may be performed in whole or in part by a client device, such as device 104 of FIGS. 1 and 2. Similarly, the operations of the process 2400 may be distributed among one or more servers, one or more client devices, and/or other computing systems.

The process 2400 can be used to generate customized technology recommendations for individuals, groups of individuals, or a cohort as a whole. The computer system 110 can track the usage of technology items by individuals in the studies that the system 110 supports. The system 110 also and store information about the attributes of individuals in the studies. For example, the computer system 110 can store age, height, weight, health status, sex, location, occupation, and other information. This data allows the computer system 110 to determine correlations between attributes of individuals or groups and their likelihood to effectively use different technology items in the manner needed. This information in turn allows the computer system 110 to select technology items that are best suited to the individuals or groups of interest.

The process 2400 includes receiving information indicating one or more of individuals (2402). The information may include, for example, a cohort identifier, a study identifier, names of individuals, identifiers of individuals, or other reference information that indicates an individual or group of individuals. The individuals may be study participants, for example, members enrolled in a cohort for a research study. As another example, the individuals can be candidates for a cohort, e.g., users who meet selection criteria but are not yet enrolled for the study. The computer system 110 may store or access data that indicates the entirety of a cohort, a portion of a cohort, or a single individual. The computer system 110 may then use information about the one or more individuals to customize the evaluation and selection of technology items for the one or more individuals.

The process 2400 includes accessing attribute data from a database that indicates attributes of the one or more individuals (2404). The computer system 110 can access a database that indicates demographic attributes, health attributes, behavioral attributes, and so on. For example, the demographic attributes can include one or more of age, sex, geographical location, education level, income level, occupation, and so on. As additional examples, the health attributes can indicate one or more of height, weight, heart rate, blood pressure, physical limitations, diseases or chronic conditions (e.g., asthma, heart disease, stroke, diabetes, arthritis, etc.), etc. As additional examples, the behavioral attributes can indicate one or more of physical activity level, diet, patterns of using phones or other technology, sleep patterns, and so on. Other attributes can also be indicated, such as levels of experience with different technologies, rates of use of technologies in prior studies, etc. The computer system 110 may obtain these attributes from users through enrollment processes, surveys, questions, user interactions with devices or software, data collection during studies, and so on. In some cases, the attribute data for the user can be from a user profile for the user, such as a user profile that the computer system 110 or another system maintains in order to evaluate individuals for their suitability for inclusion in study cohorts.

The process 2400 includes determining suitability scores for different technology options based on the attribute data for the one or more individuals (2406). Because different individuals have different capabilities, needs, and preferences, the same technology items may not be ideal for everyone. Researchers generally desire for as many study participants as possible to comply with study protocols, so the appropriate technology interactions, monitoring, and data collection can be performed. To increase the rate of compliance with a study and the quality and consistency of data collection, the computer system 110 can consider the needs and preferences of individuals, groups, and/or the cohort as a whole. This allows the computer system 110 to recommend technology options that are customized for the cohort (or for individuals or groups within the cohort) to have the highest likelihood of successful use during the study.

In one example, the computer system 110 can evaluate the suitability of technology options for a cohort as a whole. This may not require determining technology suitability for individuals, but the data for the individuals can be used to determine the overall attribute distribution or makeup of the cohort. The computer system 110 can use that information about members of the specific cohort (or a candidate pool for the cohort) to customize the assessment and scoring of technology options. This can be done by determining suitability scores for technology options based on the composition of the cohort (e.g., the attributes of those study participants in the aggregate), rather than considering only capabilities and general usage rates. For example, two studies with two different cohorts may both be designed to monitor the same participant information, such as sleep quality. However, due to differences in the makeup of the cohorts, the scoring, ranking, and selection of technology options may be different. For example, one cohort may involve a group of people who are younger and are experienced with smart phones, so a smartphone application may be indicated as most appropriate. The other cohort may involve older people who are less likely to have smart phones or are less comfortable using them consistently, and so a bed sensor may be indicated as more appropriate.

In another example, the computer system 110 may evaluate the suitability of technology options for subsets of a cohort, such as different groups of individuals in different age ranges. For a given technology option, different suitability scores can be generated for the different cohort subsets, with the technology selection for each cohort subset being determined separately. Thus, different subsets within a cohort may be recommended to use different technology options if the computer system 110 determines that this would result in better participation (e.g., technology usage, successful data collection, compliance with study protocols, etc.).

In another example, may evaluate the suitability of technology options for individuals, such as individual members of a cohort or individual candidates for a cohort. In this case, the computer system 110 can use the attributes of a single individual to customize suitability scores for different technology options.

Different user attributes can affect the likelihood that individuals will successfully use different technology. For example, a device with small controls or small writing may be difficult for an elderly person to use effectively. As another example, different age groups or demographic groups may be familiar with different technologies and thus be more likely to use the devices as needed in the study. In many cases, the effects are not clear from the nature of the technologies and individuals involved. Nevertheless, the computer system 110 can learn or infer the factors that increase or decrease the likelihood of successful use based on examples of use or non-use of technology items by users.

As discussed above, the computer system 110 has information about user compliance and data quality from different technology items from prior studies and from research literature. Based on the historical usage or compliance information, and information about the members of prior cohorts, the computer system 110 can determine which attributes are predictive of usage rates of different technologies. These may be different for different classes of technology items or for specific technology items. For example, the usage of a particular model of smart watch may vary according to user age, while the usage of a particular application may vary according to sex or location. In some cases, even different features or functions of a technology item may vary according to user attributes, e.g., with one feature being used consistently across age ranges, but another feature having usage that varies widely due to age. The computer system 110 can perform statistical analysis to determine the correlations between different attributes and combinations of attributes with the usage of, or other results from, different technology items.

In some implementations, the computer system 110 can generate rules or scoring functions based on the relationships determined through analysis of study cohort characteristics (e.g., attributes of individuals or groups), the technology items used in the studies, and the outcomes (e.g., usage measures, data quality, compliance with study protocols, etc.). The computer system 110 can then use the rules or scoring functions to generate or adjust suitability scores for the technology options based on the attributes that are determined to affect the results for different technology options. For example, the computer system 110 may determine that the rate of successful use of one device is affected by age of participants, while the rate of successful use of another device is affected by the location of participants. From these technology-item-specific relationships, the computer system 110 can set rules or scoring functions that reward or penalize the suitability of different technologies when considered for use with individuals of certain attributes or combinations of attributes. For example, the computer system 110 can set scoring factors, offsets, weightings, or other values that will adjust the suitability score when the target individual(s) have certain attributes.

In addition to statistical or rule-based analysis, or as an alternative, the computer system 110 may also learn relationships between individuals' attributes and technology items using machine learning. For example, the computer system 110 can train one or more machine learning models to predict the likelihood of successful use (e.g., achieving a result such as collecting and reporting a desired type of data with appropriate data quality) based on subject attributes. One or more machine learning models can be used to generate the suitability scores, as discussed further below. The one or more machine learning models may include at least one of a neural network, a support vector machine, a classifier, a regression model, a reinforcement learning model, a clustering model, a decision tree, a random forest model, a genetic algorithm, a Bayesian model, or a Gaussian mixture model. Each of the models discussed below may be trained using examples from research literature, studies designed or carried out using features of the computer system 110, or other examples.

As one example, the computer system 110 can train a machine learning model to predict a score or likelihood of successful usage of a technology item by one or more individuals, based on input feature values indicating attributes of the one or more individuals. For example, a neural network can have an output layer that provides values that respectively correspond to various different technology items. Given input of feature values indicating a set of attributes, the neural network can produce a score (e.g., a likelihood of usage by an individual, a compliance or usage rate for a group, etc.) for each of the different technology items that is based on the attributes indicated by the input. As another example, a model may be structured to receive input indicating attributes of one or more individuals and data that describes and/or identifies a specific technology option. In response, the neural network can process the data to determine a score (e.g., usage likelihood, compliance or usage rate, etc.) for the specific technology option indicated at the input. As another example, different models can be generated for different technology options, each mode being trained to receive input indicating attributes of one or more individuals and provide an output score for the predicted usage for the technology option that the model corresponds to. The score for predicted usage can be combined with, e.g., weighted with or used to adjust, a general suitability score in order to customize the suitability score.

In some implementations, a machine learning model uses attribute information to generate a suitability score for a technology option. For example, a model can combine the evaluation of how well a technology meets a study's requirements with the evaluation of how likely a technology is to be used effectively by one or more individuals. One example machine learning model is configured to receive input features representing (i) criteria for technology selection (e.g., study data and/or technology requirements derived from the study data, such as types of data to be collected, quality of data needed, etc.), (ii) characteristics of a technology option (e.g., from data about the technology option in the technology database 112) and/or an identifier for a technology option, and (iii) attributes of an individual or aggregate representation (e.g., attribute distribution) for multiple individuals. The model can be trained to provide an output, such as a likelihood score, confidence score, or classification score, indicating how well the model predicts the technology option described by the input features meets the criteria indicated by the input features.

Another example of a machine learning model that may be used is a model that receives input indicating (i) criteria for technology selection (e.g., study data or needs or requirements such as types of data to be collected) and (ii) attributes of an individual or an aggregate representation of attributes (e.g., attribute distributions or statistical measures) for multiple individuals. The model can output a score for each of a set of technology options, where the scores indicate their relative suitability to meet the criteria. For example, the model can be a neural network having an output layer that includes a node for output of a score for each of a set of different technology items and/or technology item combinations.

The process 2400 includes selecting one or more technology options for the one or more individuals based on the suitability scores (2408). This step can be performed using the techniques discussed for step 2310 of process 2300, e.g., selecting a number or portion of highest-ranking technology options, filtering the set of technology options to those assigned a suitability score that satisfies a threshold, etc. When the one or more individuals represent an entire cohort, the selection can occur as in step 2310 and the same technology option(s) can be selected for all members of the cohort. In some cases, however, a different set of suitability scores are determined for different subsets of a cohort, leading to a different ranking or selection of technology options for different groups within the cohort. In some cases a set of suitability scores is determined for each individual, and the computer system 110 can use these to make a different ranking or selection of technology options for each individual. In this manner, the computer system 110 can select the technology option(s) that are predicted or expected, based on historical behavior of individuals with different backgrounds (e.g., combinations of attributes), to result in the highest likelihood of being used in the manner that meets the needs of the study. In this case, the suitability scores for technology options are customized for the one or more individuals, and so incorporate information about the likelihoods of successful use by those one or more individuals. The suitability scores and the selection can be personalized for single individuals in some cases.

As discussed above, the suitability scores, and thus the selection process, can be based on implicit user preferences for the one or more individuals, as inferred from the historical results in research literature, prior studies, tracking data showing general technology usage outside of studies, and other sources. In some implementations, explicit user preferences regarding technology may be available for the one or more individuals, and this information may also be used to generate the suitability scores or otherwise adjust the selection process. For example, users may provide information in an enrollment process or through surveys or other user inputs that indicate which technologies the individuals use, enjoy, or prefer, and which technologies the individuals do not use or prefer not to use.

The process 2400 includes providing output data that indicates the one or more technology options selected for the one or more individuals (2410). The output data can be include content as discussed in step 2312 above and can be provided in the manner discussed for step 2312 above. For example, the selected technology options can be provided as recommendations of technologies to add to a study, e.g., for participants in a cohort to use during the study. Accordingly, the selected technology options can be provided as recommendations for updating the data collection procedures or study protocol for the study. Because different technology options can be selected for different groups or individuals in a study cohort, the output data may include multiple rankings, lists, or other indications of selected technology options, with different options indicated for different individuals or groups. An example is shown in recommendations 822 in FIG. 8A.

Variations of the techniques in the process 2400 can be used. In some implementations, the process 2300 can be performed, but with suitability scores generated to take into account the attributes of members of a cohort or of individuals, e.g., with suitability scores determined as in step 2406.

As another example, the techniques of estimating the likelihood of successful use for individuals of different attributes can be determined and provided separate from the selection of technology options. For example, a user may specify certain technology items for a study and uses of the technology items in the study, with or without recommendations from the computer system 110. Once this user selection is made, the computer system 110 can generate usage likelihood scores based on machine learning models and/or the analysis of relationships between attributes and technology usage (e.g., actual use of technology items and/or achieving the data collection with needed frequency, accuracy, etc.). For example, a researcher designing a cohort may specify that a particular wearable device should be used, and the computer system 110 can provide a predicted usage rate or study compliance rate based on the attributes of the members in the cohort. If the researcher selects a different device or if the cohort composition changes, the computer system 110 can estimate a different usage rate or study compliance rate. As another example, the same techniques can be used to provide predictions of the future usage or compliance of a cohort for each of multiple technology options. In a list of available technology options for a user to browse, the computer system 110 can provide measures corresponding to the different options, such as historical usage rates, predicted usage rates given the composition of the cohort or candidate pool, etc.

Figure 25:
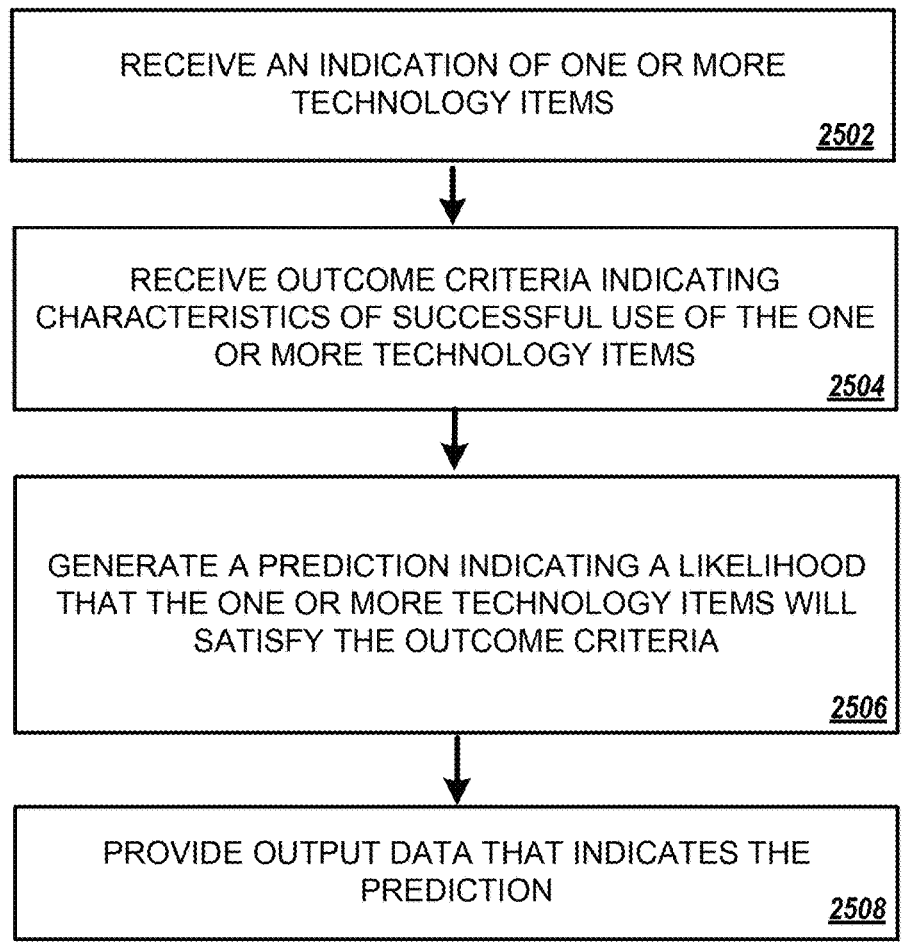
FIG. 25 is flowchart diagram that illustrates an example process for predicting outcomes of using one or more technologies.

FIG. 25 is a flowchart diagram that illustrates an example process 2500 for predicting outcomes of using one or more technologies. The process 2500 may be performed by one or more computers, such as the computer system 110 shown in FIGS. 1 and 2. As another example, the process 2500 may be performed in whole or in part by a client device, such as device 104 of FIGS. 1 and 2. Similarly, the operations of the process 2500 may be distributed among one or more servers, one or more client devices, and/or other computing systems.

The process 2500 includes receiving an indication of one or more technology items (step 2502). Examples include determining that a technology option satisfies at least some requirements of a study (e.g., step 2306 of FIG. 23), receiving data indicating a user selection of a recommended technology option, receiving user input that specifies a technology option, or receiving data indicating technology item(s) specified for use in a study protocol that is being created for a new study or is for an ongoing study.

The process 2500 includes receiving outcome criteria indicating characteristics of successful use of the one or more technology items (step 2504). The computer system 110 can perform this using any or all of the techniques for determining criteria as discussed below for step 2606 of FIG. 26. More generally, this can include extracting reference values or minimum requirements for use of the one or more technology items from study data, standard default requirements, aggregated data representing typical requirements of prior studies, and so on. As an example, study data may specify that a minimum number or percentage of study participants need to provide a certain type of data (e.g., sleep tracking data, heart rate data, step count, survey responses, etc.) with at least a minimum data quality (e.g., frequency of measurement, accuracy of measurement, consistency, etc.). The criteria can be a representation of these factors, such as specifying that a successful usage outcome would include study compliance of 80%, where study compliance includes daily step counts for 14 consecutive days. The outcome criteria may be defined for a group of individuals (e.g., based on aggregate performance of the cohort) and/or for single individuals (e.g., specifying what level of usage is needed for a single individual to comply with the study protocol).

The process 2500 includes generating a prediction indicating a likelihood that the one or more technology items will satisfy the outcome criteria (step 2506). The computer system 110 can generate the predictions through analysis of records of prior studies, including the technology items selected for the studies, the usage needs of those studies, and the usage results or compliance results reported for those studies. By identifying a subset of studies that involve the same or similar technology item and identifying the rate of successful usage achieved in those studies, the computer system 110 can determine likely rates of successful usage in the current study. The analysis can include techniques for predicting likelihoods as discussed in step 2406 of the process 2400.

In some implementations, the computer system 100 uses one or more machine learning models to generate the prediction. For example, machine learning models can be trained based on examples in research literature and/or prior studies, e.g., their requirements or study protocols and resulting usage rates. Models as discussed in step 2406 of the process 2400 can be used to make the predictions regarding successful usage. The models may take into account attributes of individuals and cohorts, but are not required to do so. For example, the models as discussed in step 2406 of the process 2400 can be structured to not receive attribute date as input, or to receive input of attributes for a generalized population, so that the predictions are not specific to a cohort or individual.

The prediction can be not merely whether a user or group is capable of successfully using a technology item once, but whether the user or group can use the technology item repeatedly, in whatever manner is needed by the study. In other words, the outcome criteria can specify not just the type of use the study needs but also the consistency and duration of multiple uses, e.g., the patterns of use of the technology that need to occur or continue over multiple time periods according to the study protocol.

The process 2500 includes providing output data that indicates the prediction (step 2508). For example, the computer system 110 can provide an indication in an alert, notification, or data for presentation on a user interface of an application, web page, or other interface. The indication can include providing a determined likelihood or expected success rate. For example, the indication can indicate that an individual is expected to has an 76% likelihood of complying with the study protocol, or that 80 out of 100 participants are expected to comply with the study protocol (e.g., based an assessment of a study as a whole or by predicting compliance for a cohort individual by individual), or that the study protocol is predicted to have an 80% rate of compliance (e.g., determined with or without taking into account a specific cohort for the study). The indication can be classification, for example, color coding different likelihood ranges or providing a binary indication a check mark vs. "X" to signify whether the outcome meets a likelihood threshold.

The techniques of the process 2500 can be performed for each of multiple technology items, for example, to determine and provide information about predictions for each of the technology options to be recommended based on the processes 2300 and 2400. In some implementations, the predictions can be used to filter or score technology options, so that technology options predicted to be less likely to satisfy the outcome criteria are indicated to be less suitable for a study.

In some implementations, the process 2500 can be used to predict the failure probability or failure rate that may occur if a technology item is selected. This failure rate may be defined as failure of the technology item itself. However, it can be more helpful to define the failure as not merely the possibility of technical failure but the failure of the device and user together to fail to produce the desired use, data collection and reporting, or other outcome. Thus, even if the technology item works as intended, improper use or lack of use may be considered a failure in this context. In other words, when a user selects a DHT, the computer system 110 can provide predicted success rate that assigning or providing that DHT will cause the results desired in the study. Alternatively, the computer system can provide a predicted failure rate at how frequently or how likely the DHT will not result in the desired outcome.

As an example, a user may might want to use an activity tracker (e.g., FITBIT device) to determine peak output heart rate. However, if the study is intending to measure peak heart rate as a measure for a possible drug toxicity event, then a consumer-level activity tracker likely does not have the capability for this sensitive use (e.g., may not provide sufficient measurement frequency, measurement precision, etc.). Thus, the computer system 110 should provide a success rate or failure rate showing that this activity tracker is unlikely to successfully provide the needed information. Even though the activity tracker provides measurement of heart rate, the computer system 110 can determine and predict that using this device to measure resting heart rate is appropriate, but using the device to measure peak heart rate is not.

To capture relationships like this, research literature and results of other studies may reveal that for one use case, a technology achieved standards for the study but the same device may not achieve the standards for another use. This helps the computer system 110 determine a predictive success rate or failure rate for a certain technology item, for individuals and across groups (e.g., for a cohort as a whole). As discussed above, the relationships and predictions can be based on results from research evidence and clinical evidence, and/or characteristics of the technology item itself (e.g., what is known about the structure and operation of a device or software program).

Figure 26:
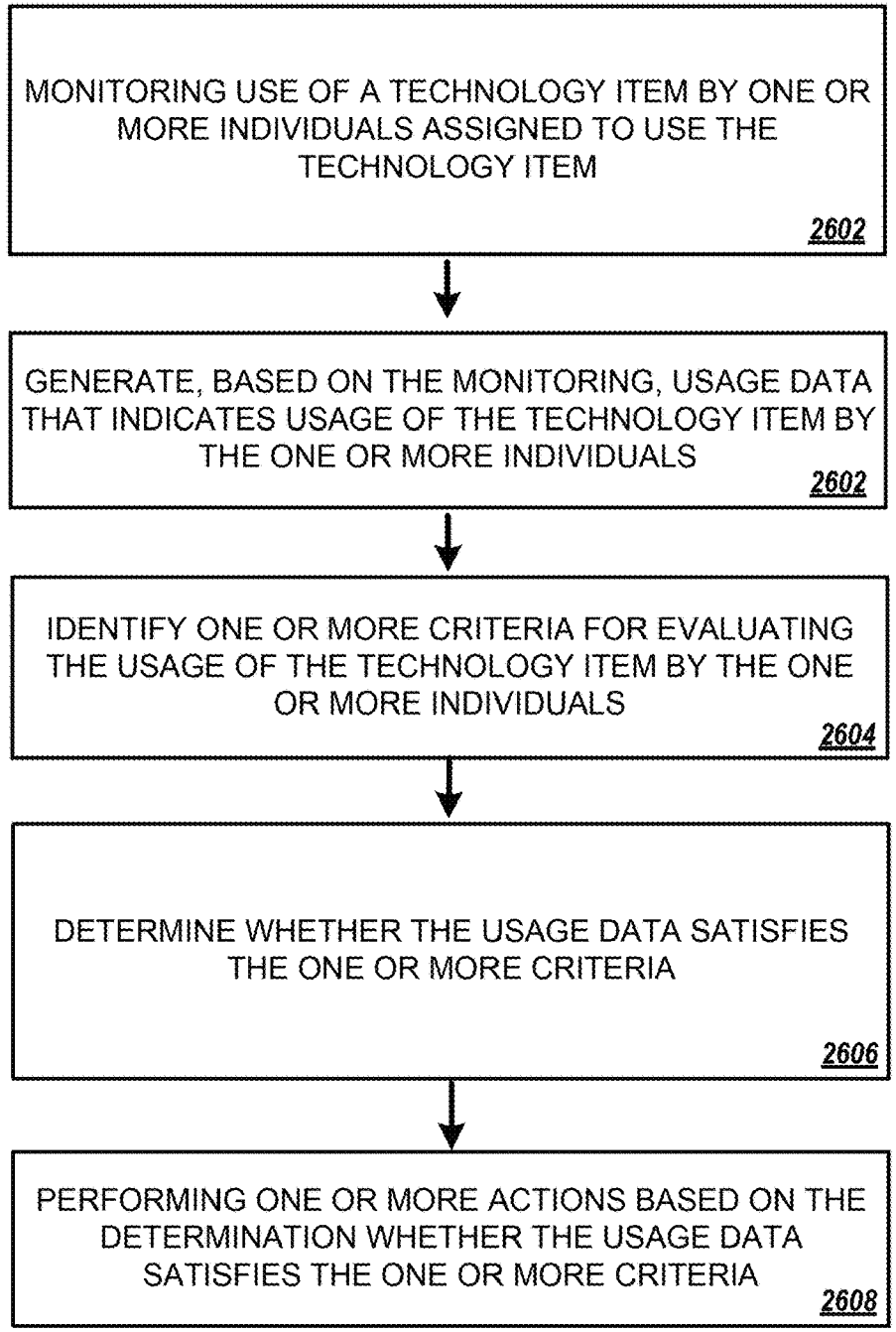
FIG. 26 is flowchart diagram that illustrates an example process for monitoring the use of technologies.

FIG. 26 is a flowchart diagram that illustrates an example process 2600 for monitoring the use of technologies. The process 2600 may be performed by one or more computers, such as the computer system 110 shown in FIGS. 1 and 2. As another example, the process 2600 may be performed in whole or in part by a client device, such as device 104 of FIGS. 1 and 2. Similarly, the operations of the process 2600 may be distributed among one or more servers, one or more client devices, and/or other computing systems.

Once technology is selected for a research study, clinical use, digital therapeutic delivery, diagnostic use, or other use, the computer system 110 can monitor the usage and performance of the technology to determine if it is achieving the results desired. For example, if usage of a device is made part of a research study, once the study begins the computer system 110 can receive collected data (e.g., measurements, sensor data, tracking data, user inputs, etc.) from devices of study participants. The computer system 110 can assess the collected data to determine if it provides, for example, the correct type of information, the appropriate data quality (e.g., frequency of measurement and reporting, accuracy, precision, etc.), and data from a sufficient number of study participants. More generally, the computer system 110 may evaluate the collected data with respect to any of the study parameters or study requirements. The computer system 110 can report the results of the monitoring, for example, to indicate measures of usage and tracked results periodically or in response to user requests.

For example, the computer system 110 can generate usage data that indicates usage of a technology item, identifying criteria for evaluating the usage of the technology elements by the one or more individuals, determine whether usage data satisfies the one or more criteria, and provide output data indicating whether the usage data satisfies the criteria. Monitoring of usage of a technology item can be performed in an ongoing manner throughout the study. For example, the usage can be evaluated periodically as the study progresses, e.g., each day, each week, and so on. The monitoring and evaluation of monitoring results can enable the computer system 110 to quickly detect usage rates or usage trends that could endanger the success of the study. The computer system 110 can then take action to improve the technology usage, such as to recommend different technology, provide instruction or education to individuals having low compliance with study requirements, etc.

The computer system 110 can send alerts in response to determining that technology is not providing the desired results, whether that is due to lack of use or misuse by the study participants or other users (e.g., usage rate is below a target level) or due to the technology not performing as desired (e.g., a device providing data that is not sufficiently accurate or reliable). In addition to alerting a researcher, doctor, or other associated user of desired usage or performance targets that are not being met, the computer system 110 can generate and provide recommendations for correcting the problem. For example, if usage by participants or technology performance does not meet the needs specified for a study, the computer system 110 can initiate a process to re-evaluate which technology options are best suited for the study or for individuals or groups of individuals, e.g., using process 2300, process 2400, or the other techniques discussed herein. The computer system 110 can then recommend that the study be updated to change which technology items are used, the manner in which the technology items are used, or to update other study parameters.

The computer system 110 can also take other actions based on monitoring technology usage and results of using technology items. For example, the computer system 110 can identify subsets of a cohort or even individuals whose usage or collected data does not meet a standard. For example, if collected data for a user indicates improper use of a technology item, perhaps resulting in incomplete or poor quality of data being collected, the computer system 110 can send instructions or educational media to the user's phone or other device for display to the user to help the user learn to use the device correctly. Similarly, the computer system 110 can send a survey asking the user about difficulties using the technology, to help identify the reasons for low usage or unsatisfactory results. The interactions with individuals can be personalized or tailored for the specific issues encountered. For example, the computer system 110 can send a different set of communications to a user that did not use a device at all than another user that used a device inconsistently or improperly.

The process 2600 can include monitoring use of a technology item by one or more individuals assigned to use the technology item (step 2602). The technology item may be assigned, for example, for use in a research study, for health monitoring, for providing clinical care, for providing digital therapeutics, for diagnostic use, etc. For example, the computer system 110 can monitor the use of technology items that are to be used by members of a research study cohort, to determine if the use complies with the study protocol. The computer system 110 can receive data generated using the technology item, for example, over a communication network such as the Internet, and store the received data in a database. From data transmissions received or other interactions, the computer system 110 can determine whether and how the technology item is being used.

Each member in a group (e.g., a study cohort) may have a respective instance of a technology item, e.g., with each member in the group using the same type of technology item. The computer system 110 can collect data from each member's technology item of that type. For example, the technology item can be a particular mobile application or software module that a research study designates to be used. For each member of the research study cohort, the computer system 110 collects data generated by the particular application and/or data generated about the use or non-use of the application (e.g., as tracked by an operating system or by the application itself). In some cases, different individuals in a group may be assigned to use different technology items, or individuals may be permitted to choose to use any from among a set of approved technology items. In these cases, the computer system 110 can track any or all of the technology items in the set that is assigned for use, e.g., designated or approved according to the study protocol.

Technology items can be configured to automatically report data to the computer system 110 or another system. As part of monitoring use, the computer system 110 can store data submissions that the technology items provide, whether directly over a network or indirectly, such as to a phone or other device that forwards the data to the computer system 110.

The system 110 may actively request data about usage as part of the monitoring process. For example, the computer system 110 may periodically send requests to the phones, wearable devices, or other technology items of individuals in a research study over a communication network. The requests can solicit sensor data, measurement data, records of instances of use, aggregate usage statistics, status information or configuration information, etc. about any or all technology items involved in the study.

The computer system 110 can monitor usage of at technology item by detecting and recording any of various different events, actions, uses, or conditions of the technology item. For example, the computer system can track at least one of: user interactions with the technology item; a frequency of use of the technology item; times that the technology item is used; a duration of use of the technology item; a location of use of the technology item; portions, features, or functions of the technology item that are used; transmissions from the technology item; interactions of the technology item with one or more other technology items; errors of the technology item; types of data collected or provided by the technology item; amounts of data collected or provided by the technology item; data quality of data provided by the technology item; or measurements or sensor data from the technology item.

As part of monitoring use, the computer system 110 can determine and store metadata that indicates information about the context of use, such as the time, location, environment that use occurred. The computer system 110 can also monitor use by receiving and evaluating results of using the technology item. For example, the computer system 110 can receive sensor data or measurement results that a device generated, and use those results as indications of use of a particular type.

The process 2600 can include, based on the monitoring, generating usage data that indicates usage of the technology item (step 2604). Using the various events and instances of data collection monitored, the computer system 110 can generate data that indicates the manner in which the technology item has been used. The generated usage data can include data specifying patterns, trends, and sequences of user actions over time. The generated usage data can include measures for different items being tracked, such as a count of times the technology item is used, average duration of use, and so on. Beyond tracking whether usage occurred and the instances of use, the usage data can specify the manner in which the technology item was used. For example, the usage data can indicate which portions or functions of a technology item were used (e.g., specific elements of a device or portions of an application), the context in which use occurred, how many of the attempts to use the technology item were successful or not, and so on.

The usage data can be generated and stored for an individual, for a group of individuals, or for a cohort as a whole. In many cases, even when the usage for a cohort is tracked, usage data for each individual member is determined. Generating the usage data may include generating an aggregate measure of usage across multiple individuals, such as computing an average, distribution, or histogram of usage measures for a cohort as a whole or for a subset of a cohort (e.g., participants that have an age in a particular age range or have a particular set of attributes). The usage data can also indicate a measure that reflects usage of a group as a whole, such as a usage rate for a cohort (e.g., indicating that 89 people out of 120 members of a cohort used the technology item in the manner specified by a study).

The process 2600 can include identifying, by the one or more computers, one or more criteria for evaluating the usage of the technology item by the one or more individuals (step 2606). This can include evaluating study data that describes the data collection needs or other technology usage needs of a study. Different studies may involve different interactions with users (e.g., outputs, display of content to users, etc.), collection of different types of data (e.g., measuring behavior, measuring physiological attributes, etc.), or collection of data at different levels of consistency or frequency. The computer system 110 may access records for the study and extract from those records the type of usage of the technology item that the particular study needs. For example, a study protocol or other information describing a study may indicate types of data to be collected, the frequency of measurements or data entry, and/or parameters indicating the quality of data needed (e.g., accuracy, precision, etc.). The computer system 110 thus identifies technology usage needs (e.g., requirements for user interactions, measurement, data collection or reporting, etc.) that should be fulfilled in order to maintain compliance with the study.

In some implementations, the criteria can include values, thresholds, or ranges that can serve as references with which to measure usage. For example, the criteria may include a minimum number of measurements, a maximum interval of time permitted between measurements, a range of measured values considered valid measurement results, and so on.

In some implementations, the criteria may include reference information that is not specified in study data. For example, information about the technology item itself may provide a typical range or acceptable range of usage needed for effectiveness. Specifications for the technology item, information from research literature, and/or information from other studies may provide examples of acceptable use of the technology item and unacceptable use. This can allowing the computer system 110 to determine whether the usage of the technology falls within typical usage patterns and acceptable ranges of data collected.

In some cases, the criteria for successful usage of technology can be determined or inferred based on the intended function or use of the technology item, or based on the type of data to be collected. For example, a study may involve a step counting function of a phone or wearable device. A user may have the needed device with step counting activated, but then leave the device off, out of battery, or not worn for most of the day. The study data may simply specify that step count data is needed from participants, without specifying a duration of use of the device each day. Nevertheless, the computer system 110 may still determine criteria that specifies of a minimum threshold amount of daily use needed for compliance with the study. Any of various pieces of data may be used by the computer system 110 to set a constraint or criterion for evaluating the usage. For example, a classification for the step count data type may indicate that it is cumulative or measured in an ongoing manner throughout the day, signifying that less than a minimum amount of use (e.g., 8 hours, or 12 hours, etc.) results in inaccurate data. As another example, other studies or research literature may specify constraints on the validity of step count data, and those constraints can be used as criteria for evaluation. As another example, a measure of typical usage of the technology item for step counting, such an average daily usage or a distribution of daily usage for a group, may be used as a reference value to be compared with.

The process 2600 can include determining whether usage data satisfies the one or more criteria (step 2608). In making this determination, the computer system 110 can determine whether and/or to what extent the one or more individuals are carrying out the planned usage of the technology item. This can take into account not only whether the technology item is used in a general sense (e.g., merely turned on, interacted with, etc.), but also whether the technology item is being used correctly or used to achieve the results needed.

The computer system 110 can compare the types of data being collected for one or more individuals with the types of data that the criteria indicates are needed for a research study or another purpose. For example, if sleep data and exercise data are needed for a study, the computer system 110 can determine which members of a cohort have used the technology item in a manner to collect those types of data. The computer system 110 can compare measures of usage in the usage data to corresponding values (e.g., thresholds, ranges, etc.) of the criteria. This can include determining whether collected data for individuals meets applicable standards or reference levels for, e.g., frequency, quantity, consistency, accuracy, precision, and so on.

In some implementations, the computer system 110 compares aggregate measures for multiple individuals with reference values corresponding to the aggregate measures. For example, the usage data may indicate 80% of members of a cohort acquired needed data using a technology item, and the computer system 110 can compare that amount with a reference measure or criterion for success of the cohort, e.g., a minimum level of 75% of cohort members. Alternatively, the comparison may be made for the number of members of a cohort that use the technology item as desired, compared with a minimum number of individuals that the study needs to participate actively.

The computer system 110 can determine whether each of the criteria for successful use of the technology item (e.g., in a manner that complies with the requirements or goals of a research study) is satisfied. The determinations can be made on an individual level, such as determining whether each individual is in compliance with the study's requirements for use of the technology item. The computer system 110 can also determine aggregate measures for groups of individuals, such as for a cohort as a whole, e.g., a number or percentage of participants in a study that are using the technology item as intended in the study.

The process 2600 can include performing one or more actions based on the determination whether usage data satisfies the one or more criteria (step 2610). For example, if the computer system 110 determines that the criteria are not met, the computer system 110 may initiate actions to attempt to improve usage and compliance with the study protocol. The monitoring and evaluation of usage (and results of usage) can quickly indicate when the rate of compliance is low, or the quality of data is insufficient, or when other conditions involving a technology item occur. This can provide a feedback mechanism so the computer system 110 can take action to boost compliance with the study protocol or to recommend changes to the study protocol to improve the likelihood of success of the study.

In some implementations, based on the determination, the computer system may evaluate an alternative technology item for the one or more individuals. For example, if the criteria are not met, the computer system 110 may initiate an evaluation of technologies indicated in the technology database 112 with respect to the needs of the study for data collection, user interaction, etc. This can include any or all of the steps in the processes 2300 and 2400 discussed above. The computer system 110 can then recommend a different technology item to use in the study (e.g., a substitute or alternative item). The recommendation may be a change for the cohort overall or for a subset, such as for groups or individuals that have not demonstrated the pattern of usage needed for the study. For example, having identified individuals whose usage did not satisfy the criteria, the computer system 110 can use the techniques of the process 2400 to select one or more technology items that are predicted to result in greater usage and study compliance based on the attributes of the individuals.

In some implementations, the computer system 110 provides, for display on a user interface, output data indicating whether the usage data satisfies the one or more criteria. For example, the computer system 110 determining that the usage does not meet the criteria can trigger the computer system 110 send a notification alerting a researcher. The notification can indicate the criteria not met and measures of the aspects of usage that do not satisfy the corresponding criteria. As with other outputs and notifications discussed herein, the notification can be provided over a communication network to a client device, provided in a message (e.g., email, SMS text message, mobile device notification, etc.), provided through a web site or web application, provided through an application of a mobile device or other device, etc. The output data can be provided in a user interface as, for example, a status view listing of needs of the study and whether those needs are met, potentially with measures of usage, trends of usage, and the criteria or standards used for evaluation also provided.

In some implementations, the computer system 110 can identify, and provide output data indicating, a limiting factor or cause of low usage or low study compliance. For example, having identified individuals whose usage does not satisfy the needs of the study, the computer system 110 can send surveys to those individuals requesting input about the reasons for lack of use or lack of success (e.g., whether the user finds the technology item bulky, has low battery life, confusing to use, etc.). The computer system 110 can use this information to inform the researcher and/or recommend new technologies that better fit the user's preferences or needs (e.g., by reducing the issue noted by the user if possible). In some implementations, the computer system 110 may infer the cause for which usage does not meet the criteria, without user input. For example, the computer system 110 may infer a cause based on a pattern of collected data, events in usage logs, etc. For example, if a device loses communication abruptly and doesn't begin collecting until a charge cycle, the computer system 110 can infer that the issue is likely related to low battery life or not charging frequently enough. Similarly, the computer system 110 may review a log of events such as battery charge being low (e.g., reaching 20%, 10%, 5%, and then log ends) indicating that data collection ended due to the battery running out of charge.

In some implementations, the techniques of the process 2600 are used to monitor and evaluate performance of the technology item. For example, in addition to or instead of monitoring usage, the computer system can monitor aspects of the performance of the technology item, to determine if it is performing according to the requirements of a study or meeting other criteria. The computer system 110 may monitor performance and generate measures of, e.g., battery life, power consumption, data quality, response time, reliability, processing speed, latency, and bandwidth, and then compare these performance measures with performance criteria (e.g., performance standards, thresholds or ranges representing standard or acceptable performance, etc.). The performance criteria may be specified in study data, specifications of the technology item, or other data. The computer system 110 may use the evaluation of performance, in addition to or instead of evaluation of usage, to initiate evaluation of alternative technology items to find one better suited for a study, to provide output characterizing how the device performs, and so on.

Figure 27:
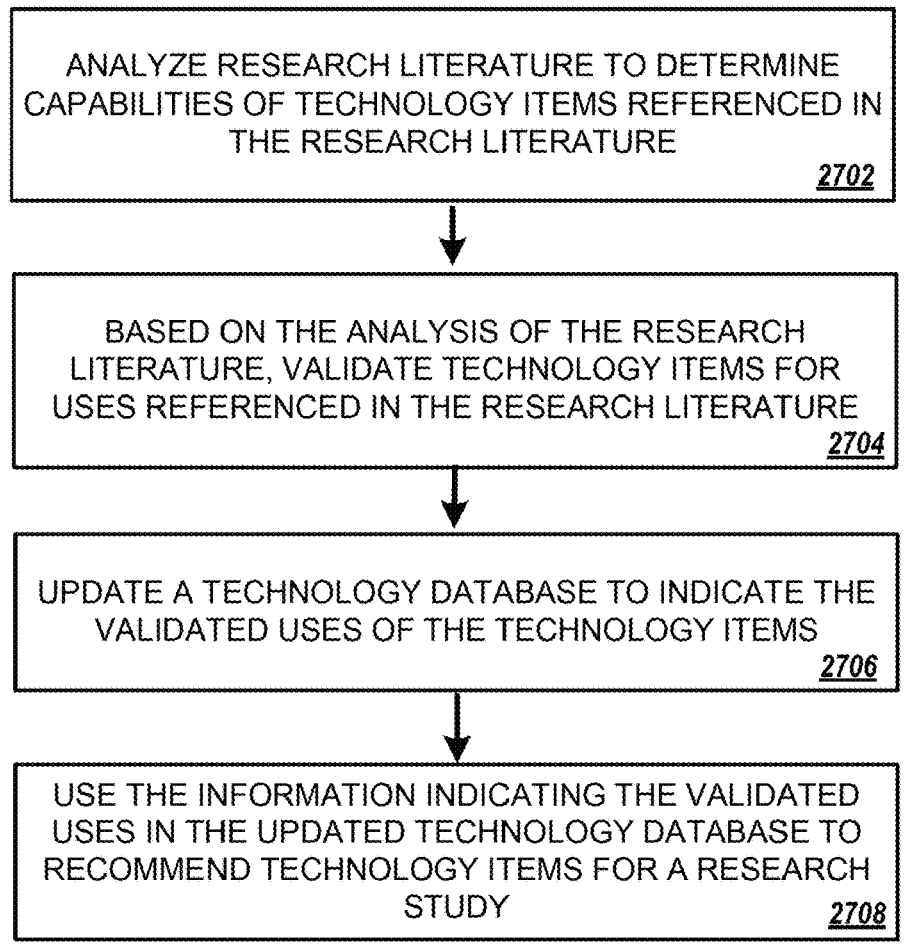
FIG. 27 is flowchart diagram that illustrates an example process for analyzing research literature.

FIG. 27 is a flowchart diagram that illustrates an example process 2700 for analyzing research literature. The process 2700 may be performed by one or more computers, such as the computer system 110 shown in FIGS. 1 and 2. As another example, the process 2700 may be performed in whole or in part by a client device, such as device 104 of FIGS. 1 and 2. Similarly, the operations of the process 2700 may be distributed among one or more servers, one or more client devices, and/or other computing systems.

The process 2700 includes analyzing research literature to determine capabilities of technology items referenced in the research literature (step 2702). This can include identifying, in publications and other data sources, references to technology items and associated mentions of the uses made of those technology items, the data collected using the technology items, and so on. Through semantic analysis or other natural language processing, and with the benefit of the taxonomy discussed above, the computer system 110 can determine how keywords and other references correspond to elements in the taxonomy. In general, research literature can include published information or materials, such as peer-reviewed journal articles, conference papers, pre-prints, or preliminary reports. Nevertheless, research literature can more broadly include information published on web pages or other public data sources. In addition to or instead of using these data sources, the computer system 110 can perform the process 2700 using records of private or unpublished studies, such as those designed or carried out using the computer system 110.

The computer system 110 also identifies criteria used by the studies (e.g., study protocol requirements regarding use of technology items) and indications of success or failure of technology items to meet the needs of the studies (e.g., participant compliance rates, statements of achieved precision, confidence intervals, error bands, etc.). Naturally, different studies have different needs. Among studies that involve heart rate tracking, for example, a level of precision that is insufficient for one study may be adequate and successful for another. The computer system 110 can extract and/or generate measures of absolute performance (e.g., the actual levels of precision achieved) in addition to or as an alternative to measures of relative performance (e.g., whether the achieved precision met the study's requirements). In some cases, the relative measures can be used by the computer system 110 to infer the absolute performance. For example, if study required precision within 5% for a measure, and study results indicate that the technology item performed adequately, the computer system 110 can use this as a data point that precision of at least 5% was achieved for that measure.

The process 2700 includes, based on the analysis of the research literature, validating technology items for uses referenced in the research literature (step 2704). The uses assessed can include including collection of specific types of data, potentially with specific levels of data quality. The assessment can be done by comparing results in the research literature to one or more predetermined criteria. For example, to be validated, a minimum number of studies using the technology item may be required (e.g., a minimum of 10 studies showing use of a particular aspect of the technology to be validated), as well as a minimum percentage of those studies showing successful use (e.g., a minimum of 70% of the studies that use the technology item for the purpose indicating success).

The process 2700 includes updating a technology database to indicate the validated uses of the technology items (step 2706). For example, this can include specifying in the database which uses of the technology items have been qualified or certified as reaching a level of reliability and effectiveness. Different levels of validation can be provided based on the variability of results among different studies and/or breakdown of successful uses and unsuccessful uses in studies. In some cases, where a use of a technology is indicated as giving poor results, the technology database can be updated to demote or warn against using technology item generally or for a specific type of use.

The process 2700 includes using the information indicating the validated uses in the updated technology database to recommend technology items for a research study (step 2708). For example, the processes 2300 of FIG. 23 and 2400 of FIG. 24 can be used, with the scoring of technology options being weighted to indicate higher suitability scores for technology items that are validated. In particular, the suitability can be boosted when the particular use that a study would need (e.g., collection of a particular type of data, providing a particular type of treatment, etc.) has been validated based on use research literature and/or success in prior studies.

The computer system 110 can also provide data for presentation to a user indicating whether the use(s) of a technology item have been validated, as well as potential statistics about the validation (e.g., a number of studies successfully using the technology, a rate of successful use in studies where the technology item was used, etc.). Information about whether a technology item has been validated can be provided for technology items recommended by the system 110, technology items added or specified by a researcher or other user, technology items specified in a study protocol, and so on.

As described above, there are many different techniques and uses of the systems and methods above. These include selecting DHTs for a health program (e.g., for research or therapeutic use), for a cohort as a whole, for an individual, for pharmaceutical applications (e.g., drug safety testing, drug effectiveness testing, drug side effects, etc.), and for medical device research. The system can select DHTs with an adjustable tradeoff between various factors: precision, cost, reliability, ease of use, statistical validity, etc. The system can perform outcome prediction, e.g., given a proposed set of DHTs and data needs using machine learning to predict the outcomes or characterize likely distributions of results, either in general or for a specific cohort. The computer system 110 can generate recommendations for study enhancement, such as given a proposed set of DHTs, recommending how a study design might be enhanced (e.g., recommending capabilities of the selected DHTs that are currently unused, showing the additional data types that come along "free"-whether simply providing a list or in a more fine-grained way predicting which available features might be most relevant to the research topic). The computer system 110 can select between a single DHT vs. a combination of DHTs. Even among options that all meet the researcher's needs, the system can consider the differences in cost and convenience of different options, and meet a budget or other constraint on resources. The computer system 110 can select the DHTs for a cohort or study based on the characteristics of individual members of the cohort, potentially resulting in a mixed set of DHTs where different members of the cohort are assigned different DHTs predicted to be best suited for them. The computer system 110 can identify the DHT needs for a study Starting with a research question or study design, the computer system can predict which data types need to be gathered, and with what level of precision, based on data about prior studies and the user's needs. This can involve using machine learning based on what previous studies have used, and/or rule-based or evaluative approach based on data tables, mappings, manually set or automatically derived rules, etc. From a set of data needs, the computer system can identify which DHTs are best suited to provide the needed types of data, with the needed quality (e.g., quantity, accuracy, frequency, consistency, diversity, etc.).

To aid in this process, the system can include a database characterizing available DHTs—e.g., their capabilities, limitations, specifications, data types, compatibilities, incompatibilities—and make the database queryable. The computer system 110 can also monitor and evaluate the usage and performance of DHTs during an ongoing study. For example, the system can monitor data streams for DHTs, detecting unusual results/lack of use and suggesting & carrying out interventions to correct issues identified (e.g., identifying members of a cohort whose data streams are unusual or lacking, and recommending education or a switch in DHTs for those members). The computer system 110 can monitor to warn the researcher of problems with DHTs in use: detect malfunctioning DHTs out in the field, evaluate incoming data streams against the study criteria to determine if the needed data is of sufficient quality (e.g., quantity, accuracy, frequency, consistency, diversity, etc.), provide a dashboard to visualize the issues (distribution of how well they are performing across the cohort); alert to risks that would jeopardize the effectiveness of the study; etc. Any of the functions of the computer system 110 can be based on machine learning models trained based on usage data and the data streams or data quality from other users and other studies.

The computer system 110 can be used to select technologies for collecting any of various types of information. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected by technology items selected or recommended by the computer system 110 can include technology items that can be used to collect any of various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNA-comics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data, and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group —OH, e.g., Isopropyl $C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

In the claims, the term "or" is generally intended to be inclusive, not exclusive. For example, the phrase "A or B" should be interpreted as encompassing (1) A only, (2) B only, and (3) A and B together. Thus, absent any modifying word or phrase to specify exclusivity (e.g., "either A or B" or "only one of A or B"), listed items are not mutually exclusive.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a cathode ray tube or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

The invention claimed is:

1. A method of facilitating compliance with requirements of clinical trials, the method being performed by one or more computers, the method comprising:
  accessing, by the one or more computers, (i) study data indicating a particular type of data to be collected in a research study and (ii) attribute data indicating attributes of participants in a cohort for the research study;
  identifying, by the one or more computers, a multiple types of devices or software items that are each capable of collecting the particular type of data indicated by the study data;
  determining, by the one or more computers, a predicted level of compliance for each of the multiple types of devices or software items, each predicted level of compliance indicating an expected level of compliance by participants in the cohort in using the corresponding type of device or software item to collect the particular type of data indicated by the study data, the predicted levels of compliance being determined based on the attribute data indicating attributes of participants in the cohort;

selecting, by the one or more computers, a type of device or software item for participants in the cohort to use in the research study based on the predicted levels of compliance;

updating, by the one or more computers, records for the research study to specify the selected type of device or software item; and sending, by the one or more computers, configuration data or a software module over a communication network to remote devices of the participants in the cohort, wherein the configuration data or software module is configured to cause the remote devices to initiate collection of the particular type of data using the selected type of device or software item.

2. The method of claim 1, wherein the research study is a clinical trial that involves use of a pharmaceutical by participants in the research study for a period of time.

3. The method of claim 1, wherein determining the predicted levels of compliance comprises determining, for each of the multiple types of devices or software items, levels of predicted compliance for different individuals in the cohort based on the respective attributes of the different individuals in the cohort.

4. The method of claim 1, wherein determining the predicted levels of compliance comprises determining, for each of the multiple types of devices or software items, levels of predicted compliance for different groups of individuals within the cohort.

5. The method of claim 1, wherein determining the predicted levels of compliance comprises determining the predicted levels of compliance based on requirements, in a study protocol for the research study, for actions requested to be performed by the participants in the cohort.

6. The method of claim 1, comprising providing, over a communication network and to a device of a researcher associated with the research study, a recommendation for participants in the cohort to use the selected type of device or software item in the research study.

7. The method of claim 1, wherein determining the predicted levels of compliance comprises determining the predicted levels of compliance based on outputs of a trained machine learning model.

8. The method of claim 1, wherein determining the predicted levels of compliance comprises determining the predicted levels of compliance based on historical data indicating levels of compliance achieved participants in other research studies for using technology items devices or software items in the other research studies.

9. A system comprising:
one or more computers; and
one or more computer-readable media storing instructions that are operable, when executed by the one or more computers, to cause the one or more computers to perform operations comprising:
   accessing, by the one or more computers, (i) study data indicating a particular type of data to be collected in a research study and (ii) attribute data indicating attributes of participants in a cohort for the research study;
   identifying, by the one or more computers, a multiple types of devices or software items that are each capable of collecting the particular type of data indicated by the study data;
   determining, by the one or more computers, a predicted level of compliance for each of the multiple types of devices or software items, each predicted level of compliance indicating an expected level of compliance by participants in the cohort in using the corresponding type of device or software item to collect the particular type of data indicated by the study data, the predicted levels of compliance being determined based on the attribute data indicating attributes of participants in the cohort;
   selecting, by the one or more computers, a type of device or software item for participants in the cohort to use in the research study based on the predicted levels of compliance;
   updating, by the one or more computers, records for the research study to specify the selected type of device or software item; and
   sending, by the one or more computers, configuration data or a software module over a communication network to remote devices of the participants in the cohort, wherein the configuration data or software module is configured to cause the remote devices to initiate collection of the particular type of data using the selected type of device or software item.

10. The system of claim 9, wherein the research study is a clinical trial that involves use of a pharmaceutical by participants in the research study for a period of time.

11. The system of claim 9, wherein determining the predicted levels of compliance comprises determining, for each of the multiple types of devices or software items, levels of predicted compliance for different individuals in the cohort based on the respective attributes of the different individuals in the cohort.

12. The system of claim 9, wherein determining the predicted levels of compliance comprises determining, for each of the multiple types of devices or software items, levels of predicted compliance for different groups of individuals within the cohort.

13. The system of claim 9, wherein determining the predicted levels of compliance comprises determining the predicted levels of compliance based on requirements, in a study protocol for the research study, for actions requested to be performed by the participants in the cohort.

14. The system of claim 9, wherein the operations comprise providing, over a communication network and to a device of a researcher associated with the research study, a recommendation for participants in the cohort to use the selected type of device or software item in the research study.

15. The system of claim 9, wherein determining the predicted levels of compliance comprises determining the predicted levels of compliance based on outputs of a trained machine learning model.

16. The system of claim 9, wherein determining the predicted levels of compliance comprises determining the predicted levels of compliance based on historical data indicating levels of compliance achieved participants in other research studies for using devices or software items in the other research studies.

17. One or more non-transitory computer-readable media storing instructions that are operable, when executed by one or more computers, to cause the one or more computers to perform operations comprising:
   accessing, by the one or more computers, (i) study data indicating a particular type of data to be collected in a research study and (ii) attribute data indicating attributes of participants in a cohort for the research study;
   identifying, by the one or more computers, a multiple types of devices or software items that are each capable of collecting the particular type of data indicated by the study data;

determining, by the one or more computers, a predicted level of compliance for each of the multiple types of devices or software items, each predicted level of compliance indicating an expected level of compliance by participants in the cohort in using the corresponding type of device or software item to collect the particular type of data indicated by the study data, the predicted levels of compliance being determined based on the attribute data indicating attributes of participants in the cohort;

selecting, by the one or more computers, a type of device or software item for participants in the cohort to use in the research study based on the predicted levels of compliance;

updating, by the one or more computers, records for the research study to specify the selected type of device or software item; and sending, by the one or more computers, configuration data or a software module over a communication network to remote devices of the participants in the cohort, wherein the configuration data or software module is configured to cause the remote devices to initiate collection of the particular type of data using the selected type of device or software item.

18. The one or more non-transitory computer-readable media of claim 17, wherein the research study is a clinical trial that involves use of a pharmaceutical by participants in the research study for a period of time.

19. The one or more non-transitory computer-readable media of claim 17, wherein determining the predicted levels of compliance comprises determining, for each of the multiple types of devices or software items, levels of predicted compliance for different individuals in the cohort based on the respective attributes of the different individuals in the cohort.

20. The one or more non-transitory computer-readable media of claim 17, wherein determining the predicted levels of compliance comprises determining, for each of the multiple types of devices or software items, levels of predicted compliance for different groups of individuals within the cohort.

21. The method of claim 1, further comprising:
accessing study data for each of multiple previous research studies, wherein the study data indicates attributes of participants of the previous research studies, types of devices of software items used to collect data in the previous research studies, and levels of compliance of the participants with study protocols for the previous research studies;

training one or more machine learning models based on the study data to predict, based on input indicating participant attributes, levels of compliance with data collection requirements that would be achieved for participants having the participant attributes;

wherein determining the predicted level of compliance for each of the multiple types of devices or software items comprises determining the predicted level of compliance for each of the multiple types of devices or software items based on output that the one or more machine learning models generated in response to input indicating the attributes of the participants in the cohort.

\* \* \* \* \*